United States Patent
Cohen et al.

(10) Patent No.: US 10,723,798 B2
(45) Date of Patent: Jul. 28, 2020

(54) ANTIBODIES TO LILRB2

(71) Applicant: Jounce Therapeutics, Inc., Cambridge, MA (US)

(72) Inventors: Heather B. Cohen, Somerville, MA (US); Lauren Pepper Mackenzie, Watertown, MA (US); Yasmin Ramsay, Boston, MA (US); Donald Raymond Shaffer, Boston, MA (US); Jeffrey Yan-Fei Smith, Somerville, MA (US)

(73) Assignee: Jounce Therapeutics, Inc., Cambridge, MA (US)

( * ) Notice: Subject to any disclaimer, the term of this patent is extended or adjusted under 35 U.S.C. 154(b) by 0 days.

(21) Appl. No.: 16/228,084

(22) Filed: Dec. 20, 2018

(65) Prior Publication Data

US 2019/0194327 A1  Jun. 27, 2019

Related U.S. Application Data

(60) Provisional application No. 62/610,050, filed on Dec. 22, 2017.

(51) Int. Cl.

| | | |
|---|---|---|
| *A61K 39/395* | (2006.01) | |
| *C07K 16/28* | (2006.01) | |
| *A61P 35/00* | (2006.01) | |
| *C07K 16/46* | (2006.01) | |
| *C07K 16/30* | (2006.01) | |
| *C12Q 1/6886* | (2018.01) | |
| *A61K 38/00* | (2006.01) | |
| *A61K 45/06* | (2006.01) | |

(52) U.S. Cl.
CPC .......... *C07K 16/2818* (2013.01); *A61P 35/00* (2018.01); *C07K 16/2803* (2013.01); *C07K 16/2896* (2013.01); *C07K 16/3061* (2013.01); *C07K 16/46* (2013.01); *C12Q 1/6886* (2013.01); *A61K 38/00* (2013.01); *A61K 45/06* (2013.01); *C07K 2317/24* (2013.01); *C07K 2317/31* (2013.01); *C07K 2317/32* (2013.01); *C07K 2317/33* (2013.01); *C07K 2317/51* (2013.01); *C07K 2317/515* (2013.01); *C07K 2317/565* (2013.01); *C07K 2317/76* (2013.01); *C07K 2317/92* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 7,014,853 | B2 | 3/2006 | Cosman |
| 7,834,157 | B2 | 11/2010 | Cosman |
| 7,943,329 | B2 | 5/2011 | Atwal et al. |
| 8,901,281 | B2 | 12/2014 | Ponath et al. |
| 2004/0241167 | A1 | 12/2004 | Suciu-Foca et al. |
| 2004/0253674 | A1 | 12/2004 | Cosman |
| 2005/0238643 | A1 | 10/2005 | Arm et al. |
| 2009/0169542 | A1 | 7/2009 | Atwal et al. |
| 2009/0280109 | A1 | 11/2009 | Suciu-Foca et al. |
| 2012/0315269 | A1 | 12/2012 | Klechevsky et al. |
| 2015/0174203 | A1 | 6/2015 | Chen et al. |
| 2016/0200815 | A1 | 7/2016 | Feldman et al. |

FOREIGN PATENT DOCUMENTS

| | | | |
|---|---|---|---|
| WO | WO-98/48017 A1 | 10/1998 | |
| WO | WO-00/68383 A2 | 11/2000 | |
| WO | WO-03/000199 A2 | 1/2003 | |
| WO | WO-03/041650 A2 | 5/2003 | |
| WO | WO-2009/076359 A2 | 6/2009 | |
| WO | WO-2009/140361 A1 | 11/2009 | |
| WO | WO-2013/181438 A2 | 12/2013 | |
| WO | WO-2015/179633 A1 | 11/2015 | |
| WO | WO-2016/111947 A2 | 7/2016 | |
| WO | WO-2016/127247 A1 | 8/2016 | |
| WO | WO-2016/144728 A2 | 9/2016 | |
| WO | WO-2018/187518 A1 | 10/2018 | |
| WO | WO-2018187518 A1 * | 10/2018 | .............. A61P 35/00 |

OTHER PUBLICATIONS

Edwards et al.,J Mol Biol. Nov. 14, 2003;334(1): 103-18.*
Llyod et al., Protein Eng Des Sel. Mar. 2009;22(3):159-68. doi: 10.1093/protein/gzn058. Epub Oct. 29, 2008.*
Goel et al., J Immunol. Dec. 15, 2004; 173(12):7358-67.*
Janeway et al., Immunobiology, 3rd edition, Garland Publishing Inc., 1997, pp. 3:1-3:11.*
Rudikoff et al., Proc Natl Acad Sci USA. Mar. 1982;79(6):1979-83.*
Kipriyanov et al., Mol Biotechnol. Jan. 2004;26(1):39-60.*
Affymetrix, "Staining Intracellular Antigens for Flow Cytometry," eBioscience—Flow Cytometry—BestProtocols. Revised Nov. 25, 2015 (10 pges).
Agaugué et al., "Role of HLA-G in tumor escape through expansion of myeloid-derived suppressor cells and cytokinic balance in favor of Th2 versus Th1/Th17," Blood. 117(26):7021-31 (2011).
Alaoui et al., "Early SIV and HIV infection promotes the LILRB2/MHC-I inhibitory axis in cDCs," Cell. Mol. Life Sci. (2017), https://doi.org/10.1007/s00018-017-2712-9 (including supplement) (27 pages).
Allan et al., "Tetrameric Complexes of Human Histocompatibility Leukocyte Antigen (HLA)-G Bind to Peripheral Blood Myelomonocytic Cells," J. Exp. Med. 189(7):1149-55 (1999).
Alvarado-Guerri et al., "TAP1 and TAP2 Polymorphisms and Their Linkage Disequilibrium With HLA-DR, -DP, and -DQ in an Eastern Andalusian Population," Hum. Immunol. 66:921-30 (2005).
Amodio et al., "HLA-G expression levels influence the tolerogenic activity of human DC-10," Haematologica 100(4):548-57 (2015) (including supplement) (20 pages).
Amodio et al., "Human tolerogenic DC-10: perspectives for clinical applications," Transplant. Res. 1:14 (2012) (10 pages).

(Continued)

*Primary Examiner* — Michael Szperka
(74) *Attorney, Agent, or Firm* — Jones Day

(57) ABSTRACT

Provided herein are various embodiments relating to antibodies that bind LILRB2. Anti-LILRB2 antibodies can be used in methods to treat disease, for example, cancer.

21 Claims, 41 Drawing Sheets

Specification includes a Sequence Listing.

(56) References Cited

OTHER PUBLICATIONS

Aoi et al., "Angiopoietin-like Protein 2 is an Important Facilitator of Inflammatory Carcinogenesis and Metastasis," Cancer Res. 71(24):7502-12 (2011).
Aoto et al., "Immunogenic tumor cell death induced by chemotherapy in patients with breast cancer and esophageal squamous cell carcinoma," Oncol. Rep. 39:151-59 (2018).
Apps et al., "A homodimeric complex of HLA-G on normal trophoblast cells modulates antigen-presenting cells via LILRB1," Eur. J. Immunol. 37:1924-37 (2007).
Aras et al., "TAMeless traitors: macrophages in cancer progression and metastasis," Br. J. Cancer 117:1583-91 (2017).
Atwal et al., "PirB is a Functional Receptor for Myelin Inhibitors of Axonal Regeneration," Science 322:967-70 (2008).
Baer et al., "Suppression of microRNA activity amplifies IFN-gamma-induced macrophage activation and promotes anti-tumour immunity," Nat. Cell Biol. (2016), DOI: 10.1038/ncb3371 (30 pages).
Balas et al., "HLA-DQA1 Introns 2 and 3 Sequencing: DQA1 Sequencing-Based Typing and Characterization of a Highly Polymorphic Microsatellite at Intron 3 of DQA1*0505," Hum. Immunol. 66:903-11 (2005).
Banchereau et al., "Immunoglobulin-like transcript receptors on human dermal CD14+ dendritic cells act as a CD8-antagonist to control cytotoxic T cell priming," Proc. Natl. Acad. Sci. U.S.A. 109(46):18885-90 (2012) (including supplement) (15 pages).
Barkal et al., "Engagement of MHC class I by the inhibitory receptor LILRB1 suppresses macrophages and is a target of cancer immunotherapy," Nat. Immunol. (2017), doi: 10.1038/s41590-017-0004-z (11 pages).
Baruch-Morgenstern et al., "Paired immunoglobulin-like receptor A is an intrinsic, self-limiting suppressor of IL-5-induced eosinophil development," available in PMC Jul. 1, 2014, published in final edited form as: Nat. Immunol. 15(1):36-44 (2014), doi:10.1038/ni.2757 (22 pages).
Bashirova et al., "LILRB2 Interaction with HLA Class I Correlates with Control of HIV-1 Infection," PLoS Genet. 10(3):e1004196. (2014) (10 pages).
Baudhuin et al., "Exocytosis acts as a modulator of the ILT4-mediated inhibition of neutrophil functions," Proc. Natl. Acad. Sci. U.S.A. 110(44):17957-62 (2013) (including supplement) (11 pages).
Baumgart et al., "Transient Cytokine-Induced Liver Injury Following Administration of the Humanized Anti-CD3 Antibody Visilizumab (HuM291) in Crohn's Disease," Am. J. Gastroenterol. 104:868-76 (2009).
Bondarenko et al., "Characterization of cynomolgus and vervet monkey placental MHC class I expression: diversity of the nonhuman primate AG locus," available in PMC Jan. 25, 2010, published in final edited form as: Immunogenetics 61(6):431-42 (2009), doi:10.1007/s00251-009-0376-9 (19 pages).
Bouchez et al., "Development of a Delayed-Type Hypersensitivity (DTH) Model in the Cynomolgus Monkey," J. Toxicol. Pathol. 25:183-88 (2012).
Boyson et al., "Identification of a Novel MHC Class I Gene, Mamu-AG, Expressed in the Placenta of a Primate with an Inactivated G Locus," J. Immunol. 159:3311-21 (1997) (12 pages).
Boyson et al., "Identification of the Rhesus Monkey HLA-G Ortholog; Mamu-G is a Pseudogene," J. Immunol. 157:5428-37 (1996) (11 pages).
Brown et al., "CD86+ or HLA-G+ can be transferred via trogocytosis from myeloma cells to T cells and are associated with poor prognosis," Blood. 120(10):2055-63 (2012).
Brown et al., "The LILR family: modulators of innate and adaptive immune pathways in health and disease," Tissue Antigens. 64:215-25 (2004).
Burshtyn et al., "The Expanding Spectrum of Ligands for Leukocyte Ig-like Receptors," J. Immunol. 196:947-955 (2016).
Bylinska et al., "The impact of HLA-G, LILRB1 and LILRB2 gene polymorphisms on susceptibility to and severity of endometriosis," Mol. Genet. Genomics (2017), https://doi.org/10.1007/s00438-017-1404-3 (13 pages).
Canavez et al., "Comparison of Chimpanzee and Human Leukocyte Ig-Like Receptor Genes Reveals Framework and Rapidly Evolving Genes," J. Immunol. 167:5786-94 (2001) (10 pages).
Carosella et al., "Beyond the increasing complexity of the immunomodulatory HLA-G molecule," Blood. 111(10):4862-70 (2008).
Carosella et al., "Chapter Two: HLA-G: An Immune Checkpoint Molecule," Adv. Immunol. 127:33-144 (2015), doi: 10.1016/bs.ai.2015.04.001 (112 pages).
Carosella et al., "HLA-G: from biology to clinical benefits," Trends Immunol. 29(3):125-32 (2008).
Castelli et al., "Transcriptional and Posttranscriptional Regulations of the HLA-G Gene," J. Immunol. Res. 2014:Article ID 734068 (2014), http://dx.doi.org/10.1155/2014/734068 (15 pages).
Chang et al., "Dose-Dense Chemotherapy Improves Mechanisms of Antitumor Immune Response," Cancer Res. 73(1):119-27 (2012).
Chattopadhyay et al., "Continuous Presence of Th1 Conditions Is Necessary for Longer Lasting Tumor-Specific CTL Activity in Stimulation Cultures With PBL," Hum. Immunol. 66:884-91 (2005).
Chen et al., "Blocking immunoinhibitory receptor LILRB2 reprograms tumor-associated myeloid cells and promotes antitumor immunity," J. Clin. Invest. (2018), https://doi.org/10.1172/JCI97570. (including supplement) (28 pages).
Choi et al., "Reference values of hematology, biochemistry, and blood type in cynomolgus monkeys from cambodia origin," Lab Anim. Res. 32(1):46-55 (2016).
Colonna et al., "Cutting Edge: Human Myelomonocytic Cells Express an Inhibitory Receptor for Classical and Nonclassical MHC Class I Molecules," J. Immunol. 160:3096-3100 (1998). (6 pages).
Comiskey et al., "Evidence That HLA-G is the Functional Homolog of Mouse Qa-2, the Ped Gene Product," available in PMC Sep. 5, 2008, published in final edited form as: Hum. Immunol. 64(11):999-1004 (2003), doi:10.1016/j.humimm.2003.08.352. (9 pages).
Carosella et al., "The tolerogenic interplay(s) among HLA-G, myeloid APCs, and regulatory cells," Blood .118(25):6499-505 (2011).
Córdoba et al., "Modeling of delayed type hypersensitivity (DTH) in the non-human primate (NHP)," Drug. Discov. Today Dis. Models. 5(2):63-71 (2008).
Curigliano et al., "Molecular Pathways: Human Leukocyte Antigen G(HLA-G)," Clin. Cancer Res. 19(20):5564-71 (2013).
Da Silva Nardi et al., "Soluble monomers, dimers and HLA-G-expressing extracellular vesicles: the three dimensions of structural complexity to use HLA-G as a clinical biomarker," HLA 88:77-86 (2016).
Das et al., "Microenvironment-dependent growth of preneoplastic and malignant plasma cells in humanized mice," Nat. Med. 22(11):1351-57 (2016) (9 pages).
David et al., "The IL-8/IL-8R Axis: A Double Agent in Tumor Immune Resistance," Vaccines 4:22 (2016), doi:10.3390/vaccines4030022 (15 pages).
De Biasi et al., "Cisplatin-Induced Antitumor Immunomodulation: A Review of Preclinical and Clinical Evidence," Clin. Cancer Res. 20(21):5384-91 (2014).
De Kruijf et al., "HLA-E and HLA-G Expression in Classical HLA Class I-Negative Tumors Is of Prognostic Value for Clinical Outcome of Early Breast Cancer Patients," J. Immunol. 185:7452-7459 (2010).
DeNardo et al., "Leukocyte Complexity Predicts Breast Cancer Survival and Functionally Regulates Response to Chemotherapy," Cancer Discov. 1:54-67 (2011) (15 pages).
Deng et al., "A motif in LILRB2 critical for Angptl2 binding and activation," Blood. 124(6):924-35 (2014) (28 pages).
Di Caro et al., "Dual prognostic significance of tumour-associated macrophages in human pancreatic adenocarcinoma treated or untreated with chemotherapy," Gut. (2016), doi: 10.1136/gutjnl-2015-309193 (11 pages).
Dudal et al., "Application of a MABEL Approach for a T-Cell-Bispecific Monoclonal Antibody: CEA TCB," J. Immunother. 00(00) (2016) (11 pages).

(56) References Cited

OTHER PUBLICATIONS

Dupin et al., "Inhibition of T Cell Alloreactivity by Bronchial Epithelium Is Impaired in Lung Transplant Recipients, Through Pathways Involving TGF-beta, IL-10 and HLA-G," Transplantation. 101(9):2192-99 (2017).
Endo et al., "Regulation of cytotoxic T lymphocyte triggering by PIR-B on dendritic cells," Proc. Natl. Acad. Sci. U.S.A. 105(38):14515-20 (2008) (including supplement) (14 pages).
Engblom et al., "The role of myeloid cells in cancer therapies," Nat. Rev. Cancer. 16:447-62 (2016).
Exley, M. A., Wilson, S. B., & Balk, S. P. (2017). Isolation and functional use of human NKT cells. Current Protocols in Immunology, 119, 14.11.1-14.11.20. doi: 10.1002/cpim.33 (20 pages).
Favier et al., "Tolerogenic Function of Dimeric Forms of HLA-G Recombinant Proteins: A Comparative Study In Vivo," PLoS One 6(7):e21011 (2011) (8 pages).
Ferns et al., "Classical and non-classical HLA class I aberrations in primary cervical squamous- and adenocarcinomas and paired lymph node metastases," J. Immunother. Cancer. 4:78 (2016), DOI 10.1186/s40425-016-0184-3 (11 pages).
Ferris et al., "Immune escape associated with functional defects in antigen-processing machinery in head and neck cancer," Clin. Cancer Res. 12(13):3890-95 (2006).
Fournel et al., "Comparative reactivity of different HLA-G monoclonal antibodies to soluble HLA-G molecules," Tissue Antigens. 55:510-18 (2000).
Fulmer, "New strategies for CNS regeneration," SciBX 1(43): (2008), doi:10.1038/scibx.2008.1036 (3 pages).
Giavridis et al., "CAR T cell—induced cytokine release syndrome is mediated by macrophages and abated by IL-1 blockade," Nat. Med. (2018), https://doi.org/10.1038/s41591-018-0041-7 (14 pages).
Giles et al., "HLA-B27 Homodimers and Free H Chains are Stronger Ligands for Leukocyte Ig-like Receptor B2 than Classical HLA Class I," J. Immunol. 188:6184-93 (2012) (11 pages).
Gonen-Gross et al., "Complexes of HLA-G Protein on the Cell Surface Are Important for Leukocyte Ig-Like Receptor-1 Function," J. Immunol. 171:1343-51 (2003). (10 pages).
Gonzalez et al., "Identification of Circulating Nonclassic Human Leukocyte Antigen G (HLA-G)—Like Molecules in Exudates," Clin. Chem. 57(7):1013-22 (2011).
Guerriero et al., "Class IIA HDAC inhibition reduces breast tumours and metastases through anti-tumour macrophages," Nature. 000(1) (2017), doi:10.1038/nature21409 (21 pages).
Haanstra et al., "Blocking T cell co-stimulation using a CD80 blocking small molecule reduces delayed type hypersensitivity responses in rhesus monkeys," Clin. Exp. Immunol. 158:91-8 (2009).
Hato et al., "Molecular Pathways: The Immunogenic Effects of Platinum-Based Chemotherapeutics," Clin. Cancer Res. 20(11):2831-7 (2014).
Hirayasu et al., "Evidence for Natural Selection on Leukocyte Immunoglobulin-like Receptors for HLA Class I in Northeast Asians," Am. J. Hum. Genet. 82:1075-83 (2008).
Hirayasu et al., "Functional and genetic diversity of leukocyte immunoglobulin-like receptor and implication for disease associations," J. Hum. Genet. 60:703-8 (2015).
Hofer et al., "Ig-like transcript 4 as a cellular receptor for soluble complement fragment C4d," FASEB J. 30(4):1492-503 (2016).
Hopkins et al., "MHC Class I—Associated Peptides Identified From Normal Platelets and From Individuals With Idiopathic Thrombocytopenic Purpura," Hum. Immunol. 66:874-83 (2005).
HoWangYin et al., "Multimeric Structures of HLA-G Isoforms Function Through Differential Binding to LILRB Receptors," available in PMC Jan. 17, 2014, published in final edited form as: Cell Mol. Life Sci. 69(23):4041-9 (2012), doi:10.1007/s00018-012-1069-3 (16 pages).
Hsi et al., "CS1, a Potential New Therapeutic Antibody Target for the Treatment of Multiple Myeloma," available in PMC May 15, 2015, published in final edited form as: Clin. Cancer Res. 14(9):2775-84 (2008), doi:10.1158/1078-0432.CCR-07-4246 (23 pages).

Hu et al., "The effects of chemotherapeutic drugs on human monocyte-derived dendritic cell differentiation and antigen presentation," Clin. Exp. Immunol. 172:490-9 (2012).
Huang et al., "HLA-B*35-Px—mediated acceleration of HIV-1 infection by increased inhibitory immunoregulatory impulses," J. Exp. Med. 206(13):2959-66 (2009).
Huang et al., "Soluble HLA-G Inhibits Myeloid Dendritic Cell Function in HIV-1 Infection by Interacting with Leukocyte Immunoglobulin-Like Receptor B2," J. Virol. 84(20):10784-91 (2010).
Hudson et al., "Leukocyte Ig-Like Receptors—A Model for MHC Class I Disease Associations," Front. Immunol. 7(281) (2016), doi: 10.3389/fimmu.2016.00281 (8 pages).
Im et al., "Defining CD8+ T cells that provide the proliferative burst after PD-1 therapy," Nature (2016), doi:10.1038/nature19330 (20 pages).
Janssen, CNTO-888/Carlumab Information (2014) (2 pages).
Jasinski-Bergner et al., "Clinical relevance of miR-mediated HLA-G regulation and the associated immune cell infiltration in renal cell carcinoma," Oncoimmunology 4(6): e1008805-1-14 (2015) (14 pages).
Jones et al., "HLA Class I Allelic Sequence and Conformation Regulate Leukocyte Ig-Like Receptor Binding," J. Immunol. 186:2990-97 (2011) (25 pages).
Kadomatsu et al., "Diverse roles of ANGPTL2 in physiology and pathophysiology," Trends Endocrinol. Metab. 25(5):245-54 (2014).
Kang et al., "Inhibitory leukocyte immunoglobulin-like receptors: Immune checkpoint proteins and tumor sustaining factors," Cell Cycle. 15(1):25-40 (2016).
Ketroussi et al., "Lymphocyte Cell-Cycle Inhibition by HLA-G is Mediated by Phosphatase SHP-2 and Acts on the mTOR Pathway," PLoS One. 6(8):e22776 (2011), doi:10.1371/journal.pone.0022776 (8 pages).
Khan et al., "Decorin Is a Novel VEGFR-2-Binding Antagonist for the Human Extravillous Trophoblast," Mol. Endocrinol. 25(8):1431-43 (2011).
Kim et al., "Human LilrB2 is a beta-Amyloid Receptor and Its Murine Homolog PirB Regulates Synaptic Plasticity in an Alzheimer's Model," available in PMC Mar. 20, 2014, published in final edited form as: Science. 341(6152); doi:10.1126/science.1242077 (2013) (including supplement) (39 pages).
Kim et al., "Serum cytokine profiles in healthy young and elderly population assessed using multiplexed bead-based immunoassays," J. Transl. Med. 9:113 (2011) (7 pages).
Kleiner et al., "Cytokine Levels in the Serum of Healthy Subjects," Mediators Inflamm. 2013; Article ID 434010 (2013), http://dx.doi.org/10.1155/2013/434010 (6 pages).
Komohara et al., "HLA-G as a target molecule in specific immunotherapy against renal cell carcinoma," Oncol. Rep. 18:1463-68 (2007).
König et al., "The prognostic impact of soluble and vesicular HLA-G and its relationship to circulating tumor cells in neoadjuvant treated breast cancer patients," Hum. Immunol. 77:791-99 (2016).
Koshkin et al., "Clinical activity of nivolumab in patients with non-clear cell renal cell carcinoma," J. Immunother. Cancer 6:9 (2018), doi: 10.1186/s40425-018-0319-9 (7 pages).
Kostlin et al., "HLA-G promotes myeloid-derived suppressor cell (MDSC) accumulation and suppressive activity during human pregnancy through engagement of the receptor ILT4," Eur. J. Immunol. (2017), doi: 10.1002/eji.201646564 (42 pages).
Kuroki et al., "Cutting Edge: Class II-like Structural Features and Strong Receptor Binding of the Nonclassical HLA-G2 Isoform Homodimer," J. Immunol. 198:3399-3403 (2017). (6 pages).
Kuroki et al., "Molecular recognition of paired receptors in the immune system," Front. Microbiol. 3(429) (2012), doi: 10.3389/fmicb.2012.00429 (12 pages).
Langat et al., "Do Nonhuman Primates Comprise Appropriate Experimental Models for Studying the Function of Human Leukocyte Antigen-G?" Biol. Reprod. 67:1367-74 (2002).
Lee et al., "Soluble human leukocyte antigen G5 polarizes differentiation of macrophages toward a decidual macrophage-like phenotype," Hum. Reprod. 30(10):2263-74 (2015).

(56) References Cited

OTHER PUBLICATIONS

Leidi et al., "M2 Macrophages Phagocytose Rituximab-Opsonized Leukemic Targets More Efficiently than M1 Cells In Vitro," J. Immunol. 182:4415-22 (2009) (9 pages).

LeMaoult et al., "HLA-G1-expressing antigen-presenting cells induce immunosuppressive CD4+ T cells," Proc. Natl. Acad. Sci. U.S.A. 101(18):7064-9 (2004).

Lesterhuis et al., "Platinum-based drugs disrupt STAT6-mediated suppression of immune responses against cancer in humans and mice," J. Clin. Invest. 121(8):3100-8 (2011).

Li et al., "A novel role of CD1c in regulating CD1d-mediated NKT cell recognition by competitive binding to Ig-like transcript 4," Int. Immunol. 24(11):729-37 (2012).

Li et al., "Cis association of leukocyte Ig-like receptor 1 with MHC class I modulates accessibility to antibodies and HCMV UL18," Eur. J. Immunol. 43:1042-52 (2013).

Li et al., "HLA-G homodimer-induced cytokine secretion through HLA-G receptors on human decidual macrophages and natural killer cells," Proc. Natl. Acad. Sci. U.S.A. 106(14):5767-72 (2009).

Li et al., "Immunoglobulin-like Transcript 4 (ILT4) Inhibits Lipid Antigen Presentation through Direct CD1d Interaction," available in PMC Jan. 15, 2010, published in final edited form as: J. Immunol. 182(2):1033-40 (2009) (17 pages).

Li et al., "Low-dose cisplatin administration to septic mice improves bacterial clearance and programs peritoneal macrophage polarization to M1 phenotype," Pathog. Dis. 72:111-23 (2014).

Liang et al., "HLA-G inhibits the functions of murine dendritic cells via the PIR-B immune inhibitory receptor," Eur. J. Immunol. 32:2418-26 (2002).

Liang et al., "Mobilizing Dendritic Cells for Tolerance by Engagement of Immune Inhibitory Receptors for HLA-G," Hum. Immunol. 64:1025-32 (2003).

Liang et al., "Modulation of dendritic cell differentiation by HLA-G and ILT4 requires the IL-6-STAT3 signaling pathway," Proc. Natl. Acad. Sci. U.S.A. 105(24):8357-62 (including supplement) (2008) (9 pages).

Lichterfeld et al., "A viral CTL escape mutation leading to immunoglobulin-like transcript 4-mediated functional inhibition of myelomonocytic cells," J. Exp. Med. 204(12):2813-24 (2007).

Lin et al., "Human Leukocyte Antigen-G (HLA-G) Expression in Cancers: Roles in Immune Evasion, Metastasis and Target for Therapy," Mol. Med. 21:782-91 (2015).

Liu et al., "ANGPTL2/LILRB2 signaling promotes the propagation of lung cancer cells," Oncotarget 6(25):21004-15 (2015).

Loumagne et al., "In vivo evidence that secretion of HLA-G by immunogenic tumor cells allows their evasion from immunosurveillance," Int. J. Cancer. 135:2107-17 (2014).

Lowe et al., "On Setting the First Dose in Man: Quantitating Biotherapeutic Drug-Target Binding through Pharmacokinetic and Pharmacodynamic Models," Basic Clin. Pharmacol. Toxicol. 106:195-209 (2009).

Lu et al., "Human Semaphorin-4A drives Th2 responses by binding to receptor ILT-4," Nat. Commun. (2018), DOI: 10.1038/s41467-018-03128-9 (11 pages).

Ma et al., "Paired Immunoglobin-like Receptor-B Regulates the Suppressive Function and Fate of Myeloid-Derived Suppressor Cells," available in PMC Mar. 25, 2012, published in final edited form as: Immunity. 34:385-95 (2011) (22 pages).

Ma et al., "Paired Immunoglobin-like Receptor-B Regulates the Suppressive Function and Fate of Myeloid-Derived Suppressor Cells," Immunity. 34:385-95 (2011).

Majumder et al., "Predicting clinical response to anticancer drugs using an ex vivo platform that captures tumour heterogeneity," Nat. Commun. 6:6169 (2015), DOI: 10.1038/ncomms7169 (14 pages).

Mantovani et al., "Tumour-associated macrophages as treatment targets in oncology," Nat. Rev. Clin. Oncol. (2017), doi: 10.1038/nrclinonc.2016.217 (18 pages).

Marchesi et al., "HLA-dependent tumour development: a role for tumour associate macrophages?" J. Transl. Med. 11:247 (2013), doi:10.1186/1479-5876-11-247 (15 pages).

Martí et al., "Quantifying soluble HLA-G in supernatants of cultured embryos as a marker of implantation potential in an assisted reproduction program," Inmunología 26(3):127-134 (2007).

Masuda et al., "Cis binding between inhibitory receptors and MHC class I can regulate mast cell activation," J. Exp. Med. 204(4):907-20 (2007).

Menier et al., "Characterization of Monoclonal Antibodies Recognizing HLA-G or HLA-E: New Tools to Analyze the Expression of Nonclassical HLA Class I Molecules," Hum. Immunol. 64:315-26 (2003).

Michea et al., "Adjustment of dendritic cells to the breast-cancer microenvironment is subset specific," Nature Immunol. 19:885-897 (2018).

Morandi et al., "Human Neuroblastoma Cells Trigger an Immunosuppressive Program in Monocytes by Stimulating Soluble HLA-G Release," Cancer Res. 67(13):6433-41 (2007).

Morandi et al., "Intrathecal Soluble HLA-E Correlates with Disease Activity in Patients with Multiple Sclerosis and may Cooperate with Soluble HLA-G in the Resolution of Neuroinflammation," J. Neuroimmune Pharmacol. 8:944-955 (2013).

Morandi et al., "Recent Advances in Our Understanding of HLA-G Biology: Lessons from a Wide Spectrum of Human Diseases," J. Immunol. Res. 2016:Article ID 4326495 (2016), doi: 10.1155/2016/4326495 (14 pages).

Munitz et al., "A dual activation and inhibition role for the paired immunoglobulin-like receptor B in eosinophils," Blood .111(12):5694-5703 (2008).

Munitz et al., "Paired immunoglobulin-like Receptor B (PIR-B) Negatively Regulates Macrophage Activation in Experimental Colitis," available in PMC Aug. 21, 2012, published in final edited form as: Gastroenterology. 139(2):530-41 (2010), doi:10.1053/j.gastro.2010.04.006 (20 pages).

Nguyen-Lefebvre et al., "Mouse models for studies of HLA-G functions in basic science and pre-clinical research," Hum. Immunol. 77:711-19 (2016).

Ning et al., "A Rapid Culture Technique Produces Functional Dendritic-Like Cells from Human Acute Myeloid Leukemia Cell Lines," J. Biomed. Biotechnol. 2011:172965 (2011), doi:10.1155/2011/172965 (9 pages).

Noel et al., "Phase Ib study of PF-04136309 (an oral CCR2 inhibitor) in combination with nab-paclitaxel/gemcitabine in first-line treatment of metastatic pancreatic adenocarcinoma," Ann. Oncol. 28(5):257 (2017) (1 page) (abstract only).

Nywening et al., "Phase 1 b study targeting tumour associated macrophages with CCR2 inhibition plus FOLFIRINOX in locally advanced and borderline resectable pancreatic cancer," available in PMC Apr. 27, 2017, published in final form as: Lancet. Oncol. 17(5):651-62 (2016), doi:10.1016/S1470-2045(16)00078-4 (22 pages).

Okada et al., "Synoviocyte-Derived Angiopoietin-Like Protein 2 Contributes to Synovial Chronic Inflammation in Rheumatoid Arthritis," Am. J. Pathol. 176(5):2309-19 (2010).

Okamoto et al., "Toll-like Receptors (TLRs) are expressed by myeloid leukaemia cell lines, but fail to trigger differentiation in response to the respective TLR ligands," Br. J. Haematol. 147:585-587 (2009).

Okimura et al., "Characterization of ASKP1240, a Fully Human Antibody Targeting Human CD40 With Potent Immunosuppressive Effects," Am. J. Transplant. 14:1290-99 (2014).

Ouji-Sageshima et al., "Establishment of optimized ELISA system specific for HLA-G in body fluids," HLA (2016), doi: 10.1111/tan.12919 (7 pages).

Piancatelli et al., "MICA Polymorphism in a Population From North Morocco, Metalsa Berbers, Using Sequence-Based Typing," Hum. Immunol. 66:931-36 (2005).

Piccolo et al., "Opposing macrophage polarization programs show extensive epigenomic and transcriptional cross-talk," Nat. Immunol. (2017), doi:10.1038/ni.3710 (12 pages).

Poirier et al., "Antibody-mediated depletion of lymphocyte-activation gene-3 (LAG-3+)-activated T lymphocytes prevents delayed-type hypersensitivity in non-human primates," Clin. Exp. Immunol. 164:265-74 (2011).

(56) References Cited

OTHER PUBLICATIONS

Poláková et al., "Expression of the non-classical HLA-G antigen in tumor cell lines is extremely restricted," Neoplasma. 47(6):342-48 (2000).
Pontes et al., "Characterization of Mannose-Binding Lectin Gene Polymorphism Among Human T-Cell Lymphotropic Virus 1 and 2-Infected Asymptomatic Subjects," Hum. Immunol. 66:892-96 (2005).
Quail et al., "Molecular Pathways: Deciphering Mechanisms of Resistance to Macrophage-Targeted Therapies," Clin. Cancer Res. 23(4):876-84 (2017), published OnlineFirst on Nov. 26, 2016, doi:10.1158/1078-0432.CCR-16/0133.
Rebmann et al., "Report of the Wet Workshop for Quantification of Soluble HLA-G in Essen, 2004," Hum. Immunol. 66:853-63 (2005).
Rebmann et al., "Soluble HLA-G and -E (sHLA-G/E) as Potential Biomarkers of Clinical Outcomes in Patients With Advanced, Refractory Squamous NSCLC Treated With Nivolumab (NIVO): CheckMate 063," Presented at the American Association for Cancer Research (AACR) Annual Meeting; Apr. 1-5, 2017; Washington, DC, USA. CT126 (5 pages).
Rebmann et al., "The Potential of HLA-G-Bearing Extracellular Vesicles as a Future Element in HLA-G Immune Biology," Front. Immunol. 7(173) (2016), doi: 10.3389/fimmu.2016.00173 (8 pages).
Reinders et al., "Identification of HLA-A*0111N: A Synonymous Substitution, Introducing an Alternative Splice Site in Exon 3, Silenced the Expression of an HLA-A Allele," Hum. Immunol. 66:912-20 (2005).
Reits et al., "Radiation modulates the peptide repertoire, enhances MHC class I expression, and induces successful antitumor immunotherapy," J. Exp. Med. 203(5):1259-71 (2006).
Ristich et al., "Mechanisms of Prolongation of Allograft Survival by HLA-G/ILT4-Modified Dendritic Cells," Hum. Immunol. 68:264-71 (2007).
Ristich et al., "Tolerization of dendritic cells by HLA-G," Eur. J. Immunol. 35:1133-42 (2005).
Riteau et al., "Exosomes Bearing HLA-G are Released by Melanoma Cells," Hum. Immunol. 64:1064-72 (2003).
Riteau et al., "HLA-G inhibits the allogeneic proliferative response," J. Reprod. Immunol. 43:203-11 (1999).
Rizzo et al., "Matrix metalloproteinase-2 (MMP-2) generates soluble HLA-G1 by cell surface proteolytic shedding," Mol. Cell Biochem. 381:243-55 (2013).
Rolland et al., "Human Leukocyte Antigen Class I Antigen Expression is an Independent Prognostic Factor in Ovarian Cancer," Clin. Cancer Res. 13(12):3591-96 (2007).
Romano et al., "Ipilimumab-dependent cell-mediated cytotoxicity of regulatory T cells ex vivo by nonclassical monocytes in melanoma patients," Proc. Natl. Acad. Sci. U.S.A. 112(19):6140-45 (2015).
Rosso et al., "Biologic Data of Cynomolgus Monkeys Maintained under Laboratory Conditions," PLoS One 11(6):e0157003 (2016), doi:10.1371/journal.pone.0157003 (17 pages).
Rouas-Freiss et al., "HLA-G Proteins in Cancer: Do They Provide Tumor Cells with an Escape Mechanism?" Cancer Res. 65(22):10139-44 (2005).
Rouas-Freiss et al., "The Dual Role of HLA-G in Cancer," J. Immunol. Res. 2014:Article ID 359748 (2014), http://dx.doi.org/10.1155/2014/359748 (10 pages).
Rueda et al., "Analysis of Vascular Endothelial Growth Factor (VEGF) Functional Variants in Rheumatoid Arthritis," Hum. Immunol. 66:864-68 (2005).
Ruffell et al., "Macrophages and therapeutic resistance in cancer," available in PMC Apr. 13, 2016, published in final edited form as: Cancer Cell. 27(4):462-72 (2015), doi:10.1016/j.ccell.2015.02.015 (22 pages).
Sánchez et al., "Analysis of a GT Microsatellite in the Promoter of the foxp3/scurfin Gene in Autoimmune Diseases," Hum. Immunol. 66:869-73 (2005).
Santiago et al., "Th1 Cytokine Polymorphisms in Spanish Patients With Type 1 Diabetes," Hum. Immunol. 66:897-902 (2005).

Santulli, "Angiopoietin-like proteins: a comprehensive look," Front. Endocrinol. 5(4) (2014), doi: 10.3389/fendo.2014.00004 (6 pages).
Sasaki et al., "Angiopoietin Like Protein 2 (ANGPTL2) Promotes Adipose Tissue Macrophage and T lymphocyte Accumulation and Leads to Insulin Resistance," PLoS One (2015), D01:10.1371/journal.pone.0131176 (18 pages).
Satterwhite et al., "Investigation of KLH (Keyhole Limpet Hemocyanin) Antigen Dose Response in Male and Female Cynomolgus Monkeys to Establish a Sub-optimal Response," Poster—Abstract No. 1928, Poster Board No. P235 (1 page).
Satterwhite, "An In Vivo Delayed-Type Hypersensitivity (DTH) Model in Non-Human Primates and Applications in Nonclinical Studies Supporting Biotherapeutic Drug Development," Charles River Presentation. Oct. 20, 2015 (48 pages).
Satterwhite, "Key Immunoassays to Support Preclinical Vaccine Development," Slide Presentation—Charles River Laboratories (2014) (28 pages).
Satterwhite, "Strategies for Development of Pharmacodynamic and In Vitro Functional Immunoassays in Support of Preclinical and Clinical Oncology Biopharmaceutical Programs," Charles River Presentation (60 pages).
Shehata et al., "Human leukocyte antigen class I expression is an independent prognostic factor in advanced ovarian cancer resistant to first-line platinum chemotherapy," Br. J. Cancer 101(8):1321-28 (2009).
Shiroishi et al., "Human inhibitory receptors Ig-like transcript 2 (ILT2) and ILT4 compete with CD8 for MHC class I binding and bind preferentially to HLA-G," Proc. Natl. Acad. Sci. U.S.A. 100(15):8856-61 (2003).
Shiroishi et al., "Structural basis for recognition of the nonclassical MHC molecule HLA-G by the leukocyte Ig-like receptor B2 (LILRB2/LIR2/ILT4/CD85d)," Proc. Natl. Acad. Sci. U.S.A. 103(44):16412-17 (2006).
Showalter et al., "Cytokines in immunogenic cell death: Applications for cancer immunotherapy," Cytokine 97:123-32 (2017).
Sierra-Filardi et al., "CCL2 Shapes Macrophage Polarization by GM-CSF and M-CSF: Identification of CCL2/CCR2-Dependent Gene Expression Profile," J. Immunol. 192:3858-67 (2014) (11 pags).
Singh et al., "Antigen presentation by cisplatin-activated macrophages: Role of soluble factor(s) and second messengers," Immunol. Cell Biol. 76:513-19 (1998).
Slukvin et al., "Cloning of rhesus monkey LILRs," Tissue Antigens 67:331-37 (2006).
Stojanovska et al., "Platinum-based chemotherapy: gastrointestinal immunomodulation and enteric nervous system toxicity," Am. J. Physiol. Gastrointest. Liver Physiol. 308:G223-32 (2015).
Svajger et al., "IFN-gamma-rich environment programs dendritic cells toward silencing of cytotoxic immune responses," J. Leukoc. Biol. 95:33-46 (2014).
Takahashi et al., "The immunosuppressive effect of domain-deleted dimer of HLA-G2 isoform in collagen-induced arthritis mice," Hum. Immunol. 77:754-59 (2016).
Takai, "Paired immunoglobulin-like receptors and their MHC class I recognition," Immunol. 115:433-40 (2005).
Taskinen et al., "A High Tumor-Associated Macrophage Content Predicts Favorable Outcome in Follicular Lymphoma Patients Treated with Rituximab and Cyclophosphamide-Doxorubicin-Vincristine-Prednisone," Clin. Cancer Res. 13(19):5784-89 (2007).
Tazume et al., "Macrophage-Derived Angiopoietin-Like Protein 2 Accelerates Development of Abdominal Aortic Aneurysm," Arterioscler. Thromb. Vasc. Biol. 32:1400-9 (2012) (24 pages).
Tedla et al., "Activation of human eosinophils through leukocyte immunoglobulin-like receptor 7," Proc. Natl. Acad. Sci. U.S.A. 100(3):1174-79 (2003).
Tedla et al., "Differential expression of leukocyte immunoglobulin-like receptors on cord blood-derived human mast cell progenitors and mature mast cells," J. Leukoc. Biol. 83:334-43 (2008).
Ujike et al., "Impaired dendritic cell maturation and increased T(H)2 responses in PIR-B(-/-) mice," Nat. Immunol. 3(6):542-48 (2002).
Volz et al., "Genesis of the ILT/LIR/MIR clusters within the human leukocyte receptor complex," Immunol. Rev. 181:39-51 (2001).

(56) References Cited

OTHER PUBLICATIONS

Wang et al., "Molecular mechanisms that influence the macrophage M1-M2 polarization balance," Front. Immunol. 5(614) (2014), doi: 10.3389/fimmu.2014.00614 (9 pages).
Wiseman et al., "Haplessly Hoping: Macaque Major Histocompatibility Complex Made Easy," ILAR J. 54(2):196-210 (2013).
Wu et al., "Multiplex bead-based immunoassay for the free soluble forms of the HLA-G receptors, ILT2 and ILT4," Hum. Immunol. (2016), http://dx.doi.org/10.1016/j.humimm.2016.01.017 (7 pages).
Xu et al., "Elevation of HLA-G-expressing DC-10 cells in patients with gastric cancer," Hum. Immunol. 77:800-804 (2016).
Yuan et al., "Opposite Effects of M1 and M2 Macrophage Subtypes on Lung Cancer Progression," Sci. Rep. 5:14273 (2015), DOI: 10.1038/srep14273 (12 pages).
Yugami et al., "Mice deficient in Angptl2 show increased susceptibility to bacterial infection due to attenuated macrophage activity," J. Biol. Chem. (2016), doi: 10.1074/jbc.M116.720870 (26 pages).
Zhang et al., "Co-expression of ILT4/HLA-G in human non-small cell lung cancer correlates with poor prognosis and ILT4-HLA-G interaction activates ERK signaling," Tumor Biol. 37:11187-98 (2016).
Zhang et al., "Human trophoblast cells induced MDSCs from peripheral blood CD14+ myelomonocytic cells via elevated levels of CCL2," Cell Mol. Immunol. 13:615-27 (2016).
Zhang et al., "ILT4 drives B7-H3 expression via PI3K/AKT/mTOR signalling and ILT4/B7-H3 co-expression correlates with poor prognosis in non-small cell lung cancer," FEBS Lett. 589:2248-56 (2015).
Zhao et al., "Reassessment of HLA-G isoform specificity of MEM-G/9 and 4H84 monoclonal antibodies," Tissue Antigens 80:231-38 (2012).
Zheng et al., "Inhibitory receptors bind Angptls and support blood stem cells and leukemia development," available in PMC Nov. 30, 2012, published in final edited form as: Nature 485(7400):656-60 (2012) (14 pages).
Zhu et al., "Addition of CpG ODN and Poly (I:C) to a standard maturation cocktail generates monocyte-derived dendritic cells and induces a potent Th1 polarization with migratory capacity," Hum. Vaccines Immunother. 11(7):1596-1605 (2015).
Zitvogel et al., "The anticancer immune response: indispensable for therapeutic success?" J. Clin. Invest. 118:1991-2001 (2008).
Arlauckas et al., "In vivo imaging reveals a tumor-associated macrophage-mediated resistance pathway in anti-PD-1 therapy," Sci Transl Med. 9(389):eaal3604 (2017) (11 pages).
Ayers et al., "IFN-gamma-related mRNA profile predicts clinical response to PD-1 blockade," J Clin Invest. 127(8):2930-40 (2017) (12 pages).
Bailey et al., "Genomic analyses identify molecular subtypes of pancreatic cancer," Nature. 531(7592):47-52 (including supplement) (2016) (19 pages).
Baker et al., "Tumour gene expression predicts response to cetuximab in patients with KRAS wild-type metastatic colorectal cancer," Br J Cancer. 104(3):488-95 (2011).
Basha et al., "A CD74-dependent MHC class I endolysosomal cross-presentation pathway," Nat Immunol. 13(3):237-45 (2012) (10 pages).
Bass et al., The Cancer Genome Atlas Research Network, "Comprehensive molecular characterization of gastric adenocarcinoma," Nature. 513(7517):202-9 (2014).
Biswas et al., "Macrophage plasticity and interaction with lymphocyte subsets: cancer as a paradigm," Nat Immunol. 11(10):889-96 (2010).
Bonneville et al., "Landscape of Microsatellite Instability Across 39 Cancer Types," available in PMC May 28, 2018, published in final edited form as: JCO Precis Oncol. (2017) (21 pages).
Brannon et al., "Molecular Stratification of Clear Cell Renal Cell Carcinoma by Consensus Clustering Reveals Distinct Subtypes and Survival Patterns," Genes Cancer. 1(2):152-63 (2010).
Bristol-Myers Squibb Company, Prescribing Information and Medication Guide for "OPDIVO® (nivolumab) injection, for intravenous use," U.S. License No. 1713, revised Apr. 2018 (83 pages).
Burk et al., The Cancer Genomic Atlas Research Network, "Integrated genomic and molecular characterization of cervical cancer," Nature. 543(7645):378-84 (2017) (23 pages).
Böttcher et al., "NK Cells Stimulate Recruitment of cDC1 into the Tumor Microenvironment Promoting Cancer Immune Control," Cell. 172(5):1022-37.e1-5 (2018) (31 pages).
Candido et al., "CSF1R+ Macrophages Sustain Pancreatic Tumor Growth through T Cell Suppression and Maintenance of Key Gene Programs that Define the Squamous Subtype," Cell Rep. 23(5):1448-60 (2018) (14 pages).
Cannarile et al., "Colony-stimulating factor 1 receptor (CSF1 R) inhibitors in cancer therapy," J Immunother Cancer. 5(1):53 (2017) (13 pages).
Chang et al., "Tolerization of dendritic cells by T(S) cells: the crucial role of inhibitory receptors ILT3 and ILT4," Nat Immunol. 3(3):237-43 (2002).
Chapuy et al., "Molecular subtypes of diffuse large B cell lymphoma are associated with distinct pathogenic mechanisms and outcomes," Nat Med. 24(5):679-90 (2018) (19 pages).
Chen et al., "Analysis of Immune Signatures in Longitudinal Tumor Samples Yields Insight into Biomarkers of Response and Mechanisms of Resistance to Immune Checkpoint Blockade," Cancer Discov. 6(8):827-37 (2016) (12 pages).
Chevrier et al., "An Immune Atlas of Clear Cell Renal Cell Carcinoma," Cell. 169(4):736-49.e1-7 (2017) (33 pages).
Chowell et al., "Patient HLA class I genotype influences cancer response to checkpoint blockade immunotherapy," Science. 359(6375):582-7 (2018) (7 pages).
Ciriello et al., "Emerging landscape of oncogenic signatures across human cancers," Nat Genet. 45(10):1127-33 (2013) (9 pages).
Clouthier et al., "An interim report on the investigator-initiated phase 2 study of pembrolizumab immunological response evaluation (INSPIRE)," J Immunother Cancer. 7(1):72 (2019) (12 pages).
Collisson et al., "Subtypes of pancreatic ductal adenocarcinoma and their differing responses to therapy," Nat Med. 17(4):500-3 (including supplement) (2011) (5 pages).
Creighton et al., The Cancer Genome Atlas Research Network, "Comprehensive molecular characterization of clear cell renal cell carcinoma," Nature. 499(7456):43-9 (2013).
Cui et al., "Targeting tumor-associated macrophages to combat pancreatic cancer," Oncotarget. 7(31):50735-54 (2016).
Deshmukh et al., "Gemcitabine treatment promotes immunosuppressive microenvironment in pancreatic tumors by supporting the infiltration, growth, and polarization of macrophages," Sci Rep. 8(1):12000 (2018) (10 pages).
Dietel et al., "Real-world prevalence of PD-L1 expression in locally advanced or metastatic non-small cell lung cancer (NSCLC): The global, multicentre EXPRESS study," Journal of Thoracic Oncology. 13(4S):S74-5, Abstract 130O (2018).
Dijkgraaf et al., "Chemotherapy alters monocyte differentiation to favor generation of cancer-supporting M2 macrophages in the tumor microenvironment," published OnlineFirst on Feb. 22, 2013, published in final edited form as: Cancer Res. 73(8):2480-92 (2013) (32 pages).
Gao et al., "ILT4 functions as a potential checkpoint molecule for tumor immunotherapy," Biochim Biophys Acta Rev Cancer. 1869(2):278-85 (2018).
Gleissner et al., "IL-10 inhibits endothelium-dependent T cell costimulation by up-regulation of ILT3/4 in human vascular endothelial cells," Eur J Immunol. 37(1):177-92 (2007).
Gnjatic et al., "Identifying baseline immune-related biomarkers to predict clinical outcome of immunotherapy," J Immunother Cancer. 5:44 (2017) (18 pages).
Greene et al., "Impairment of antigen-presenting cell function by ultraviolet radiation," Proc Natl Acad Sci USA. 76(12):6591-5 (1979).
Hachiya et al., "Association of HLA-G 3' Untranslated Region Polymorphisms with Systemic Lupus Erythematosus in a Japanese Population: A Case-Control Association Study," PLoS One. 11(6):e0158065 (2016) (14 pages).

(56) References Cited

OTHER PUBLICATIONS

Halbrook et al., "Macrophage-Released Pyrimidines Inhibit Gemcitabine Therapy in Pancreatic Cancer," Cell Metab. 29:1-10.e1-6 (2019) (17 pages).
Hammerman et al., The Cancer Genome Atlas Research Network, "Comprehensive genomic characterization of squamous cell lung cancers," Nature. 489(7417):519-25 (2012) (8 pages).
Hmeljak et al., "Integrative Molecular Characterization of Malignant Pleural Mesothelioma," Cancer Discov. 8(12):1548-65 (2018) (19 pages).
Hughes et al., "Perivascular M2 Macrophages Stimulate Tumor Relapse after Chemotherapy," Cancer Res. 75(17):3479-91 (2015) (14 pages).
Hugo et al., "Genomic and Transcriptomic Features of Response to Anti-PD-1 Therapy in Metastatic Melanoma," Cell. 165(1):35-44 (2016) (14 pages).
Jamieson et al., "Gene-expression profiling to predict responsiveness to immunotherapy," Cancer Gene Ther. 24(3):134-40 (2017).
Johnson et al., "Melanoma-specific MHC-II expression represents a tumour-autonomous phenotype and predicts response to anti-PD-1/PD-L1 therapy," Nat Comm. 7:10582 (2016) (10 pages).
Kawai et al., "Predominant infiltration of macrophages and CD8(+) T Cells in cancer nests is a significant predictor of survival in stage IV nonsmall cell lung cancer," Cancer. 113(6):1387-95 (2008).
Kim et al., "Comprehensive molecular characterization of clinical responses to PD-1 inhibition in metastatic gastric cancer," Nat Med. 24(9):1449-58 (2018) (14 pages).
Kim et al., "Three-gene predictor of clinical outcome for gastric cancer patients treated with chemotherapy," Pharmacogenomics J. 12(2):119-27 (2012).
Kumar et al., "Cancer-associated fibroblasts neutralize the antitumor effect of CSF1 receptor blockade by inducing PMN-MDSC infiltration of tumors," available in PMC Nov. 13, 2018, published in final edited form as: Cancer Cell. 32(5):654-68.e5 (2017) (34 pages).
Lawrence et al., The Cancer Genome Atlas Network, "Comprehensive genomic characterization of head and neck squamous cell carcinomas," available in PMC Jul. 29, 2015, published in final edited form as: Nature. 517(7536):576-82 (2015) (16 pages).
Lehmann et al., "Tumor location determines tissue-specific recruitment of tumor-associated macrophages and antibody-dependent immunotherapy response," Sci Immunol. 2(7):eaah6413 (2017) (12 pages).
Lenz et al., "Stromal gene signatures in large-B-cell lymphomas," N Engl J Med. 359(22):2313-23 (2008).
Lepin et al., "Functional characterization of HLA-F and binding of HLA-F tetramers to ILT2 and ILT4 receptors," Eur J Immunol. 30(12):3552-61 (2000).
Li et al., "Dysfunctional CD8 T Cells Form a Proliferative, Dynamically Regulated Compartment within Human Melanoma," Cell. 176(4):775-89.e18 (2019) (34 pages).
Li et al., "Immune profiling of pre- and post-treatment breast cancer tissues from the SWOG S0800 randomized neoadjuvant trial of weekly nab-paclitaxel with or without bevacizumab and dose dense doxorubicin and cyclophosphamide," J Clin Oncol. 36(15):578 (2018) (1 page).
Liu et al., "Pre-treatment with chemotherapy can enhance the antigenicity and immunogenicity of tumours by promoting adaptive immune responses," Br J Cancer. 102(1):115-23 (2010).
Malumbres et al., "Paraffin-based 6-gene model predicts outcome in diffuse large B-cell lymphoma patients treated with R-CHOP," Blood. 111(12):5509-14 (2008) (7 pages).
Mantovani et al., "Macrophage plasticity and polarization in tissue repair and remodelling," J Pathol. 229(2):176-85 (2013).
Mantovani et al., "The chemokine system in diverse forms of macrophage activation and polarization," Trends Immunol. 25(12):677-86 (2004).
Mantovani et al., "The interaction of anticancer therapies with tumor-associated macrophages," J Exp Med. 212(4):435-45 (2015).

Mantovani et al., "Tumor-Associated Macrophages in Treatment Targets in Oncology," available in PMC Jul. 1, 2018, published in final edited form as: Nat Rev Clin Oncol. 14(7):399-416 (2017) (34 pages).
Martinez et al., "The M1 and M2 paradigm of macrophage activation: time for reassessment," F1000Prime Rep. 6:13 (2014) (13 pages).
Martinez et al., "Transcriptional profiling of the human monocyte-to-macrophage differentiation and polarization: new molecules and patterns of gene expression," J Immunol. 177(10):7303-11 (2006) (10 pages).
Martins et al., "Restoration of the immunogenicity of cisplatin-induced cancer cell death by endoplasmic reticulum stress," Oncogene. 30(1):1147-58 (2011).
Martín et al., "PAM50 proliferation score as a predictor of weekly paclitaxel benefit in breast cancer," Breast Cancer Res Treat. 138(2):457-66 (2013).
McGranahan et al., "Allele-Specific HLA Loss and Immune Escape in Lung Cancer Evolution," Cell. 171(6):1259-71.e11 (2017) (25 pages).
Merck & Co., Inc., Prescribing Information for "KEYTRUDA® (pembrolizumab)," U.S. License No. 0002, revised Apr. 2019 (63 pages).
Miao et al., "Genomic correlates of response to immune checkpoint blockade in microsatellite-stable solid tumors," Nat Genet. 50(9):1271-81 (2018) (16 pages).
Moffitt et al., "Virtual microdissection identifies distinct tumor- and stroma-specific subtypes of pancreatic ductal adenocarcinoma," Nat Genet. 47(10):1168-78 (including supplement) (2015) (13 pages).
Mosser et al., "Exploring the full spectrum of macrophage activation," available in PMC Aug. 11, 2009, published in final edited form as: Nat Rev Immunol. 8(12):958-69 (2008) (26 pages).
Murray et al., "Macrophage activation and polarization: nomenclature and experimental guidelines," Immunity. 41(1):14-20 (2014).
Müller et al., "Single-cell profiling of human gliomas reveals macrophage ontogeny as a basis for regional differences in macrophage activation in the tumor microenvironment," Genome Biol. 18(1):234 (2017) (14 pages).
Nowakowski et al., "ABC, GCB, and Double-Hit Diffuse Large B-Cell Lymphoma: Does Subtype Make a Difference in Therapy Selection?" Am Soc Clin Oncol Educ Book. 2015:e499-57 (2015).
Ober et al., "Variation in the HLA-G promoter region influences miscarriage rates," Am J Hum Genet. 72(6):1425-35 (2003).
Ocaña-Guzman et al., "TIM-3 Regulates Distinct Functions in Macrophages," Front Immunol. 7:229 (2016) (9 pages).
Papadopoulos et al., "First-in-Human Study of AMG 820, a Monoclonal Anti-Colony-Stimulating Factor 1 Receptor Antibody, in Patients with Advanced Solid Tumors," Clin Cancer Res. 23(19):5703-10 (2017) (9 pages).
Parker et al., "Supervised risk predictor of breast cancer based on intrinsic subtypes," J Clin Oncol. 27(8):1160-7 (2009).
Pham et al., "The Role of Macrophage/B-Cell Interactions in the Pathophysiology of B-Cell Lymphomas," Front Oncol. 8:147 (2018) (14 pages).
Pistoia et al., "Soluble HLA-G: Are they clinically relevant?" available in PMC Dec. 1, 2008, published in final edited form as: Semin Cancer Biol. 17(6):469-79 (2007) (20 pages).
Pyonteck et al., "CSF-1 R inhibition alters macrophage polarization and blocks glioma progression," available in PMC Apr. 1, 2014, published in final edited form as: Nat Med. 19(10):1264-72 (2013) (23 pages).
Raphael et al., The Cancer Genome Atlas Research Network, "Integrated Genomic Characterization of Pancreatic Ductal Adenocarcinoma," Cancer Cell. 32(2):185-203 (including supplement) (2017) (39 pages).
Reche et al., "Sequence variability analysis of human class I and class II MHC molecules: functional and structural correlates of amino acid polymorphisms," J Mol Biol. 331(3):623-41 (2003).
Ries et al., "Targeting tumor-associated macrophages with anti-CSF-1R antibody reveals a strategy for cancer therapy," Cancer Cell. 25(6):846-59 (including supplement) (2014) (24 pages).
Rizvi et al., "Molecular Determinants of Response to Anti-Programmed Cell Death (PD)-1 and Anti-Programmed Death-

(56) References Cited

OTHER PUBLICATIONS

Ligand 1 (PD-L1) Blockade in Patients With Non-Small-Cell Lung Cancer Profiled With Targeted Next-Generation Sequencing," J Clin Oncol. 36(7):633-41 (including supplement) (2018) (35 pages).
Roberti et al., "Overexpression of CD85j in TNBC patients inhibits Cetuximab-mediated NK-cell ADCC but can be restored with CD85j functional blockade," Eur J Immunol. 45(5):1560-9 (2015).
Ruffell et al., "Macrophages and therapeutic resistance in cancer," Cancer Cell. 27(4):462-72 (2015).
Sade-Feldman et al., "Defining T Cell States Associated with Response to Checkpoint Immunotherapy in Melanoma," Cell. 175(4):998-1013 (including supplement) (2018) (37 pages).
Sharabi et al., "Stereotactic Radiation Therapy Augments Antigen-Specific PD-1-Mediated Antitumor Immune Responses via Cross-Presentation of Tumor Antigen," Cancer Immunol Res. 3(4):345-55 (2015) (12 pages).
Sharma et al., "Primary, Adaptive, and Acquired Resistance to Cancer Immunotherapy," Cell. 168(4):707-23 (2017).
Sica et al., "Macrophage plasticity and polarization: in vivo veritas," J Clin Invest. 122(3):787-95 (2012).
Sidaway, "Immunotherapy-responsive gastric cancers identified," Nat Rev Clin Oncol. 15(10):590 (2018).
Subramanian et al., "Gene set enrichment analysis: a knowledge-based approach for interpreting genome-wide expression profiles," Proc Natl Acad Sci USA. 102(43):15545-50 (2005).
Suda, "Tumor-associated macrophages-additional effectors at anti-PD-1/PD-L1 therapy?" J Thorac Dis. 9(11):4197-200 (2017).
Talebian Yazdi et al., "The positive prognostic effect of stromal CD8+ tumor-infiltrating T cells is restrained by the expression of HLA-E in non-small cell lung carcinoma," Oncotarget. 7(3):3477-88 (2016).
Tesniere et al., "Immunogenic death of colon cancer cells treated with oxaliplatin," Oncogene. 29(4):482-91 (2010).
Thorsson et al., "The Immune Landscape of Cancer," Immunity. 48(4):812-30 (including supplement) (2018) (49 pages).
Tunger et al., "Immune Monitoring of Cancer Patients Prior to and During CTLA-4 or PD-1/PD-L1 Inhibitor Treatment," Biomedicines. 6(1):E26 (2018) (14 pages).
Varn et al., "Systematic Pan-Cancer Analysis Reveals Immune Cell Interactions in the Tumor Microenvironment," Cancer Res. 77(6):1271-82 (2017) (13 pages).
Wan et al., "M2 Kupffer cells promote M1 Kupffer cell apoptosis: a protective mechanism against alcoholic and nonalcoholic fatty liver disease," Hepatology. 59(1):130-42 (2014).
Wang et al., "Human leucocyte antigen-G 14-bp InDel polymorphism and oral squamous cell carcinoma risk in Chinese Han population: a case-control study," Int J Immunogenet. (2018) (9 pages).
Weizman et al., "Macrophages mediate gemcitabine resistance of pancreatic adenocarcinoma by upregulating cytidine deaminase," Oncogene. 33(29):3812-9 (2014).
Wilkerson et al., "Lung squamous cell carcinoma mRNA expression subtypes are reproducible, clinically important, and correspond to normal cell types," Clin Cancer Res. 16(19):4864-75 (2010) (13 pages).
Wilson, "SOCS Proteins in Macrophage Polarization and Function," Front Immunol. 5:357 (2014) (5 pages).
Xue et al., "Transcriptome-based network analysis reveals a spectrum model of human macrophage activation," Immunity. 40(2):274-88 (2014).
Yu et al., "Correlation of PD-L1 Expression with Tumor Mutation Burden and Gene Signatures for Prognosis in Early-Stage Squamous Cell Lung Carcinoma," publicly available on Sep. 22, 2018, published as: J Thorac Oncol. 14(1):25-36 (2019).
Zhu et al., "CSF1/CSF1R blockade reprograms tumor-infiltrating macrophages and improves response to T-cell checkpoint immunotherapy in pancreatic cancer models," Cancer Res. 74(18):5057-69 (2014) (14 pages).
Anonymous, "Data-sheet: Human LILRB2/CD85d/ILT4 Antibody; Monoclonal Mouse IgG2A, Clone # 287219; Catalog No. MAB2078," R&D Systems—a Biotechne brand, Jan. 1, 2016, revised Feb. 7, 2018 (2 pages).
Anonymous, "Invitrogen Data sheet: CF85d (ILT4) Monoclonal Antibody (42D1), Functional Grade, eBioscience, Catalog No. 16-5149-85," Thermo Fisher Scientific, Jan. 1, 2015, retrieved from <https://www.thermofisher.com/order/genome-database/generatePdf?productName-D85d%20(ILT4)&assayType=PRANT&detailed=true&productId=16-5149-85> on Feb. 11, 2019 (3 pages).
International Search Report and Written Opinion dated Jul. 5, 2019 for PCT International Application No. PCT/US2018/066819, Cohen et al., "Antibodies to LILRB2," filed Dec. 20, 2018 (22 pages).
Van der Touw et al., "LILRB receptor-mediated regulation of myeloid cell maturation and function," available in PMC Sep. 9, 2017, published in final edited form as: Cancer Immunol Immunother. 66(8):1079-87 (2017) (16 pages).

\* cited by examiner

FIG. 3A-1

| Reference | Hybridoma clone isotype | LILRB1 CHOs binding (fold over iso) | LILRB2 CHOs binding (fold over iso) | LILRB3 CHOs binding (fold over iso) | LILRB4 CHOs binding (fold over iso) | LILRB5 CHOs binding (fold over iso) | LILRA1 CHOs binding (fold over iso) |
|---|---|---|---|---|---|---|---|
| J-01 | mG1 | 0.96 | 19.95 | 2.49 | 0.87 | 1.23 | 0.90 |
| J-02 | mG1 | 1.03 | 12.18 | 1.00 | 1.00 | 1.09 | 0.98 |
| J-03 | mG2b | 0.94 | 30.14 | 0.97 | 1.02 | 1.00 | 0.89 |
| J-04 | mG2b | 0.95 | 33.80 | 0.90 | 0.83 | 1.08 | 0.88 |
| J-05 | mG2b | 0.95 | 25.09 | 0.91 | 0.76 | 1.03 | 0.87 |
| J-06 | mG1 | 0.83 | 9.58 | 0.89 | 0.83 | 1.00 | 1.42 |
| J-07 | mG2b | 0.97 | 38.66 | 0.93 | 0.91 | 1.29 | 0.96 |
| J-08 | mG1 | 1.00 | 25.19 | 1.03 | 0.98 | 1.40 | 1.01 |
| J-09 | mG1 | 0.96 | 13.19 | 1.01 | 0.90 | 1.18 | 1.06 |
| J-10 | mG1 | 1.04 | 19.03 | 1.22 | 0.94 | 1.36 | 1.13 |
| J-11 | mG2b | 1.07 | 3.49 | 1.09 | 1.03 | 1.22 | -1.63 |
| J-12 | mG2a | 0.99 | 1.25 | 0.99 | 0.99 | 0.98 | 1.28 |
| J-13 | mG1 | 0.86 | 14.40 | 0.90 | 0.84 | 1.01 | 0.89 |
| J-14 | mG1 | 0.92 | 25.97 | 0.92 | 1.01 | 1.03 | 0.94 |
| J-15 | mG2b | 1.00 | 28.06 | 1.02 | 0.95 | 1.24 | 1.17 |
| J-16 | rG1 | 1.03 | 3.75 | 1.11 | 1.01 | 1.10 | 611.88 |
| J-17 | mG1 | 1.05 | 3.68 | 0.99 | 1.00 | 1.03 | 7.31 |

FIG. 3A-2

| LILRA2 CHOs binding (fold over iso) | LILRA3 CHOs binding (fold over iso) | LILRA4 CHOs binding (fold over iso) | LILRA5 CHOs binding (fold over iso) | LILRA6 CHOs binding (fold over iso) |
|---|---|---|---|---|
| 1.34 | 1.06 | 1.90 | 0.77 | 1.23 |
| 1.34 | 1.08 | 1.63 | 1.03 | 1.14 |
| 1.58 | 1.05 | 2.01 | 0.96 | 1.23 |
| 1.62 | 0.93 | 2.07 | 0.74 | 1.30 |
| 1.34 | 0.90 | 1.69 | 0.82 | 1.23 |
| 1.09 | 1.04 | 1.85 | 0.73 | 1.28 |
| 1.57 | 1.02 | 1.39 | 0.98 | 1.09 |
| 1.64 | 1.03 | 0.28 | 1.06 | 1.08 |
| 1.28 | 1.03 | 1.32 | 0.91 | 0.90 |
| 1.49 | 1.10 | 1.00 | 0.99 | 0.19 |
| -2.52 | 1.02 | -1.27 | 1.34 | 1.00 |
| 1.24 | 1.23 | 0.20 | 1.12 | 0.41 |
| 1.08 | 0.99 | 1.93 | 0.76 | 1.19 |
| 1.42 | 1.01 | 1.46 | 0.99 | 1.17 |
| 1.86 | 1.17 | 0.43 | 1.19 | 0.92 |
| -31.56 | 182.92 | -35.47 | 3.09 | 0.62 |
| -1.05 | 1.35 | -36.53 | 0.82 | 0.94 |

| | | | | | | | |
|---|---|---|---|---|---|---|---|
| J-18 | | 0.98 | 1.23 | 0.81 | 0.96 | 0.97 | -12.44 |
| J-19 | rG1 | 1.05 | 3.78 | 1.09 | 1.03 | 1.19 | -3.31 |
| J-20 | rG1 | 1.02 | 3.43 | 1.00 | 0.99 | 1.03 | 375.00 |
| J-21 | rG1 | 1.08 | 2.50 | 1.22 | 1.10 | 1.06 | 13.94 |
| J-22 | mG2a | 1.05 | 1.46 | 1.01 | 0.97 | 1.00 | -19.25 |
| J-23 | mG1 | 0.99 | 1.15 | 1.36 | 0.99 | 0.94 | 11.00 |
| J-24 | mG2b | 1.06 | 1.01 | 1.00 | 0.99 | 0.95 | 22.44 |
| J-25 | mG1 | 0.98 | 1.57 | 1.06 | 0.99 | 0.96 | -6.31 |
| Isotype | mG1 | 1.00 | 1.00 | 1.00 | 1.00 | 1.00 | 1.00 |
| Total screened | | 25 | 25 | 25 | 25 | 25 | 25 |
| Hit cut-off | | 2 | 2 | 2 | 2 | 2 | 2 |
| Total hits | | 0 | 18 | 1 | 0 | 0 | 6 |
| % hit | | 0.0 | 72.0 | 4.0 | 0.0 | 0.0 | 24.0 |

FIG. 3A-3

| 1.91 | 0.45 | 2.67 | -1.93 | -0.64 |
|---|---|---|---|---|
| -0.51 | 0.97 | -26.80 | -0.62 | 1.07 |
| 3.12 | 0.18 | 19.73 | -3.65 | -0.08 |
| -1.26 | 1.46 | -26.33 | 1.63 | 1.21 |
| 3.03 | 0.51 | 16.00 | -1.05 | -0.20 |
| 0.34 | 1.33 | -16.13 | 1.33 | 0.70 |
| 0.04 | 1.36 | -17.67 | 0.59 | 1.19 |
| 1.85 | 0.51 | 29.73 | -1.33 | 0.26 |
| 1.00 | 1.00 | 1.00 | 1.00 | 1.00 |
| 25 | 25 | 25 | 25 | 25 |
| 2 | 2 | 2 | 2 | 2 |
| 2 | 1 | 6 | 1 | 0 |
| 8.0 | 4.0 | 24.0 | 4.0 | 0.0 |

| Reference | Hybridoma clone isotype | HLA-G:LILRB2 CHOs blocking (% blocked) | HLA-A2:LILRB2 CHOs blocking (% blocked) | TNFa production (fold over LPS alone) | IL-6 production (fold over LPS alone) | IL-10 production (fold over LPS alone) | CCL2 production (fold over LPS alone) |
|---|---|---|---|---|---|---|---|
| J-01 | mG1 | -40.25 | 15.12 | 3.86 | 2.55 | 0.78 | 0.88 |
| J-02 | mG1 | 50.41 | 43.21 | 1.58 | 1.38 | 0.79 | 0.79 |
| J-03 | mG2b | -156.17 | -208.49 | 1.27 | 1.10 | 0.97 | 0.95 |
| J-04 | mG2b | -255.13 | -319.42 | 1.18 | 1.36 | 0.95 | 1.00 |
| J-05 | mG2b | -21.97 | 15.16 | 1.16 | 1.00 | 1.01 | 1.02 |
| J-06 | mG1 | -62.70 | -59.10 | 0.56 | 1.10 | 0.92 | 0.84 |
| J-07 | mG2b | 44.29 | 70.93 | 2.66 | 1.58 | 0.91 | 0.95 |
| J-08 | mG1 | -186.51 | -177.77 | 3.63 | 2.64 | 0.75 | 0.89 |
| J-09 | mG1 | -13.66 | 2.46 | 3.32 | 1.68 | 0.90 | 0.92 |
| J-10 | mG1 | -73.72 | -34.77 | 2.44 | 1.97 | 1.01 | 1.01 |
| J-11 | mG2b | 99.86 | 94.44 | 7.61 | 3.06 | 0.81 | 0.96 |
| J-12 | mG2a | -7.16 | -10.40 | 0.31 | 0.87 | 0.89 | 0.94 |
| J-13 | mG1 | -61.85 | -61.85 | n/a | n/a | n/a | n/a |
| J-14 | mG1 | -160.30 | -204.08 | 0.91 | 2.97 | 0.75 | 0.84 |
| J-15 | mG2b | -243.96 | -288.39 | 1.07 | 1.29 | 0.92 | 0.93 |
| J-16 | rG1 | 96.77 | 94.80 | 2.49 | 1.41 | 1.09 | 1.31 |
| J-17 | mG1 | 96.56 | 93.44 | 8.12 | 2.57 | 0.89 | 1.85 |

FIG. 3B-2

| Human Monocytes binding (fold over iso) | Human Neutrophils binding (fold over iso) | Cyno Monocytes binding (fold over iso) | Cyno Neutrophils binding (fold over iso) | Rhesus Monocytes binding (fold over iso) | Rhesus Neutrophils binding (fold over iso) |
|---|---|---|---|---|---|
| | | | | | |
| | | | | | |
| | | | | | |
| | | | | | |
| | | | | | |
| | | | | | |
| | | | | | |
| 8.54 | 2.89 | 0.71 | 0.94 | 0.88 | 0.64 |
| | | | | | |
| | | | | | |
| | | | | | |
| 11.35 | 4.55 | 0.92 | 0.87 | 1.41 | 1.44 |
| | | | | | |
| | | | | | |

| | | | | | | |
|---|---|---|---|---|---|---|
| J-18 | | -15.14 | 16.04 | 0.92 | 1.08 | 0.99 | 1.00 |
| J-19 | rG1 | 97.01 | 95.32 | 8.90 | 2.72 | 0.80 | 1.69 |
| J-20 | rG1 | -188.75 | 11.03 | 9.02 | 2.58 | 0.67 | 1.64 |
| J-21 | rG1 | 95.61 | 56.57 | 5.46 | 2.23 | 1.00 | 1.48 |
| J-22 | mG2a | -24.90 | 21.76 | 2.62 | 1.39 | 1.10 | 1.24 |
| J-23 | mG1 | 58.97 | 16.27 | 2.07 | 1.14 | 1.03 | 1.12 |
| J-24 | mG2b | 0.08 | 6.30 | 1.16 | 0.84 | 0.83 | 0.87 |
| J-25 | mG1 | -139.70 | 7.12 | 1.82 | 1.57 | 1.20 | 1.29 |
| Isotype | mG1 | -8.00 | -12.49 | 0.82 | 1.08 | 0.96 | 1.02 |
| Total screened | | 25 | 25 | 24 | 24 | 24 | 24 |
| Hit cut-off | | 50 | 50 | 1.5 | 1.5 | 0.85 | 0.85 |
| Total hits | | 7 | 6 | 15 | 12 | 8 | 3 |
| % hit | | 28.0 | 24.0 | 62.5 | 50.0 | 33.3 | 12.5 |

FIG. 3B-3

| mAb | LILRB1 CHOs binding (fold over iso) | LILRB2 CHOs binding (fold over iso) | LILRB3 CHOs binding (fold over iso) | LILRB4 CHOs binding (fold over iso) | LILRB5 CHOs binding (fold over iso) | LILRA1 CHOs binding (fold over iso) | LILRA2 CHOs binding (fold over iso) | LILRA3 CHOs binding (fold over iso) | LILRA4 CHOs binding (fold over iso) | LILRA5 CHOs binding (fold over iso) | LILRA6 CHOs binding (fold over iso) |
|---|---|---|---|---|---|---|---|---|---|---|---|
| J-19.h1 | 0.79 | 73.25 | 1.00 | 1.22 | 1.01 | 0.95 | 0.88 | 0.97 | 0.95 | 1.34 | 0.98 |
| J-19.h2 | 0.73 | 74.45 | 0.81 | 0.90 | 0.76 | 0.89 | 0.66 | 0.83 | 0.84 | 0.86 | 0.74 |
| J-19.h3 | 0.84 | 79.40 | 0.97 | 1.16 | 0.95 | 1.00 | 0.83 | 0.92 | 0.99 | 1.22 | 1.03 |
| J-19.h4 | 0.87 | 76.50 | 1.24 | 2.02 | 1.27 | 0.99 | 0.96 | 0.99 | 1.09 | 2.14 | 1.27 |
| Isotype | 1.00 | 1.00 | 1.00 | 1.00 | 1.00 | 1.00 | 1.00 | 1.00 | 1.00 | 1.00 | 1.00 |

*FIG. 11A*

| mAb | EC50 (nM) hLILRB2 CHOs binding | EC50 (nM) HLA-G: LILRB2 blocking | EC50 (nM) HLA-A2: LILRB2 blocking | EC50 (nM) TNFα production | EC50 (nM) IL-6 production | IC50 (nM) IL-10 production | IC50 (nM) CCL2 production |
|---|---|---|---|---|---|---|---|
| J-19.h1 | 0.03204 | 0.162 | 0.083 | 0.076 | 0.085 | 0.450 | 0.005 |
| J-19.h2 | 0.4467 | 0.122 | 0.087 | 0.120 | 0.186 | 0.702 | 0.011 |
| J-19.h3 | 0.03248 | 0.113 | 0.103 | 0.087 | 0.083 | 0.270 | 5.902 |
| J-19.h4 | 0.001749 | 0.131 | 0.106 | 0.084 | 0.091 | 0.190 | 0.010 |
| Isotype | N/A | N/A | N/A | N/A | N/A | N/A | N/A |

*FIG. 11B*

J-19.h1 Heavy Chain Variable Region

QITLKESGPTLVKPTQTLTLTCTFSGFSLNTYAMGVSW
IRQPPGKALEWLASIWWNGNKYNNPSLKSRLTVTKDT
SKNQVVLTMTNMDPVDTATYYCAHSRIIR*FTDYVMDA
WGQGTLVTVSS (SEQ ID NO: 53)

J-19.h1 Light Chain Variable Region

DIQMTQSPSSLSTSVGDRVTITCRASEDIYNDLAWYQ
QKPGKAPKLLIYNANSLHTGVASRFSGSGSGTDFTFTI
SSLQPEDVATYFCQQYYDYPLTFGQGTKLEIK (SEQ
ID NO: 54)

*FIG. 30*

Distribution of Normalized IFNγ PD Response to Palivizumab

PD Response Rates to J-19.h1 Across 3 Indications

| Indication | Monoculture Signature | Keytruda Signature | IFNγ Signature |
|---|---|---|---|
| Renal Cell Carcinoma | 5/44 = 11% | 3/44 = 7% | 2/44 = 5% |
| Head and Neck Cancer | 4/42 = 10% | 8/42 = 19% | 8/42 = 19% |
| Lung Cancer | 7/28 = 25% | 5/28 = 18% | 3/28 = 11% |

SEQUENCE LISTING

<160> NUMBER OF SEQ ID NOS: 235

<210> SEQ ID NO 1
<211> LENGTH: 444
<212> TYPE: PRT
<213> ORGANISM: Artificial Sequence
<220> FEATURE:
<223> OTHER INFORMATION: Synthetic Construct

<400> SEQUENCE: 1

```
Gln Val Gln Leu Gln Gln Ser Gly Ala Glu Leu Met Lys Pro Gly Ala
 1               5                  10                  15

Ser Val Lys Leu Ser Cys Lys Ala Thr Gly Tyr Ile Leu Thr Gly Tyr
             20                  25                  30

Trp Ile Glu Trp Val Lys Gln Arg Pro Gly His Gly Leu Glu Trp Ile
         35                  40                  45

Gly Glu Ile Leu Pro Gly Ser Gly Ser Thr Asn Tyr Asn Glu Asn Phe
     50                  55                  60

Lys Gly Lys Ala Thr Phe Thr Ala Asp Thr Ser Ser Asn Thr Ala Tyr
 65                  70                  75                  80

Met Gln Leu Ser Ser Leu Thr Thr Glu Asp Ser Ala Ile Tyr Tyr Cys
                 85                  90                  95

Ala Arg Ala Val Leu Gly Tyr Phe Asp Tyr Trp Gly Gln Gly Thr Thr
            100                 105                 110

Leu Thr Val Ser Ser Ala Ser Thr Lys Gly Pro Ser Val Phe Pro Leu
        115                 120                 125

Ala Pro Cys Ser Arg Ser Thr Ser Glu Ser Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Lys Thr Tyr Thr Cys Asn Val Asp His Lys Pro Ser Asn
        195                 200                 205

Thr Lys Val Asp Lys Arg Val Glu Ser Lys Tyr Gly Pro Pro Cys Pro
    210                 215                 220

Pro Cys Pro Ala Pro Glu Phe Leu Gly Gly Pro Ser Val Phe Leu Phe
225                 230                 235                 240

Pro Pro Lys Pro Lys Asp Thr Leu Met Ile Ser Arg Thr Pro Glu Val
                245                 250                 255

Thr Cys Val Val Val Asp Val Ser Gln Glu Asp Pro Glu Val Gln Phe
            260                 265                 270

Asn Trp Tyr Val Asp Gly Val Glu Val His Asn Ala Lys Thr Lys Pro
        275                 280                 285

Arg Glu Glu Gln Phe Asn Ser Thr Tyr Arg Val Val Ser Val Leu Thr
    290                 295                 300

Val Leu His Gln Asp Trp Leu Asn Gly Lys Glu Tyr Lys Cys Lys Val
305                 310                 315                 320

Ser Asn Lys Gly Leu Pro Ser Ser Ile Glu Lys Thr Ile Ser Lys Ala
                325                 330                 335

Lys Gly Gln Pro Arg Glu Pro Gln Val Tyr Thr Leu Pro Pro Ser Gln
            340                 345                 350

Glu Glu Met Thr Lys Asn Gln Val Ser Leu Thr Cys Leu Val Lys Gly
```

```
                355                 360                 365
Phe Tyr Pro Ser Asp Ile Ala Val Glu Trp Glu Ser Asn Gly Gln Pro
    370                 375                 380

Glu Asn Asn Tyr Lys Thr Thr Pro Pro Val Leu Asp Ser Asp Gly Ser
385                 390                 395                 400

Phe Phe Leu Tyr Ser Arg Leu Thr Val Asp Lys Ser Arg Trp Gln Glu
                405                 410                 415

Gly Asn Val Phe Ser Cys Ser Val Met His Glu Ala Leu His Asn His
            420                 425                 430

Tyr Thr Gln Lys Ser Leu Ser Leu Ser Leu Gly Lys
        435                 440

<210> SEQ ID NO 2
<211> LENGTH: 213
<212> TYPE: PRT
<213> ORGANISM: Artificial Sequence
<220> FEATURE:
<223> OTHER INFORMATION: Synthetic Construct

<400> SEQUENCE: 2

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
                20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
    50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys His Gln His Tyr Ser Thr Tyr Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 3
<211> LENGTH: 117
<212> TYPE: PRT
<213> ORGANISM: Artificial Sequence
<220> FEATURE:
<223> OTHER INFORMATION: Synthetic Construct

<400> SEQUENCE: 3
```

```
Gln Val Gln Leu Gln Gln Ser Gly Ala Glu Leu Met Lys Pro Gly Ala
1               5                   10                  15

Ser Val Lys Leu Ser Cys Lys Ala Thr Gly Tyr Ile Leu Thr Gly Tyr
            20                  25                  30

Trp Ile Glu Trp Val Lys Gln Arg Pro Gly His Gly Leu Glu Trp Ile
            35                  40                  45

Gly Glu Ile Leu Pro Gly Ser Gly Ser Thr Asn Tyr Asn Glu Asn Phe
        50                  55                  60

Lys Gly Lys Ala Thr Phe Thr Ala Asp Thr Ser Asn Thr Ala Tyr
65                  70                  75                  80

Met Gln Leu Ser Ser Leu Thr Thr Glu Asp Ser Ala Ile Tyr Tyr Cys
                85                  90                  95

Ala Arg Ala Val Leu Gly Tyr Phe Asp Tyr Trp Gly Gln Gly Thr Thr
            100                 105                 110

Leu Thr Val Ser Ser
        115
```

<210> SEQ ID NO 4
<211> LENGTH: 106
<212> TYPE: PRT
<213> ORGANISM: Artificial Sequence
<220> FEATURE:
<223> OTHER INFORMATION: Synthetic Construct

<400> SEQUENCE: 4

```
Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
            35                  40                  45

Tyr Trp Ala Ser Thr Arg His Thr Gly Val Pro Asp Arg Phe Thr Gly
        50                  55                  60

Ser Gly Ser Gly Thr Asp Tyr Thr Leu Thr Ile Ser Ser Val Gln Ala
65                  70                  75                  80

Glu Asp Leu Ala Leu Tyr Tyr Cys His Gln His Tyr Ser Thr Tyr Thr
                85                  90                  95

Phe Gly Gly Gly Thr Lys Leu Glu Ile Lys
            100                 105
```

<210> SEQ ID NO 5
<211> LENGTH: 5
<212> TYPE: PRT
<213> ORGANISM: Artificial Sequence
<220> FEATURE:
<223> OTHER INFORMATION: Synthetic Construct

<400> SEQUENCE: 5

```
Gly Tyr Trp Ile Glu
1               5
```

<210> SEQ ID NO 6
<211> LENGTH: 17
<212> TYPE: PRT
<213> ORGANISM: Artificial Sequence
<220> FEATURE:
<223> OTHER INFORMATION: Synthetic Construct

<400> SEQUENCE: 6

Glu Ile Leu Pro Gly Ser Gly Ser Thr Asn Tyr Asn Glu Asn Phe Lys

```
1               5                   10                  15
Gly

<210> SEQ ID NO 7
<211> LENGTH: 8
<212> TYPE: PRT
<213> ORGANISM: Artificial Sequence
<220> FEATURE:
<223> OTHER INFORMATION: Synthetic Construct

<400> SEQUENCE: 7

Ala Val Leu Gly Tyr Phe Asp Tyr
1               5

<210> SEQ ID NO 8
<211> LENGTH: 11
<212> TYPE: PRT
<213> ORGANISM: Artificial Sequence
<220> FEATURE:
<223> OTHER INFORMATION: Synthetic Construct

<400> SEQUENCE: 8

Lys Ala Ser Gln Asp Val Ser Thr Ala Val Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Synthetic Construct

<400> SEQUENCE: 9

Trp Ala Ser Thr Arg His Thr
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic Construct

<400> SEQUENCE: 10

His Gln His Tyr Ser Thr Tyr Thr
1               5

<210> SEQ ID NO 11
<211> LENGTH: 450
<212> TYPE: PRT
<213> ORGANISM: Artificial Sequence
<220> FEATURE:
<223> OTHER INFORMATION: Synthetic Construct

<400> SEQUENCE: 11

Gln Val Thr Leu Lys Glu Ser Gly Pro Gly Ile Leu Gln Pro Ser His
1               5                   10                  15

Thr Leu Ser Leu Thr Cys Ser Phe Ser Gly Phe Ser Leu Asn Thr Tyr
                20                  25                  30

Ala Met Gly Val Ser Trp Ile Arg Gln Pro Ser Gly Lys Gly Leu Glu
            35                  40                  45

Trp Leu Ala Ser Ile Trp Trp Asn Gly Asn Lys Tyr Asn Asn Pro Ser
        50                  55                  60

Leu Lys Ser Arg Leu Thr Val Ser Lys Asp Thr Ser Asn Asn Gln Ala
```

```
             65                  70                  75                  80
        Phe Leu Lys Val Thr Ser Val Asp Thr Ala Asp Thr Ala Thr Tyr Tyr
                         85                  90                  95
        Cys Ala His Ser Arg Ile Ile Arg Phe Thr Asp Tyr Val Met Asp Ala
                        100                 105                 110
        Trp Gly Gln Gly Ala Ser Val Thr Val Ser Ser Ala Ser Thr Lys Gly
                        115                 120                 125
        Pro Ser Val Phe Pro Leu Ala Pro Cys Ser Arg Ser Thr Ser Glu Ser
            130                 135                 140
        Thr Ala Ala Leu Gly Cys Leu Val Lys Asp Tyr Phe Pro Glu Pro Val
        145                 150                 155                 160
        Thr Val Ser Trp Asn Ser Gly Ala Leu Thr Ser Gly Val His Thr Phe
                        165                 170                 175
        Pro Ala Val Leu Gln Ser Ser Gly Leu Tyr Ser Leu Ser Ser Val Val
                        180                 185                 190
        Thr Val Pro Ser Ser Ser Leu Gly Thr Lys Thr Tyr Thr Cys Asn Val
                        195                 200                 205
        Asp His Lys Pro Ser Asn Thr Lys Val Asp Lys Arg Val Glu Ser Lys
            210                 215                 220
        Tyr Gly Pro Pro Cys Pro Pro Cys Pro Ala Pro Glu Phe Leu Gly Gly
        225                 230                 235                 240
        Pro Ser Val Phe Leu Phe Pro Pro Lys Pro Lys Asp Thr Leu Met Ile
                        245                 250                 255
        Ser Arg Thr Pro Glu Val Thr Cys Val Val Val Asp Val Ser Gln Glu
                        260                 265                 270
        Asp Pro Glu Val Gln Phe Asn Trp Tyr Val Asp Gly Val Glu Val His
                        275                 280                 285
        Asn Ala Lys Thr Lys Pro Arg Glu Glu Gln Phe Asn Ser Thr Tyr Arg
            290                 295                 300
        Val Val Ser Val Leu Thr Val Leu His Gln Asp Trp Leu Asn Gly Lys
        305                 310                 315                 320
        Glu Tyr Lys Cys Lys Val Ser Asn Lys Gly Leu Pro Ser Ser Ile Glu
                        325                 330                 335
        Lys Thr Ile Ser Lys Ala Lys Gly Gln Pro Arg Glu Pro Gln Val Tyr
                        340                 345                 350
        Thr Leu Pro Pro Ser Gln Glu Glu Met Thr Lys Asn Gln Val Ser Leu
                        355                 360                 365
        Thr Cys Leu Val Lys Gly Phe Tyr Pro Ser Asp Ile Ala Val Glu Trp
            370                 375                 380
        Glu Ser Asn Gly Gln Pro Glu Asn Asn Tyr Lys Thr Thr Pro Pro Val
        385                 390                 395                 400
        Leu Asp Ser Asp Gly Ser Phe Phe Leu Tyr Ser Arg Leu Thr Val Asp
                        405                 410                 415
        Lys Ser Arg Trp Gln Glu Gly Asn Val Phe Ser Cys Ser Val Met His
                        420                 425                 430
        Glu Ala Leu His Asn His Tyr Thr Gln Lys Ser Leu Ser Leu Ser Leu
                        435                 440                 445
        Gly Lys
            450

<210> SEQ ID NO 12
<211> LENGTH: 214
<212> TYPE: PRT
<213> ORGANISM: Artificial Sequence
```

```
<220> FEATURE:
<223> OTHER INFORMATION: Synthetic Construct

<400> SEQUENCE: 12

Asp Ile Gln Met Thr Gln Ser Pro Ala Ser Leu Ser Thr Phe Leu Gly
1               5                   10                  15

Glu Pro Val Thr Ile Glu Cys Arg Ala Ser Glu Asp Ile Tyr Asn Asp
            20                  25                  30

Leu Ala Trp Tyr Gln Gln Lys Pro Gly Lys Ser Pro Gln Leu Leu Ile
        35                  40                  45

Tyr Asn Ala Asn Ser Leu His Thr Gly Val Pro Ser Arg Phe Ser Gly
50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Asp Tyr Pro Leu
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 13
<211> LENGTH: 123
<212> TYPE: PRT
<213> ORGANISM: Artificial Sequence
<220> FEATURE:
<223> OTHER INFORMATION: Synthetic Construct

<400> SEQUENCE: 13

Gln Val Thr Leu Lys Glu Ser Gly Pro Gly Ile Leu Gln Pro Ser His
1               5                   10                  15

Thr Leu Ser Leu Thr Cys Ser Phe Ser Gly Phe Ser Leu Asn Thr Tyr
            20                  25                  30

Ala Met Gly Val Ser Trp Ile Arg Gln Pro Ser Gly Lys Gly Leu Glu
        35                  40                  45

Trp Leu Ala Ser Ile Trp Trp Asn Gly Asn Lys Tyr Asn Asn Pro Ser
50                  55                  60

Leu Lys Ser Arg Leu Thr Val Ser Lys Asp Thr Ser Asn Asn Gln Ala
65                  70                  75                  80

Phe Leu Lys Val Thr Ser Val Asp Thr Ala Asp Thr Ala Thr Tyr Tyr
                85                  90                  95

Cys Ala His Ser Arg Ile Ile Arg Phe Thr Asp Tyr Val Met Asp Ala
            100                 105                 110

Trp Gly Gln Gly Ala Ser Val Thr Val Ser Ser
```

```
                115                 120

<210> SEQ ID NO 14
<211> LENGTH: 107
<212> TYPE: PRT
<213> ORGANISM: Artificial Sequence
<220> FEATURE:
<223> OTHER INFORMATION: Synthetic Construct

<400> SEQUENCE: 14

Asp Ile Gln Met Thr Gln Ser Pro Ala Ser Leu Ser Thr Phe Leu Gly
1               5                   10                  15

Glu Pro Val Thr Ile Glu Cys Arg Ala Ser Glu Asp Ile Tyr Asn Asp
            20                  25                  30

Leu Ala Trp Tyr Gln Gln Lys Pro Gly Lys Ser Pro Gln Leu Leu Ile
        35                  40                  45

Tyr Asn Ala Asn Ser Leu His Thr Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Val Ala Ser Tyr Phe Cys Gln Gln Tyr Tyr Asp Tyr Pro Leu
                85                  90                  95

Thr Phe Gly Ser Gly Thr Lys Leu Glu Ile Lys
            100                 105

<210> SEQ ID NO 15
<211> LENGTH: 7
<212> TYPE: PRT
<213> ORGANISM: Artificial Sequence
<220> FEATURE:
<223> OTHER INFORMATION: Synthetic Construct

<400> SEQUENCE: 15

Thr Tyr Ala Met Gly Val Ser
1               5

<210> SEQ ID NO 16
<211> LENGTH: 16
<212> TYPE: PRT
<213> ORGANISM: Artificial Sequence
<220> FEATURE:
<223> OTHER INFORMATION: Synthetic Construct

<400> SEQUENCE: 16

Ser Ile Trp Trp Asn Gly Asn Lys Tyr Asn Asn Pro Ser Leu Lys Ser
1               5                   10                  15

<210> SEQ ID NO 17
<211> LENGTH: 13
<212> TYPE: PRT
<213> ORGANISM: Artificial Sequence
<220> FEATURE:
<223> OTHER INFORMATION: Synthetic Construct

<400> SEQUENCE: 17

Ser Arg Ile Ile Arg Phe Thr Asp Tyr Val Met Asp Ala
1               5                   10

<210> SEQ ID NO 18
<211> LENGTH: 11
<212> TYPE: PRT
<213> ORGANISM: Artificial Sequence
<220> FEATURE:
<223> OTHER INFORMATION: Synthetic Construct
```

<400> SEQUENCE: 18

Arg Ala Ser Glu Asp Ile Tyr Asn Asp Leu Ala
1               5                   10

<210> SEQ ID NO 19
<211> LENGTH: 7
<212> TYPE: PRT
<213> ORGANISM: Artificial Sequence
<220> FEATURE:
<223> OTHER INFORMATION: Synthetic Construct

<400> SEQUENCE: 19

Asn Ala Asn Ser Leu His Thr
1               5

<210> SEQ ID NO 20
<211> LENGTH: 9
<212> TYPE: PRT
<213> ORGANISM: Artificial Sequence
<220> FEATURE:
<223> OTHER INFORMATION: Synthetic Construct

<400> SEQUENCE: 20

Gln Gln Tyr Tyr Asp Tyr Pro Leu Thr
1               5

<210> SEQ ID NO 21
<211> LENGTH: 447
<212> TYPE: PRT
<213> ORGANISM: Artificial Sequence
<220> FEATURE:
<223> OTHER INFORMATION: Synthetic Construct

<400> SEQUENCE: 21

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
                20                  25                  30

Gly Leu Ser Trp Val Lys Gln Thr Pro Gly Lys Gly Leu Lys Trp Met
            35                  40                  45

Gly Trp Ile Asn Thr Tyr Ser Gly Val Pro Thr Tyr Thr Asp Asp Phe
        50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Pro Tyr Asp Phe Asp Gln Val Gly Phe Ala Tyr Trp Gly Gln
            100                 105                 110

Gly Thr Leu Val Thr Val Ser Ala Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys

```
            195                 200                 205
Pro Ser Asn Thr Lys Val Asp Lys Arg Val Glu Ser Lys Tyr Gly Pro
    210                 215                 220

Pro Cys Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 22
<211> LENGTH: 214
<212> TYPE: PRT
<213> ORGANISM: Artificial Sequence
<220> FEATURE:
<223> OTHER INFORMATION: Synthetic Construct

<400> SEQUENCE: 22

Ser Ile Val Met Thr Gln Thr Pro Lys Phe Leu Leu Val Ser Ala Gly
1               5                   10                  15

Asp Arg Val Ser Ile Thr Cys Lys Ala Ser Gln Thr Val Ser Ser Asp
            20                  25                  30

Val Ala Trp Tyr Gln Gln Lys Ala Gly Gln Ser Pro Lys Leu Leu Ile
        35                  40                  45

Tyr Tyr Ala Ser Asn Arg Tyr Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Ser Pro Phe
                85                  90                  95

Thr Phe Gly Gly Gly Ser Lys Leu Glu Ile Lys Arg Thr Val Ala Ala
            100                 105                 110

Pro Ser Val Phe Ile Phe Pro Pro Ser Asp Glu Gln Leu Lys Ser Gly
```

```
                115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
            195                 200                 205
Phe Asn Arg Gly Glu Cys
    210

<210> SEQ ID NO 23
<211> LENGTH: 120
<212> TYPE: PRT
<213> ORGANISM: Artificial Sequence
<220> FEATURE:
<223> OTHER INFORMATION: Synthetic Construct

<400> SEQUENCE: 23

Gln Ile Gln Leu Val Gln Ser Gly Pro Glu Leu Lys Lys Pro Gly Glu
1               5                   10                  15
Thr Val Lys Ile Ser Cys Lys Ala Ser Gly Tyr Thr Phe Thr Thr Tyr
                20                  25                  30
Gly Leu Ser Trp Val Lys Gln Thr Pro Gly Lys Gly Leu Lys Trp Met
            35                  40                  45
Gly Trp Ile Asn Thr Tyr Ser Gly Val Pro Tyr Thr Asp Asp Phe
    50                  55                  60
Lys Gly Arg Phe Ala Phe Ser Leu Glu Thr Ser Ala Ser Thr Ala Tyr
65                  70                  75                  80
Leu Gln Ile Asn Asn Leu Lys Asn Glu Asp Thr Ala Thr Tyr Phe Cys
                85                  90                  95
Ala Arg Pro Tyr Asp Phe Asp Val Gly Phe Ala Tyr Trp Gly Gln
            100                 105                 110
Gly Thr Leu Val Thr Val Ser Ala
        115                 120

<210> SEQ ID NO 24
<211> LENGTH: 107
<212> TYPE: PRT
<213> ORGANISM: Artificial Sequence
<220> FEATURE:
<223> OTHER INFORMATION: Synthetic Construct

<400> SEQUENCE: 24

Ser Ile Val Met Thr Gln Thr Pro Lys Phe Leu Leu Val Ser Ala Gly
1               5                   10                  15
Asp Arg Val Ser Ile Thr Cys Lys Ala Ser Gln Thr Val Ser Ser Asp
                20                  25                  30
Val Ala Trp Tyr Gln Gln Lys Ala Gly Gln Ser Pro Lys Leu Leu Ile
            35                  40                  45
Tyr Tyr Ala Ser Asn Arg Tyr Thr Gly Val Pro Asp Arg Phe Thr Gly
        50                  55                  60
Ser Gly Tyr Gly Thr Asp Phe Thr Phe Thr Ile Ser Thr Val Gln Ala
65                  70                  75                  80
```

Glu Asp Leu Ala Val Tyr Phe Cys Gln Gln Asp Tyr Ser Ser Pro Phe
            85                  90                  95

Thr Phe Gly Gly Gly Ser Lys Leu Glu Ile Lys
            100                 105

<210> SEQ ID NO 25
<211> LENGTH: 5
<212> TYPE: PRT
<213> ORGANISM: Artificial Sequence
<220> FEATURE:
<223> OTHER INFORMATION: Synthetic Construct

<400> SEQUENCE: 25

Thr Tyr Gly Leu Ser
1               5

<210> SEQ ID NO 26
<211> LENGTH: 17
<212> TYPE: PRT
<213> ORGANISM: Artificial Sequence
<220> FEATURE:
<223> OTHER INFORMATION: Synthetic Construct

<400> SEQUENCE: 26

Trp Ile Asn Thr Tyr Ser Gly Val Pro Thr Tyr Thr Asp Asp Phe Lys
1               5                   10                  15

Gly

<210> SEQ ID NO 27
<211> LENGTH: 11
<212> TYPE: PRT
<213> ORGANISM: Artificial Sequence
<220> FEATURE:
<223> OTHER INFORMATION: Synthetic Construct

<400> SEQUENCE: 27

Pro Tyr Asp Phe Asp Gln Val Gly Phe Ala Tyr
1               5                   10

<210> SEQ ID NO 28
<211> LENGTH: 11
<212> TYPE: PRT
<213> ORGANISM: Artificial Sequence
<220> FEATURE:
<223> OTHER INFORMATION: Synthetic Construct

<400> SEQUENCE: 28

Lys Ala Ser Gln Thr Val Ser Ser Asp Val Ala
1               5                   10

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Tyr Ala Ser Asn Arg Tyr Thr
1               5

<210> SEQ ID NO 30
<211> LENGTH: 9
<212> TYPE: PRT
<213> ORGANISM: Artificial Sequence
<220> FEATURE:

<223> OTHER INFORMATION: Synthetic Construct

<400> SEQUENCE: 30

Gln Gln Asp Tyr Ser Ser Pro Phe Thr
1               5

<210> SEQ ID NO 31
<211> LENGTH: 446
<212> TYPE: PRT
<213> ORGANISM: Artificial Sequence
<220> FEATURE:
<223> OTHER INFORMATION: Synthetic Construct

<400> SEQUENCE: 31

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ala Asp Tyr
            20                  25                  30

Glu Ile His Trp Val Lys Gln Thr Pro Val His Gly Leu Glu Trp Ile
        35                  40                  45

Gly Ala Ile Asp Pro Glu Thr Gly Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Tyr Tyr Asp Tyr Asp Asp Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Cys Ser Arg Ser Thr Ser Glu Ser Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Lys Thr Tyr Thr Cys Asn Val Asp His Lys Pro
        195                 200                 205

Ser Asn Thr Lys Val Asp Lys Arg Val Glu Ser Lys Tyr Gly Pro Pro
    210                 215                 220

Cys Pro Pro Cys Pro Ala Pro Glu Phe Leu Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
            260                 265                 270

Gln Phe Asn Trp Tyr Val Asp Gly Val Glu Val His Asn Ala Lys Thr
        275                 280                 285

Lys Pro Arg Glu Glu Gln Phe Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

```
Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
        355                 360                 365

Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
            420                 425                 430

Asn His Tyr Thr Gln Lys Ser Leu Ser Leu Ser Leu Gly Lys
            435                 440                 445

<210> SEQ ID NO 32
<211> LENGTH: 213
<212> TYPE: PRT
<213> ORGANISM: Artificial Sequence
<220> FEATURE:
<223> OTHER INFORMATION: Synthetic Construct

<400> SEQUENCE: 32

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Phe Met
            20                  25                  30

His Trp Tyr Gln Gln Lys Ser Gly Thr Ser Pro Lys Arg Trp Ile Tyr
        35                  40                  45

Gly Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Gly Asn Pro Phe Thr
                85                  90                  95

Phe Gly Ser Gly Thr Lys Leu Glu Thr Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 33
<211> LENGTH: 119
<212> TYPE: PRT
<213> ORGANISM: Artificial Sequence
```

```
<220> FEATURE:
<223> OTHER INFORMATION: Synthetic Construct

<400> SEQUENCE: 33

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Thr Phe Ala Asp Tyr
            20                  25                  30

Glu Ile His Trp Val Lys Gln Thr Pro Val His Gly Leu Glu Trp Ile
        35                  40                  45

Gly Ala Ile Asp Pro Glu Thr Gly Thr Ala Tyr Asn Gln Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Tyr Tyr Asp Tyr Asp Asp Ala Met Asp Tyr Trp Gly Gln Gly
            100                 105                 110

Thr Ser Val Thr Val Ser Ser
        115

<210> SEQ ID NO 34
<211> LENGTH: 106
<212> TYPE: PRT
<213> ORGANISM: Artificial Sequence
<220> FEATURE:
<223> OTHER INFORMATION: Synthetic Construct

<400> SEQUENCE: 34

Gln Ile Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Phe Met
            20                  25                  30

His Trp Tyr Gln Gln Lys Ser Gly Thr Ser Pro Lys Arg Trp Ile Tyr
        35                  40                  45

Gly Thr Ser Lys Leu Ala Ser Gly Val Pro Ala Arg Phe Ser Gly Ser
    50                  55                  60

Gly Ser Gly Thr Ser Tyr Ser Leu Thr Ile Ser Ser Met Glu Ala Glu
65                  70                  75                  80

Asp Ala Ala Thr Tyr Tyr Cys Gln Gln Trp Asn Gly Asn Pro Phe Thr
                85                  90                  95

Phe Gly Ser Gly Thr Lys Leu Glu Thr Lys
            100                 105

<210> SEQ ID NO 35
<211> LENGTH: 5
<212> TYPE: PRT
<213> ORGANISM: Artificial Sequence
<220> FEATURE:
<223> OTHER INFORMATION: Synthetic Construct

<400> SEQUENCE: 35

Asp Tyr Glu Ile His
1               5

<210> SEQ ID NO 36
<211> LENGTH: 17
<212> TYPE: PRT
<213> ORGANISM: Artificial Sequence
<220> FEATURE:
```

<223> OTHER INFORMATION: Synthetic Construct

<400> SEQUENCE: 36

Ala Ile Asp Pro Glu Thr Gly Gly Thr Ala Tyr Asn Gln Lys Phe Lys
1               5                   10                  15

Gly

<210> SEQ ID NO 37
<211> LENGTH: 10
<212> TYPE: PRT
<213> ORGANISM: Artificial Sequence
<220> FEATURE:
<223> OTHER INFORMATION: Synthetic Construct

<400> SEQUENCE: 37

Tyr Tyr Asp Tyr Asp Asp Ala Met Asp Tyr
1               5                   10

<210> SEQ ID NO 38
<211> LENGTH: 10
<212> TYPE: PRT
<213> ORGANISM: Artificial Sequence
<220> FEATURE:
<223> OTHER INFORMATION: Synthetic Construct

<400> SEQUENCE: 38

Ser Ala Ser Ser Ser Val Ser Phe Met His
1               5                   10

<210> SEQ ID NO 39
<211> LENGTH: 7
<212> TYPE: PRT
<213> ORGANISM: Artificial Sequence
<220> FEATURE:
<223> OTHER INFORMATION: Synthetic Construct

<400> SEQUENCE: 39

Gly Thr Ser Lys Leu Ala Ser
1               5

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

Gln Gln Trp Asn Gly Asn Pro Phe Thr
1               5

<210> SEQ ID NO 41
<211> LENGTH: 447
<212> TYPE: PRT
<213> ORGANISM: Artificial Sequence
<220> FEATURE:
<223> OTHER INFORMATION: Synthetic Construct

<400> SEQUENCE: 41

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Lys Phe Thr Asp Tyr
                20                  25                  30

Glu Met His Trp Val Lys Gln Thr Pro Val His Gly Leu Glu Trp Ile
            35                  40                  45

Gly Ala Ile Asp Pro Glu Thr Asn Gly Thr Ala Tyr Asn Lys Lys Phe
        50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                    85                  90                  95

Thr Arg Gly Asp Tyr Asp Phe Ser Ala Trp Phe Ala Tyr Trp Gly Gln
                100                 105                 110

Gly Thr Leu Val Thr Val Ser Ala Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Asp Val Ser Gln Glu Asp Pro Glu
                260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
            435                 440                 445

<210> SEQ ID NO 42
<211> LENGTH: 218

-continued

```
<212> TYPE: PRT
<213> ORGANISM: Artificial Sequence
<220> FEATURE:
<223> OTHER INFORMATION: Synthetic Construct

<400> SEQUENCE: 42

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Asp Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Arg Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 43
<211> LENGTH: 120
<212> TYPE: PRT
<213> ORGANISM: Artificial Sequence
<220> FEATURE:
<223> OTHER INFORMATION: Synthetic Construct

<400> SEQUENCE: 43

Gln Val Gln Leu Gln Gln Ser Gly Ala Glu Leu Val Arg Pro Gly Ala
1               5                   10                  15

Ser Val Thr Leu Ser Cys Lys Ala Ser Gly Tyr Lys Phe Thr Asp Tyr
            20                  25                  30

Glu Met His Trp Val Lys Gln Thr Pro Val His Gly Leu Glu Trp Ile
        35                  40                  45

Gly Ala Ile Asp Pro Glu Thr Asn Gly Thr Ala Tyr Asn Lys Lys Phe
    50                  55                  60

Lys Gly Lys Ala Ile Leu Thr Ala Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Thr Arg Gly Asp Tyr Asp Phe Ser Ala Trp Phe Ala Tyr Trp Gly Gln
            100                 105                 110
```

Gly Thr Leu Val Thr Val Ser Ala
        115                 120

<210> SEQ ID NO 44
<211> LENGTH: 111
<212> TYPE: PRT
<213> ORGANISM: Artificial Sequence
<220> FEATURE:
<223> OTHER INFORMATION: Synthetic Construct

<400> SEQUENCE: 44

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Asp Ile Ser Phe Met His Trp Tyr Gln Gln Lys Pro Gly Gln Pro Pro
        35                  40                  45

Lys Leu Leu Ile Tyr Arg Ala Ser Asn Leu Glu Ser Gly Ile Pro Ala
    50                  55                  60

Arg Phe Ser Gly Ser Gly Ser Arg Thr Asp Phe Thr Leu Thr Ile Asn
65                  70                  75                  80

Pro Val Glu Thr Asp Asp Val Ala Thr Tyr Tyr Cys Gln Gln Ser Asn
                85                  90                  95

Lys Asp Pro Arg Thr Phe Gly Gly Gly Thr Lys Leu Glu Ile Lys
            100                 105                 110

<210> SEQ ID NO 45
<211> LENGTH: 5
<212> TYPE: PRT
<213> ORGANISM: Artificial Sequence
<220> FEATURE:
<223> OTHER INFORMATION: Synthetic Construct

<400> SEQUENCE: 45

Asp Tyr Glu Met His
1               5

<210> SEQ ID NO 46
<211> LENGTH: 17
<212> TYPE: PRT
<213> ORGANISM: Artificial Sequence
<220> FEATURE:
<223> OTHER INFORMATION: Synthetic Construct

<400> SEQUENCE: 46

Ala Ile Asp Pro Glu Thr Asn Gly Thr Ala Tyr Asn Lys Lys Phe Lys
1               5                   10                  15

Gly

<210> SEQ ID NO 47
<211> LENGTH: 11
<212> TYPE: PRT
<213> ORGANISM: Artificial Sequence
<220> FEATURE:
<223> OTHER INFORMATION: Synthetic Construct

<400> SEQUENCE: 47

Gly Asp Tyr Asp Phe Ser Ala Trp Phe Ala Tyr
1               5                   10

<210> SEQ ID NO 48
<211> LENGTH: 15

```
<212> TYPE: PRT
<213> ORGANISM: Artificial Sequence
<220> FEATURE:
<223> OTHER INFORMATION: Synthetic Construct

<400> SEQUENCE: 48

Arg Ala Ser Glu Ser Val Asp Asn Tyr Asp Ile Ser Phe Met His
1               5                   10                  15

<210> SEQ ID NO 49
<211> LENGTH: 7
<212> TYPE: PRT
<213> ORGANISM: Artificial Sequence
<220> FEATURE:
<223> OTHER INFORMATION: Synthetic Construct

<400> SEQUENCE: 49

Arg Ala Ser Asn Leu Glu Ser
1               5

<210> SEQ ID NO 50
<211> LENGTH: 9
<212> TYPE: PRT
<213> ORGANISM: Artificial Sequence
<220> FEATURE:
<223> OTHER INFORMATION: Synthetic Construct

<400> SEQUENCE: 50

Gln Gln Ser Asn Lys Asp Pro Arg Thr
1               5

<210> SEQ ID NO 51
<211> LENGTH: 450
<212> TYPE: PRT
<213> ORGANISM: Artificial Sequence
<220> FEATURE:
<223> OTHER INFORMATION: Synthetic Construct

<400> SEQUENCE: 51

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
                20                  25                  30

Ala Met Gly Val Ser Trp Ile Arg Gln Pro Pro Gly Lys Ala Leu Glu
            35                  40                  45

Trp Leu Ala Ser Ile Trp Trp Asn Gly Asn Lys Tyr Asn Asn Pro Ser
        50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Arg Phe Thr Asp Tyr Val Met Asp Ala
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175
```

```
Pro Ala Val Leu Gln Ser Ser Gly Leu Tyr Ser Leu Ser Ser Val Val
            180                 185                 190

Thr Val Pro Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 52
<211> LENGTH: 214
<212> TYPE: PRT
<213> ORGANISM: Artificial Sequence
<220> FEATURE:
<223> OTHER INFORMATION: Synthetic Construct

<400> SEQUENCE: 52

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Lys Leu Leu Ile
        35                  40                  45

Tyr Asn Ala Asn Ser Leu His Thr Gly Val Ala Ser Arg Phe Ser Gly
    50                  55                  60

Ser Gly Ser Gly Thr Asp Phe Thr Phe Thr Ile Ser Ser Leu Gln Pro
65                  70                  75                  80
```

Glu Asp Val Ala Thr Tyr Phe Cys Gln Gln Tyr Tyr Asp Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 53
<211> LENGTH: 123
<212> TYPE: PRT
<213> ORGANISM: Artificial Sequence
<220> FEATURE:
<223> OTHER INFORMATION: Synthetic Construct

<400> SEQUENCE: 53

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
                20                  25                  30

Ala Met Gly Val Ser Trp Ile Arg Gln Pro Pro Gly Lys Ala Leu Glu
            35                  40                  45

Trp Leu Ala Ser Ile Trp Trp Asn Gly Asn Lys Tyr Asn Asn Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Arg Phe Thr Asp Tyr Val Met Asp Ala
            100                 105                 110

Trp Gly Gln Gly Thr Leu Val Thr Val Ser Ser
            115                 120

<210> SEQ ID NO 54
<211> LENGTH: 107
<212> TYPE: PRT
<213> ORGANISM: Artificial Sequence
<220> FEATURE:
<223> OTHER INFORMATION: Synthetic Construct

<400> SEQUENCE: 54

Asp Ile Gln Met Thr Gln Ser Pro Ser Ser Leu Ser Ser Val Gly
1               5                   10                  15

Asp Arg Val Thr Ile Thr Cys Arg Ala Ser Glu Asp Ile Tyr Asn Asp
                20                  25                  30

Leu Ala Trp Tyr Gln Gln Lys Pro Gly Lys Ala Pro Lys Leu Leu Ile
            35                  40                  45

Tyr Asn Ala Asn Ser Leu His Thr Gly Val Ala Ser Arg Phe Ser Gly
            50                  55                  60

Ser Gly Ser Gly Thr Asp Phe Thr Phe Thr Ile Ser Ser Leu Gln Pro
 65                  70                  75                  80

Glu Asp Val Ala Thr Tyr Phe Cys Gln Gln Tyr Asp Tyr Pro Leu
                 85                  90                  95

Thr Phe Gly Gln Gly Thr Lys Leu Glu Ile Lys
            100                 105

<210> SEQ ID NO 55
<211> LENGTH: 7
<212> TYPE: PRT
<213> ORGANISM: Artificial Sequence
<220> FEATURE:
<223> OTHER INFORMATION: Synthetic Construct

<400> SEQUENCE: 55

Thr Tyr Ala Met Gly Val Ser
1               5

<210> SEQ ID NO 56
<211> LENGTH: 16
<212> TYPE: PRT
<213> ORGANISM: Artificial Sequence
<220> FEATURE:
<223> OTHER INFORMATION: Synthetic Construct

<400> SEQUENCE: 56

Ser Ile Trp Trp Asn Gly Asn Lys Tyr Asn Asn Pro Ser Leu Lys Ser
1               5                   10                  15

<210> SEQ ID NO 57
<211> LENGTH: 13
<212> TYPE: PRT
<213> ORGANISM: Artificial Sequence
<220> FEATURE:
<223> OTHER INFORMATION: Synthetic Construct

<400> SEQUENCE: 57

Ser Arg Ile Ile Arg Phe Thr Asp Tyr Val Met Asp Ala
1               5                   10

<210> SEQ ID NO 58
<211> LENGTH: 11
<212> TYPE: PRT
<213> ORGANISM: Artificial Sequence
<220> FEATURE:
<223> OTHER INFORMATION: Synthetic Construct

<400> SEQUENCE: 58

Arg Ala Ser Glu Asp Ile Tyr Asn Asp Leu Ala
1               5                   10

<210> SEQ ID NO 59
<211> LENGTH: 7
<212> TYPE: PRT
<213> ORGANISM: Artificial Sequence
<220> FEATURE:
<223> OTHER INFORMATION: Synthetic Construct

<400> SEQUENCE: 59

Asn Ala Asn Ser Leu His Thr
1               5

```
<210> SEQ ID NO 60
<211> LENGTH: 9
<212> TYPE: PRT
<213> ORGANISM: Artificial Sequence
<220> FEATURE:
<223> OTHER INFORMATION: Synthetic Construct

<400> SEQUENCE: 60

Gln Gln Tyr Tyr Asp Tyr Pro Leu Thr
1               5

<210> SEQ ID NO 61
<211> LENGTH: 450
<212> TYPE: PRT
<213> ORGANISM: Artificial Sequence
<220> FEATURE:
<223> OTHER INFORMATION: Synthetic Construct

<400> SEQUENCE: 61

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Arg Phe Thr Asp Tyr Val Met Asp Ala
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300
```

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
            355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
            435                 440                 445

Gly Lys
    450

<210> SEQ ID NO 62
<211> LENGTH: 214
<212> TYPE: PRT
<213> ORGANISM: Artificial Sequence
<220> FEATURE:
<223> OTHER INFORMATION: Synthetic Construct

<400> SEQUENCE: 62

Asp Ile Val Met Thr Gln Ser Pro Ser Ser Leu Ser Ala Ser Val Gly
1               5                   10                  15

Asp Thr Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Gln Leu Leu Leu
        35                  40                  45

Tyr Asn Ala Asn Ser Leu His Thr Gly Val Pro Ser Arg Phe Ser Gly
50                  55                  60

Ser Gly Ser Gly Thr Asp Tyr Thr Leu Thr Ile Ser Thr Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Pro Gly Thr Lys Val His Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
            210

<210> SEQ ID NO 63
<211> LENGTH: 123
<212> TYPE: PRT
<213> ORGANISM: Artificial Sequence
<220> FEATURE:
<223> OTHER INFORMATION: Synthetic Construct

<400> SEQUENCE: 63

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Arg Phe Thr Asp Tyr Val Met Asp Ala
            100                 105                 110

Trp Gly Gln Gly Thr Leu Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: Synthetic Construct

<400> SEQUENCE: 64

Asp Ile Val Met Thr Gln Ser Pro Ser Ser Leu Ser Ala Ser Val Gly
1               5                   10                  15

Asp Thr Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Gln Leu Leu Leu
        35                  40                  45

Tyr Asn Ala Asn Ser Leu His Thr Gly Val Pro Ser Arg Phe Ser Gly
50                  55                  60

Ser Gly Ser Gly Thr Asp Tyr Thr Leu Thr Ile Ser Thr Leu Gln Pro
65                  70                  75                  80

Glu Asp Phe Ala Thr Tyr Tyr Cys Gln Gln Tyr Asp Tyr Pro Leu
                85                  90                  95

Thr Phe Gly Pro Gly Thr Lys Val His Ile Lys
            100                 105

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Thr Tyr Ala Met Gly Val Ser

```
1               5

<210> SEQ ID NO 66
<211> LENGTH: 16
<212> TYPE: PRT
<213> ORGANISM: Artificial Sequence
<220> FEATURE:
<223> OTHER INFORMATION: Synthetic Construct

<400> SEQUENCE: 66

Ser Ile Trp Trp Asn Gly Asn Lys Tyr Asn Asn Pro Ser Leu Lys Ser
1               5                   10                  15

<210> SEQ ID NO 67
<211> LENGTH: 13
<212> TYPE: PRT
<213> ORGANISM: Artificial Sequence
<220> FEATURE:
<223> OTHER INFORMATION: Synthetic Construct

<400> SEQUENCE: 67

Ser Arg Ile Ile Arg Phe Thr Asp Tyr Val Met Asp Ala
1               5                   10

<210> SEQ ID NO 68
<211> LENGTH: 11
<212> TYPE: PRT
<213> ORGANISM: Artificial Sequence
<220> FEATURE:
<223> OTHER INFORMATION: Synthetic Construct

<400> SEQUENCE: 68

Arg Ala Ser Glu Asp Ile Tyr Asn Asp Leu Ala
1               5                   10

<210> SEQ ID NO 69
<211> LENGTH: 7
<212> TYPE: PRT
<213> ORGANISM: Artificial Sequence
<220> FEATURE:
<223> OTHER INFORMATION: Synthetic Construct

<400> SEQUENCE: 69

Asn Ala Asn Ser Leu His Thr
1               5

<210> SEQ ID NO 70
<211> LENGTH: 9
<212> TYPE: PRT
<213> ORGANISM: Artificial Sequence
<220> FEATURE:
<223> OTHER INFORMATION: Synthetic Construct

<400> SEQUENCE: 70

Gln Gln Tyr Tyr Asp Tyr Pro Leu Thr
1               5

<210> SEQ ID NO 71
<211> LENGTH: 450
<212> TYPE: PRT
<213> ORGANISM: Artificial Sequence
<220> FEATURE:
<223> OTHER INFORMATION: Synthetic Construct

<400> SEQUENCE: 71

Gln Val Thr Leu Lys Glu Ser Gly Pro Ser Leu Val Lys Pro Thr Gln
1               5                   10                  15
```

-continued

```
Thr Leu Thr Leu Thr Cys Thr Phe Ser Gly Phe Ser Leu Asn Thr Tyr
             20                  25                  30

Ala Met Gly Val Ser Trp Ile Arg Gln Pro Pro Gly Lys Ala Leu Glu
         35                  40                  45

Trp Leu Ala Ser Ile Trp Trp Asn Gly Asn Lys Tyr Asn Asn Pro Ser
 50                  55                  60

Leu Lys Ser Arg Leu Thr Ile Thr Lys Asp Thr Ser Lys Asn Gln Val
 65                  70                  75                  80

Val Leu Lys Val Thr Asn Met Asp Pro Ala Asp Thr Ala Thr Tyr Tyr
                 85                  90                  95

Cys Ala His Ser Arg Ile Ile Arg Phe Thr Asp Tyr Val Met Asp Ala
             100                 105                 110

Trp Gly Gln Gly Thr Thr Val Thr Val Ser Ser Ala Ser Thr Lys Gly
         115                 120                 125

Pro Ser Val Phe Pro Leu Ala Pro Cys Ser Arg Ser Thr Ser Glu Ser
     130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                 165                 170                 175

Pro Ala Val Leu Gln Ser Ser Gly Leu Tyr Ser Leu Ser Ser Val Val
             180                 185                 190

Thr Val Pro Ser Ser Ser Leu Gly Thr Lys Thr Tyr Thr Cys Asn Val
         195                 200                 205

Asp His Lys Pro Ser Asn Thr Lys Val Asp Lys Arg Val Glu Ser Lys
     210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                 245                 250                 255

Ser Arg Thr Pro Glu Val Thr Cys Val Val Val Asp Val Ser Gln Glu
             260                 265                 270

Asp Pro Glu Val Gln Phe Asn Trp Tyr Val Asp Gly Val Glu Val His
         275                 280                 285

Asn Ala Lys Thr Lys Pro Arg Glu Glu Gln Phe Asn Ser Thr Tyr Arg
     290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                 325                 330                 335

Lys Thr Ile Ser Lys Ala Lys Gly Gln Pro Arg Glu Pro Gln Val Tyr
             340                 345                 350

Thr Leu Pro Pro Ser Gln Glu Glu Met Thr Lys Asn Gln Val Ser Leu
         355                 360                 365

Thr Cys Leu Val Lys Gly Phe Tyr Pro Ser Asp Ile Ala Val Glu Trp
     370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                 405                 410                 415

Lys Ser Arg Trp Gln Glu Gly Asn Val Phe Ser Cys Ser Val Met His
             420                 425                 430
```

Glu Ala Leu His Asn His Tyr Thr Gln Lys Ser Leu Ser Leu Ser Leu
            435                 440                 445

Gly Lys
    450

<210> SEQ ID NO 72
<211> LENGTH: 214
<212> TYPE: PRT
<213> ORGANISM: Artificial Sequence
<220> FEATURE:
<223> OTHER INFORMATION: Synthetic Construct

<400> SEQUENCE: 72

Asp Ile Val Met Thr Gln Ser Pro Ser Ser Leu Ser Ala Ser Val Gly
1               5                   10                  15

Asp Thr Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Gln Leu Leu Leu
        35                  40                  45

Tyr Asn Ala Asn Ser Leu His Thr Gly Val Pro Ser Arg Phe Ser Gly
50                  55                  60

Ser Gly Ser Gly Thr Asp Tyr Thr Leu Thr Ile Ser Thr Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Pro Gly Thr Lys Val His Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 73
<211> LENGTH: 123
<212> TYPE: PRT
<213> ORGANISM: Artificial Sequence
<220> FEATURE:
<223> OTHER INFORMATION: Synthetic Construct

<400> SEQUENCE: 73

Gln Val Thr Leu Lys Glu Ser Gly Pro Ser Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
50                  55                  60

Leu Lys Ser Arg Leu Thr Ile Thr Lys Asp Thr Ser Lys Asn Gln Val
65                  70                  75                  80

Val Leu Lys Val Thr Asn Met Asp Pro Ala Asp Thr Ala Thr Tyr Tyr
                85                  90                  95

Cys Ala His Ser Arg Ile Ile Arg Phe Thr Asp Tyr Val Met Asp Ala
            100                 105                 110

Trp Gly Gln Gly Thr Thr Val Thr Val Ser Ser
        115                 120

<210> SEQ ID NO 74
<211> LENGTH: 107
<212> TYPE: PRT
<213> ORGANISM: Artificial Sequence
<220> FEATURE:
<223> OTHER INFORMATION: Synthetic Construct

<400> SEQUENCE: 74

Asp Ile Val Met Thr Gln Ser Pro Ser Ser Leu Ser Ala Ser Val Gly
1               5                   10                  15

Asp Thr Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Gln Leu Leu Leu
        35                  40                  45

Tyr Asn Ala Asn Ser Leu His Thr Gly Val Pro Ser Arg Phe Ser Gly
    50                  55                  60

Ser Gly Ser Gly Thr Asp Tyr Thr Leu Thr Ile Ser Thr Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Pro Gly Thr Lys Val His Ile Lys
            100                 105

<210> SEQ ID NO 75
<211> LENGTH: 7
<212> TYPE: PRT
<213> ORGANISM: Artificial Sequence
<220> FEATURE:
<223> OTHER INFORMATION: Synthetic Construct

<400> SEQUENCE: 75

Thr Tyr Ala Met Gly Val Ser
1               5

<210> SEQ ID NO 76
<211> LENGTH: 16
<212> TYPE: PRT
<213> ORGANISM: Artificial Sequence
<220> FEATURE:
<223> OTHER INFORMATION: Synthetic Construct

<400> SEQUENCE: 76

Ser Ile Trp Trp Asn Gly Asn Lys Tyr Asn Asn Pro Ser Leu Lys Ser
1               5                   10                  15

<210> SEQ ID NO 77
<211> LENGTH: 13
<212> TYPE: PRT
<213> ORGANISM: Artificial Sequence
<220> FEATURE:
<223> OTHER INFORMATION: Synthetic Construct

<400> SEQUENCE: 77

```
Ser Arg Ile Ile Arg Phe Thr Asp Tyr Val Met Asp Ala
1               5                   10
```

<210> SEQ ID NO 78
<211> LENGTH: 11
<212> TYPE: PRT
<213> ORGANISM: Artificial Sequence
<220> FEATURE:
<223> OTHER INFORMATION: Synthetic Construct

<400> SEQUENCE: 78

```
Arg Ala Ser Glu Asp Ile Tyr Asn Asp Leu Ala
1               5                   10
```

<210> SEQ ID NO 79
<211> LENGTH: 7
<212> TYPE: PRT
<213> ORGANISM: Artificial Sequence
<220> FEATURE:
<223> OTHER INFORMATION: Synthetic Construct

<400> SEQUENCE: 79

```
Asn Ala Asn Ser Leu His Thr
1               5
```

<210> SEQ ID NO 80
<211> LENGTH: 9
<212> TYPE: PRT
<213> ORGANISM: Artificial Sequence
<220> FEATURE:
<223> OTHER INFORMATION: Synthetic Construct

<400> SEQUENCE: 80

```
Gln Gln Tyr Tyr Asp Tyr Pro Leu Thr
1               5
```

<210> SEQ ID NO 81
<211> LENGTH: 450
<212> TYPE: PRT
<213> ORGANISM: Artificial Sequence
<220> FEATURE:
<223> OTHER INFORMATION: Synthetic Construct

<400> SEQUENCE: 81

```
Gln Val Thr Leu Lys Glu Ser Gly Pro Ala Leu Val Lys Pro Thr His
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Glu Asp Thr Ala Thr Phe Tyr
                85                  90                  95

Cys Ala His Ser Arg Ile Ile Arg Phe Thr Asp Tyr Val Met Asp Ala
            100                 105                 110

Trp Gly Arg Gly Thr Thr Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140
```

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
        180                 185                 190

Thr Val Pro Ser Ser Ser Leu Gly Thr Lys Thr Tyr Thr Cys Asn Val
    195                 200                 205

Asp His Lys Pro Ser Asn Thr Lys Val Asp Lys Arg Val Glu Ser Lys
210                 215                 220

Tyr Gly Pro Pro Cys Pro Cys Pro Ala Pro Glu Phe Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser Gln Glu
        260                 265                 270

Asp Pro Glu Val Gln Phe Asn Trp Tyr Val Asp Gly Val Glu Val His
    275                 280                 285

Asn Ala Lys Thr Lys Pro Arg Glu Glu Gln Phe Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Gln Glu Glu Met Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
            405                 410                 415

Lys Ser Arg Trp Gln Glu Gly Asn Val Phe Ser Cys Ser Val Met His
        420                 425                 430

Glu Ala Leu His Asn His Tyr Thr Gln Lys Ser Leu Ser Leu Ser Leu
    435                 440                 445

Gly Lys
    450

<210> SEQ ID NO 82
<211> LENGTH: 214
<212> TYPE: PRT
<213> ORGANISM: Artificial Sequence
<220> FEATURE:
<223> OTHER INFORMATION: Synthetic Construct

<400> SEQUENCE: 82

Asp Ile Val Met Thr Gln Ser Pro Ser Ser Leu Ser Ala Ser Val Gly
1               5                   10                  15

Asp Thr Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Gln Leu Leu Leu
        35                  40                  45

Tyr Asn Ala Asn Ser Leu His Thr Gly Val Pro Ser Arg Phe Ser Gly
             50                  55                  60

Ser Gly Ser Gly Thr Asp Tyr Thr Leu Thr Ile Ser Thr Leu Gln Pro
 65                  70                  75                  80

Glu Asp Phe Ala Thr Tyr Tyr Cys Gln Gln Tyr Tyr Asp Tyr Pro Leu
                 85                  90                  95

Thr Phe Gly Pro Gly Thr Lys Val His Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 83
<211> LENGTH: 123
<212> TYPE: PRT
<213> ORGANISM: Artificial Sequence
<220> FEATURE:
<223> OTHER INFORMATION: Synthetic Construct

<400> SEQUENCE: 83

Gln Val Thr Leu Lys Glu Ser Gly Pro Ala Leu Val Lys Pro Thr His
 1               5                  10                  15

Thr Leu Thr Leu Thr Cys Thr Phe Ser Gly Phe Ser Leu Asn Thr Tyr
             20                  25                  30

Ala Met Gly Val Ser Trp Ile Arg Gln Pro Pro Gly Lys Ala Leu Glu
         35                  40                  45

Trp Leu Ala Ser Ile Trp Trp Asn Gly Asn Lys Tyr Asn Asn Pro Ser
 50                  55                  60

Leu Lys Ser Arg Leu Thr Ile Ser Lys Asp Thr Ser Lys Asn Gln Val
 65                  70                  75                  80

Val Leu Thr Met Thr Asn Met Asp Pro Glu Asp Thr Ala Thr Phe Tyr
                 85                  90                  95

Cys Ala His Ser Arg Ile Ile Arg Phe Thr Asp Tyr Val Met Asp Ala
            100                 105                 110

Trp Gly Arg Gly Thr Thr Val Thr Val Ser Ser
        115                 120

<210> SEQ ID NO 84
<211> LENGTH: 107
<212> TYPE: PRT
<213> ORGANISM: Artificial Sequence
<220> FEATURE:
<223> OTHER INFORMATION: Synthetic Construct

<400> SEQUENCE: 84

Asp Ile Val Met Thr Gln Ser Pro Ser Ser Leu Ser Ala Ser Val Gly

```
            1               5                  10                 15
Asp Thr Val Thr Ile Thr Cys Arg Ala Ser Glu Asp Ile Tyr Asn Asp
                20                  25                 30

Leu Ala Trp Tyr Gln Gln Lys Pro Gly Lys Ala Pro Gln Leu Leu Leu
            35                  40                 45

Tyr Asn Ala Asn Ser Leu His Thr Gly Val Pro Ser Arg Phe Ser Gly
        50                  55                 60

Ser Gly Ser Gly Thr Asp Tyr Thr Leu Thr Ile Ser Thr Leu Gln Pro
65                  70                  75                 80

Glu Asp Phe Ala Thr Tyr Tyr Cys Gln Gln Tyr Tyr Asp Tyr Pro Leu
                85                  90                 95

Thr Phe Gly Pro Gly Thr Lys Val His Ile Lys
                100                 105
```

<210> SEQ ID NO 85
<211> LENGTH: 7
<212> TYPE: PRT
<213> ORGANISM: Artificial Sequence
<220> FEATURE:
<223> OTHER INFORMATION: Synthetic Construct

<400> SEQUENCE: 85

```
Thr Tyr Ala Met Gly Val Ser
1               5
```

<210> SEQ ID NO 86
<211> LENGTH: 16
<212> TYPE: PRT
<213> ORGANISM: Artificial Sequence
<220> FEATURE:
<223> OTHER INFORMATION: Synthetic Construct

<400> SEQUENCE: 86

```
Ser Ile Trp Trp Asn Gly Asn Lys Tyr Asn Asn Pro Ser Leu Lys Ser
1               5                   10                  15
```

<210> SEQ ID NO 87
<211> LENGTH: 13
<212> TYPE: PRT
<213> ORGANISM: Artificial Sequence
<220> FEATURE:
<223> OTHER INFORMATION: Synthetic Construct

<400> SEQUENCE: 87

```
Ser Arg Ile Ile Arg Phe Thr Asp Tyr Val Met Asp Ala
1               5                   10
```

<210> SEQ ID NO 88
<211> LENGTH: 11
<212> TYPE: PRT
<213> ORGANISM: Artificial Sequence
<220> FEATURE:
<223> OTHER INFORMATION: Synthetic Construct

<400> SEQUENCE: 88

```
Arg Ala Ser Glu Asp Ile Tyr Asn Asp Leu Ala
1               5                   10
```

<210> SEQ ID NO 89
<211> LENGTH: 7
<212> TYPE: PRT
<213> ORGANISM: Artificial Sequence
<220> FEATURE:
<223> OTHER INFORMATION: Synthetic Construct

<400> SEQUENCE: 89

Asn Ala Asn Ser Leu His Thr
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Construct

<400> SEQUENCE: 90

Gln Gln Tyr Tyr Asp Tyr Pro Leu Thr
1               5

<210> SEQ ID NO 91
<211> LENGTH: 450
<212> TYPE: PRT
<213> ORGANISM: Artificial Sequence
<220> FEATURE:
<223> OTHER INFORMATION: Synthetic Construct

<400> SEQUENCE: 91

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Ala Phe Thr Asp Tyr Val Met Asp Ala
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 92
<211> LENGTH: 214
<212> TYPE: PRT
<213> ORGANISM: Artificial Sequence
<220> FEATURE:
<223> OTHER INFORMATION: Synthetic Construct

<400> SEQUENCE: 92

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Lys Leu Leu Ile
        35                  40                  45

Tyr Asn Ala Asn Ser Leu His Thr Gly Val Ala Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Phe Cys Gln Gln Tyr Tyr Asp Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
            210

<210> SEQ ID NO 93
<211> LENGTH: 123
<212> TYPE: PRT
<213> ORGANISM: Artificial Sequence
<220> FEATURE:
<223> OTHER INFORMATION: Synthetic Construct

<400> SEQUENCE: 93

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Ala Phe Thr Asp Tyr Val Met Asp Ala
            100                 105                 110

Trp Gly Gln Gly Thr Leu Val Thr Val Ser Ser
        115                 120

<210> SEQ ID NO 94
<211> LENGTH: 107
<212> TYPE: PRT
<213> ORGANISM: Artificial Sequence
<220> FEATURE:
<223> OTHER INFORMATION: Synthetic Construct

<400> SEQUENCE: 94

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Lys Leu Leu Ile
        35                  40                  45

Tyr Asn Ala Asn Ser Leu His Thr Gly Val Ala Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Phe Cys Gln Gln Tyr Tyr Asp Tyr Pro Leu
                85                  90                  95

Thr Phe Gly Gln Gly Thr Lys Leu Glu Ile Lys
            100                 105

<210> SEQ ID NO 95
<211> LENGTH: 7
<212> TYPE: PRT

```
<213> ORGANISM: Artificial Sequence
<220> FEATURE:
<223> OTHER INFORMATION: Synthetic Construct

<400> SEQUENCE: 95

Thr Tyr Ala Met Gly Val Ser
1               5

<210> SEQ ID NO 96
<211> LENGTH: 16
<212> TYPE: PRT
<213> ORGANISM: Artificial Sequence
<220> FEATURE:
<223> OTHER INFORMATION: Synthetic Construct

<400> SEQUENCE: 96

Ser Ile Trp Trp Asn Gly Asn Lys Tyr Asn Asn Pro Ser Leu Lys Ser
1               5                   10                  15

<210> SEQ ID NO 97
<211> LENGTH: 13
<212> TYPE: PRT
<213> ORGANISM: Artificial Sequence
<220> FEATURE:
<223> OTHER INFORMATION: Synthetic Construct

<400> SEQUENCE: 97

Ser Arg Ile Ile Ala Phe Thr Asp Tyr Val Met Asp Ala
1               5                   10

<210> SEQ ID NO 98
<211> LENGTH: 11
<212> TYPE: PRT
<213> ORGANISM: Artificial Sequence
<220> FEATURE:
<223> OTHER INFORMATION: Synthetic Construct

<400> SEQUENCE: 98

Arg Ala Ser Glu Asp Ile Tyr Asn Asp Leu Ala
1               5                   10

<210> SEQ ID NO 99
<211> LENGTH: 7
<212> TYPE: PRT
<213> ORGANISM: Artificial Sequence
<220> FEATURE:
<223> OTHER INFORMATION: Synthetic Construct

<400> SEQUENCE: 99

Asn Ala Asn Ser Leu His Thr
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic Construct

<400> SEQUENCE: 100

Gln Gln Tyr Tyr Asp Tyr Pro Leu Thr
1               5

<210> SEQ ID NO 101
<211> LENGTH: 450
<212> TYPE: PRT
<213> ORGANISM: Artificial Sequence
```

<220> FEATURE:
<223> OTHER INFORMATION: Synthetic Construct

<400> SEQUENCE: 101

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Asp Phe Thr Asp Tyr Val Met Asp Ala
            100                 105                 110

Trp Gly Gln Gly Thr Leu Val Thr Val Ser Ser Ala Ser Thr Lys Gly
        115                 120                 125

Pro Ser Val Phe Pro Leu Ala Pro Cys Ser Arg Ser Thr Ser Glu Ser
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
        195                 200                 205

Asp His Lys Pro Ser Asn Thr Lys Val Asp Lys Arg Val Glu Ser Lys
    210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

```
Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 102
<211> LENGTH: 214
<212> TYPE: PRT
<213> ORGANISM: Artificial Sequence
<220> FEATURE:
<223> OTHER INFORMATION: Synthetic Construct

<400> SEQUENCE: 102

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Lys Leu Leu Ile
        35                  40                  45

Tyr Asn Ala Asn Ser Leu His Thr Gly Val Ala Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Phe Cys Gln Gln Tyr Tyr Asp Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 103
<211> LENGTH: 123
<212> TYPE: PRT
<213> ORGANISM: Artificial Sequence
<220> FEATURE:
<223> OTHER INFORMATION: Synthetic Construct

<400> SEQUENCE: 103

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
```

20                  25                  30

Ala Met Gly Val Ser Trp Ile Arg Gln Pro Pro Gly Lys Ala Leu Glu
            35                  40                  45

Trp Leu Ala Ser Ile Trp Trp Asn Gly Asn Lys Tyr Asn Asn Pro Ser
        50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Asp Phe Thr Asp Tyr Val Met Asp Ala
            100                 105                 110

Trp Gly Gln Gly Thr Leu Val Thr Val Ser Ser
        115                 120

<210> SEQ ID NO 104
<211> LENGTH: 107
<212> TYPE: PRT
<213> ORGANISM: Artificial Sequence
<220> FEATURE:
<223> OTHER INFORMATION: Synthetic Construct

<400> SEQUENCE: 104

Asp Ile Gln Met Thr Gln Ser Pro Ser Ser Leu Ser Thr Ser Val Gly
1               5                   10                  15

Asp Arg Val Thr Ile Thr Cys Arg Ala Ser Glu Asp Ile Tyr Asn Asp
                20                  25                  30

Leu Ala Trp Tyr Gln Gln Lys Pro Gly Lys Ala Pro Lys Leu Leu Ile
            35                  40                  45

Tyr Asn Ala Asn Ser Leu His Thr Gly Val Ala Ser Arg Phe Ser Gly
        50                  55                  60

Ser Gly Ser Gly Thr Asp Phe Thr Phe Thr Ile Ser Ser Leu Gln Pro
65                  70                  75                  80

Glu Asp Val Ala Thr Tyr Phe Cys Gln Gln Tyr Asp Tyr Pro Leu
                85                  90                  95

Thr Phe Gly Gln Gly Thr Lys Leu Glu Ile Lys
            100                 105

<210> SEQ ID NO 105
<211> LENGTH: 7
<212> TYPE: PRT
<213> ORGANISM: Artificial Sequence
<220> FEATURE:
<223> OTHER INFORMATION: Synthetic Construct

<400> SEQUENCE: 105

Thr Tyr Ala Met Gly Val Ser
1               5

<210> SEQ ID NO 106
<211> LENGTH: 16
<212> TYPE: PRT
<213> ORGANISM: Artificial Sequence
<220> FEATURE:
<223> OTHER INFORMATION: Synthetic Construct

<400> SEQUENCE: 106

Ser Ile Trp Trp Asn Gly Asn Lys Tyr Asn Asn Pro Ser Leu Lys Ser
1               5                   10                  15

<210> SEQ ID NO 107

```
<211> LENGTH: 13
<212> TYPE: PRT
<213> ORGANISM: Artificial Sequence
<220> FEATURE:
<223> OTHER INFORMATION: Synthetic Construct

<400> SEQUENCE: 107

Ser Arg Ile Ile Asp Phe Thr Asp Tyr Val Met Asp Ala
1               5                   10

<210> SEQ ID NO 108
<211> LENGTH: 11
<212> TYPE: PRT
<213> ORGANISM: Artificial Sequence
<220> FEATURE:
<223> OTHER INFORMATION: Synthetic Construct

<400> SEQUENCE: 108

Arg Ala Ser Glu Asp Ile Tyr Asn Asp Leu Ala
1               5                   10

<210> SEQ ID NO 109
<211> LENGTH: 7
<212> TYPE: PRT
<213> ORGANISM: Artificial Sequence
<220> FEATURE:
<223> OTHER INFORMATION: Synthetic Construct

<400> SEQUENCE: 109

Asn Ala Asn Ser Leu His Thr
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Construct

<400> SEQUENCE: 110

Gln Gln Tyr Tyr Asp Tyr Pro Leu Thr
1               5

<210> SEQ ID NO 111
<211> LENGTH: 450
<212> TYPE: PRT
<213> ORGANISM: Artificial Sequence
<220> FEATURE:
<223> OTHER INFORMATION: Synthetic Construct

<400> SEQUENCE: 111

Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Ala Met Gly Val Ser Trp Ile Arg Gln Pro Pro Gly Lys Ala Leu Glu
        35                  40                  45

Trp Leu Ala Ser Ile Trp Trp Asn Gly Asn Lys Tyr Asn Asn Pro Ser
    50                  55                  60

Leu Lys Ser Arg Leu Thr Val Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala His Ser Arg Ile Ile Glu Phe Thr Asp Tyr Val Met Asp Ala
```

100                 105                 110
Trp Gly Gln Gly Thr Leu Val Thr Val Ser Ser Ala Ser Thr Lys Gly
            115                 120                 125

Pro Ser Val Phe Pro Leu Ala Pro Cys Ser Arg Ser Thr Ser Glu Ser
130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
            165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Lys Thr Tyr Thr Cys Asn Val
            195                 200                 205

Asp His Lys Pro Ser Asn Thr Lys Val Asp Lys Arg Val Glu Ser Lys
        210                 215                 220

Tyr Gly Pro Pro Cys Pro Pro Cys Pro Ala Pro Glu Phe Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser Gln Glu
            260                 265                 270

Asp Pro Glu Val Gln Phe Asn Trp Tyr Val Asp Gly Val Glu Val His
        275                 280                 285

Asn Ala Lys Thr Lys Pro Arg Glu Glu Gln Phe Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Gly Leu Pro Ser Ser Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Gln Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Arg Leu Thr Val Asp
                405                 410                 415

Lys Ser Arg Trp Gln Glu Gly Asn Val Phe Ser Cys Ser Val Met His
            420                 425                 430

Glu Ala Leu His Asn His Tyr Thr Gln Lys Ser Leu Ser Leu Ser Leu
        435                 440                 445

Gly Lys
    450

<210> SEQ ID NO 112
<211> LENGTH: 214
<212> TYPE: PRT
<213> ORGANISM: Artificial Sequence
<220> FEATURE:
<223> OTHER INFORMATION: Synthetic Construct

<400> SEQUENCE: 112

Asp Ile Gln Met Thr Gln Ser Pro Ser Ser Leu Ser Thr Ser Val Gly

-continued

```
                1               5                  10                 15
        Asp Arg Val Thr Ile Thr Cys Arg Ala Ser Glu Asp Ile Tyr Asn Asp
                        20                  25                 30

Leu Ala Trp Tyr Gln Gln Lys Pro Gly Lys Ala Pro Lys Leu Leu Ile
                        35                  40                 45

Tyr Asn Ala Asn Ser Leu His Thr Gly Val Ala Ser Arg Phe Ser Gly
                    50              55                 60

Ser Gly Ser Gly Thr Asp Phe Thr Phe Thr Ile Ser Ser Leu Gln Pro
        65                  70                  75                 80

Glu Asp Val Ala Thr Tyr Phe Cys Gln Gln Tyr Tyr Asp Tyr Pro Leu
                        85                  90                 95

Thr Phe Gly Gln Gly Thr Lys Leu Glu Ile Lys Arg Thr Val Ala Ala
                        100                 105                110

Pro Ser Val Phe Ile Phe Pro Pro Ser Asp Glu Gln Leu Lys Ser Gly
                        115                 120                125

Thr Ala Ser Val Val Cys Leu Leu Asn Asn Phe Tyr Pro Arg Glu Ala
                    130             135                140

Lys Val Gln Trp Lys Val Asp Asn Ala Leu Gln Ser Gly Asn Ser Gln
        145                 150                 155                160

Glu Ser Val Thr Glu Gln Asp Ser Lys Asp Ser Thr Tyr Ser Leu Ser
                        165                 170                175

Ser Thr Leu Thr Leu Ser Lys Ala Asp Tyr Glu Lys His Lys Val Tyr
                    180             185                190

Ala Cys Glu Val Thr His Gln Gly Leu Ser Ser Pro Val Thr Lys Ser
                        195                 200                205

Phe Asn Arg Gly Glu Cys
                    210

<210> SEQ ID NO 113
<211> LENGTH: 123
<212> TYPE: PRT
<213> ORGANISM: Artificial Sequence
<220> FEATURE:
<223> OTHER INFORMATION: Synthetic Construct

<400> SEQUENCE: 113

Gln Ile Thr Leu Lys Glu Ser Gly Pro Thr Leu Val Lys Pro Thr Gln
        1               5                   10                 15

Thr Leu Thr Leu Thr Cys Thr Phe Ser Gly Phe Ser Leu Asn Thr Tyr
                        20                  25                 30

Ala Met Gly Val Ser Trp Ile Arg Gln Pro Pro Gly Lys Ala Leu Glu
                        35                  40                 45

Trp Leu Ala Ser Ile Trp Trp Asn Gly Asn Lys Tyr Asn Asn Pro Ser
                    50              55                 60

Leu Lys Ser Arg Leu Thr Val Thr Lys Asp Thr Ser Lys Asn Gln Val
        65                  70                  75                 80

Val Leu Thr Met Thr Asn Met Asp Pro Val Asp Thr Ala Thr Tyr Tyr
                        85                  90                 95

Cys Ala His Ser Arg Ile Ile Glu Phe Thr Asp Tyr Val Met Asp Ala
                        100                 105                110

Trp Gly Gln Gly Thr Leu Val Thr Val Ser Ser
                    115             120

<210> SEQ ID NO 114
<211> LENGTH: 107
<212> TYPE: PRT
```

```
<213> ORGANISM: Artificial Sequence
<220> FEATURE:
<223> OTHER INFORMATION: Synthetic Construct

<400> SEQUENCE: 114

Asp Ile Gln Met Thr Gln Ser Pro Ser Leu Ser Thr Ser Val Gly
1               5                   10                  15

Asp Arg Val Thr Ile Thr Cys Arg Ala Ser Glu Asp Ile Tyr Asn Asp
            20                  25                  30

Leu Ala Trp Tyr Gln Gln Lys Pro Gly Lys Ala Pro Lys Leu Leu Ile
        35                  40                  45

Tyr Asn Ala Asn Ser Leu His Thr Gly Val Ala Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Val Ala Thr Tyr Phe Cys Gln Gln Tyr Tyr Asp Tyr Pro Leu
                85                  90                  95

Thr Phe Gly Gln Gly Thr Lys Leu Glu Ile Lys
            100                 105

<210> SEQ ID NO 115
<211> LENGTH: 7
<212> TYPE: PRT
<213> ORGANISM: Artificial Sequence
<220> FEATURE:
<223> OTHER INFORMATION: Synthetic Construct

<400> SEQUENCE: 115

Thr Tyr Ala Met Gly Val Ser
1               5

<210> SEQ ID NO 116
<211> LENGTH: 16
<212> TYPE: PRT
<213> ORGANISM: Artificial Sequence
<220> FEATURE:
<223> OTHER INFORMATION: Synthetic Construct

<400> SEQUENCE: 116

Ser Ile Trp Trp Asn Gly Asn Lys Tyr Asn Asn Pro Ser Leu Lys Ser
1               5                   10                  15

<210> SEQ ID NO 117
<211> LENGTH: 13
<212> TYPE: PRT
<213> ORGANISM: Artificial Sequence
<220> FEATURE:
<223> OTHER INFORMATION: Synthetic Construct

<400> SEQUENCE: 117

Ser Arg Ile Ile Glu Phe Thr Asp Tyr Val Met Asp Ala
1               5                   10

<210> SEQ ID NO 118
<211> LENGTH: 11
<212> TYPE: PRT
<213> ORGANISM: Artificial Sequence
<220> FEATURE:
<223> OTHER INFORMATION: Synthetic Construct

<400> SEQUENCE: 118

Arg Ala Ser Glu Asp Ile Tyr Asn Asp Leu Ala
1               5                   10
```

<210> SEQ ID NO 119
<211> LENGTH: 7
<212> TYPE: PRT
<213> ORGANISM: Artificial Sequence
<220> FEATURE:
<223> OTHER INFORMATION: Synthetic Construct

<400> SEQUENCE: 119

Asn Ala Asn Ser Leu His Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic Construct

<400> SEQUENCE: 120

Gln Gln Tyr Tyr Asp Tyr Pro Leu Thr
1               5

<210> SEQ ID NO 121
<211> LENGTH: 489
<212> TYPE: PRT
<213> ORGANISM: Artificial Sequence
<220> FEATURE:
<223> OTHER INFORMATION: Synthetic Construct

<400> SEQUENCE: 121

Met Thr Pro Ile Val Thr Val Leu Ile Cys Leu Arg Leu Ser Leu Gly
1               5                   10                  15

Pro Arg Thr His Val Gln Ala Gly Thr Leu Pro Lys Pro Thr Leu Trp
            20                  25                  30

Ala Glu Pro Gly Ser Val Ile Thr Gln Gly Ser Pro Val Thr Leu Trp
        35                  40                  45

Cys Gln Gly Ile Leu Glu Thr Gln Glu Tyr Arg Leu Tyr Arg Glu Lys
    50                  55                  60

Lys Thr Ala Pro Trp Ile Thr Arg Ile Pro Gln Glu Ile Val Lys Lys
65                  70                  75                  80

Gly Gln Phe Pro Ile Pro Ser Ile Thr Trp Glu His Thr Gly Arg Tyr
                85                  90                  95

Arg Cys Phe Tyr Gly Ser His Thr Ala Gly Trp Ser Glu Pro Ser Asp
            100                 105                 110

Pro Leu Glu Leu Val Val Thr Gly Ala Tyr Ile Lys Pro Thr Leu Ser
        115                 120                 125

Ala Leu Pro Ser Pro Val Val Thr Ser Gly Gly Asn Val Thr Leu His
    130                 135                 140

Cys Val Ser Gln Val Ala Phe Gly Ser Phe Ile Leu Cys Lys Glu Gly
145                 150                 155                 160

Glu Asp Glu His Pro Gln Cys Leu Asn Ser Gln Pro Arg Thr His Gly
                165                 170                 175

Trp Ser Arg Ala Ile Phe Ser Val Gly Pro Val Ser Pro Ser Arg Arg
            180                 185                 190

Trp Ser Tyr Arg Cys Tyr Ala Tyr Asp Ser Asn Ser Pro His Val Trp
        195                 200                 205

Ser Leu Pro Ser Asp Leu Leu Glu Leu Leu Val Leu Gly Val Ser Lys
    210                 215                 220

Lys Pro Ser Leu Ser Val Gln Pro Gly Pro Ile Val Ala Pro Gly Glu

```
            225                 230                 235                 240
        Ser Leu Thr Leu Gln Cys Val Ser Asp Val Ser Tyr Asp Arg Phe Val
                        245                 250                 255
        Leu Tyr Lys Glu Gly Glu Arg Asp Phe Leu Gln Leu Pro Gly Pro Gln
                        260                 265                 270
        Pro Gln Ala Gly Leu Ser Gln Ala Asn Phe Thr Leu Gly Pro Val Ser
                        275                 280                 285
        Arg Ser Tyr Gly Gly Gln Tyr Arg Cys Ser Gly Ala Tyr Asn Leu Ser
                        290                 295                 300
        Ser Glu Trp Ser Ala Pro Ser Asp Pro Leu Asp Ile Leu Ile Ala Gly
        305                 310                 315                 320
        Gln Phe Arg Gly Arg Pro Phe Ile Ser Val His Pro Gly Pro Thr Val
                        325                 330                 335
        Ala Ser Gly Glu Asn Val Thr Leu Leu Cys Gln Ser Trp Gly Pro Phe
                        340                 345                 350
        His Thr Phe Leu Leu Thr Lys Ala Gly Ala Ala Asp Ala Pro Leu Arg
                        355                 360                 365
        Leu Arg Ser Ile His Glu Tyr Pro Lys Tyr Gln Ala Glu Phe Pro Met
                        370                 375                 380
        Ser Pro Val Thr Ser Ala His Ser Gly Thr Tyr Arg Cys Tyr Gly Ser
        385                 390                 395                 400
        Leu Ser Ser Asn Pro Tyr Leu Leu Ser His Pro Ser Asp Ser Leu Glu
                        405                 410                 415
        Leu Met Val Ser Gly Ala Ala Glu Thr Leu Ser Pro Pro Gln Asn Lys
                        420                 425                 430
        Ser Asp Ser Lys Ala Gly Ala Ala Asn Thr Leu Ser Pro Ser Gln Asn
                        435                 440                 445
        Lys Thr Ala Ser His Pro Gln Asp Tyr Thr Val Glu Asn Leu Ile Arg
                        450                 455                 460
        Met Gly Ile Ala Gly Leu Val Leu Val Val Leu Gly Ile Leu Leu Phe
        465                 470                 475                 480
        Glu Ala Gln His Ser Gln Arg Ser Leu
                        485

<210> SEQ ID NO 122
<211> LENGTH: 483
<212> TYPE: PRT
<213> ORGANISM: Artificial Sequence
<220> FEATURE:
<223> OTHER INFORMATION: Synthetic Construct

<400> SEQUENCE: 122

Met Thr Pro Ile Leu Thr Val Leu Ile Cys Leu Gly Leu Ser Leu Gly
        1               5                   10                  15
        Pro Arg Thr His Val Gln Ala Gly His Leu Pro Lys Pro Thr Leu Trp
                        20                  25                  30
        Ala Glu Pro Gly Ser Val Ile Ile Gln Gly Ser Pro Val Thr Leu Arg
                        35                  40                  45
        Cys Gln Gly Ser Leu Gln Ala Glu Glu Tyr His Leu Tyr Arg Glu Asn
                        50                  55                  60
        Lys Ser Ala Ser Trp Val Arg Arg Ile Gln Glu Pro Gly Lys Asn Gly
        65                  70                  75                  80
        Gln Phe Pro Ile Pro Ser Ile Thr Trp Glu His Ala Gly Arg Tyr His
                        85                  90                  95
        Cys Gln Tyr Tyr Ser His Asn His Ser Ser Glu Tyr Ser Asp Pro Leu
```

```
            100                 105                 110
Glu Leu Val Val Thr Gly Ala Tyr Ser Lys Pro Thr Leu Ser Ala Leu
            115                 120                 125

Pro Ser Pro Val Val Thr Leu Gly Gly Asn Val Thr Leu Gln Cys Val
            130                 135                 140

Ser Gln Val Ala Phe Asp Gly Phe Ile Leu Cys Lys Glu Gly Glu Asp
145                 150                 155                 160

Glu His Pro Gln Arg Leu Asn Ser His Ser His Ala Arg Gly Trp Ser
                165                 170                 175

Trp Ala Ile Phe Ser Val Gly Pro Val Ser Pro Ser Arg Arg Trp Ser
                180                 185                 190

Tyr Arg Cys Tyr Ala Tyr Asp Ser Asn Ser Pro Tyr Val Trp Ser Leu
                195                 200                 205

Pro Ser Asp Leu Leu Glu Leu Leu Val Pro Gly Val Ser Lys Lys Pro
            210                 215                 220

Ser Leu Ser Val Gln Pro Gly Pro Met Val Ala Pro Gly Glu Ser Leu
225                 230                 235                 240

Thr Leu Gln Cys Val Ser Asp Val Gly Tyr Asp Arg Phe Val Leu Tyr
                245                 250                 255

Lys Glu Gly Glu Arg Asp Phe Leu Gln Arg Pro Gly Trp Gln Pro Gln
                260                 265                 270

Ala Gly Leu Ser Gln Ala Asn Phe Thr Leu Gly Pro Val Ser Pro Ser
                275                 280                 285

His Gly Gly Gln Tyr Arg Cys Tyr Ser Ala His Asn Leu Ser Ser Glu
            290                 295                 300

Trp Ser Ala Pro Ser Asp Pro Leu Asp Ile Leu Ile Thr Gly Gln Phe
305                 310                 315                 320

Tyr Asp Arg Pro Ser Leu Ser Val Gln Pro Val Pro Thr Val Ala Pro
                325                 330                 335

Gly Lys Asn Val Thr Leu Leu Cys Gln Ser Arg Gly Gln Phe His Thr
                340                 345                 350

Phe Leu Leu Thr Lys Glu Gly Ala Gly His Pro Pro Leu His Leu Arg
                355                 360                 365

Ser Glu His Gln Ala Gln Gln Asn Gln Ala Glu Phe Arg Met Gly Pro
            370                 375                 380

Val Thr Ser Ala His Val Gly Thr Tyr Arg Cys Tyr Ser Ser Leu Ser
385                 390                 395                 400

Ser Asn Pro Tyr Leu Leu Ser Leu Pro Ser Asp Pro Leu Glu Leu Val
                405                 410                 415

Val Ser Glu Ala Ala Glu Thr Leu Ser Pro Ser Gln Asn Lys Thr Asp
                420                 425                 430

Ser Thr Thr Thr Ser Leu Gly Gln His Pro Gln Asp Tyr Thr Val Glu
                435                 440                 445

Asn Leu Ile Arg Met Gly Val Ala Gly Leu Val Leu Val Val Leu Gly
            450                 455                 460

Ile Leu Leu Phe Glu Ala Gln His Ser Gln Arg Ser Leu Gln Asp Ala
465                 470                 475                 480

Ala Gly Arg

<210> SEQ ID NO 123
<211> LENGTH: 439
<212> TYPE: PRT
<213> ORGANISM: Artificial Sequence
<220> FEATURE:
```

<223> OTHER INFORMATION: Synthetic Construct

<400> SEQUENCE: 123

```
Met Thr Pro Ile Leu Thr Val Leu Ile Cys Leu Gly Leu Ser Leu Asp
1               5                   10                  15

Pro Arg Thr His Val Gln Ala Gly Pro Leu Pro Lys Pro Thr Leu Trp
            20                  25                  30

Ala Glu Pro Gly Ser Val Ile Thr Gln Gly Ser Pro Val Thr Leu Arg
        35                  40                  45

Cys Gln Gly Ser Leu Glu Thr Gln Glu Tyr His Leu Tyr Arg Glu Lys
    50                  55                  60

Lys Thr Ala Leu Trp Ile Thr Arg Ile Pro Gln Glu Leu Val Lys Lys
65                  70                  75                  80

Gly Gln Phe Pro Ile Leu Ser Ile Thr Trp Glu His Ala Gly Arg Tyr
                85                  90                  95

Cys Cys Ile Tyr Gly Ser His Thr Ala Gly Leu Ser Glu Ser Ser Asp
            100                 105                 110

Pro Leu Glu Leu Val Val Thr Gly Ala Tyr Ser Lys Pro Thr Leu Ser
        115                 120                 125

Ala Leu Pro Ser Pro Val Val Thr Ser Gly Gly Asn Val Thr Ile Gln
130                 135                 140

Cys Asp Ser Gln Val Ala Phe Asp Gly Phe Ile Leu Cys Lys Glu Gly
145                 150                 155                 160

Glu Asp Glu His Pro Gln Cys Leu Asn Ser His Ser His Ala Arg Gly
                165                 170                 175

Ser Ser Arg Ala Ile Phe Ser Val Gly Pro Val Ser Pro Ser Arg Arg
            180                 185                 190

Trp Ser Tyr Arg Cys Tyr Gly Tyr Asp Ser Arg Ala Pro Tyr Val Trp
        195                 200                 205

Ser Leu Pro Ser Asp Leu Leu Gly Leu Leu Val Pro Gly Val Ser Lys
210                 215                 220

Lys Pro Ser Leu Ser Val Gln Pro Gly Pro Val Val Ala Pro Gly Glu
225                 230                 235                 240

Lys Leu Thr Phe Gln Cys Gly Ser Asp Ala Gly Tyr Asp Arg Phe Val
                245                 250                 255

Leu Tyr Lys Glu Trp Gly Arg Asp Phe Leu Gln Arg Pro Gly Arg Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Thr Cys Ser Gly Ala Tyr Asn Leu Ser
290                 295                 300

Ser Glu Trp Ser Ala Pro Ser Asp Pro Leu Asp Ile Leu Ile Thr Gly
305                 310                 315                 320

Gln Ile Arg Ala Arg Pro Phe Leu Ser Val Arg Pro Gly Pro Thr Val
                325                 330                 335

Ala Ser Gly Glu Asn Val Thr Leu Leu Cys Gln Ser Gln Gly Gly Met
            340                 345                 350

His Thr Phe Leu Leu Thr Lys Glu Gly Ala Ala Asp Ser Pro Leu Arg
        355                 360                 365

Leu Lys Ser Lys Arg Gln Ser His Lys Tyr Gln Ala Glu Phe Pro Met
370                 375                 380

Ser Pro Val Thr Ser Ala His Ala Gly Thr Tyr Arg Cys Tyr Gly Ser
385                 390                 395                 400
```

```
Leu Ser Ser Asn Pro Tyr Leu Leu Thr His Pro Ser Asp Pro Leu Glu
            405                 410                 415

Leu Val Val Ser Gly Ala Ala Glu Thr Leu Ser Pro Pro Gln Asn Lys
            420                 425                 430

Ser Asp Ser Lys Ala Gly Glu
            435

<210> SEQ ID NO 124
<211> LENGTH: 499
<212> TYPE: PRT
<213> ORGANISM: Artificial Sequence
<220> FEATURE:
<223> OTHER INFORMATION: Synthetic Construct

<400> SEQUENCE: 124

Met Thr Leu Ile Leu Thr Ser Leu Leu Phe Phe Gly Leu Ser Leu Gly
1               5                   10                  15

Pro Arg Thr Arg Val Gln Ala Glu Asn Leu Pro Lys Pro Ile Leu Trp
            20                  25                  30

Ala Glu Pro Gly Pro Val Ile Thr Trp His Asn Pro Val Thr Ile Trp
            35                  40                  45

Cys Gln Gly Thr Leu Glu Ala Gln Gly Tyr Arg Leu Asp Lys Glu Gly
        50                  55                  60

Asn Ser Met Ser Arg His Ile Leu Lys Thr Leu Glu Ser Glu Asn Lys
65                  70                  75                  80

Val Lys Leu Ser Ile Pro Ser Met Met Trp Glu His Ala Gly Arg Tyr
            85                  90                  95

His Cys Tyr Tyr Gln Ser Pro Ala Gly Trp Ser Glu Pro Ser Asp Pro
            100                 105                 110

Leu Glu Leu Val Val Thr Ala Tyr Ser Arg Pro Thr Leu Ser Ala Leu
            115                 120                 125

Pro Ser Pro Val Val Thr Ser Gly Val Asn Val Thr Leu Arg Cys Ala
        130                 135                 140

Ser Arg Leu Gly Leu Gly Arg Phe Thr Leu Ile Glu Glu Gly Asp His
145                 150                 155                 160

Arg Leu Ser Trp Thr Leu Asn Ser His Gln His Asn His Gly Lys Phe
                165                 170                 175

Gln Ala Leu Phe Pro Met Gly Pro Leu Thr Phe Ser Asn Arg Gly Thr
            180                 185                 190

Phe Arg Cys Tyr Gly Tyr Glu Asn Asn Thr Pro Tyr Val Trp Ser Glu
            195                 200                 205

Pro Ser Asp Pro Leu Gln Leu Leu Val Ser Gly Val Ser Arg Lys Pro
            210                 215                 220

Ser Leu Leu Thr Leu Gln Gly Pro Val Val Thr Pro Gly Glu Asn Leu
225                 230                 235                 240

Thr Leu Gln Cys Gly Ser Asp Val Gly Tyr Ile Arg Tyr Thr Leu Tyr
                245                 250                 255

Lys Glu Gly Ala Asp Gly Leu Pro Gln Arg Pro Gly Arg Gln Pro Gln
            260                 265                 270

Ala Gly Leu Ser Gln Ala Asn Phe Thr Leu Ser Pro Val Ser Arg Ser
            275                 280                 285

Tyr Gly Gly Gln Tyr Arg Cys Tyr Gly Ala His Asn Val Ser Ser Glu
            290                 295                 300

Trp Ser Ala Pro Ser Asp Pro Leu Asp Ile Leu Ile Ala Gly Gln Ile
305                 310                 315                 320
```

Ser Asp Arg Pro Ser Leu Ser Val Gln Pro Gly Pro Thr Val Thr Ser
            325                 330                 335

Gly Glu Lys Val Thr Leu Leu Cys Gln Ser Trp Asp Pro Met Phe Thr
        340                 345                 350

Phe Leu Leu Thr Lys Glu Gly Ala Ala His Pro Pro Leu Arg Leu Arg
            355                 360                 365

Ser Met Tyr Gly Ala His Lys Tyr Gln Ala Glu Phe Pro Met Ser Pro
        370                 375                 380

Val Thr Ser Ala His Ala Gly Thr Tyr Arg Cys Tyr Gly Ser Arg Ser
385                 390                 395                 400

Ser Asn Pro Tyr Leu Leu Ser His Pro Ser Glu Pro Leu Glu Leu Val
                405                 410                 415

Val Ser Gly Ala Thr Glu Thr Leu Asn Pro Ala Gln Lys Lys Ser Asp
            420                 425                 430

Ser Lys Thr Ala Pro His Leu Gln Asp Tyr Thr Val Glu Asn Leu Ile
        435                 440                 445

Arg Met Gly Val Ala Gly Leu Val Leu Leu Phe Leu Gly Ile Leu Leu
    450                 455                 460

Phe Glu Ala Gln His Ser Gln Arg Ser Pro Pro Arg Cys Ser Gln Glu
465                 470                 475                 480

Ala Asn Ser Arg Lys Asp Asn Ala Pro Phe Arg Val Val Glu Pro Trp
                485                 490                 495

Glu Gln Ile

<210> SEQ ID NO 125
<211> LENGTH: 299
<212> TYPE: PRT
<213> ORGANISM: Artificial Sequence
<220> FEATURE:
<223> OTHER INFORMATION: Synthetic Construct

<400> SEQUENCE: 125

Met Ala Pro Trp Ser His Pro Ser Ala Gln Leu Gln Pro Val Gly Gly
1               5                   10                  15

Asp Ala Val Ser Pro Ala Leu Met Val Leu Leu Cys Leu Gly Leu Ser
            20                  25                  30

Leu Gly Pro Arg Thr His Val Gln Ala Gly Asn Leu Ser Lys Ala Thr
        35                  40                  45

Leu Trp Ala Glu Pro Gly Ser Val Ile Ser Arg Gly Asn Ser Val Thr
    50                  55                  60

Ile Arg Cys Gln Gly Thr Leu Glu Ala Gln Glu Tyr Arg Leu Val Lys
65                  70                  75                  80

Glu Gly Ser Pro Glu Pro Trp Asp Thr Gln Asn Pro Leu Glu Pro Lys
                85                  90                  95

Asn Lys Ala Arg Phe Ser Ile Pro Ser Met Thr Glu His His Ala Gly
            100                 105                 110

Arg Tyr Arg Cys Tyr Tyr Ser Pro Ala Gly Trp Ser Glu Pro Ser
        115                 120                 125

Asp Pro Leu Glu Leu Val Val Thr Gly Phe Tyr Asn Lys Pro Thr Leu
    130                 135                 140

Ser Ala Leu Pro Ser Pro Val Val Thr Ser Gly Glu Asn Val Thr Leu
145                 150                 155                 160

Gln Cys Gly Ser Arg Leu Arg Phe Asp Arg Phe Ile Leu Thr Glu Glu
                165                 170                 175

Gly Asp His Lys Leu Ser Trp Thr Leu Asp Ser Gln Leu Thr Pro Ser

```
            180                 185                 190
Gly Gln Phe Gln Ala Leu Phe Pro Val Gly Pro Val Thr Pro Ser His
            195                 200                 205

Arg Trp Met Leu Arg Cys Tyr Gly Ser Arg Arg His Ile Leu Gln Val
            210                 215                 220

Trp Ser Glu Pro Ser Asp Leu Leu Glu Ile Pro Val Ser Gly Ala Ala
225                 230                 235                 240

Asp Asn Leu Ser Pro Ser Gln Asn Lys Ser Asp Ser Gly Thr Ala Ser
            245                 250                 255

His Leu Gln Asp Tyr Ala Val Glu Asn Leu Ile Arg Met Gly Met Ala
            260                 265                 270

Gly Leu Ile Leu Val Val Leu Gly Ile Leu Ile Phe Gln Asp Trp His
            275                 280                 285

Ser Gln Arg Ser Pro Gln Ala Ala Ala Gly Arg
            290                 295
```

```
<210> SEQ ID NO 126
<211> LENGTH: 481
<212> TYPE: PRT
<213> ORGANISM: Artificial Sequence
<220> FEATURE:
<223> OTHER INFORMATION: Synthetic Construct

<400> SEQUENCE: 126

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
            20                  25                  30

Ala Glu Pro Gly Ser Val Ile Ser Trp Gly Ser Pro Val Thr Ile Trp
            35                  40                  45

Cys Gln Gly Ser Leu Glu Ala Gln Glu Tyr Gln Leu Asp Lys Glu Gly
            50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Gln His His Ala Gly Arg Tyr
            85                  90                  95

Arg Cys His Tyr Tyr Ser Ser Ala Gly Trp Ser Glu Pro Ser Asp Pro
            100                 105                 110

Leu Glu Leu Val Met Thr Gly Phe Tyr Asn Lys Pro Thr Leu Ser Ala
            115                 120                 125

Leu Pro Ser Pro Val Val Ala Ser Gly Gly Asn Met Thr Leu Arg Cys
            130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Gly Gly
            165                 170                 175

Phe Gln Ala Leu Phe Pro Val Gly Pro Val Thr Pro Ser His Arg Trp
            180                 185                 190

Arg Phe Thr Cys Tyr Tyr Tyr Tyr Thr Asn Thr Pro Arg Val Trp Ser
            195                 200                 205

His Pro Ser Asp Pro Leu Glu Ile Leu Pro Ser Gly Val Ser Arg Lys
            210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asp Arg Phe Val Leu
```

Tyr Lys Glu Gly Glu Arg Asp Phe Leu Gln Arg Pro Gly Gln Gln Pro
                245                 250                 255
                    260                 265                 270

Gln Ala Gly Leu Ser Gln Ala Asn Phe Thr Leu Gly Pro Val Ser Pro
            275                 280                 285

Ser His Gly Gly Gln Tyr Arg Cys Tyr Gly Ala His Asn Leu Ser Ser
    290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Arg Gly Tyr Phe Asp
            340                 345                 350

Thr Phe Leu Leu Thr Lys Glu Gly Ala Ala His Pro Pro Leu Arg Leu
                355                 360                 365

Arg Ser Met Tyr Gly Ala His Lys Tyr Gln Ala Glu Phe Pro Met Ser
    370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser Phe Pro Ser Glu Pro Leu Glu Leu
                405                 410                 415

Met Val Ser Gly His Ser Gly Ser Ser Leu Pro Pro Thr Gly Pro
            420                 425                 430

Pro Ser Thr Pro Ala Ser His Ala Lys Asp Tyr Thr Val Glu Asn Leu
                435                 440                 445

Ile Arg Met Gly Met Ala Gly Leu Val Leu Val Phe Leu Gly Ile Leu
    450                 455                 460

Leu Phe Glu Ala Gln His Ser Gln Arg Asn Pro Gln Asp Ala Ala Gly
465                 470                 475                 480

Arg

<210> SEQ ID NO 127
<211> LENGTH: 650
<212> TYPE: PRT
<213> ORGANISM: Artificial Sequence
<220> FEATURE:
<223> OTHER INFORMATION: Synthetic Construct

<400> SEQUENCE: 127

Met Thr Pro Ile Leu Thr Val Leu Ile Cys Leu Gly Leu Ser Leu Gly
1               5                   10                  15

Pro Arg Thr His Val Gln Ala Gly His Leu Pro Lys Pro Thr Leu Trp
                20                  25                  30

Ala Glu Pro Gly Ser Val Ile Thr Gln Gly Ser Pro Val Thr Leu Arg
            35                  40                  45

Cys Gln Gly Gly Gln Glu Thr Gln Glu Tyr Arg Leu Tyr Arg Glu Lys
        50                  55                  60

Lys Thr Ala Leu Trp Ile Thr Arg Ile Pro Gln Glu Leu Val Lys Lys
65                  70                  75                  80

Gly Gln Phe Pro Ile Pro Ser Ile Thr Trp Glu His Ala Gly Arg Tyr
                85                  90                  95

Arg Cys Tyr Tyr Gly Ser Asp Thr Ala Gly Arg Ser Glu Ser Ser Asp
            100                 105                 110

Pro Leu Glu Leu Val Val Thr Gly Ala Tyr Ile Lys Pro Thr Leu Ser
        115                 120                 125

-continued

```
Ala Gln Pro Ser Pro Val Val Asn Ser Gly Gly Asn Val Ile Leu Gln
    130                 135                 140

Cys Asp Ser Gln Val Ala Phe Asp Gly Phe Ser Leu Cys Lys Glu Gly
145                 150                 155                 160

Glu Asp Glu His Pro Gln Cys Leu Asn Ser Gln Pro His Ala Arg Gly
                165                 170                 175

Ser Ser Arg Ala Ile Phe Ser Val Gly Pro Val Ser Pro Ser Arg Arg
            180                 185                 190

Trp Trp Tyr Arg Cys Tyr Ala Tyr Asp Ser Asn Ser Pro Tyr Glu Trp
        195                 200                 205

Ser Leu Pro Ser Asp Leu Glu Leu Leu Val Leu Gly Val Ser Lys
    210                 215                 220

Lys Pro Ser Leu Ser Val Gln Pro Gly Pro Ile Val Ala Pro Glu Glu
225                 230                 235                 240

Thr Leu Thr Leu Gln Cys Gly Ser Asp Ala Gly Tyr Asn Arg Phe Val
                245                 250                 255

Leu Tyr Lys Asp Gly Glu Arg Asp Phe Leu Gln Leu Ala Gly Ala Gln
            260                 265                 270

Pro Gln Ala Gly Leu Ser Gln Ala Asn Phe Thr Leu Gly Pro Val Ser
        275                 280                 285

Arg Ser Tyr Gly Gly Gln Tyr Arg Cys Tyr Gly Ala His Asn Leu Ser
    290                 295                 300

Ser Glu Trp Ser Ala Pro Ser Asp Pro Leu Asp Ile Leu Ile Ala Gly
305                 310                 315                 320

Gln Phe Tyr Asp Arg Val Ser Leu Ser Val Gln Pro Gly Pro Thr Val
                325                 330                 335

Ala Ser Gly Glu Asn Val Thr Leu Leu Cys Gln Ser Gln Gly Trp Met
            340                 345                 350

Gln Thr Phe Leu Leu Thr Lys Glu Gly Ala Ala Asp Asp Pro Trp Arg
        355                 360                 365

Leu Arg Ser Thr Tyr Gln Ser Gln Lys Tyr Gln Ala Glu Phe Pro Met
    370                 375                 380

Gly Pro Val Thr Ser Ala His Ala Gly Thr Tyr Arg Cys Tyr Gly Ser
385                 390                 395                 400

Gln Ser Ser Lys Pro Tyr Leu Leu Thr His Pro Ser Asp Pro Leu Glu
                405                 410                 415

Leu Val Val Ser Gly Pro Ser Gly Pro Ser Ser Pro Thr Thr Gly
            420                 425                 430

Pro Thr Ser Thr Ser Gly Pro Glu Asp Gln Pro Leu Thr Pro Thr Gly
        435                 440                 445

Ser Asp Pro Gln Ser Gly Leu Gly Arg His Leu Gly Val Val Ile Gly
    450                 455                 460

Ile Leu Val Ala Val Ile Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
            500                 505                 510

Thr Asp Arg Gly Leu Gln Trp Arg Ser Ser Pro Ala Ala Asp Ala Gln
        515                 520                 525

Glu Glu Asn Leu Tyr Ala Ala Val Lys His Thr Gln Pro Glu Asp Gly
    530                 535                 540
```

```
Val Glu Met Asp Thr Arg Ser Pro His Asp Glu Asp Pro Gln Ala Val
545                 550                 555                 560

Thr Tyr Ala Glu Val Lys His Ser Arg Pro Arg Arg Glu Met Ala Ser
                565                 570                 575

Pro Pro Ser Pro Leu Ser Gly Glu Phe Leu Asp Thr Lys Asp Arg Gln
            580                 585                 590

Ala Glu Glu Asp Arg Gln Met Asp Thr Glu Ala Ala Ser Glu Ala
        595                 600                 605

Pro Gln Asp Val Thr Tyr Ala Gln Leu His Ser Leu Thr Leu Arg Arg
        610                 615                 620

Glu Ala Thr Glu Pro Pro Ser Gln Glu Gly Pro Ser Pro Ala Val
625                 630                 635                 640

Pro Ser Ile Tyr Ala Thr Leu Ala Ile His
                645                 650

<210> SEQ ID NO 128
<211> LENGTH: 598
<212> TYPE: PRT
<213> ORGANISM: Artificial Sequence
<220> FEATURE:
<223> OTHER INFORMATION: Synthetic Construct

<400> SEQUENCE: 128

Met Thr Pro Ile Val Thr Val Leu Ile Cys Leu Gly Leu Ser Leu Gly
1               5                   10                  15

Pro Arg Thr His Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
        50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
                100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
        130                 135                 140

Glu Ser Gln Val Ala Phe Gly Gly Phe Ile Leu Cys Lys Glu Gly Glu
145                 150                 155                 160

Glu Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
        195                 200                 205

Ser Pro Ser Asp Leu Leu Glu Leu Leu Val Pro Gly Val Ser Lys Lys
210                 215                 220

Pro Ser Leu Ser Val Gln Pro Gly Pro Val Val Ala Pro Gly Glu Ser
225                 230                 235                 240

Leu Thr Leu Gln Cys Val Ser Asp Val Gly Tyr Asp Arg Phe Val Leu
            245                 250                 255
```

Tyr Lys Glu Gly Glu Arg Asp Leu Arg Gln Leu Pro Gly Arg Gln Pro
              260                 265                 270

Gln Ala Gly Leu Ser Gln Ala Asn Phe Thr Leu Gly Pro Val Ser Arg
          275                 280                 285

Ser Tyr Gly Gly Gln Tyr Arg Cys Tyr Gly Ala His Asn Leu Ser Ser
      290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
              325                 330                 335

Ser Gly Glu Asn Val Thr Leu Leu Cys Gln Ser Trp Arg Gln Phe His
          340                 345                 350

Thr Phe Leu Leu Thr Lys Ala Gly Ala Ala Asp Ala Pro Leu Arg Leu
      355                 360                 365

Arg Ser Ile His Glu Tyr Pro Lys Tyr Gln Ala Glu Phe Pro Met Ser
370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
              405                 410                 415

Val Val Ser Gly Pro Ser Met Gly Ser Ser Pro Pro Thr Gly Pro
          420                 425                 430

Ile Ser Thr Pro Ala Gly Pro Glu Asp Gln Pro Leu Thr Pro Thr Gly
      435                 440                 445

Ser Asp Pro Gln Ser Gly Leu Gly Arg His Leu Gly Val Val Ile Gly
450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
              485                 490                 495

Arg Lys Ala Asp Phe Gln His Pro Ala Gly Ala Val Gly Pro Glu Pro
          500                 505                 510

Thr Asp Arg Gly Leu Gln Trp Arg Ser Ser Pro Ala Ala Asp Ala Gln
      515                 520                 525

Glu Glu Asn Leu Tyr Ala Ala Val Lys Asp Thr Gln Pro Glu Asp Gly
530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
              565                 570                 575

Pro Pro Pro Ser Gln Glu Arg Glu Pro Pro Ala Glu Pro Ser Ile Tyr
          580                 585                 590

Ala Thr Leu Ala Ile His
          595

<210> SEQ ID NO 129
<211> LENGTH: 598
<212> TYPE: PRT
<213> ORGANISM: Artificial Sequence
<220> FEATURE:
<223> OTHER INFORMATION: Synthetic Construct

<400> SEQUENCE: 129

Met Thr Pro Ile Val Thr Val Leu Ile Cys Leu Gly Leu Ser Leu Gly
1               5                   10                  15

```
Pro Arg Thr Arg Val Gln Thr Gly Thr Ile Pro Lys Pro Thr Leu Trp
                20                  25                  30

Ala Glu Pro Asp Ser Val Ile Thr Gln Gly Ser Pro Val Thr Leu Ser
            35                  40                  45

Cys Gln Gly Ser Leu Glu Ala Gln Glu Tyr Arg Leu Tyr Arg Glu Lys
50                  55                  60

Lys Ser Ala Ser Trp Ile Thr Arg Ile Arg Pro Glu Leu Val Lys Asn
65                  70                  75                  80

Gly Gln Phe His Ile Pro Ser Ile Thr Trp Glu His Thr Gly Arg Tyr
                85                  90                  95

Gly Cys Gln Tyr Tyr Ser Arg Ala Arg Trp Ser Glu Leu Ser Asp Pro
            100                 105                 110

Leu Val Leu Val Met Thr Gly Ala Tyr Pro Lys Pro Thr Leu Ser Ala
            115                 120                 125

Gln Pro Ser Pro Val Val Thr Ser Gly Gly Arg Val Thr Leu Gln Cys
            130                 135                 140

Glu Ser Gln Val Ala Phe Gly Gly Phe Ile Leu Cys Lys Glu Gly Glu
145                 150                 155                 160

Asp Glu His Pro Gln Cys Leu Asn Ser Gln Pro His Ala Arg Gly Ser
                165                 170                 175

Ser Arg Ala Ile Phe Ser Val Gly Pro Val Ser Pro Asn Arg Arg Trp
            180                 185                 190

Ser His Arg Cys Tyr Gly Tyr Asp Leu Asn Ser Pro Tyr Val Trp Ser
            195                 200                 205

Ser Pro Ser Asp Leu Leu Glu Leu Leu Val Pro Gly Val Ser Lys Lys
210                 215                 220

Pro Ser Leu Ser Val Gln Pro Gly Pro Val Met Ala Pro Gly Glu Ser
225                 230                 235                 240

Leu Thr Leu Gln Cys Val Ser Asp Val Gly Tyr Asp Arg Phe Val Leu
                245                 250                 255

Tyr Lys Glu Gly Glu Arg Asp Leu Arg Gln Leu Pro Gly Arg Gln Pro
            260                 265                 270

Gln Ala Gly Leu Ser Gln Ala Asn Phe Thr Leu Gly Pro Val Ser Arg
            275                 280                 285

Ser Tyr Gly Gly Gln Tyr Arg Cys Tyr Gly Ala His Asn Leu Ser Ser
290                 295                 300

Glu Cys Ser Ala Pro Ser Asp Pro Leu Asp Ile Leu Ile Thr Gly Gln
305                 310                 315                 320

Ile Arg Gly Thr Pro Phe Ile Ser Val Gln Pro Gly Pro Thr Val Ala
                325                 330                 335

Ser Gly Glu Asn Val Thr Leu Leu Cys Gln Ser Trp Arg Gln Phe His
            340                 345                 350

Thr Phe Leu Leu Thr Lys Ala Gly Ala Ala Asp Ala Pro Leu Arg Leu
            355                 360                 365

Arg Ser Ile His Glu Tyr Pro Lys Tyr Gln Ala Glu Phe Pro Met Ser
370                 375                 380

Pro Val Thr Ser Ala His Ala Gly Thr Tyr Arg Cys Tyr Gly Ser Leu
385                 390                 395                 400

Asn Ser Asp Pro Tyr Leu Leu Ser His Pro Ser Glu Pro Leu Glu Leu
                405                 410                 415

Val Val Ser Gly Pro Ser Met Gly Ser Ser Pro Pro Thr Gly Pro
            420                 425                 430

Ile Ser Thr Pro Ala Gly Pro Glu Asp Gln Pro Leu Thr Pro Thr Gly
```

```
                 435                 440                 445
Ser Asp Pro Gln Ser Gly Leu Gly Arg His Leu Gly Val Val Ile Gly
450                 455                 460

Ile Leu Val Ala Val Val Leu Leu Leu Leu Leu Leu Leu Leu Leu Phe
465                 470                 475                 480

Leu Ile Leu Arg His Arg Arg Gln Gly Lys His Trp Thr Ser Thr Gln
                485                 490                 495

Arg Lys Ala Asp Phe Gln His Pro Ala Gly Ala Val Gly Pro Glu Pro
                500                 505                 510

Thr Asp Arg Gly Leu Gln Trp Arg Ser Ser Pro Ala Ala Asp Ala Gln
                515                 520                 525

Glu Glu Asn Leu Tyr Ala Ala Val Lys Asp Thr Gln Pro Glu Asp Gly
                530                 535                 540

Val Glu Met Asp Thr Arg Ala Ala Ala Ser Glu Ala Pro Gln Asp Val
545                 550                 555                 560

Thr Tyr Ala Gln Leu His Ser Leu Thr Leu Arg Arg Lys Ala Thr Glu
                565                 570                 575

Pro Pro Pro Ser Gln Glu Arg Glu Pro Pro Ala Glu Pro Ser Ile Tyr
                580                 585                 590

Ala Thr Leu Ala Ile His
                595

<210> SEQ ID NO 130
<211> LENGTH: 631
<212> TYPE: PRT
<213> ORGANISM: Artificial Sequence
<220> FEATURE:
<223> OTHER INFORMATION: Synthetic Construct

<400> SEQUENCE: 130

Met Thr Pro Ala Leu Thr Ala Leu Leu Cys Leu Gly Leu Ser Leu Gly
1               5                   10                  15

Pro Arg Thr Arg Val Gln Ala Gly Pro Phe Pro Lys Pro Thr Leu Trp
                20                  25                  30

Ala Glu Pro Gly Ser Val Ile Ser Trp Gly Ser Pro Val Thr Ile Trp
                35                  40                  45

Cys Gln Gly Ser Gln Glu Ala Gln Glu Tyr Arg Leu His Lys Glu Gly
            50                  55                  60

Ser Pro Glu Pro Leu Asp Arg Asn Asn Pro Leu Glu Pro Lys Asn Lys
65                  70                  75                  80

Ala Arg Phe Ser Ile Pro Ser Met Thr Glu His His Ala Gly Arg Tyr
                85                  90                  95

Arg Cys His Tyr Tyr Ser Ser Ala Gly Trp Ser Glu Pro Ser Asp Pro
                100                 105                 110

Leu Glu Met Val Met Thr Gly Ala Tyr Ser Lys Pro Thr Leu Ser Ala
                115                 120                 125

Leu Pro Ser Pro Val Val Ala Ser Gly Gly Asn Met Thr Leu Arg Cys
            130                 135                 140

Gly Ser Gln Lys Gly Tyr His His Phe Val Leu Met Lys Glu Gly Glu
145                 150                 155                 160

His Gln Leu Pro Arg Thr Leu Asp Ser Gln Gln Leu His Ser Arg Gly
                165                 170                 175

Phe Gln Ala Leu Phe Pro Val Gly Pro Val Thr Pro Ser His Arg Trp
                180                 185                 190

Arg Phe Thr Cys Tyr Tyr Tyr Tyr Thr Asn Thr Pro Trp Val Trp Ser
```

-continued

```
            195                 200                 205
His Pro Ser Asp Pro Leu Glu Ile Leu Pro Ser Gly Val Ser Arg Lys
210                 215                 220

Pro Ser Leu Leu Thr Leu Gln Gly Pro Val Leu Ala Pro Gly Gln Ser
225                 230                 235                 240

Leu Thr Leu Gln Cys Gly Ser Asp Val Gly Tyr Asn Arg Phe Val Leu
                245                 250                 255

Tyr Lys Glu Gly Glu Arg Asp Phe Leu Gln Arg Pro Gly Gln Gln Pro
            260                 265                 270

Gln Ala Gly Leu Ser Gln Ala Asn Phe Thr Leu Gly Pro Val Ser Pro
        275                 280                 285

Ser Asn Gly Gly Gln Tyr Arg Cys Tyr Gly Ala His Asn Leu Ser Ser
290                 295                 300

Glu Trp Ser Ala Pro Ser Asp Pro Leu Asn Ile Leu Met Ala Gly Gln
305                 310                 315                 320

Ile Tyr Asp Thr Val Ser Leu Ser Ala Gln Pro Gly Pro Thr Val Ala
                325                 330                 335

Ser Gly Glu Asn Val Thr Leu Leu Cys Gln Ser Trp Trp Gln Phe Asp
            340                 345                 350

Thr Phe Leu Leu Thr Lys Glu Gly Ala Ala His Pro Pro Leu Arg Leu
        355                 360                 365

Arg Ser Met Tyr Gly Ala His Lys Tyr Gln Ala Glu Phe Pro Met Ser
370                 375                 380

Pro Val Thr Ser Ala His Ala Gly Thr Tyr Arg Cys Tyr Gly Ser Tyr
385                 390                 395                 400

Ser Ser Asn Pro His Leu Leu Ser His Pro Ser Glu Pro Leu Glu Leu
                405                 410                 415

Val Val Ser Gly His Ser Gly Gly Ser Ser Leu Pro Pro Thr Gly Pro
            420                 425                 430

Pro Ser Thr Pro Gly Leu Gly Arg Tyr Leu Glu Val Leu Ile Gly Val
        435                 440                 445

Ser Val Ala Phe Val Leu Leu Leu Phe Leu Leu Leu Phe Leu Leu Leu
450                 455                 460

Arg Arg Gln Arg His Ser Lys His Arg Thr Ser Asp Gln Arg Lys Thr
465                 470                 475                 480

Asp Phe Gln Arg Pro Ala Gly Ala Ala Glu Thr Glu Pro Lys Asp Arg
                485                 490                 495

Gly Leu Leu Arg Arg Ser Ser Pro Ala Ala Asp Val Gln Glu Glu Asn
            500                 505                 510

Leu Tyr Ala Ala Val Lys Asp Thr Gln Ser Glu Asp Arg Val Glu Leu
        515                 520                 525

Asp Ser Gln Ser Pro His Asp Glu Asp Pro Gln Ala Val Thr Tyr Ala
530                 535                 540

Pro Val Lys His Ser Ser Pro Arg Arg Glu Met Ala Ser Pro Pro Ser
545                 550                 555                 560

Ser Leu Ser Gly Glu Phe Leu Asp Thr Lys Asp Arg Gln Val Glu Glu
                565                 570                 575

Asp Arg Gln Met Asp Thr Glu Ala Ala Ala Ser Glu Ala Ser Gln Asp
            580                 585                 590

Val Thr Tyr Ala Gln Leu His Ser Leu Thr Leu Arg Arg Lys Ala Thr
        595                 600                 605

Glu Pro Pro Pro Ser Gln Glu Gly Glu Pro Pro Ala Glu Pro Ser Ile
610                 615                 620
```

Tyr Ala Thr Leu Ala Ile His
625                 630

<210> SEQ ID NO 131
<211> LENGTH: 448
<212> TYPE: PRT
<213> ORGANISM: Artificial Sequence
<220> FEATURE:
<223> OTHER INFORMATION: Synthetic Construct

<400> SEQUENCE: 131

Met Ile Pro Thr Phe Thr Ala Leu Leu Cys Leu Gly Leu Ser Leu Gly
1               5                   10                  15

Pro Arg Thr His Met Gln Ala Gly Pro Leu Pro Lys Pro Thr Leu Trp
                20                  25                  30

Ala Glu Pro Gly Ser Val Ile Ser Trp Gly Asn Ser Val Thr Ile Trp
            35                  40                  45

Cys Gln Gly Thr Leu Glu Ala Arg Glu Tyr Arg Leu Asp Lys Glu Glu
        50                  55                  60

Ser Pro Ala Pro Trp Asp Arg Gln Asn Pro Leu Glu Pro Lys Asn Lys
65                  70                  75                  80

Ala Arg Phe Ser Ile Pro Ser Met Thr Glu Asp Tyr Ala Gly Arg Tyr
                85                  90                  95

Arg Cys Tyr Tyr Arg Ser Pro Val Gly Trp Ser Gln Pro Ser Asp Pro
            100                 105                 110

Leu Glu Leu Val Met Thr Gly Ala Tyr Ser Lys Pro Thr Leu Ser Ala
        115                 120                 125

Leu Pro Ser Pro Leu Val Thr Ser Gly Lys Ser Val Thr Leu Leu Cys
130                 135                 140

Gln Ser Arg Ser Pro Met Asp Thr Phe Leu Leu Ile Lys Glu Arg Ala
145                 150                 155                 160

Ala His Pro Leu Leu His Leu Arg Ser Glu His Gly Ala Gln Gln His
                165                 170                 175

Gln Ala Glu Phe Pro Met Ser Pro Val Thr Ser Val His Gly Gly Thr
            180                 185                 190

Tyr Arg Cys Phe Ser Ser His Gly Phe Ser His Tyr Leu Leu Ser His
        195                 200                 205

Pro Ser Asp Pro Leu Glu Leu Ile Val Ser Gly Ser Leu Glu Asp Pro
210                 215                 220

Arg Pro Ser Pro Thr Arg Ser Val Ser Thr Ala Ala Gly Pro Glu Asp
225                 230                 235                 240

Gln Pro Leu Met Pro Thr Gly Ser Val Pro His Ser Gly Leu Arg Arg
                245                 250                 255

His Trp Glu Val Leu Ile Gly Val Leu Val Val Ser Ile Leu Leu Leu
            260                 265                 270

Ser Leu Leu Leu Phe Leu Leu Leu Gln His Trp Arg Gln Gly Lys His
        275                 280                 285

Arg Thr Leu Ala Gln Arg Gln Ala Asp Phe Gln Arg Pro Pro Gly Ala
290                 295                 300

Ala Glu Pro Glu Pro Lys Asp Gly Gly Leu Gln Arg Arg Ser Ser Pro
305                 310                 315                 320

Ala Ala Asp Val Gln Gly Glu Asn Phe Cys Ala Ala Val Lys Asn Thr
                325                 330                 335

Gln Pro Glu Asp Gly Val Glu Met Asp Thr Arg Gln Ser Pro His Asp
            340                 345                 350

Glu Asp Pro Gln Ala Val Thr Tyr Ala Lys Val Lys His Ser Arg Pro
                355                 360                 365

Arg Arg Glu Met Ala Ser Pro Ser Pro Leu Ser Gly Glu Phe Leu
370                 375                 380

Asp Thr Lys Asp Arg Gln Ala Glu Glu Asp Arg Gln Met Asp Thr Glu
385                 390                 395                 400

Ala Ala Ala Ser Glu Ala Pro Gln Asp Val Thr Tyr Ala Gln Leu His
                405                 410                 415

Ser Phe Thr Leu Arg Gln Lys Ala Thr Glu Pro Pro Ser Gln Glu
                420                 425                 430

Gly Ala Ser Pro Ala Glu Pro Ser Val Tyr Ala Thr Leu Ala Ile His
                435                 440                 445

<210> SEQ ID NO 132
<211> LENGTH: 590
<212> TYPE: PRT
<213> ORGANISM: Artificial Sequence
<220> FEATURE:
<223> OTHER INFORMATION: Synthetic Construct

<400> SEQUENCE: 132

Met Thr Leu Thr Leu Ser Val Leu Ile Cys Leu Gly Leu Ser Val Gly
1               5                   10                  15

Pro Arg Thr Cys Val Gln Ala Gly Thr Leu Pro Lys Pro Thr Leu Trp
                20                  25                  30

Ala Glu Pro Ala Ser Val Ile Ala Arg Gly Lys Pro Val Thr Leu Trp
                35                  40                  45

Cys Gln Gly Pro Leu Glu Thr Glu Glu Tyr Arg Leu Asp Lys Glu Gly
    50                  55                  60

Leu Pro Trp Ala Arg Lys Arg Gln Asn Pro Leu Glu Pro Gly Ala Lys
65                  70                  75                  80

Ala Lys Phe His Ile Pro Ser Thr Val Tyr Asp Ser Ala Gly Arg Tyr
                85                  90                  95

Arg Cys Tyr Tyr Glu Thr Pro Ala Gly Trp Ser Glu Pro Ser Asp Pro
                100                 105                 110

Leu Glu Leu Val Ala Thr Gly Phe Tyr Ala Glu Pro Thr Leu Leu Ala
                115                 120                 125

Leu Pro Ser Pro Val Val Ala Ser Gly Gly Asn Val Thr Leu Gln Cys
                130                 135                 140

Asp Thr Leu Asp Gly Leu Leu Thr Phe Val Leu Val Glu Glu Glu Gln
145                 150                 155                 160

Lys Leu Pro Arg Thr Leu Tyr Ser Gln Lys Leu Pro Lys Gly Pro Ser
                165                 170                 175

Gln Ala Leu Phe Pro Val Gly Pro Val Thr Pro Ser Cys Arg Trp Arg
                180                 185                 190

Phe Arg Cys Tyr Tyr Tyr Tyr Arg Lys Asn Pro Gln Val Trp Ser Asn
                195                 200                 205

Pro Ser Asp Leu Leu Glu Ile Leu Val Pro Gly Val Ser Arg Lys Pro
                210                 215                 220

Ser Leu Leu Ile Pro Gln Gly Ser Val Val Ala Arg Gly Gly Ser Leu
225                 230                 235                 240

Thr Leu Gln Cys Arg Ser Asp Val Gly Tyr Asp Ile Phe Val Leu Tyr
                245                 250                 255

Lys Glu Gly Glu His Asp Leu Val Gln Gly Ser Gly Gln Gln Pro Gln
                260                 265                 270

```
Ala Gly Leu Ser Gln Ala Asn Phe Thr Leu Gly Pro Val Ser Arg Ser
            275                 280                 285

His Gly Gly Gln Tyr Arg Cys Tyr Gly Ala His Asn Leu Ser Pro Arg
        290                 295                 300

Trp Ser Ala Pro Ser Asp Pro Leu Asp Ile Leu Ile Ala Gly Leu Ile
305                 310                 315                 320

Pro Asp Ile Pro Ala Leu Ser Val Gln Pro Gly Pro Lys Val Ala Ser
                325                 330                 335

Gly Glu Asn Val Thr Leu Leu Cys Gln Ser Trp His Gln Ile Asp Thr
                340                 345                 350

Phe Phe Leu Thr Lys Glu Gly Ala Ala His Pro Pro Leu Cys Leu Lys
            355                 360                 365

Ser Lys Tyr Gln Ser Tyr Arg His Gln Ala Glu Phe Ser Met Ser Pro
        370                 375                 380

Val Thr Ser Ala Gln Gly Gly Thr Tyr Arg Cys Tyr Ser Ala Ile Arg
385                 390                 395                 400

Ser Tyr Pro Tyr Leu Leu Ser Ser Pro Ser Tyr Pro Gln Glu Leu Val
                405                 410                 415

Val Ser Gly Pro Ser Gly Asp Pro Ser Leu Ser Pro Gly Ser Thr
            420                 425                 430

Pro Thr Pro Gly Pro Glu Asp Gln Pro Leu Thr Pro Thr Gly Leu Asp
        435                 440                 445

Pro Gln Ser Gly Leu Gly Arg His Leu Gly Val Val Thr Gly Val Ser
    450                 455                 460

Val Ala Phe Val Leu Leu Leu Phe Leu Leu Leu Phe Leu Leu Leu Arg
465                 470                 475                 480

His Arg His Gln Ser Lys His Arg Thr Ser Ala His Phe Tyr Arg Pro
                485                 490                 495

Ala Gly Ala Ala Gly Pro Glu Pro Lys Asp Gln Gly Leu Gln Lys Arg
            500                 505                 510

Ala Ser Pro Val Ala Asp Ile Gln Glu Glu Ile Leu Asn Ala Ala Val
        515                 520                 525

Lys Asp Thr Gln Pro Lys Asp Gly Val Glu Met Asp Ala Arg Ala Ala
530                 535                 540

Ala Ser Glu Ala Pro Gln Asp Val Thr Tyr Ala Gln Leu His Ser Leu
545                 550                 555                 560

Thr Leu Arg Arg Glu Ala Thr Glu Pro Pro Pro Ser Gln Glu Arg Glu
                565                 570                 575

Pro Pro Ala Glu Pro Ser Ile Tyr Ala Pro Leu Ala Ile His
            580                 585                 590

<210> SEQ ID NO 133
<211> LENGTH: 598
<212> TYPE: PRT
<213> ORGANISM: Artificial Sequence
<220> FEATURE:
<223> OTHER INFORMATION: Synthetic Construct

<400> SEQUENCE: 133

Met Thr Pro Ile Leu Met Val Leu Ile Cys Leu Gly Leu Ser Leu Gly
1               5                   10                  15

Pro Arg Thr His Val Gln Ala Gly Ile Leu Pro Lys Pro Thr Leu Trp
            20                  25                  30

Ala Glu Pro Gly Ser Val Ile Ser Glu Gly Ser Pro Val Thr Leu Arg
        35                  40                  45
```

-continued

```
Cys Gln Gly Ser Leu Gln Val Gln Glu Tyr His Leu Tyr Arg Glu Lys
    50                  55                  60

Asn Pro Ala Ser Trp Val Arg Gln Ile Arg Gln Glu Leu Val Lys Lys
65                  70                  75                  80

Gly Tyr Phe Ala Ile Gly Phe Ile Thr Trp Glu His Thr Gly Gln Tyr
                85                  90                  95

Arg Cys Gln Tyr Tyr Ser His Ser Trp Trp Ser Glu Pro Ser Asp Pro
                100                 105                 110

Leu Glu Leu Val Val Thr Gly Ala Tyr Ser Lys Pro Thr Leu Ser Ala
            115                 120                 125

Leu Pro Ser Pro Val Val Ala Ser Gly Gly Asn Val Thr Leu Gln Cys
    130                 135                 140

Asp Ser Gln Val Ala Phe Asp Ser Phe Thr Leu Cys Lys Glu Gly Glu
145                 150                 155                 160

Asp Glu His Pro Gln Arg Leu Asn Cys Gln Ser His Ala Arg Gly Trp
                165                 170                 175

Ser Trp Ala Val Phe Ser Val Gly Pro Val Ser Pro Ser Arg Arg Trp
                180                 185                 190

Ser Tyr Arg Cys Tyr Gly Tyr Ile Ser Ser Ala Pro Asn Val Trp Ser
            195                 200                 205

Leu Pro Ser Asp Leu Leu Glu Leu Leu Val Pro Gly Val Ser Lys Lys
    210                 215                 220

Pro Ser Leu Ser Val Gln Pro Gly Pro Val Val Ala Pro Gly Asp Lys
225                 230                 235                 240

Leu Thr Leu Gln Cys Gly Ser Asp Ala Gly Tyr Asp Arg Phe Ala Leu
                245                 250                 255

Tyr Lys Glu Gly Glu Gly Asp Phe Leu Gln Arg Pro Val Arg Gln Pro
                260                 265                 270

Gln Ala Gly Leu Ser Gln Ala Asn Phe Leu Leu Gly Pro Val Ser Arg
            275                 280                 285

Ser His Gly Gly Gln Tyr Arg Cys Ser Gly Ala His Asn Leu Ser Ser
    290                 295                 300

Glu Trp Ser Ala Pro Ser Asp Pro Leu Asp Ile Leu Ile Ala Gly Gln
305                 310                 315                 320

Ile Arg Gly Arg Pro Phe Leu Ser Val Gln Pro Gly Pro Lys Val Val
                325                 330                 335

Ser Gly Glu Asn Val Thr Leu Leu Cys Gln Ser Ser Trp Gln Phe His
                340                 345                 350

Ala Phe Leu Leu Thr Gln Ala Gly Ala Ala Asp Ala His Leu His Leu
            355                 360                 365

Arg Ser Met Tyr Lys Tyr Pro Lys Tyr Gln Ala Glu Phe Pro Met Ser
    370                 375                 380

Pro Val Thr Ser Ala His Ala Gly Thr Tyr Arg Cys Tyr Gly Ser Arg
385                 390                 395                 400

Ser Ser Asn Pro Tyr Leu Leu Ser Val Pro Ser Asp Pro Leu Glu Leu
                405                 410                 415

Val Val Ser Gly Pro Ser Gly Gly Pro Ser Ser Pro Thr Thr Gly Pro
            420                 425                 430

Thr Ser Thr Cys Ala Gly Pro Glu Asp Gln Pro Leu Thr Pro Thr Gly
            435                 440                 445

Ser Ala Pro Gln Ser Gly Leu Gly Arg His Leu Gly Val Val Thr Gly
    450                 455                 460
```

Val Leu Val Ala Phe Val Leu Leu Phe Leu Leu Leu Leu Phe
465                 470                 475                 480

Leu Val Leu Arg Tyr Arg Arg Gln Gly Lys Arg Trp Thr Ser Ala Gln
            485                 490                 495

Arg Lys Ala Asp Phe Gln His Pro Ala Gly Ala Val Glu Pro Glu Pro
            500                 505                 510

Arg Asp Arg Gly Leu Gln Arg Ser Ser Pro Ala Ala Asp Thr Gln
            515                 520                 525

Glu Glu Asn Leu Tyr Ala Ala Val Lys Asp Thr Gln Pro Glu Asp Gly
            530                 535                 540

Val Glu Leu Asp Ser Arg Ala Ala Ser Glu Asp Pro Gln Asp Val
545                 550                 555                 560

Thr Tyr Ala Gln Leu Gln Ser Leu Thr Leu Arg Arg Glu Ala Thr Glu
            565                 570                 575

Pro Pro Pro Ser Gln Glu Arg Ala Pro Pro Val Glu Ser Ser Ile Tyr
            580                 585                 590

Ala Thr Leu Thr Ile His
            595

<210> SEQ ID NO 134
<211> LENGTH: 580
<212> TYPE: PRT
<213> ORGANISM: Artificial Sequence
<220> FEATURE:
<223> OTHER INFORMATION: Synthetic Construct

<400> SEQUENCE: 134

Gly Leu Ser Leu Gly Ser Arg Thr Arg Val Gln Ala Gly Thr Leu Pro
1               5                   10                  15

Lys Pro Thr Leu Trp Ala Glu Pro Asp Ser Val Ile Thr Gln Gly Ser
            20                  25                  30

Pro Val Thr Leu Arg Cys Gln Gly Ser Leu Gln Val Gln Glu Tyr Arg
            35                  40                  45

Leu Tyr Arg Glu Arg Lys Pro Ala Ser Trp Val Arg Arg Ile Arg Gln
    50                  55                  60

Glu Leu Val Lys Lys Gly Tyr Phe Ala Ile Gly Phe Ile Thr Trp Glu
65                  70                  75                  80

His Thr Gly Gln Tyr His Cys Gln Tyr Tyr Ser His Ser Trp Trp Pro
            85                  90                  95

Glu Pro Ser Asp Pro Leu Glu Leu Val Met Thr Gly Ala Tyr Ser Lys
            100                 105                 110

Pro Thr Leu Ser Ala Leu Pro Ser Pro Met Val Ala Ser Gly Gly Asn
            115                 120                 125

Val Thr Leu Gln Cys Asp Ser Gln Val Ala Phe Asp Gly Phe Ile Leu
            130                 135                 140

Cys Lys Glu Gly Glu Asp Glu His Pro Gln Arg Leu Asn Ser His Phe
145                 150                 155                 160

His Ala Tyr Gly Trp Ser Arg Ala Val Phe Ser Val Gly Pro Val Ser
            165                 170                 175

Pro Ser Arg Arg Trp Ser Tyr Arg Cys Tyr Gly Tyr Asp Ser Arg Ser
            180                 185                 190

Pro Tyr Val Trp Ser Leu Pro Ser Asp Leu Leu Glu Leu Leu Val Pro
            195                 200                 205

Gly Val Ser Lys Lys Pro Ser Leu Ser Val Gln Pro Gly Pro Val Val
            210                 215                 220

```
Ala Pro Gly Asp Lys Leu Thr Leu Gln Cys Gly Ser Asp Ala Gly Tyr
225                 230                 235                 240

Asn Arg Phe Ala Leu Tyr Lys Glu Gly Glu Gly Asn Phe Leu Gln His
            245                 250                 255

Pro Gly Arg Gln Arg Gln Ala Gly Leu Ser Gln Ala Asn Phe Leu Leu
        260                 265                 270

Gly Pro Val Ser Arg Ser His Gly Gly Gln Tyr Arg Cys Tyr Gly Ala
    275                 280                 285

His Asn Leu Ser Ser Glu Trp Ser Ala Pro Ser Asp Pro Leu Asp Ile
290                 295                 300

Leu Ile Ala Gly Gln Ile Arg Gly Arg Pro Ser Leu Val Gln Pro
305                 310                 315                 320

Gly Arg Thr Val Ala Ser Gly Glu Asn Val Thr Leu Leu Cys Gln Ser
                325                 330                 335

Ser Trp Gln Phe His Val Phe Leu Leu Thr Gln Ala Gly Ala Ala Asp
            340                 345                 350

Ala His Leu His Leu Arg Ser Met Tyr Lys Tyr Pro Lys Tyr Gln Ala
        355                 360                 365

Glu Phe Pro Met Ser Pro Val Thr Ser Ala His Ala Gly Thr Tyr Arg
    370                 375                 380

Cys Tyr Gly Ser His Ser Ser Asp Ser Tyr Leu Leu Ser Val Pro Ser
385                 390                 395                 400

Asp Pro Leu Glu Leu Val Val Ser Gly Pro Ser Gly Gly Pro Ser Ser
                405                 410                 415

Pro Thr Thr Gly Pro Thr Ser Thr Cys Gly Pro Glu Asp Gln Pro Leu
            420                 425                 430

Thr Pro Thr Gly Ser Ala Pro Gln Ser Gly Leu Gly Arg His Leu Gly
        435                 440                 445

Val Val Thr Gly Val Leu Val Ala Phe Val Leu Leu Phe Leu Leu
    450                 455                 460

Leu Leu Leu Phe Leu Val Leu Arg His Arg Arg Gln Gly Lys Arg Trp
465                 470                 475                 480

Thr Ser Ala Gln Arg Lys Ala Asp Phe Gln His Pro Ala Gly Ala Val
                485                 490                 495

Glu Pro Glu Pro Arg Asp Arg Gly Leu Gln Arg Arg Ser Ser Pro Ala
            500                 505                 510

Ala Asn Thr Gln Glu Glu Asn Leu Tyr Ala Ala Met Lys Asp Thr Gln
        515                 520                 525

Pro Glu Asp Gly Val Glu Leu Asp Ser Gln Ala Ala Ser Glu Asp
    530                 535                 540

Pro Gln Asp Val Thr Tyr Ala Gln Leu Gln Ser Leu Thr Leu Arg Arg
545                 550                 555                 560

Glu Thr Thr Glu Pro Pro Pro Ser Gln Glu Arg Ala Pro Pro Val Glu
                565                 570                 575

Ser Ser Ile Tyr
            580

<210> SEQ ID NO 135
<211> LENGTH: 20
<212> TYPE: DNA
<213> ORGANISM: Artificial Sequence
<220> FEATURE:
<223> OTHER INFORMATION: Synthetic Construct

<400> SEQUENCE: 135
```
cacacagctc aacctggaca                                            20

<210> SEQ ID NO 136
<211> LENGTH: 19
<212> TYPE: DNA
<213> ORGANISM: Artificial Sequence
<220> FEATURE:
<223> OTHER INFORMATION: Synthetic Construct

<400> SEQUENCE: 136
agctcaacct ggacagcac                                             19

<210> SEQ ID NO 137
<211> LENGTH: 20
<212> TYPE: DNA
<213> ORGANISM: Artificial Sequence
<220> FEATURE:
<223> OTHER INFORMATION: Synthetic Construct

<400> SEQUENCE: 137
acacacagct caacctggac                                            20

<210> SEQ ID NO 138
<211> LENGTH: 20
<212> TYPE: DNA
<213> ORGANISM: Artificial Sequence
<220> FEATURE:
<223> OTHER INFORMATION: Synthetic Construct

<400> SEQUENCE: 138
cacacagctc aacctggaca                                            20

<210> SEQ ID NO 139
<211> LENGTH: 20
<212> TYPE: DNA
<213> ORGANISM: Artificial Sequence
<220> FEATURE:
<223> OTHER INFORMATION: Synthetic Construct

<400> SEQUENCE: 139
cctgcatttc tcctctgtgc                                            20

<210> SEQ ID NO 140
<211> LENGTH: 20
<212> TYPE: DNA
<213> ORGANISM: Artificial Sequence
<220> FEATURE:
<223> OTHER INFORMATION: Synthetic Construct

<400> SEQUENCE: 140
tcgcacaggt gctatggtta                                            20

<210> SEQ ID NO 141
<211> LENGTH: 22
<212> TYPE: DNA
<213> ORGANISM: Artificial Sequence
<220> FEATURE:
<223> OTHER INFORMATION: Synthetic Construct

<400> SEQUENCE: 141
agtagaagga gactcaggac tg                                         22

<210> SEQ ID NO 142
<211> LENGTH: 21
<212> TYPE: DNA
<213> ORGANISM: Artificial Sequence

```
<220> FEATURE:
<223> OTHER INFORMATION: Synthetic Construct

<400> SEQUENCE: 142
ttccacactt tccttctgac c                                              21

<210> SEQ ID NO 143
<211> LENGTH: 19
<212> TYPE: DNA
<213> ORGANISM: Artificial Sequence
<220> FEATURE:
<223> OTHER INFORMATION: Synthetic Construct

<400> SEQUENCE: 143
cgtcaccctc agttgtcag                                                 19

<210> SEQ ID NO 144
<211> LENGTH: 21
<212> TYPE: DNA
<213> ORGANISM: Artificial Sequence
<220> FEATURE:
<223> OTHER INFORMATION: Synthetic Construct

<400> SEQUENCE: 144
cctacttccc tgcatttctc c                                              21

<210> SEQ ID NO 145
<211> LENGTH: 25
<212> TYPE: DNA
<213> ORGANISM: Artificial Sequence
<220> FEATURE:
<223> OTHER INFORMATION: Synthetic Construct

<400> SEQUENCE: 145
ttcttcccct acttccctgc atttc                                          25

<210> SEQ ID NO 146
<211> LENGTH: 23
<212> TYPE: DNA
<213> ORGANISM: Artificial Sequence
<220> FEATURE:
<223> OTHER INFORMATION: Synthetic Construct

<400> SEQUENCE: 146
gaagtcaact tttcttcccc tac                                            23

<210> SEQ ID NO 147
<211> LENGTH: 20
<212> TYPE: DNA
<213> ORGANISM: Artificial Sequence
<220> FEATURE:
<223> OTHER INFORMATION: Synthetic Construct

<400> SEQUENCE: 147
cacacagctc aacctggaca                                                20

<210> SEQ ID NO 148
<211> LENGTH: 23
<212> TYPE: DNA
<213> ORGANISM: Artificial Sequence
<220> FEATURE:
<223> OTHER INFORMATION: Synthetic Construct

<400> SEQUENCE: 148
gtcaactttt cttcccctac ttc                                            23
```

```
<210> SEQ ID NO 149
<211> LENGTH: 22
<212> TYPE: DNA
<213> ORGANISM: Artificial Sequence
<220> FEATURE:
<223> OTHER INFORMATION: Synthetic Construct

<400> SEQUENCE: 149
aagaagccat cactctcagt gc                                              22

<210> SEQ ID NO 150
<211> LENGTH: 20
<212> TYPE: DNA
<213> ORGANISM: Artificial Sequence
<220> FEATURE:
<223> OTHER INFORMATION: Synthetic Construct

<400> SEQUENCE: 150
tgggtaggct cctgtcatca                                                 20

<210> SEQ ID NO 151
<211> LENGTH: 20
<212> TYPE: DNA
<213> ORGANISM: Artificial Sequence
<220> FEATURE:
<223> OTHER INFORMATION: Synthetic Construct

<400> SEQUENCE: 151
cttggggatg gtccctgtct                                                 20

<210> SEQ ID NO 152
<211> LENGTH: 20
<212> TYPE: DNA
<213> ORGANISM: Artificial Sequence
<220> FEATURE:
<223> OTHER INFORMATION: Synthetic Construct

<400> SEQUENCE: 152
caggcagact cagatcagca                                                 20

<210> SEQ ID NO 153
<211> LENGTH: 20
<212> TYPE: DNA
<213> ORGANISM: Artificial Sequence
<220> FEATURE:
<223> OTHER INFORMATION: Synthetic Construct

<400> SEQUENCE: 153
ctgcaggcag actcagatca                                                 20

<210> SEQ ID NO 154
<211> LENGTH: 20
<212> TYPE: DNA
<213> ORGANISM: Artificial Sequence
<220> FEATURE:
<223> OTHER INFORMATION: Synthetic Construct

<400> SEQUENCE: 154
ctgtccaggt tgagctgtgt                                                 20

<210> SEQ ID NO 155
<211> LENGTH: 23
<212> TYPE: DNA
<213> ORGANISM: Artificial Sequence
<220> FEATURE:
<223> OTHER INFORMATION: Synthetic Construct
```

```
<400> SEQUENCE: 155
gcactgagag tgatggcttc tta                                           23

<210> SEQ ID NO 156
<211> LENGTH: 19
<212> TYPE: DNA
<213> ORGANISM: Artificial Sequence
<220> FEATURE:
<223> OTHER INFORMATION: Synthetic Construct

<400> SEQUENCE: 156
tcccaaagtt cccagcatc                                                19

<210> SEQ ID NO 157
<211> LENGTH: 22
<212> TYPE: DNA
<213> ORGANISM: Artificial Sequence
<220> FEATURE:
<223> OTHER INFORMATION: Synthetic Construct

<400> SEQUENCE: 157
gggaattcag cctggtactt ag                                            22

<210> SEQ ID NO 158
<211> LENGTH: 21
<212> TYPE: DNA
<213> ORGANISM: Artificial Sequence
<220> FEATURE:
<223> OTHER INFORMATION: Synthetic Construct

<400> SEQUENCE: 158
tccgtgtaat ccaagatgct g                                             21

<210> SEQ ID NO 159
<211> LENGTH: 19
<212> TYPE: DNA
<213> ORGANISM: Artificial Sequence
<220> FEATURE:
<223> OTHER INFORMATION: Synthetic Construct

<400> SEQUENCE: 159
caggcagact cagatcagc                                                19

<210> SEQ ID NO 160
<211> LENGTH: 21
<212> TYPE: DNA
<213> ORGANISM: Artificial Sequence
<220> FEATURE:
<223> OTHER INFORMATION: Synthetic Construct

<400> SEQUENCE: 160
cttcaaggct cccctgacaa c                                             21

<210> SEQ ID NO 161
<211> LENGTH: 19
<212> TYPE: DNA
<213> ORGANISM: Artificial Sequence
<220> FEATURE:
<223> OTHER INFORMATION: Synthetic Construct

<400> SEQUENCE: 161
caaggctccc ctgacaact                                                19

<210> SEQ ID NO 162
```

-continued

```
<211> LENGTH: 20
<212> TYPE: DNA
<213> ORGANISM: Artificial Sequence
<220> FEATURE:
<223> OTHER INFORMATION: Synthetic Construct

<400> SEQUENCE: 162
agactcagcc cgagacagat                                                     20

<210> SEQ ID NO 163
<211> LENGTH: 19
<212> TYPE: DNA
<213> ORGANISM: Artificial Sequence
<220> FEATURE:
<223> OTHER INFORMATION: Synthetic Construct

<400> SEQUENCE: 163
aaggctcccc tgacaactg                                                      19

<210> SEQ ID NO 164
<211> LENGTH: 18
<212> TYPE: DNA
<213> ORGANISM: Artificial Sequence
<220> FEATURE:
<223> OTHER INFORMATION: Synthetic Construct

<400> SEQUENCE: 164
gtaggagcgg ctcacagg                                                       18

<210> SEQ ID NO 165
<211> LENGTH: 23
<212> TYPE: DNA
<213> ORGANISM: Artificial Sequence
<220> FEATURE:
<223> OTHER INFORMATION: Synthetic Construct

<400> SEQUENCE: 165
agcctggacc cctaacaaag acc                                                 23

<210> SEQ ID NO 166
<211> LENGTH: 27
<212> TYPE: DNA
<213> ORGANISM: Artificial Sequence
<220> FEATURE:
<223> OTHER INFORMATION: Synthetic Construct

<400> SEQUENCE: 166
tgccccactc cgtctaagat caataca                                             27

<210> SEQ ID NO 167
<211> LENGTH: 25
<212> TYPE: DNA
<213> ORGANISM: Artificial Sequence
<220> FEATURE:
<223> OTHER INFORMATION: Synthetic Construct

<400> SEQUENCE: 167
ccttgaagcc caggagtacc gtcta                                               25

<210> SEQ ID NO 168
<211> LENGTH: 20
<212> TYPE: DNA
<213> ORGANISM: Artificial Sequence
<220> FEATURE:
<223> OTHER INFORMATION: Synthetic Construct

<400> SEQUENCE: 168
```
agctcaacct ggacggcaca                                         20

<210> SEQ ID NO 169
<211> LENGTH: 29
<212> TYPE: DNA
<213> ORGANISM: Artificial Sequence
<220> FEATURE:
<223> OTHER INFORMATION: Synthetic Construct

<400> SEQUENCE: 169
agtcccgtca ccctcagttg tcaggggag                               29

<210> SEQ ID NO 170
<211> LENGTH: 31
<212> TYPE: DNA
<213> ORGANISM: Artificial Sequence
<220> FEATURE:
<223> OTHER INFORMATION: Synthetic Construct

<400> SEQUENCE: 170
tcgtatccgt gtaatccaag atgctgattt t                            31

<210> SEQ ID NO 171
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (3)..(4)
<223> OTHER INFORMATION: Xaa is any naturally occurring amino acid
<220> FEATURE:
<221> NAME/KEY: MISC_FEATURE
<222> LOCATION: (6)..(7)
<223> OTHER INFORMATION: Xaa is any naturally occurring amino acid

<400> SEQUENCE: 171

Xaa Tyr Xaa Xaa Gly Xaa Xaa
1               5

<210> SEQ ID NO 172
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is any naturally occurring amino acid
<220> FEATURE:
<221> NAME/KEY: MISC_FEATURE
<222> LOCATION: (4)..(14)
<223> OTHER INFORMATION: Xaa is any naturally occurring amino acid
<220> FEATURE:
<221> NAME/KEY: MISC_FEATURE
<222> LOCATION: (16)..(16)
<223> OTHER INFORMATION: Xaa is any naturally occurring amino acid

<400> SEQUENCE: 172

Xaa Xaa Trp Xaa Xaa Xaa Xaa Xaa Xaa Xaa Xaa Xaa Xaa Xaa Lys Xaa
1               5                   10                  15

<210> SEQ ID NO 173

```
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is any naturally occurring amino acid
<220> FEATURE:
<221> NAME/KEY: MISC_FEATURE
<222> LOCATION: (4)..(6)
<223> OTHER INFORMATION: Xaa is any naturally occurring amino acid
<220> FEATURE:
<221> NAME/KEY: MISC_FEATURE
<222> LOCATION: (11)..(13)
<223> OTHER INFORMATION: Xaa is any naturally occurring amino acid

<400> SEQUENCE: 173

Xaa Xaa Ile Xaa Xaa Xaa Thr Asp Tyr Val Xaa Xaa Xaa
1               5                   10

<210> SEQ ID NO 174
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(8)
<223> OTHER INFORMATION: Xaa is any naturally occurring amino acid
<220> FEATURE:
<221> NAME/KEY: MISC_FEATURE
<222> LOCATION: (11)..(11)
<223> OTHER INFORMATION: Xaa is any naturally occurring amino acid

<400> SEQUENCE: 174

Xaa Xaa Xaa Xaa Xaa Xaa Xaa Xaa Asp Leu Xaa
1               5                   10

<210> SEQ ID NO 175
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(7)
<223> OTHER INFORMATION: Xaa is any naturally occurring amino acid

<400> SEQUENCE: 175

Xaa Xaa Xaa Xaa Xaa Xaa Xaa
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(3)
<223> OTHER INFORMATION: Xaa is any naturally occurring amino acid
<220> FEATURE:
<221> NAME/KEY: MISC_FEATURE
<222> LOCATION: (5)..(5)
<223> OTHER INFORMATION: Xaa is any naturally occurring amino acid
<220> FEATURE:
<221> NAME/KEY: MISC_FEATURE
<222> LOCATION: (9)..(9)
```

<223> OTHER INFORMATION: Xaa is any naturally occurring amino acid

<400> SEQUENCE: 176

Xaa Xaa Xaa Tyr Xaa Tyr Pro Leu Xaa
1               5

<210> SEQ ID NO 177
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid
<220> FEATURE:
<221> NAME/KEY: MISC_FEATURE
<222> LOCATION: (4)..(14)
<223> OTHER INFORMATION: Xaa is any naturally occurring amino acid
<220> FEATURE:
<221> NAME/KEY: MISC_FEATURE
<222> LOCATION: (16)..(16)
<223> OTHER INFORMATION: Xaa is any naturally occurring amino acid

<400> SEQUENCE: 177

Ser Xaa Trp Xaa Xaa Xaa Xaa Xaa Xaa Xaa Xaa Xaa Xaa Xaa Lys Xaa
1               5                   10                  15

<210> SEQ ID NO 178
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(3)
<223> OTHER INFORMATION: Xaa is any naturally occurring amino acid
<220> FEATURE:
<221> NAME/KEY: MISC_FEATURE
<222> LOCATION: (9)..(9)
<223> OTHER INFORMATION: Xaa is any naturally occurring amino acid

<400> SEQUENCE: 178

Xaa Xaa Xaa Tyr Asp Tyr Pro Leu Xaa
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid

<400> SEQUENCE: 179

Xaa Tyr Ala Met Gly Val Ser
1               5

<210> SEQ ID NO 180
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE -continued

```
<222> LOCATION: (3)..(3)
<223> OTHER INFORMATION: Xaa is any naturally occurring amino acid

<400> SEQUENCE: 180

Thr Tyr Xaa Met Gly Val Ser
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is any naturally occurring amino acid

<400> SEQUENCE: 181

Thr Tyr Ala Xaa Gly Val Ser
1               5

<210> SEQ ID NO 182
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 182

Thr Tyr Ala Met Gly Xaa Ser
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is any naturally occurring amino acid

<400> SEQUENCE: 183

Thr Tyr Ala Met Gly Val Xaa
1               5

<210> SEQ ID NO 184
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid

<400> SEQUENCE: 184

Ser Xaa Trp Trp Asn Gly Asn Lys Tyr Asn Asn Pro Ser Leu Lys Ser
1               5                   10                  15

<210> SEQ ID NO 185
<211> LENGTH: 16
```

```
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is any naturally occurring amino acid

<400> SEQUENCE: 185

Ser Ile Trp Xaa Asn Gly Asn Lys Tyr Asn Asn Pro Ser Leu Lys Ser
1               5                   10                  15

<210> SEQ ID NO 186
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid

<400> SEQUENCE: 186

Ser Ile Trp Trp Xaa Gly Asn Lys Tyr Asn Asn Pro Ser Leu Lys Ser
1               5                   10                  15

<210> SEQ ID NO 187
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 187

Ser Ile Trp Trp Asn Xaa Asn Lys Tyr Asn Asn Pro Ser Leu Lys Ser
1               5                   10                  15

<210> SEQ ID NO 188
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is any naturally occurring amino acid

<400> SEQUENCE: 188

Ser Ile Trp Trp Asn Gly Xaa Lys Tyr Asn Asn Pro Ser Leu Lys Ser
1               5                   10                  15

<210> SEQ ID NO 189
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is any naturally occurring amino acid

<400> SEQUENCE: 189
```

-continued

Ser Ile Trp Trp Asn Gly Asn Xaa Tyr Asn Asn Pro Ser Leu Lys Ser
1               5                   10                  15

<210> SEQ ID NO 190
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is any naturally occurring amino acid

<400> SEQUENCE: 190

Ser Ile Trp Trp Asn Gly Asn Lys Xaa Asn Asn Pro Ser Leu Lys Ser
1               5                   10                  15

<210> SEQ ID NO 191
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (10)..(10)
<223> OTHER INFORMATION: Xaa is any naturally occurring amino acid

<400> SEQUENCE: 191

Ser Ile Trp Trp Asn Gly Asn Lys Tyr Xaa Asn Pro Ser Leu Lys Ser
1               5                   10                  15

<210> SEQ ID NO 192
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is any naturally occurring amino acid

<400> SEQUENCE: 192

Ser Ile Trp Trp Asn Gly Asn Lys Tyr Asn Xaa Pro Ser Leu Lys Ser
1               5                   10                  15

<210> SEQ ID NO 193
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is any naturally occurring amino acid

<400> SEQUENCE: 193

Ser Ile Trp Trp Asn Gly Asn Lys Tyr Asn Asn Xaa Ser Leu Lys Ser
1               5                   10                  15

<210> SEQ ID NO 194
<211> LENGTH: 16
<212> TYPE: PRT
<213> ORGANISM: Artificial Sequence
<220> FEATURE:
<223> OTHER INFORMATION: Synthetic Construct
<220> FEATURE:

```
<221> NAME/KEY: MISC_FEATURE
<222> LOCATION: (13)..(13)
<223> OTHER INFORMATION: Xaa is any naturally occurring amino acid

<400> SEQUENCE: 194

Ser Ile Trp Trp Asn Gly Asn Lys Tyr Asn Asn Pro Xaa Leu Lys Ser
1               5                   10                  15

<210> SEQ ID NO 195
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is any naturally occurring amino acid

<400> SEQUENCE: 195

Ser Ile Trp Trp Asn Gly Asn Lys Tyr Asn Asn Pro Ser Xaa Lys Ser
1               5                   10                  15

<210> SEQ ID NO 196
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (16)..(16)
<223> OTHER INFORMATION: Xaa is any naturally occurring amino acid

<400> SEQUENCE: 196

Ser Ile Trp Trp Asn Gly Asn Lys Tyr Asn Asn Pro Ser Leu Lys Xaa
1               5                   10                  15

<210> SEQ ID NO 197
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid

<400> SEQUENCE: 197

Xaa Arg Ile Ile Arg Phe Thr Asp Tyr Val Met Asp Ala
1               5                   10

<210> SEQ ID NO 198
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid

<400> SEQUENCE: 198

Ser Xaa Ile Ile Arg Phe Thr Asp Tyr Val Met Asp Ala
1               5                   10

<210> SEQ ID NO 199
```

```
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is any naturally occurring amino acid

<400> SEQUENCE: 199

Ser Arg Ile Xaa Arg Phe Thr Asp Tyr Val Met Asp Ala
1               5                   10

<210> SEQ ID NO 200
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid

<400> SEQUENCE: 200

Ser Arg Ile Ile Xaa Phe Thr Asp Tyr Val Met Asp Ala
1               5                   10

<210> SEQ ID NO 201
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 201

Ser Arg Ile Ile Arg Xaa Thr Asp Tyr Val Met Asp Ala
1               5                   10

<210> SEQ ID NO 202
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is any naturally occurring amino acid

<400> SEQUENCE: 202

Ser Arg Ile Ile Arg Phe Thr Asp Tyr Val Xaa Asp Ala
1               5                   10

<210> SEQ ID NO 203
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (12)..(12)
<223> OTHER INFORMATION: Xaa is any naturally occurring amino acid

<400> SEQUENCE: 203
```

```
Ser Arg Ile Ile Arg Phe Thr Asp Tyr Val Met Xaa Ala
1               5                   10

<210> SEQ ID NO 204
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (13)..(13)
<223> OTHER INFORMATION: Xaa is any naturally occurring amino acid

<400> SEQUENCE: 204

Ser Arg Ile Ile Arg Phe Thr Asp Tyr Val Met Asp Xaa
1               5                   10

<210> SEQ ID NO 205
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid

<400> SEQUENCE: 205

Xaa Ala Ser Glu Asp Ile Tyr Asn Asp Leu Ala
1               5                   10

<210> SEQ ID NO 206
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid

<400> SEQUENCE: 206

Arg Xaa Ser Glu Asp Ile Tyr Asn Asp Leu Ala
1               5                   10

<210> SEQ ID NO 207
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 207

Arg Ala Xaa Glu Asp Ile Tyr Asn Asp Leu Ala
1               5                   10

<210> SEQ ID NO 208
<211> LENGTH: 11
<212> TYPE: PRT
<213> ORGANISM: Artificial Sequence
<220> FEATURE:
<223> OTHER INFORMATION: Synthetic Construct
```

```
<220> FEATURE:
<221> NAME/KEY: MISC_FEATURE
<222> LOCATION: (4)..(4)
<223> OTHER INFORMATION: Xaa is any naturally occurring amino acid

<400> SEQUENCE: 208

Arg Ala Ser Xaa Asp Ile Tyr Asn Asp Leu Ala
1               5                   10

<210> SEQ ID NO 209
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid

<400> SEQUENCE: 209

Arg Ala Ser Glu Xaa Ile Tyr Asn Asp Leu Ala
1               5                   10

<210> SEQ ID NO 210
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 210

Arg Ala Ser Glu Asp Xaa Tyr Asn Asp Leu Ala
1               5                   10

<210> SEQ ID NO 211
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is any naturally occurring amino acid

<400> SEQUENCE: 211

Arg Ala Ser Glu Asp Ile Xaa Asn Asp Leu Ala
1               5                   10

<210> SEQ ID NO 212
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (8)..(8)
<223> OTHER INFORMATION: Xaa is any naturally occurring amino acid

<400> SEQUENCE: 212

Arg Ala Ser Glu Asp Ile Tyr Xaa Asp Leu Ala
1               5                   10
```

```
<210> SEQ ID NO 213
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (11)..(11)
<223> OTHER INFORMATION: Xaa is any naturally occurring amino acid

<400> SEQUENCE: 213

Arg Ala Ser Glu Asp Ile Tyr Asn Asp Leu Xaa
1               5                   10

<210> SEQ ID NO 214
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid

<400> SEQUENCE: 214

Xaa Ala Asn Ser Leu His Thr
1               5

<210> SEQ ID NO 215
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid

<400> SEQUENCE: 215

Asn Xaa Asn Ser Leu His Thr
1               5

<210> SEQ ID NO 216
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 216

Asn Ala Xaa Ser Leu His Thr
1               5

<210> SEQ ID NO 217
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is any naturally occurring amino acid
```

```
<400> SEQUENCE: 217

Asn Ala Asn Xaa Leu His Thr
1               5

<210> SEQ ID NO 218
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid

<400> SEQUENCE: 218

Asn Ala Asn Ser Xaa His Thr
1               5

<210> SEQ ID NO 219
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 219

Asn Ala Asn Ser Leu Xaa Thr
1               5

<210> SEQ ID NO 220
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (7)..(7)
<223> OTHER INFORMATION: Xaa is any naturally occurring amino acid

<400> SEQUENCE: 220

Asn Ala Asn Ser Leu His Xaa
1               5

<210> SEQ ID NO 221
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid

<400> SEQUENCE: 221

Xaa Gln Tyr Tyr Asp Tyr Pro Leu Thr
1               5

<210> SEQ ID NO 222
<211> LENGTH: 9
<212> TYPE: PRT
<213> ORGANISM: Artificial Sequence
<220> FEATURE:
```

```
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid

<400> SEQUENCE: 222

Gln Xaa Tyr Tyr Asp Tyr Pro Leu Thr
1               5

<210> SEQ ID NO 223
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is any naturally occurring amino acid

<400> SEQUENCE: 223

Gln Gln Xaa Tyr Asp Tyr Pro Leu Thr
1               5

<210> SEQ ID NO 224
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (9)..(9)
<223> OTHER INFORMATION: Xaa is any naturally occurring amino acid

<400> SEQUENCE: 224

Gln Gln Tyr Tyr Asp Tyr Pro Leu Xaa
1               5

<210> SEQ ID NO 225
<211> LENGTH: 16
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid

<400> SEQUENCE: 225

Xaa Ile Trp Trp Asn Gly Asn Lys Tyr Asn Asn Pro Ser Leu Lys Ser
1               5                   10                  15

<210> SEQ ID NO 226
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid

<400> SEQUENCE: 226

Gln Gln Tyr Tyr Xaa Tyr Pro Leu Thr
1               5
```

```
<210> SEQ ID NO 227
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(2)
<223> OTHER INFORMATION: Xaa is any naturally occurring amino acid
<220> FEATURE:
<221> NAME/KEY: MISC_FEATURE
<222> LOCATION: (4)..(4)
<223> OTHER INFORMATION: Xaa is any naturally occurring amino acid
<220> FEATURE:
<221> NAME/KEY: MISC_FEATURE
<222> LOCATION: (5)..(5)
<223> OTHER INFORMATION: Xaa is any naturally occurring amino acid
      except for Arg
<220> FEATURE:
<221> NAME/KEY: MISC_FEATURE
<222> LOCATION: (6)..(6)
<223> OTHER INFORMATION: Xaa is any naturally occurring amino acid
<220> FEATURE:
<221> NAME/KEY: MISC_FEATURE
<222> LOCATION: (11)..(13)
<223> OTHER INFORMATION: Xaa is any naturally occurring amino acid

<400> SEQUENCE: 227

Xaa Xaa Ile Xaa Xaa Xaa Thr Asp Tyr Val Xaa Xaa Xaa
1               5                   10

<210> SEQ ID NO 228
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (1)..(1)
<223> OTHER INFORMATION: Xaa is any naturally occurring amino acid
<220> FEATURE:
<221> NAME/KEY: MISC_FEATURE
<222> LOCATION: (5)..(5)
<223> OTHER INFORMATION: Xaa is any naturally occurring amino acid
      except for Arg

<400> SEQUENCE: 228

Xaa Arg Ile Ile Xaa Phe Thr Asp Tyr Val Met Asp Ala
1               5                   10

<210> SEQ ID NO 229
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (2)..(2)
<223> OTHER INFORMATION: Xaa is any naturally occurring amino acid
<220> FEATURE:
<221> NAME/KEY: MISC_FEATURE
<222> LOCATION: (5)..(5)
<223> OTHER INFORMATION: Xaa is any naturally occurring amino acid
      except for Arg

<400> SEQUENCE: 229

Ser Xaa Ile Ile Xaa Phe Thr Asp Tyr Val Met Asp Ala
1               5                   10
```

```
<210> SEQ ID NO 230
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (4)..(4)
<223> OTHER INFORMATION: Xaa is any naturally occurring amino acid
<220> FEATURE:
<221> NAME/KEY: MISC_FEATURE
<222> LOCATION: (5)..(5)
<223> OTHER INFORMATION: Xaa is any naturally occurring amino acid
      except for Arg

<400> SEQUENCE: 230

Ser Arg Ile Xaa Xaa Phe Thr Asp Tyr Val Met Asp Ala
1               5                   10

<210> SEQ ID NO 231
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid
      except for Arg

<400> SEQUENCE: 231

Ser Arg Ile Ile Xaa Phe Thr Asp Tyr Val Met Asp Ala
1               5                   10

<210> SEQ ID NO 232
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid
      except for Arg
<220> FEATURE:
<221> NAME/KEY: MISC_FEATURE
<222> LOCATION: (6)..(6)
<223> OTHER INFORMATION: Xaa is any naturally occurring amino acid

<400> SEQUENCE: 232

Ser Arg Ile Ile Xaa Xaa Thr Asp Tyr Val Met Asp Ala
1               5                   10

<210> SEQ ID NO 233
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid
      except for Arg
<220> FEATURE:
<221> NAME/KEY: MISC_FEATURE
<222> LOCATION: (11)..(11)
<223> OTHER INFORMATION: Xaa is any naturally occurring amino acid

<400> SEQUENCE: 233
```

```
Ser Arg Ile Ile Xaa Phe Thr Asp Tyr Val Xaa Asp Ala
1               5                   10
```

<210> SEQ ID NO 234
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid
      except for Arg
<220> FEATURE:
<221> NAME/KEY: MISC_FEATURE
<222> LOCATION: (12)..(12)
<223> OTHER INFORMATION: Xaa is any naturally occurring amino acid

<400> SEQUENCE: 234

```
Ser Arg Ile Ile Xaa Phe Thr Asp Tyr Val Met Xaa Ala
1               5                   10
```

<210> SEQ ID NO 235
<211> LENGTH: 13
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (5)..(5)
<223> OTHER INFORMATION: Xaa is any naturally occurring amino acid
      except for Arg
<220> FEATURE:
<221> NAME/KEY: MISC_FEATURE
<222> LOCATION: (13)..(13)
<223> OTHER INFORMATION: Xaa is any naturally occurring amino acid

<400> SEQUENCE: 235

```
Ser Arg Ile Ile Xaa Phe Thr Asp Tyr Val Met Asp Xaa
1               5                   10
```

ANTIBODIES TO LILRB2

SEQUENCE LISTING

The instant application contains a Sequence Listing which has been submitted electronically in ASCII format and is hereby incorporated by reference in its entirety. Said ASCII copy, created on Dec. 13, 2018 is named 51266-002002_Sequence_Listing_12.13.18_ST25 and is 206,026 bytes in size.

BACKGROUND

Myeloid cells, such as dendritic cells and macrophages, can instruct the adaptive immune system to mount a response against tumor cells and pathogens by presenting peptide antigens to T cells while expressing immunogenic cytokines and costimulatory signals, thereby promoting cytotoxic T cell activation and proliferation. Conversely, in a steady state condition, myeloid cells maintain tolerance to endogenous proteins by presenting self-antigens to T cells in the context of non-immunogenic signals, such as regulatory cytokines, which can promote regulatory T cells and suppress immunogenicity.

Cancer cells can evade the immune system by engaging signaling pathways associated with immunosuppressive or immunoregulatory antigen presentation. Such evasion events represent a major obstacle to therapeutic strategies that rely on promoting anti-tumor immunity. Therefore, there is a need for therapeutic compositions and methods that prevent tumor-induced immunosuppression and promote immunogenic presentation of tumor antigens by myeloid cells.

SUMMARY

The present invention features antibodies that specifically bind to human LILRB2. Also provided are compositions of the anti-LILRB2 antibodies and methods of using the anti-LILRB2 antibodies and compositions thereof.

In one aspect, the invention provides antibodies that specifically binds to human LILRB2, wherein the antibody comprises the following complementarity determining regions (CDRs): (a) a CDR-H1 comprising the amino acid sequence of JY(J)$_2$G(J)$_2$ (SEQ ID NO: 171); (b) a CDR-H2 comprising the amino acid sequence of (J)$_2$W(J)$_{11}$KJ (SEQ ID NO: 172); (c) a CDR-H3 comprising the amino acid sequence of (J)$_2$I(J)$_3$TDYV(J)$_3$ (SEQ ID NO: 173); (d) a CDR-L1 comprising the amino acid sequence of (J)$_8$DLJ (SEQ ID NO: 174); (e) a CDR-L2 comprising the amino acid sequence of (J)$_7$ (SEQ ID NO: 175); and (f) a CDR-L3 comprising the amino acid sequence of (J)$_3$YJYPLJ (SEQ ID NO: 176); wherein each J is independently a naturally occurring amino acid (see, e.g., Table 1, below).

In some embodiments, the CDR-H2 comprises the amino acid sequence of SJW(J)$_{11}$KJ (SEQ ID NO: 177) and/or the CDR-L3 comprises the amino acid sequence of (J)$_3$YDYPLJ (SEQ ID NO: 178).

In some embodiments, the CDR-H1 comprises the amino acid sequence of: (i) TYAMGVS (SEQ ID NO: 15); (ii) JYAMGVS (SEQ ID NO: 179); (iii) TYJMGVS (SEQ ID NO: 180); (iv) TYAJGVS (SEQ ID NO: 181); (v) TYAMGJS (SEQ ID NO: 182); (vi) TYAMGVJ (SEQ ID NO: 183); or (vii) a variant of any one of (ii) to (vi) comprising an additional J amino acid in place of a recited amino acid that is represented by a J in SEQ ID NO: 171. Thus, when a variant sequence is aligned with SEQ ID NO: 171, it maintains the non-J amino acids that are set forth in SEQ ID NO: 171. The additional J amino acid in the variant thus aligns with an amino acid that is a J in SEQ ID NO: 171.

In some embodiments, the CDR-H2 comprises the amino acid sequence of: (i) SIWWNGNKYNNPSLKS (SEQ ID NO: 16); (ii) SJWWNGNKYNNPSLKS (SEQ ID NO: 184); (iii) SIWJNGNKYNNPSLKS (SEQ ID NO: 185); (iv) SIWWJGNKYNNPSLKS (SEQ ID NO: 186); (v) SIWWNJNKYNNPSLKS (SEQ ID NO: 187); (vi) SIWWNGJKYNNPSLKS (SEQ ID NO: 188); (vii) SIWWNGNJYNNPSLKS (SEQ ID NO: 189); (viii) SIWWNGNKJNNPSLKS (SEQ ID NO: 190); (ix) SIWWNGNKYJNPSLKS (SEQ ID NO: 191); (x) SIWWNGNKYNJPSLKS (SEQ ID NO: 192); (xi) SIWWNGNKYNNJSLKS (SEQ ID NO: 193); (xii) SIWWNGNKYNNPJLKS (SEQ ID NO: 194); (xiii) SIWWNGNKYNNPSJKS (SEQ ID NO: 195); (xiv) SIWWNGNKYNNPSLKJ (SEQ ID NO: 196); or (xv) a variant of any one of (ii) to (xiv) comprising an additional J amino acid in place of a recited amino acid that is represented by a J in SEQ ID NO: 172. Thus, when a variant sequence is aligned with SEQ ID NO: 172, it maintains the non-J amino acids that are set forth in SEQ ID NO: 172. The additional J amino acid in the variant thus aligns with an amino acid that is a J in SEQ ID NO: 172

In some embodiments, the CDR-H3 comprises the amino acid sequence of: (i) SRIIRFTDYVMDA (SEQ ID NO: 17); (ii) JRIIRFTDYVMDA (SEQ ID NO: 197); (iii) SJIIRFTDYVMDA (SEQ ID NO: 198); (iv) SRIJRFTDYVMDA (SEQ ID NO: 199); (v) SRIIJFTDYVMDA (SEQ ID NO: 200); (vi) SRIIRJTDYVMDA (SEQ ID NO: 201); (vii) SRIIRFTDYVJDA (SEQ ID NO: 202); (viii) SRIIRFTDYVMJA (SEQ ID NO: 203); (ix) SRIIRFTDYVMDJ (SEQ ID NO: 204); or (x) a variant of any one of (ii) to (ix) comprising an additional J amino acid in place of a recited amino acid that is represented by a J in SEQ ID NO: 173. Thus, when a variant sequence is aligned with SEQ ID NO: 173, it maintains the non-J amino acids that are set forth in SEQ ID NO: 173. The additional J amino acid in the variant thus aligns with an amino acid that is a J in SEQ ID NO: 173.

In some embodiments, the CDR-L1 comprises the amino acid sequence of: (i) RASEDIYNDLA (SEQ ID NO: 18); (ii) JASEDIYNDLA (SEQ ID NO: 205); (iii) RJSEDIYNDLA (SEQ ID NO: 206); (iv) RAJEDIYNDLA (SEQ ID NO: 207); (v) RASJDIYNDLA (SEQ ID NO: 208); (vi) RASEJIYNDLA (SEQ ID NO: 209); (vii) RASEDJYNDLA (SEQ ID NO: 210); (viii) RASEDIJNDLA (SEQ ID NO: 211); (ix) RASEDIYJDLA (SEQ ID NO: 212); (x) RASEDIYNDLJ (SEQ ID NO: 213); or (xi) a variant of any one of (ii) to (x) comprising an additional J amino acid in place of a recited amino acid that is represented by a J in SEQ ID NO: 174. Thus, when a variant sequence is aligned with SEQ ID NO: 174, it maintains the non-J amino acids that are set forth in SEQ ID NO: 174. The additional J amino acid in the variant thus aligns with an amino acid that is a J in SEQ ID NO: 174.

In some embodiments, the CDR-L2 comprises the amino acid sequence of: (i) NANSLHT (SEQ ID NO: 19); (ii) JANSLHT (SEQ ID NO: 214); (iii) NJNSLHT (SEQ ID NO: 215); (iv) NAJSLHT (SEQ ID NO: 216); (v) NANJLHT (SEQ ID NO: 217); (vi) NANSJHT (SEQ ID NO: 218); (vii) NANSLJT (SEQ ID NO: 219); (viii) NANSLHJ (SEQ ID NO: 220); or (ix) a variant of any one of (ii) to (viii) comprising an additional J amino acid in place of a recited amino acid that is represented by a J in SEQ ID NO: 175. Thus, when a variant sequence is aligned with SEQ ID NO: 175, it maintains the non-J amino acids that are set forth in SEQ ID NO: 175. The additional J amino acid in the variant thus aligns with an amino acid that is a J in SEQ ID NO: 175.

In some embodiments, the CDR-L3 comprises the amino acid sequence of: (i) QQYYDYPLT (SEQ ID NO: 20); (ii) JQYYDYPLT (SEQ ID NO: 221); (iii) QJYYDYPLT (SEQ ID NO: 222); (iv) QQJYDYPLT (SEQ ID NO: 223); (v) QQYYDYPLJ (SEQ ID NO: 224); or (vi) a variant of any one of (ii) to (v) comprising an additional J amino acid in place of a recited amino acid that is represented by a J in SEQ ID NO: 176. Thus, when a variant sequence is aligned with SEQ ID NO: 176, it maintains the non-J amino acids that are set forth in SEQ ID NO: 176. The additional J amino acid in the variant thus aligns with an amino acid that is a J in SEQ ID NO: 176.

In some embodiments, the CDR-H2 comprises the amino acid sequence of JIWWNGNKYNNPSLKS (SEQ ID NO: 225), or a variant thereof comprising an additional J amino acid in place of a recited amino acid that is represented by a J in SEQ ID NO: 172, and/or the CDR-L3 comprises the amino acid sequence of QQYYJYPLT (SEQ ID NO: 226), or a variant thereof comprising an additional J amino acid in place of a recited amino acid that is represented by a J in SEQ ID NO: 176. Thus, when a variant sequence is aligned with SEQ ID NO: 176, it maintains the non-J amino acids that are set forth in SEQ ID NO: 176. The additional J amino acid in the variant thus aligns with an amino acid that is a J in SEQ ID NO: 176.

In various embodiments of the above, one or more of the CDRs comprises said additional J amino acid. In additional embodiments, one or more of the CDRs comprises 2, 3, 4, 5, 6, 7, 8, 9, 10, or more additional J amino acids. In these additional embodiments, each of the additional J amino acids aligns with an amino acid that is a J in the respective generic formula for the CDR. The specifically recited amino acids of a generic formula are maintained.

In some embodiments, the CDR-H3 comprises the amino acid sequence of $(J)_2IJXJTDYV(J)_3$ (SEQ ID NO: 227), wherein X is not arginine. In some embodiments, X is selected from the group consisting of aspartate, glutamate, and alanine. In some embodiments, the CDR-H3 comprises the sequence of: (i) JRIIXFTDYVMDA (SEQ ID NO: 228); (ii) SJIIXFTDYVMDA (SEQ ID NO: 229); (iii) SRIJXFT-DYVMDA (SEQ ID NO: 230); (iv) SRIIXFTDYVMDA (SEQ ID NO: 231); (v) SRIIXJTDYVMDA (SEQ ID NO: 232); (vi) SRIIXFTDYVJDA (SEQ ID NO: 233); (vii) SRIIXFTDYVMJA (SEQ ID NO: 234); (viii) SRIIXFT-DYVMDJ (SEQ ID NO: 235); or (ix) a variant of any one of (ii) to (iii) or (v) to (viii) comprising an additional J amino acid in place of a recited amino acid that is represented by a J in SEQ ID NO: 173.

In some embodiments, the antibody comprises a variable heavy chain ($V_H$) region comprising an amino acid sequence that is at least 90% identical to the amino acid sequence of SEQ ID NO: 3, 13, 23, 33, 43, 53, 63, 73, 83, 93, 103, or 113, and/or a variable light chain ($V_L$) region comprising an amino acid sequence that is at least 90% identical to the amino acid sequence of SEQ ID NO: 4, 14, 24, 34, 44, 54, 64, 74, 84, 94, 104, or 114. It is to be understood herein that if a sequence is required in an independent claim and a dependent claim permits variability in a larger sequence encompassing the sequence of the independent claim, that the variability is not applicable to the sequence required in the independent claim, In some embodiments, the antibody comprises a variable heavy chain ($V_H$) region comprising the amino acid sequence of SEQ ID NO: 3, 13, 23, 33, 43, 53, 63, 73, 83, 93, 103, or 113, and/or a variable light chain ($V_L$) region comprising the amino acid sequence of SEQ ID NO: 4, 14, 24, 34, 44, 54, 64, 74, 84, 94, 104, or 114.

In some embodiments, the antibody comprises a heavy chain comprising an amino acid sequence that is at least 90% identical to the amino acid sequence of SEQ ID NO: 1, 11, 21, 31, 41, 51, 61, 71, 81, 91, 101, or 111, and/or a light chain comprising an amino acid sequence that is at least 90% identical to the amino acid sequence of SEQ ID NO: 2, 22, 32, 42, 52, 62, 72, 82, 92, 102, or 112.

In another aspect, the invention provides an antibody that specifically binds to human LILRB2, wherein the antibody comprises the following six complementarity determining regions (CDRs): (a) a CDR-H1 comprising the amino acid sequence of SEQ ID NO: 15; (b) a CDR-H2 comprising the amino acid sequence of SEQ ID NO: 16; (c) a CDR-H3 comprising the amino acid sequence of SEQ ID NO: 17; (d) a CDR-L1 comprising the amino acid sequence of SEQ ID NO: 18; (e) a CDR-L2 comprising the amino acid sequence of SEQ ID NO: 19; and (f) a CDR-L3 comprising the amino acid sequence of SEQ ID NO: 20.

In some embodiments, the antibody comprises a variable heavy chain ($V_H$) region comprising an amino acid sequence that is at least 90% identical to the amino acid sequence of SEQ ID NO: 13 and a variable light chain ($V_L$) region comprising an amino acid sequence that is at least 90% identical to the amino acid sequence of SEQ ID NO: 14, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In some embodiments, the antibody comprises a $V_H$ region comprising the amino acid sequence of SEQ ID NO: 13 and a $V_L$ region comprising the amino acid sequence of SEQ ID NO: 14. In some embodiments, the antibody comprises a heavy chain comprising the amino acid sequence of SEQ ID NO: 11 and a light chain comprising the amino acid sequence of SEQ ID NO: 12.

In some embodiments, the antibody comprises a $V_H$ region comprising an amino acid sequence that is at least 90% identical to the amino acid sequence of SEQ ID NO: 53 and a $V_L$ region comprising an amino acid sequence that is at least 90% identical to the amino acid sequence of SEQ ID NO: 54, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In particular embodiments, the antibody comprises a $V_H$ region comprising the amino acid sequence of SEQ ID NO: 53 and a variable light chain $V_L$ region comprising the amino acid sequence of SEQ ID NO: 54. In some embodiments, the antibody comprises a heavy chain comprising the amino acid sequence of SEQ ID NO: 51 and a light chain comprising the amino acid sequence of SEQ ID NO: 52.

In other embodiments, the antibody comprises a $V_H$ region comprising an amino acid sequence that is at least 90% identical to the amino acid sequence of SEQ ID NO: 63 and a $V_L$ region comprising an amino acid sequence that is at least 90% identical to the amino acid sequence of SEQ ID NO: 64, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In some embodiments, the antibody comprises a $V_H$ region comprising the amino acid sequence of SEQ ID NO: 63 and a $V_L$ region comprising the amino acid sequence of SEQ ID NO: 64. In some embodiments, the antibody comprises a heavy chain comprising the amino acid sequence of SEQ ID NO: 61 and a light chain comprising the amino acid sequence of SEQ ID NO: 62.

In some embodiments, the antibody comprises a $V_H$ region comprising an amino acid sequence that is at least 90% identical to the amino acid sequence of SEQ ID NO: 73 and a $V_L$ region comprising an amino acid sequence that is at least 90% identical to the amino acid sequence of SEQ ID NO: 74, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In particular embodiments, the antibody comprises a $V_H$ region comprising the amino acid sequence of SEQ ID NO: 73 and a $V_L$ region comprising the amino acid sequence of SEQ ID NO: 74. In some embodiments, the antibody comprises a heavy chain comprising the amino acid sequence of SEQ ID NO: 71 and a light chain comprising the amino acid sequence of SEQ ID NO: 72.

In other embodiments, the antibody comprises a $V_H$ region comprising an amino acid sequence that is at least 90% identical to the amino acid sequence of SEQ ID NO: 83 and a $V_L$ region comprising an amino acid sequence that is at least 90% identical to the amino acid sequence of SEQ ID NO: 84, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In some embodiments, the antibody comprises a $V_H$ region comprising the amino acid sequence of SEQ ID NO: 83 and a $V_L$ region comprising the amino acid sequence of SEQ ID NO: 84. In particular embodiments, the antibody comprises a heavy chain comprising the amino acid sequence of SEQ ID NO: 81 and a light chain comprising the amino acid sequence of SEQ ID NO: 82.

In other embodiments, the antibody comprises a $V_H$ region comprising an amino acid sequence that is at least 90% identical to the amino acid sequence of SEQ ID NO: 93 and a $V_L$ region comprising an amino acid sequence that is at least 90% identical to the amino acid sequence of SEQ ID NO: 94, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In some embodiments, the antibody comprises a $V_H$ region comprising the amino acid sequence of SEQ ID NO: 93 and a $V_L$ region comprising the amino acid sequence of SEQ ID NO: 94. In particular embodiments, the antibody comprises a heavy chain comprising the amino acid sequence of SEQ ID NO: 91 and a light chain comprising the amino acid sequence of SEQ ID NO: 92.

In other embodiments, the antibody comprises a $V_H$ region comprising an amino acid sequence that is at least 90% identical to the amino acid sequence of SEQ ID NO: 103 and a $V_L$ region comprising an amino acid sequence that is at least 90% identical to the amino acid sequence of SEQ ID NO: 104, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In some embodiments, the antibody comprises a $V_H$ region comprising the amino acid sequence of SEQ ID NO: 103 and a $V_L$ region comprising the amino acid sequence of SEQ ID NO: 104. In particular embodiments, the antibody comprises a heavy chain comprising the amino acid sequence of SEQ ID NO: 101 and a light chain comprising the amino acid sequence of SEQ ID NO: 102.

In other embodiments, the antibody comprises a $V_H$ region comprising an amino acid sequence that is at least 90% identical to the amino acid sequence of SEQ ID NO: 113 and a $V_L$ region comprising an amino acid sequence that is at least 90% identical to the amino acid sequence of SEQ ID NO: 114, wherein the $V_H$ region comprises three CDRs comprising the amino acid sequences of SEQ ID NOs: 15-17, and the $V_L$ region comprises three CDRs comprising the amino acid sequences of SEQ ID NOs: 18-20. In some embodiments, the antibody comprises a $V_H$ region comprising the amino acid sequence of SEQ ID NO: 113 and a $V_L$ region comprising the amino acid sequence of SEQ ID NO: 114. In particular embodiments, the antibody comprises a heavy chain comprising the amino acid sequence of SEQ ID NO: 111 and a light chain comprising the amino acid sequence of SEQ ID NO: 112.

In another aspect, the invention provides an antibody that specifically binds to human LILRB2, wherein the antibody comprises the following six CDRs: (a) a CDR-H1 comprising the amino acid sequence of SEQ ID NO: 5; (b) a CDR-H2 comprising the amino acid sequence of SEQ ID NO: 6; (c) a CDR-H3 comprising the amino acid sequence of SEQ ID NO: 7; (d) a CDR-L1 comprising the amino acid sequence of SEQ ID NO: 8; (e) a CDR-L2 comprising the amino acid sequence of SEQ ID NO: 9; and (f) a CDR-L3 comprising the amino acid sequence of SEQ ID NO: 10.

In some embodiments, the antibody comprises a $V_H$ region comprising an amino acid sequence that is at least 90% identical to the amino acid sequence of SEQ ID NO: 3 and a $V_L$ region comprising an amino acid sequence that is at least 90% identical to the amino acid sequence of SEQ ID NO: 4, wherein the $V_H$ region comprises three CDRs comprising the amino acid sequences of SEQ ID NOs: 5-7, and the $V_L$ region comprises three CDRs comprising the amino acid sequences of SEQ ID NOs: 8-10. In some embodiments, the antibody comprises a $V_H$ region comprising the amino acid sequence of SEQ ID NO: 3 and a $V_L$ region comprising the amino acid sequence of SEQ ID NO: 4. In particular embodiments, the antibody comprises a heavy chain comprising the amino acid sequence of SEQ ID NO: 1 and a light chain comprising the amino acid sequence of SEQ ID NO: 2.

In another aspect, the invention features an antibody that specifically binds to human LILRB2, wherein the antibody comprises the following six CDRs: (a) a CDR-H1 comprising the amino acid sequence of SEQ ID NO: 25; (b) a CDR-H2 comprising the amino acid sequence of SEQ ID NO: 26; (c) a CDR-H3 comprising the amino acid sequence of SEQ ID NO: 27; (d) a CDR-L1 comprising the amino acid sequence of SEQ ID NO: 28; (e) a CDR-L2 comprising the amino acid sequence of SEQ ID NO: 29; and (f) a CDR-L3 comprising the amino acid sequence of SEQ ID NO: 30.

In some embodiments, the antibody comprises a $V_H$ region comprising an amino acid sequence that is at least 90% identical to the amino acid sequence of SEQ ID NO: 23 and a $V_L$ region comprising an amino acid sequence that is at least 90% identical to the amino acid sequence of SEQ ID NO: 24, wherein the $V_H$ region comprises three CDRs comprising the amino acid sequences of SEQ ID NOs: 25-27, and the $V_L$ region comprises three CDRs comprising the amino acid sequences of SEQ ID NOs: 28-30. In some embodiments, the antibody comprises a $V_H$ region comprising the amino acid sequence of SEQ ID NO: 23 and a $V_L$ region comprising the amino acid sequence of SEQ ID NO: 24. In some embodiments, the antibody comprises a heavy chain comprising the amino acid sequence of SEQ ID NO: 21 and a light chain comprising the amino acid sequence of SEQ ID NO: 22.

In another aspect, the invention features an antibody that specifically binds to human LILRB2, wherein the antibody comprises the following six CDRs: (a) a CDR-H1 comprising the amino acid sequence of SEQ ID NO: 35; (b) a CDR-H2 comprising the amino acid sequence of SEQ ID NO: 36; (c) a CDR-H3 comprising the amino acid sequence of SEQ ID NO: 37; (d) a CDR-L1 comprising the amino acid sequence of SEQ ID NO: 38; (e) a CDR-L2 comprising the amino acid sequence of SEQ ID NO: 39; and (f) a CDR-L3 comprising the amino acid sequence of SEQ ID NO: 40.

In some embodiments, the antibody comprises a $V_H$ region comprising an amino acid sequence that is at least 90% identical to the amino acid sequence of SEQ ID NO: 33 and a $V_L$ region comprising an amino acid sequence that is at least 90% identical to the amino acid sequence of SEQ ID NO: 34, wherein the $V_H$ region comprises three CDRs comprising the amino acid sequences of SEQ ID NOs: 35-37, and the $V_L$ region comprises three CDRs comprising the amino acid sequences of SEQ ID NOs: 38-40. In some embodiments, the antibody comprises a $V_H$ region comprising the amino acid sequence of SEQ ID NO: 33 and a $V_L$ region comprising the amino acid sequence of SEQ ID NO: 34. In some embodiments, the antibody comprises a heavy chain comprising the amino acid sequence of SEQ ID NO: 31 and a light chain comprising the amino acid sequence of SEQ ID NO: 32.

In another aspect, the invention features an antibody that specifically binds to human LILRB2, wherein the antibody comprises the following six CDRs: (a) a CDR-H1 comprising the amino acid sequence of SEQ ID NO: 45; (b) a CDR-H2 comprising the amino acid sequence of SEQ ID NO: 46; (c) a CDR-H3 comprising the amino acid sequence of SEQ ID NO: 47; (d) a CDR-L1 comprising the amino acid sequence of SEQ ID NO: 48; (e) a CDR-L2 comprising the amino acid sequence of SEQ ID NO: 49; and (f) a CDR-L3 comprising the amino acid sequence of SEQ ID NO: 50.

In some embodiments, the antibody comprises a $V_H$ region comprising an amino acid sequence that is at least 90% identical to the amino acid sequence of SEQ ID NO: 43 and a $V_L$ region comprising an amino acid sequence that is at least 90% identical to the amino acid sequence of SEQ ID NO: 44, wherein the $V_H$ region comprises three CDRs comprising the amino acid sequences of SEQ ID NOs: 45-47, and the $V_L$ region comprises three CDRs comprising the amino acid sequences of SEQ ID NOs: 48-50. In some embodiments, the antibody comprises a $V_H$ region comprising the amino acid sequence of SEQ ID NO: 43 and a $V_L$ region comprising the amino acid sequence of SEQ ID NO: 44. In some embodiments, the antibody comprises a heavy chain comprising the amino acid sequence of SEQ ID NO: 41 and a light chain comprising the amino acid sequence of SEQ ID NO: 42.

In some embodiments of any of the antibodies described herein, e.g., those described above, the heavy chain of the antibody additionally comprises a C-terminal lysine.

With respect to all of the aspects and embodiments summarized above, when a specific sequence is referenced, the invention also includes variants of the sequences. In various embodiments, a variant can be specified as including 1, 2, 3, 4, 5, 6, 7, 8, 9, 10, or more substitutions of a recited sequence.

In another aspect, the invention features an antibody that cross-competes for binding to human LILRB2 with an antibody of the preceding aspects.

In another aspect, the invention features an antibody that specifically binds to human LILRB2 and blocks the binding of HLA-G and/or HLA-A2 to human LILRB2. In some embodiments, the blocking is determined in a HLA-G tetramer blocking assay using human monocyte-derived macrophages, human myeloid cells, and/or a cell line expressing LILRB2. In some embodiments, the assay includes the use of HLA-G conjugated beads. In some embodiments, the antibody blocks HLA-G tetramer with an $EC_{50}$ of less than 20 nM (e.g., less than 10 nM, less than 5 nM, less than 2 nM, less than 1.0 nM, less than 0.5 nM, or less than 0.2 nM). In some embodiments, the antibody blocks HLA-G tetramer with an $EC_{50}$ of less than 0.2 nM. In some embodiments, the blocking is determined in a HLA-A2 tetramer blocking assay using human monocyte-derived macrophages. In some embodiments, the antibody blocks HLA-A2 tetramer with an $EC_{50}$ of less than 20 nM (e.g., less than 10 nM, less than 5 nM, less than 2 nM, less than 1.0 nM, less than 0.5 nM, or less than 0.2 nM). In some embodiments, the antibody blocks HLA-A2 tetramer with an $EC_{50}$ of less than 0.2 nM. In any of the foregoing embodiments, in which the antibody specifically binds to human LILRB2 and blocks the binding of HLA-G and/or HLA-A2 to human LILRB2, the antibody can be any of the antibodies of any other one or more aspects of the invention.

In another aspect, the invention provides an antibody that specifically binds to human LILRB2, wherein said antibody is capable of converting an M2-like macrophage to an M1-like macrophage. In some embodiments, the conversion of an M2-like macrophage to an M1-like macrophage is indicated by an increased expression of one or more genes (e.g., one, two, three, four, five, or all six genes) selected from the group consisting of CXCL9, CXCL11, IRF1, TAP1, IL6R, and IL15. Additionally or alternatively, in some embodiments, the conversion of an M2-like macrophage to an M1-like macrophage is indicated by a decreased expression of one or more genes (e.g., one, two, three, four, five, six, seven, eight, or nine genes) selected from the group consisting of IL-10, CCL2, TGFBR2, CXCL13, IL21R, CD36, CR1, C1QB, and TGFBI. In some embodiments, the conversion of an M2-like macrophage to an M1-like macrophage is detected using a tumor histoculture assay. In some embodiments, the conversion of an M2-like macrophage to an M1-like macrophage is detected using a primary human macrophage assay using human monocyte-derived macrophages. In some embodiments, the conversion of an M2-like macrophage to an M1-like macrophage is indicated by an increased expression of one, two, or all three cytokines selected from the group consisting of TNFα, IL-1β, and IL-6, and/or the conversion of an M2-like macrophage to an M1-like macrophage is indicated by decreased expression of one or both cytokines selected from the group consisting of IL-10 and CCL-2. In any of the foregoing embodiments, in which the antibody is capable of converting an M2-like macrophage to an M1-like macrophage, the antibody can be any of the antibodies of any other one or more aspects of the invention.

In some embodiments of any of the preceding aspects, the antibody binds to LILRB2 with a dissociation constant ($K_D$) of less than 3.0 nM (e.g., less than 1.5 nM, less than 1.0 nM, or less than 750 pM).

In some embodiments of any of the preceding aspects, the antibody is a monoclonal antibody. In some embodiments of any of the preceding aspects, the antibody is a chimeric antibody, a humanized antibody, a CDR-grafted antibody, or a human antibody. In some embodiments of any of the preceding aspects, the antibody includes an Fc region selected from the group consisting of a native Fc region, a variant Fc region, and a functional Fc region. In some embodiments of any of the preceding aspects, the antibody is a conjugate antibody or is detectably labeled. In some embodiments of any of the preceding aspects, the antibody is an IgG1 antibody, an IgG2 antibody, an IgG3 antibody, or an IgG4 antibody.

In all aspects of the invention, if an optional more specific embodiment is not consistent with a more general embodiment, then it may be considered as excluded from the general embodiment.

In another aspect, the invention provides a nucleic acid molecule encoding a polypeptide of the antibody of any of the preceding aspects.

In another aspect, the invention provides a host cell or vector including a nucleic acid molecule encoding a polypeptide of the antibody of any of the preceding aspects.

In another aspect, the invention features a pharmaceutical composition comprising the antibody of any of the preceding aspects or a nucleic acid molecule encoding the antibody of any of the preceding aspects.

In another aspect, the invention provides a method of treating a disease in a subject in need thereof, the method including administering to the subject a therapeutically effective amount of the antibody of any of the preceding aspects. In some embodiments, the disease is a cancer (see, e.g., examples of cancer types listed elsewhere herein). In some embodiments, the method further includes administering the antibody in combination with a second therapeutic agent (e.g., an immunotherapy or a cancer vaccine). In some embodiments, the second therapeutic agent is an immunotherapy comprising a PD-1 therapy and/or an ICOS therapy.

In another aspect, the invention provides a method of enhancing an anti-tumor immune response in a subject in need thereof, the method including administering to the subject a therapeutically effective amount of any of the preceding aspects. In some embodiments, the method further includes administering the antibody in combination with a second therapeutic agent (e.g., an immunotherapy or a cancer vaccine). In some embodiments, the second therapeutic agent is an immunotherapy comprising a PD-1 therapy and/or an ICOS therapy.

In other aspects, the invention includes use of the antibodies, pharmaceutical compositions, and combinations for preventing, treating, ameliorating one or more symptoms of a disease or condition (e.g., as described herein, for example, cancer) or the use of these agents for the preparation of a medicament for these purposes.

In another aspect, the invention provides a kit including a pharmaceutical composition comprising the antibody of any of the preceding aspects or a nucleic acid molecule encoding the antibody of any of the preceding aspects and instructions for use.

In a further aspect, the invention provides an oligonucleotide comprising a nucleic acid fragment, wherein nucleic acid fragment comprises at least 16 consecutive nucleic acid residues of the oligonucleotide sequence of CGTCACCCTCAGTTGTCAG (SEQ ID NO: 143) or TCCGTGTAATCCAAGATGCTG (SEQ ID NO: 158). In some embodiments, the nucleic acid fragment comprises at least 16 consecutive nucleic acid residues of the oligonucleotide sequence of AGTCCCGTCACCCTCAGTTGTCAGGGGAG (SEQ ID NO: 169) or TCGTATCCGTGTAATCCAAGATGCTGATTTT (SEQ ID NO: 170).

The invention also includes a qPCR primer set comprising a forward primer and a reverse primer, wherein the forward primer comprises a nucleic acid fragment comprising at least 16 consecutive nucleic acid residues of the oligonucleotide sequence of SEQ ID NO: 143 or 169, and the reverse primer comprises a nucleic acid fragment comprising at least 16 consecutive nucleic acid residues of the oligonucleotide sequence of SEQ ID NO: 158 or 170, wherein the qPCR primer set is optionally comprised within a kit that further comprises a probe comprising at least 16 consecutive residues of SEQ ID NO: 167.

In addition, the invention includes a method of quantifying a level of LILRB2 expression in a biological sample, the method comprising: (a) obtaining cDNA derived from a biological sample; (b) performing qPCR on the cDNA using an oligonucleotide of claim 87 or 88, or a qPCR primer set or kit of claim 89, to produce an amplification product, wherein the qPCR is specific for LILRB2; and (c) quantifying the amplification product to determine the level of LILRB2 expression.

In another aspect, the invention provides use of an antibody as described herein (e.g., above and elsewhere herein) for treating or preventing a disease (e.g., cancer; see, e.g., below) in a subject in need thereof by administration of a therapeutically effective amount the antibody to the subject.

In a further aspect, the invention includes use of a therapeutically effective amount of an antibody as described herein (e.g., above and elsewhere herein) for enhancing an anti-tumor immune response in a subject in need thereof by administering an effective amount of the antibody to the subject.

In either of the above aspects, the use can further include administering the antibody in combination with a second therapeutic agent (e.g., an immunotherapy (e.g., a PD-1 therapy and/or an ICOS therapy) or a cancer vaccine).

BRIEF DESCRIPTION OF THE DRAWINGS

FIGS. 2B and 2H show LILRB2 expression; FIGS. 2C and 2I show CD11c expression; FIGS. 2D and 2J show HLA-DR expression; FIGS. 2E and 2K show CD86 expression; and FIGS. 2F and 2L show CD80 expression.

FIGS. 3A and 3B are tables showing results of a chimeric anti-LILRB2 screening. Shaded boxes indicate results which met threshold criteria for each screening assay.

FIG. 7A shows TNFα production relative to isotype. FIG. 7B shows IL-10 production relative to isotype. Isotype controls are shown in gray/gray dashed lines.

FIGS. 11A and 11B are tables showing results of the humanized anti-LILRB2 characterization.

FIG. 23A shows IL-4 secretion, FIG. 23B shows IL-6 secretion, FIG. 23C shows IL-8 secretion, and FIG. 23D shows TNFα secretion. The assay was incubated for 24 hours at 37° C. Plasma was then isolated with cytokines and measured using a 10-cytokine MSD panel. Data are mean+/−SD of three donors.

FIG. 24A shows CD11b expression (as geometric mean fluorescence intensity), FIG. 24B shows the percent of CD11b high cells, FIG. 24C shows CD62L expression (as geometric mean fluorescence intensity), and FIG. 24D shows the percent of CD62L low cells, each in response to various antibody concentrations. The assay was incubated for 2 hours at 37° C. Changes in neutrophil activation markers (increase in CD1 lb and decrease in CD62L) were assessed by flow cytometry. Data are mean+/−SD of two donors.

FIG. 27A shows tumor growth in wild type (WT) mice, and FIG. 27B shows tumor growth in PirB knockout (Pirb$^{-/-}$) mice.

FIG. 28A shows tumor growth in WT mice, and FIG. 28B shows tumor growth in Pirb$^{-/-}$ mice.

FIG. 29A shows tumor growth in WT mice, and FIG. 29B shows tumor growth in Pirb$^{-/-}$ mice.

FIG. 30 shows the sequences of the heavy chain (SEQ ID NO: 53) and light chain (SEQ ID NO: 54) variable regions of J-19.h1.

DETAILED DESCRIPTION OF SOME EMBODIMENTS

Figure 1:
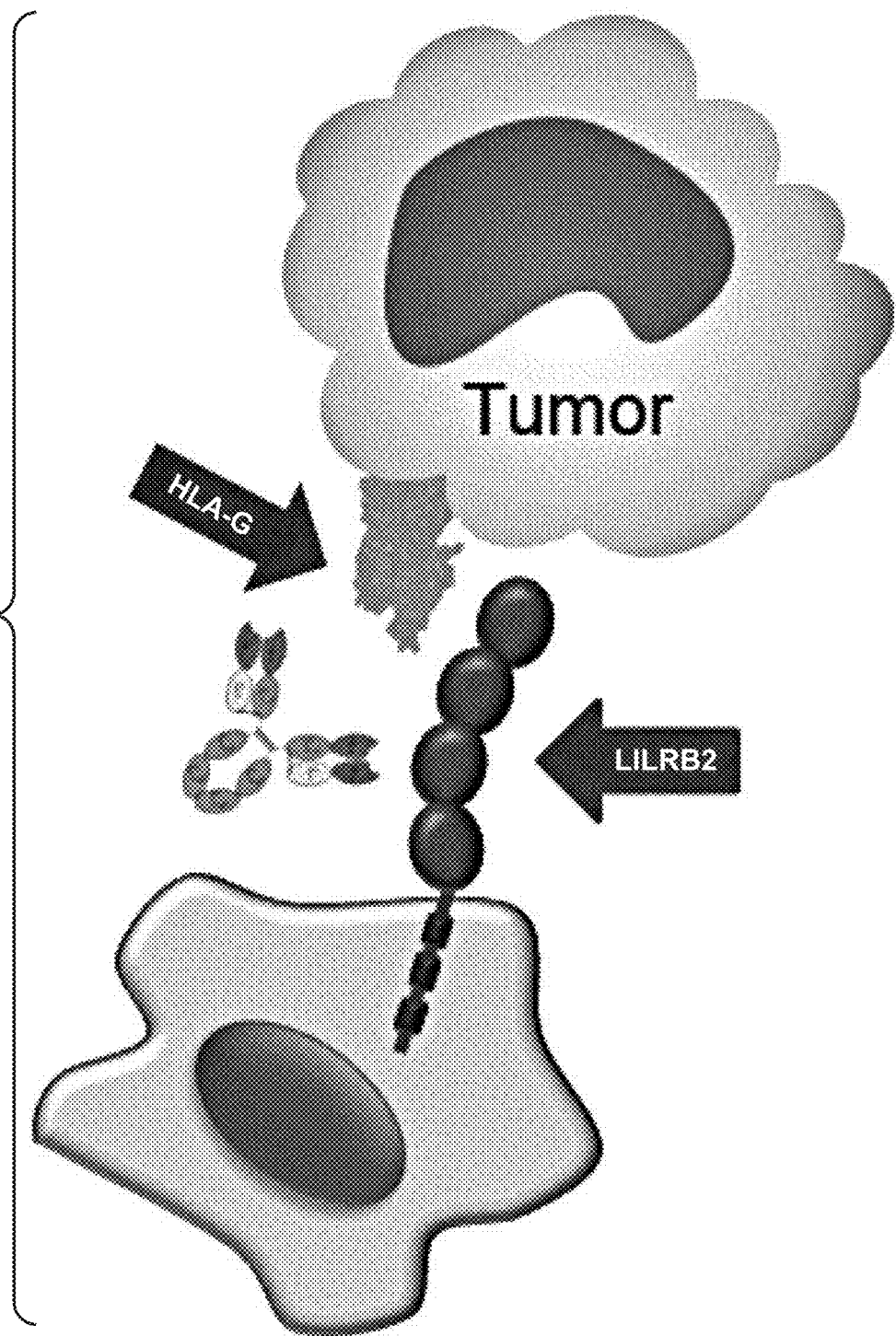
FIG. 1 is a drawing depicting a model of a LILRB2-expressing myeloid cell and a HLA-G-expressing tumor cell. A blocking anti-LILRB2 antibody is shown between the LILRB2 expressed on the myeloid cell and the HLA-G expressed on the tumor cell.
Figure 2A:
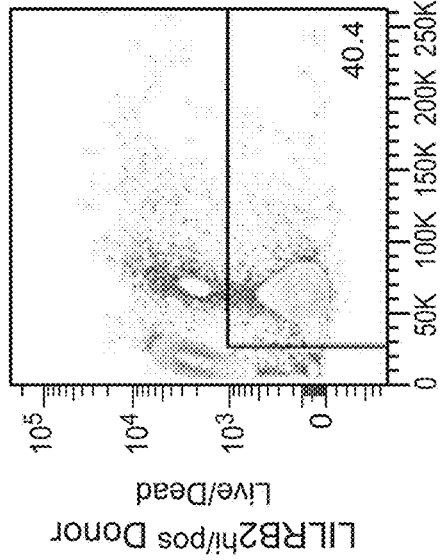
FIGS. 2A-2L are flow cytometry plots showing down-regulation of maturation markers on DCs by HLA-G tetramers. Expression of maturation markers was assessed by flow cytometry on LILRB2$^{hi/pos}$ donor (FIGS. 2A-2F) and LILRB2$^{low/neg}$ donor (FIGS. 2G-2L) immature dendritic cells (iDCs) cultured in media alone (open histograms, dotted lines), or matured with a cytokine cocktail in the absence (open histograms, solid lines) or presence (filled histograms) of HLA-G tetramer. Histograms are gated on live cells, as shown in FIGS. 2A and 2G.
Figure 2B:
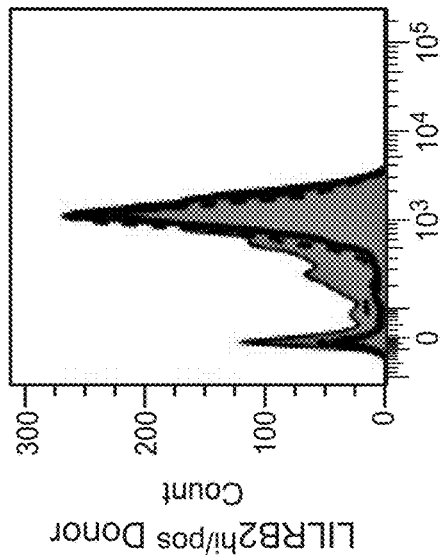
Figure 2C:
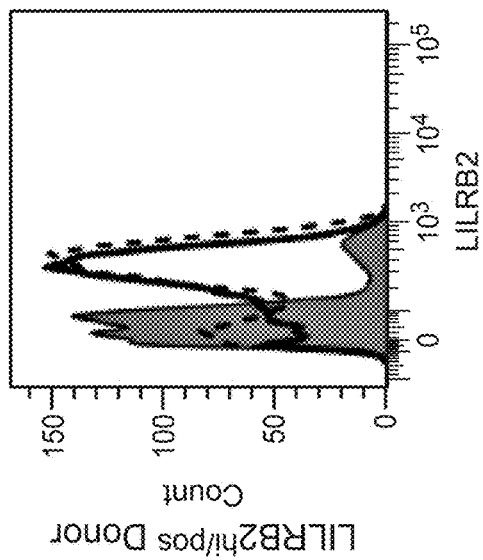
Figure 2D:
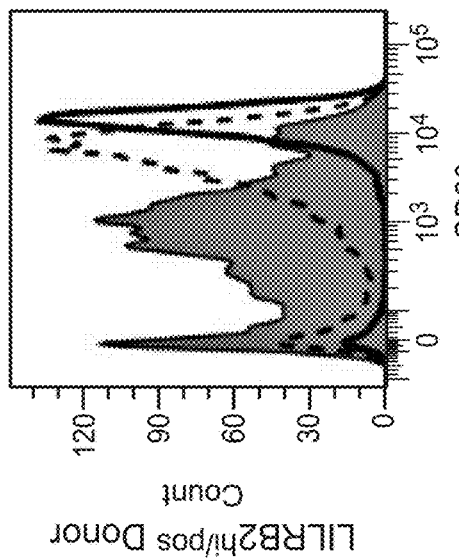
Figure 2E:
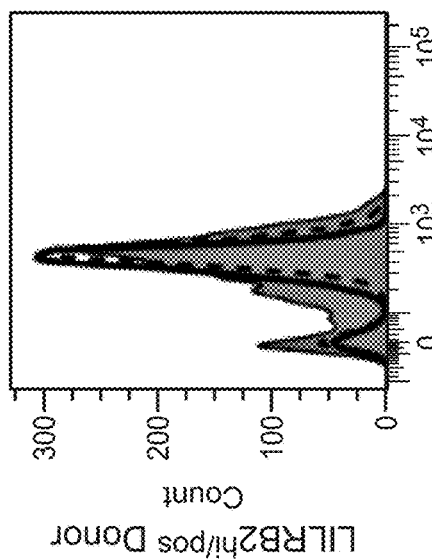
Figure 2F:
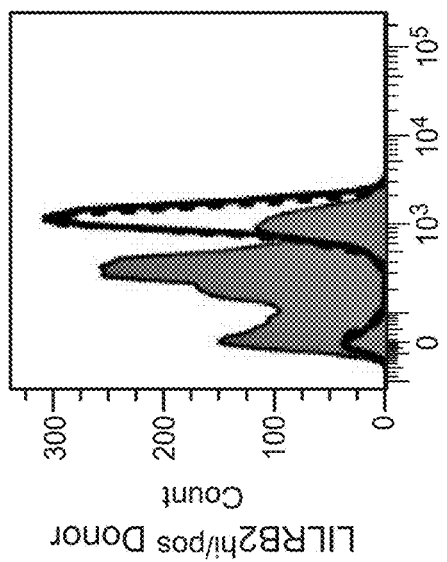
Figure 2G:
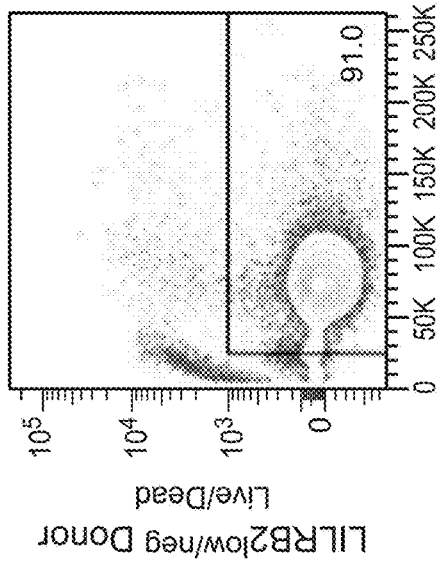
Figure 2H:
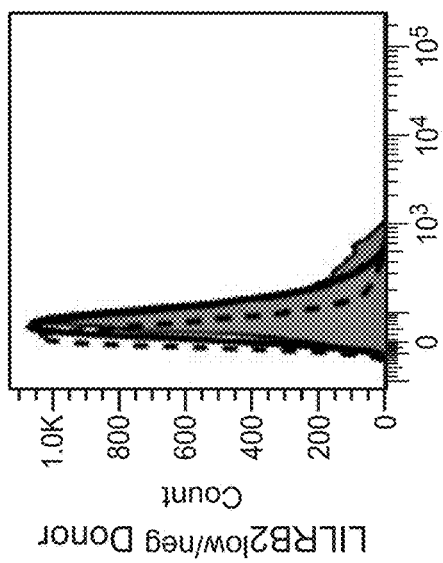
Figure 2I:
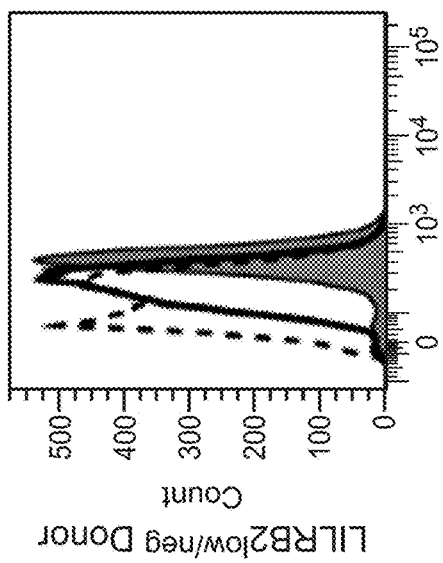
Figure 2J:
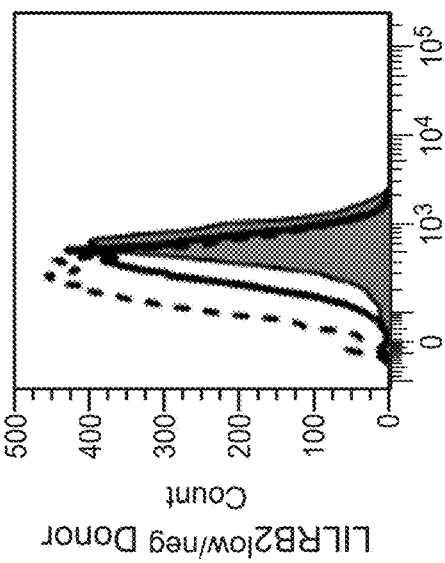
Figure 2K:
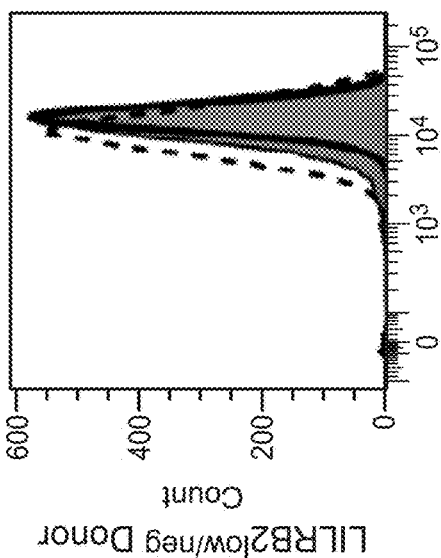
Figure 2L:
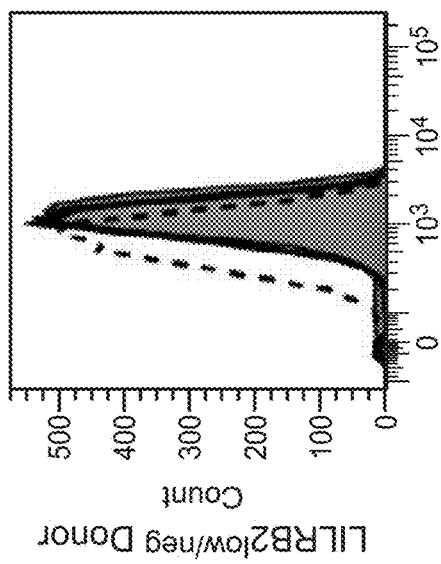

In general, the present invention features antibodies against leukocyte immunoglobulin-like receptor B2 (LILRB2), e.g., antibodies useful for treating disease (e.g., cancer). This invention is based, in part, on the discovery that it is possible to generate antibodies that are simultaneously (1) specific to LILRB2 (e.g., in that they do not bind other LILRA and LILRB family members), (2) capable of blocking HLA-G and/or HLA-A2 binding to LILRB2 on macrophages, and (3) capable of promoting a pro-inflammatory phenotype in contacted macrophages. Indeed, the present application discloses the identification of three independent families of such antibodies and discloses that antibodies with the above properties are capable of inducing tumor-associated macrophages to exhibit anti-cancer properties. Based, in part, on these properties, as well as favorable pharmacokinetic and safety properties in animal models relevant to human physiology, the disclosed antibodies are candidates for therapeutic use in humans.

Antibodies that specifically bind LILRB2 (e.g., human LILRB2) are provided. Antibody heavy chains and light chains that are capable of forming antibodies that bind LILRB2 (e.g., human LILRB2) are also provided. In addition, antibodies, heavy chains, and light chains comprising one or more particular complementarity determining region (CDR) are provided. Also provided are antibodies that cross-compete for binding to LILRB2 (e.g., human LILRB2) with any of the antibodies described herein. In some aspects, the present invention provides antibodies that specifically bind to LILRB2 (e.g., human LILRB2) and blocks the binding of HLA-G and/or HLA-A2 to human LILRB2. Also provided are antibodies that specifically bind to LILRB2 (e.g., human LILRB2) and are capable of converting an M2-like macrophage into an M1-like macrophage. Polynucleotides encoding antibodies to LILRB2 (e.g., any of the LILRB2 antibodies provided herein) are provided. Polynucleotides encoding antibody heavy chains or lights chains thereof are also provided. Host cells containing polynucleotides disclosed herein are also provided. Additionally, pharmaceutical compositions including any of the antibodies or polynucleotides provided herein are provided. Methods of treatment using antibodies to LILRB2 are provided. Such methods include, but are not limited to, methods of treating cancer.

The section headings used herein are for organizational purposes only and are not to be construed as limiting the subject matter described.

All references cited herein, including patent applications, patent publications, and Genbank Accession numbers are herein incorporated by reference, as if each individual reference were specifically and individually indicated to be incorporated by reference in its entirety.

The techniques and procedures described or referenced herein are generally well understood and commonly employed using conventional methodology by those skilled in the art, such as, for example, the widely utilized methodologies described in Sambrook et al., Molecular Cloning: A Laboratory Manual 3rd. edition (2001) Cold Spring Harbor Laboratory Press, Cold Spring Harbor, N.Y. Current Protocols in Molecular Biology (F. M. Ausubel, et al. eds., (2003)); the series Methods in Enzymology (Academic Press, Inc.): PCR 2: A Practical Approach (M. J. MacPherson, B. D. Hames and G. R. Taylor eds. (1995)), Harlow and Lane, eds. (1988) Antibodies, A Laboratory Manual, and Animal Cell Culture (R. I. Freshney, ed. (1987)); Oligonucleotide Synthesis (M. J. Gait, ed., 1984); Methods in Molecular Biology, Humana Press; Cell Biology: A Laboratory Notebook (J. E. Cellis, ed., 1998) Academic Press; Animal Cell Culture (R. I. Freshney), ed., 1987); Introduction to Cell and Tissue Culture (J. P. Mather and P. E. Roberts, 1998) Plenum Press; Cell and Tissue Culture Laboratory Procedures (A. Doyle, J. B. Griffiths, and D. G. Newell, eds., 1993-8) J. Wiley and Sons; Handbook of Experimental Immunology (D. M. Weir and C. C. Blackwell, eds.); Gene Transfer Vectors for Mammalian Cells (J. M. Miller and M. P. Calos, eds., 1987); PCR: The Polymerase Chain Reaction, (Mullis et al., eds., 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: A Practical Approach (D. Catty., ed., IRL Press, 1988-1989); Monoclonal Antibodies: A Practical Approach (P. Shepherd and C. Dean, eds., Oxford University Press, 2000); Using Antibodies: A Laboratory Manual (E. Harlow and D. Lane (Cold Spring Harbor Laboratory Press, 1999); The Antibodies (M.

Zanetti and J. D. Capra, eds., Harwood Academic Publishers, 1995); and Cancer: Principles and Practice of Oncology (V. T. DeVita et al., eds., J. B. Lippincott Company, 1993); and updated versions thereof.

I. Definitions

Unless otherwise defined, scientific and technical terms used in connection with the present disclosure shall have the meanings that are commonly understood by those of ordinary skill in the art. Further, unless otherwise required by context or expressly indicated, singular terms shall include pluralities and plural terms shall include the singular. For any conflict in definitions between various sources or references, the definition provided herein will control.

It is understood that embodiments of the invention described herein include "consisting" and/or "consisting essentially of" embodiments. As used herein, the singular form "a", "an," and "the" includes plural references unless indicated otherwise. Use of the term "or" herein is not meant to imply that alternatives are mutually exclusive.

In this application, the use of "or" means "and/or" unless expressly stated or understood by one skilled in the art. In the context of a multiple dependent claim, the use of "or" refers back to more than one preceding independent or dependent claim.

The terms "nucleic acid molecule," "nucleic acid," and "polynucleotide" may be used interchangeably, and refer to a polymer of nucleotides. Such polymers of nucleotides may contain natural and/or non-natural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "protein" are used interchangeably to refer to a polymer of amino acid residues, and are not limited to a minimum length. Such polymers of amino acid residues may contain natural or non-natural amino acid residues, and include, but are not limited to, peptides, oligopeptides, dimers, trimers, and multimers of amino acid residues. Both full-length proteins and fragments thereof are encompassed by the definition. The terms also include post-expression modifications of the polypeptide, for example, glycosylation, sialylation, acetylation, phosphorylation, and the like. Furthermore, for purposes of the present disclosure, a "polypeptide" refers to a protein which includes modifications, such as deletions, additions, and substitutions (generally conservative in nature), to the native sequence, as long as the protein maintains the desired activity. These modifications may be deliberate, as through site-directed mutagenesis, or may be accidental, such as through mutations of hosts which produce the proteins or errors due to PCR amplification.

The term "specifically binds" to an antigen or epitope is a term that is well understood in the art, and methods to determine such specific binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to an LILRB2 epitope is an antibody that binds this epitope with greater affinity, avidity, more readily, and/or with greater duration than it binds to other LILRB2 epitopes or non-LILRB2 epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding. "Specificity" refers to the ability of a binding protein to selectively bind an antigen.

As used herein, "substantially pure" refers to material which is at least 50% pure (that is, free from contaminants), e.g., at least 90% pure, at least 95% pure, at least 98% pure, or at least 99% pure.

The term "cross-competes" refers to competitive binding of one molecule with another, e.g., by binding to all or part of the same epitope. Cross-competition can be determined using the experiments described herein (e.g., biolayer interferometry), for example, by detecting no positive response signal upon addition of a second antibody to a sensor after a first antibody is bound to the signal. In particular embodiments, one LILRB2 antibody cross-competes another LILRB2 antibody for binding to LILRB2. Characterization of such cross-competition between LILRB2 antibodies is described, e.g., in Example 3.

The term "antibody" herein is used in the broadest sense and encompasses various antibody structures, including but not limited to monoclonal antibodies, polyclonal antibodies, multispecific antibodies (for example, bispecific (such as Bi-specific T-cell engagers) and trispecific antibodies), and antibody fragments so long as they exhibit the desired antigen-binding activity.

The term antibody includes, but is not limited to, fragments that are capable of binding to an antigen, such as Fv, single-chain Fv (scFv), Fab, Fab', di-scFv, sdAb (single domain antibody) and (Fab')$_2$ (including a chemically linked F(ab')$_2$). Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')2 fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc. Furthermore, for all antibody constructs provided herein, variants having the sequences from other organisms are also contemplated. Thus, if a human version of an antibody is disclosed, one of skill in the art will appreciate how to transform the human sequence based antibody into a mouse, rat, cat, dog, horse, etc. sequence. Antibody fragments also include either orientation of single chain scFvs, tandem di-scFv, diabodies, tandem tri-sdcFv, minibodies, etc. Antibody fragments also include nanobodies (sdAb, an antibody having a single, monomeric domain, such as a pair of variable domains of heavy chains, without a light chain). An antibody fragment can be referred to as being a specific species in some embodiments (for example, human scFv or a mouse scFv). This denotes the sequences of at least part of the non-CDR regions, rather than the source of the construct.

The term "monoclonal antibody" refers to an antibody of a substantially homogeneous population of antibodies, that is, the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. Thus, a sample of monoclonal antibodies can bind to the same epitope on the antigen. The modifier "monoclonal" indicates the character of the antibody as being obtained from a substantially homogeneous population of antibodies, and is not to be construed as requiring production of the antibody by any particular method. For example, the monoclonal antibodies may be made by the hybridoma method first described by Kohler and Milstein, 1975, Nature 256:495, or may be made by recombinant DNA methods such as described in U.S. Pat. No. 4,816,567. The monoclonal antibodies may also be isolated from phage libraries generated using the techniques described in McCafferty et al., 1990, *Nature* 348:552-554, for example.

The term "CDR" denotes a complementarity determining region as defined by the Kabat numbering scheme. Kabat et al., Sequences of Proteins of Immunological Interest, 5th Ed. Public Health Service, National Institutes of Health, Bethesda, Md. (1991). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. CDRs can also be provided as shown in any one or more of the accompanying figures. With the exception of CDR1 in a variable heavy chain region ($V_H$), CDRs generally comprise the amino acid residues that form the hypervariable loops. The various CDRs within an antibody can be designated by their appropriate number and chain type, including, without limitation as: a) CDR-L1, CDR-L2, CDR-L3, CDR-H1, CDR-H2, and CDR-H3; b) CDRL1, CDRL2, CDRL3, CDRH1, CDRH2, and CDRH3; c) LCDR-1, LCDR-2, LCDR-3, HCDR-1, HCDR-2, and HCDR-3; or d) LCDR1, LCDR2, LCDR3, HCDR1, HCDR2, and HCDR3; etc. The term "CDR" is used herein to also encompass HVR or a "hypervariable region", including hypervariable loops. Exemplary hypervariable loops occur at amino acid residues 26-32 (L1), 50-52 (L2), 91-96 (L3), 26-32 (H1), 53-55 (H2), and 96-101 (H3). (Chothia and Lesk, 1987, *J. Mol. Biol.* 196:901-917.)

The term "heavy chain variable region" or $V_H$ as used herein refers to a region comprising at least three heavy chain CDRs. In some embodiments, the heavy chain variable region includes the three CDRs and at least FR2 and FR3. In some embodiments, the heavy chain variable region includes at least heavy chain HCDR1, framework (FR) 2, HCDR2, FR3, and HCDR3. In some embodiments, a heavy chain variable region also comprises at least a portion of an FR1 and/or at least a portion of an FR4.

The term "heavy chain constant region" as used herein refers to a region comprising at least three heavy chain constant domains, $C_H1$, $C_H2$, and $C_H3$. Of course, non-function-altering deletions and alterations within the domains are encompassed within the scope of the term "heavy chain constant region," unless designated otherwise. Nonlimiting exemplary heavy chain constant regions include γ, δ, and α. Nonlimiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $γ_1$ constant region), IgG2 (comprising a $γ_2$ constant region), IgG3 (comprising a $γ_3$ constant region), and IgG4 (comprising a $γ_4$ constant region) antibodies; IgA antibodies include, but are not limited to, IgA1 (comprising an $α_1$ constant region) and IgA2 (comprising an $α_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain variable region" of $V_L$ as used herein refers to a region comprising at least three light chain CDRs. In some embodiments, the light chain variable region includes the three CDRs and at least FR2 and FR3. In some embodiments, the light chain variable region includes at least light chain LCDR1, framework (FR) 2, LCDR2, FR3, and LCDR3. For example, a light chain variable region may comprise light chain CDR1, framework (FR) 2, CDR2, FR3, and CDR3. In some embodiments, a light chain variable region also comprises at least a portion of an FR1 and/or at least a portion of an FR4.

The term "light chain constant region" as used herein refers to a region comprising a light chain constant domain, $C_L$. Nonlimiting exemplary light chain constant regions include λ and κ. Of course, non-function-altering deletions and alterations within the domains are encompassed within the scope of the term "light chain constant region," unless designated otherwise.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

An "acceptor human framework" for the purposes herein is a framework comprising the amino acid sequence of a light chain variable domain ($V_L$) framework or a heavy chain variable domain ($V_H$) framework derived from a human immunoglobulin framework or a human consensus framework, as defined below. An acceptor human framework derived from a human immunoglobulin framework or a human consensus framework can comprise the same amino acid sequence thereof, or it can contain amino acid sequence changes. In some embodiments, the number of amino acid changes are 10 or fewer, 9 or fewer, 8 or fewer, 7 or fewer, 6 or fewer, 5 or fewer, 4 or fewer, 3 or fewer, or 2 or fewer. In some embodiments, the $V_L$ acceptor human framework is identical in sequence to the $V_L$ human immunoglobulin framework sequence or human consensus framework sequence.

"Affinity" refers to the strength of the sum total of noncovalent interactions between a single binding site of a molecule (for example, an antibody) and its binding partner (for example, an antigen). The affinity of a molecule X for its partner Y can generally be represented by the equilibrium dissociation constant ($K_D$). Affinity can be measured by common methods known in the art (such as, for example, ELISA $K_D$, KinExA, bio-layer interferometry (BLI), and/or surface plasmon resonance devices (such as a BIACORE® device), including those described herein).

The term "$K_D$", as used herein, refers to the equilibrium dissociation constant of an antibody-antigen interaction.

In some embodiments, the "$K_D$" of the antibody is measured by using surface plasmon resonance assays using a BIACORE®-2000 or a BIACORE®-3000 (BIAcore, Inc., Piscataway, N.J.) at 25° C. with immobilized antigen CM5 chips at ~10 response units (RU). Briefly, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 μg/ml (0.2 μM), before injection at a flow rate of 5 μL/minute to achieve approximately 10 response units (RU) of coupled protein. Following the injection of antigen, 1 M ethanolamine is injected to block unreacted groups. For kinetics measurements, serial dilutions of polypeptide, for example, full length antibody, are injected in PBS with 0.05% TWEEN-20™ surfactant (PBST) at 25° C. at a flow rate of approximately 25 μL/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant ($K_D$) is calculated as the ratio $k_{off}/k_{on}$. See, for example, Chen et al., 1999, *J. Mol. Biol.* 293:865881. If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody in PBS, pH 7.2, in the presence of increasing concentrations of antigen as measured in a spectrometer, such as a stop-flow equipped spectrophometer (Aviv Instruments) or a 8000-series SLM-AMINCO™ spectrophotometer (ThermoSpectronic) with a stirred cuvette.

In some embodiments, the difference between said two values (for example, $K_D$ values) is substantially the same, for example, less than about 50%, less than about 40%, less than about 30%, less than about 20%, and/or less than about 10% as a function of the reference/comparator value.

In some embodiments, the difference between said two values (for example, $K_D$ values) is substantially different, for example, greater than about 10%, greater than about 20%, greater than about 30%, greater than about 40%, and/or greater than about 50% as a function of the value for the reference/comparator molecule.

"Surface plasmon resonance" denotes an optical phenomenon that allows for the analysis of real-time biospecific interactions by detection of alterations in protein concentrations within a biosensor matrix, for example using the BIAcore™ system (BIAcore International AB, a GE Healthcare company, Uppsala, Sweden and Piscataway, N.J.). For further descriptions, see Jonsson et al., 1993, *Ann. Biol. Clin.* 51:19-26.

"Biolayer interferometry" refers to an optical analytical technique that analyzes the interference pattern of light reflected from a layer of immobilized protein on a biosensor tip and an internal reference layer. Changes in the number of molecules bound to the biosensor tip cause shifts in the interference pattern that can be measured in real-time. A nonlimiting exemplary device for biolayer interferometry is FORTEBIO® OCTET® RED96 system (Pall Corporation). See, e.g., Abdiche et al., 2008, *Anal. Biochem.* 377: 209-277.

The term "$k_{on}$", as used herein, refers to the rate constant for association of an antibody to an antigen. Specifically, the rate constants ($k_{on}$ and $k_{on}$) and equilibrium dissociation constant ($K_D$) are measured using IgGs (bivalent) with monovalent antigen (e.g., LILRB2 antigen). "$K_{on}$", "$k_{on}$", "association rate constant", or "ka", are used interchangeably herein. The value indicates the binding rate of a binding protein to its target antigen or the rate of complex formation between an antibody and antigen, shown by the equation:

Antibody("$Ab$")+Antigen("$Ag$")→$Ab$–$Ag$. 

The term "$k_{off}$", as used herein, refers to the rate constant for dissociation of an antibody from the antibody/antigen complex. $k_{off}$ is also denoted as "$K_{off}$" or the "dissociation rate constant". This value indicates the dissociation rate of an antibody from its target antigen or separation of Ab-Ag complex over time into free antibody and antigen as shown by the equation:

$Ab$+$Ag$←$Ab$–$Ag$. 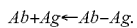

The term "biological activity" refers to any one or more biological properties of a molecule (whether present naturally as found in vivo, or provided or enabled by recombinant means). Biological properties include, but are not limited to, binding a receptor, inducing cell proliferation, inhibiting cell growth, inducing maturation or activation (e.g., myeloid cell maturation or activation), inhibiting maturation or activation (e.g., myeloid cell maturation or activation), inducing cytokine expression or secretion (e.g., inflammatory cytokines or immunosuppressive cytokines), inducing apoptosis, and enzymatic activity. In some embodiments, biological activity of an LILRB2 protein includes, for example, conversion of M2-like macrophages to M1-like macrophages.

An "M2-like macrophage," as used herein, refers to a macrophage characterized by one or more immunosuppressive characteristics, relative to a reference. Immunosuppressive characteristics include decreased maturation marker or activation marker expression (e.g., decreased expression of one or more costimulatory markers (e.g., CD80 or CD86), decreased antigen presentation (e.g., by HLA expression), decreased expression of inflammatory cytokines (e.g., TNFα, IL-6, or IL-1β), and increased regulatory or suppressive marker expression (e.g., increased IL-10 or CCL-2 expression or secretion). Immunosuppressive characteristics may additionally or alternatively be characterized by decrease in immunogenic or inflammatory gene expression, or increase in immunosuppressive or immunoregulatory gene expression, according to methods known in the art. Immunosuppressive characteristics may additionally or alternatively be characterized by one or more functional qualities, such as the ability to inhibit activation and/or expansion of other immune cells. Assays suitable for identifying a macrophage as an M2-like macrophage are known in the art and described herein. For example, a primary human macrophage assay can be used to determine whether a macrophage is an M2-like macrophage or an M1-like macrophage. In some instances, an M2-like macrophage is a tumor-associated macrophage. In the context of determining whether a macrophage is an M2-like macrophage, a reference can be provided by a control macrophage of the same or different origin (e.g., an untreated control or an LPS-treated control). In embodiments in which a candidate macrophage is a tumor-associated macrophage, a control may be a non-tumor-associated macrophage (e.g., from a healthy donor). Alternatively, a reference can be a predetermined threshold, e.g., a parameter derived from an art-known immunosuppressive threshold.

An "M1-like macrophage," as used herein, refers to a macrophage characterized by one or more immunogenic (e.g., immunostimulatory or activatory) characteristics, relative to a reference. Immunogenic characteristics include increased maturation marker or activation marker expression (e.g., increased expression of one or more costimulatory markers (e.g., CD80 or CD86), increased antigen presentation (e.g., by HLA expression), increased expression of activating cytokines (e.g., TNFα, IL-6, or IL-1β), decreased regulatory or suppressive marker expression (e.g., decreased IL-10 or CCL-2 expression or secretion). Immunogenic characteristics may additionally or alternatively be characterized by increase in immunogenic or inflammatory gene expression, or decrease in immunosuppressive or immunoregulatory gene expression, according to methods known in the art. Immunogenic characteristics may additionally or alternatively be characterized by one or more functional qualities, such as the ability to activate and/or expand other immune cells. Assays suitable for identifying a macrophage as an M1-like macrophage are known in the art and described herein. For example, a primary human macrophage assay can be used to determine whether a macrophage is an M2-like macrophage or an M1-like macrophage. In some instances, an M1-like macrophage is a tumor-associated macrophage (e.g., a tumor-associated macrophage that has been exposed to an antibody to LILRB2). In the context of determining whether a macrophage is an M1-like macrophage, a reference can be provided by a control macrophage of the same or different origin (e.g., an untreated control or an immunosuppressed control). In embodiments in which a candidate macrophage is a tumor-associated macrophage, a control may be a non-tumor-associated macrophage (e.g., from a healthy donor). Alternatively, a reference can be a predetermined threshold, e.g., a parameter derived from an art-known immunogenic threshold.

"Conversion of an M2-like macrophage to an M1-like macrophage" can be identified upon detection of an increase in any one or more characteristics of an M1-like macrophage, a decrease in any one or more characteristics of an M2-like macrophage, or any combination thereof.

As used herein, a "human monocyte-derived macrophage," a "human monocyte-differentiated macrophage," or an "HMDM" refers to a macrophage that has been derived from a primary human monocyte. In some embodiments, the primary human macrophage is derived from monocytes from whole blood (e.g., from a PBMC population). In some embodiments, primary human monocytes are incubated in the presence of M-CSF for seven days. A human monocyte-derived macrophage can be obtained using the methods described in Example 6.

As used herein, the term "tetramer blocking assay" refers to an assay including the following steps:
(1) plate $1\times10^5$ macrophages (e.g., human monocyte differentiated macrophages (HMDMs)) in a well of a 96-well round-bottom tissue culture plate;
(2) add 50 μL test antibody (e.g., LILRB2 antibody or isotype control) in buffer (e.g., FACS buffer (1×DPBS containing 2% HI-FBS (Sigma)+0.05% Sodium Azide));
(3) incubate 30 minutes at 4° C.;
(4) wash cells in buffer (e.g., FACS buffer) and resuspend in 50 μL buffer (e.g., FACS buffer) containing 1 μg/mL tetramer (e.g., fluorochrome-labeled tetramer, e.g., HLA-G or HLA-A2 tetramer);
(5) incubate protected from light for 30-60 minutes at 4° C.;
(6) wash cells in buffer (e.g., FACS buffer); and
(7) quantify tetramer binding (e.g., using flow cytometry).

A "chimeric antibody" as used herein refers to an antibody in which a portion of the heavy and/or light chain is derived from a particular source or species, while at least a part of the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species. The chimeric construct can also be a functional fragment, as noted above.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an antibody fragment, such as Fab, an scFv, a (Fab')$_2$, etc. The term humanized also denotes forms of non-human (for example, murine) antibodies that are chimeric immunoglobulins, immunoglobulin chains, or fragments thereof (such as Fv, Fab, Fab', F(ab')2 or other antigen-binding subsequences of antibodies) that contain minimal sequence of non-human immunoglobulin. Humanized antibodies can include human immunoglobulins (recipient antibody) in which residues from a complementary determining region (CDR) of the recipient are substituted by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody can comprise residues that are found neither in the recipient antibody nor in the imported CDR or framework sequences, but are included to further refine and optimize antibody performance. In general, the humanized antibody can comprise substantially all of at least one, and typically two, variable domains, in which all or substantially all of the CDR regions correspond to those of a non-human immunoglobulin and all or substantially all of the FR regions are those of a human immunoglobulin consensus sequence. In some embodiments, the humanized antibody can also comprise at least a portion of an immunoglobulin constant region or domain (Fc), typically that of a human immunoglobulin. Other forms of humanized antibodies have one or more CDRs (CDR L1, CDR L2, CDR L3, CDR H1, CDR H2, and/or CDR H3) which are altered with respect to the original antibody, which are also termed one or more CDRs "derived from" one or more CDRs from the original antibody. As will be appreciated, a humanized sequence can be identified by its primary sequence and does not necessarily denote the process by which the antibody was created.

An "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein encompasses antibodies produced in humans, antibodies produced in non-human animals that comprise human immunoglobulin genes, such as XENOMOUSE® mice, and antibodies selected using in vitro methods, such as phage display (Vaughan et al., 1996, Nat. Biotechnol., 14:309-314; Sheets et al., 1998, Proc. Natl. Acad. Sci. (USA), 95:6157-6162; Hoogenboom and Winter, 1991, J. Mol. Biol., 227:381; Marks et al., 1991, J. Mol. Biol., 222:581), wherein the antibody repertoire is based on a human immunoglobulin sequence. The term "human antibody" denotes the genus of sequences that are human sequences. Thus, the term is not designating the process by which the antibody was created, but the genus of sequences that are relevant.

A "functional Fc region" possesses an "effector function" of a native sequence Fc region. Exemplary "effector functions" include Fc receptor binding; C1q binding; CDC; ADCC; phagocytosis; down regulation of cell surface receptors (for example B cell receptor; BCR), etc. Such effector functions generally require the Fc region to be combined with a binding domain (for example, an antibody variable domain) and can be assessed using various assays.

A "native sequence Fc region" comprises an amino acid sequence identical to the amino acid sequence of an Fc region found in nature. Native sequence human Fc regions include a native sequence human IgG1 Fc region (non-A and A allotypes); native sequence human IgG2 Fc region; native sequence human IgG3 Fc region; and native sequence human IgG4 Fc region as well as naturally occurring variants thereof.

A "variant Fc region" comprises an amino acid sequence which differs from that of a native sequence Fc region by virtue of at least one amino acid modification. In some embodiments, a "variant Fc region" comprises an amino acid sequence which differs from that of a native sequence Fc region by virtue of at least one amino acid modification, yet retains at least one effector function of the native sequence Fc region. In some embodiments, the variant Fc region has at least one amino acid substitution compared to a native sequence Fc region or to the Fc region of a parent polypeptide, for example, from about one to about ten amino acid substitutions, and preferably, from about one to about five amino acid substitutions in a native sequence Fc region or in the Fc region of the parent polypeptide. In some embodiments, the variant Fc region herein will possess at least about 80% sequence identity with a native sequence Fc region and/or with an Fc region of a parent polypeptide, at least about 90% sequence identity therewith, at least about 95%, at least about 96%, at least about 97%, at least about 98%, or at least about 99% sequence identity therewith.

"Fc receptor" or "FcR" describes a receptor that binds to the Fc region of an antibody. In some embodiments, an FcγR is a native human FcR. In some embodiments, an FcR is one which binds an IgG antibody (a gamma receptor) and includes receptors of the FcγRI, FcγRII, and FcγRIII subclasses, including allelic variants and alternatively spliced forms of those receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain Inhibiting receptor FcγRIIB contains an immunoreceptor tyrosine-based inhibition motif (ITIM) in its cytoplasmic domain. See, for example, Daeron, 1997, Annu. Rev. Immunol. 15:203-234. FcRs are reviewed, for example, in Ravetch and Kinet, 1991, Annu. Rev. Immunol 9:457-92; Capel et al., 1994, Immunomethods, 4:25-34; and de Haas et al., 1995, J. Lab. Clin. Med. 126:330-41. Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus (Guyer et al., 1976, J. Immunol. 117:587 and Kim et al., 1994, J. Immunol. 24:249) and regulation of homeostasis of immunoglobulins. Methods of measuring binding to FcRn are known. See, for example, Ghetie and Ward, 1997, Immunol. Today, 18(12):592-598; Ghetie et al., 1997, Nat. Biotechnol., 15(7):637-640; Hinton et al., 2004, J. Biol. Chem. 279(8):6213-6216; and WO 2004/92219 (Hinton et al.).

"Effector functions" refer to biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (for example B cell receptor); and B cell activation.

"Antibody-dependent cell-mediated cytotoxicity" or "ADCC" refers to a form of cytotoxicity in which secreted Ig bound onto Fc receptors (FcRs) present on certain cytotoxic cells (for example NK cells, neutrophils, and macrophages) enable these cytotoxic effector cells to bind specifically to an antigen-bearing target cell and subsequently kill the target cell with cytotoxins. The primary cells for mediating ADCC, NK cells, express FcγRIII only, whereas monocytes express FcγRI, FcγRII, and FcγRIII. FcR expression on hematopoietic cells is summarized in Table 3 on page 464 of Ravetch and Kinet, 1991, Annu. Rev. Immunol 9:457-92. To assess ADCC activity of a molecule of interest, an in vitro ADCC assay, such as that described in U.S. Pat. Nos. 5,500,362, 5,821,337, or 6,737,056 (Presta), may be performed. Useful effector cells for such assays include PBMC and NK cells. Alternatively, or additionally, ADCC activity of the molecule of interest may be assessed in vivo, for example, in an animal model such as that disclosed in Clynes et al., 1998, Proc. Natl. Acad. Sci. (USA) 95:652-656. Additional polypeptide variants with altered Fc region amino acid sequences (polypeptides with a variant Fc region) and increased or decreased ADCC activity are described, for example, in U.S. Pat. Nos. 7,923,538, and 7,994,290.

"Complement dependent cytotoxicity" or "CDC" refers to the lysis of a target cell in the presence of complement. Activation of the classical complement pathway is initiated by the binding of the first component of the complement system (C1q) to antibodies (of the appropriate subclass), which are bound to their cognate antigen. To assess complement activation, a CDC assay, for example, as described in Gazzano-Santoro et al., 1996, J. Immunol. Methods 202:163, may be performed. Polypeptide variants with altered Fc region amino acid sequences (polypeptides with a variant Fc region) and increased or decreased C1q binding capability are described, for example, in U.S. Pat. No. 6,194,551 B1, U.S. Pat. Nos. 7,923,538, 7,994,290, and WO 1999/51642. See also, for example, Idusogie et al., 2000, J. Immunol. 164: 4178-4184.

A polypeptide variant with "altered" FcR binding affinity or ADCC activity is one which has either enhanced or diminished FcR binding activity and/or ADCC activity compared to a parent polypeptide or to a polypeptide comprising a native sequence Fc region. The polypeptide variant which "displays increased binding" to an FcR binds at least one FcR with better affinity than the parent polypeptide. The polypeptide variant which "displays decreased binding" to an FcR, binds at least one FcR with lower affinity than a parent polypeptide. Such variants which display decreased binding to an FcR may possess little or no appreciable binding to an FcR, for example, 0-20% binding to the FcR compared to a native sequence IgG Fc region.

The polypeptide variant which "mediates antibody-dependent cell-mediated cytotoxicity (ADCC) in the presence of human effector cells more effectively" than a parent antibody is one which in vitro or in vivo is more effective at mediating ADCC, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

The term "substantially similar" or "substantially the same," as used herein, denotes a sufficiently high degree of similarity between two or more numeric values such that one of skill in the art would consider the difference between the two or more values to be of little or no biological and/or statistical significance within the context of the biological characteristic measured by said value. In some embodiments the two or more substantially similar values differ by no more than about any one of 5%, 10%, 15%, 20%, 25%, or 50%.

The phrase "substantially different," as used herein, denotes a sufficiently high degree of difference between two numeric values such that one of skill in the art would consider the difference between the two values to be of statistical significance within the context of the biological characteristic measured by said values. In some embodiments, the two substantially different numeric values differ by greater than about any one of 10%, 20%, 25%, 30%, 35%, 40%, 45%, 50%, 60%, 70%, 80%, 90%, or 100%.

The phrase "substantially reduced," as used herein, denotes a sufficiently high degree of reduction between a numeric value and a reference numeric value such that one of skill in the art would consider the difference between the two values to be of statistical significance within the context of the biological characteristic measured by said values. In some embodiments, the substantially reduced numeric values is reduced by greater than about any one of 10%, 20%, 25%, 30%, 35%, 40%, 45%, 50%, 60%, 70%, 80%, 90%, or 100% compared to the reference value.

The term "leader sequence" refers to a sequence of amino acid residues located at the N-terminus of a polypeptide that facilitates secretion of a polypeptide from a mammalian cell. A leader sequence can be cleaved upon export of the polypeptide from the mammalian cell, forming a mature protein. Leader sequences can be natural or synthetic, and they can be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (for example, an extracellular domain sequence), naturally occurring variant forms (for example, alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN, or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, for example, retained/improved antigen binding, decreased immunogenicity, or improved ADCC or CDC.

TABLE 1

| Original Residue | Exemplary Substitutions |
|---|---|
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gin;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that can be engineered to contain a cloned polynucleotide or polynucleotides that can be propagated in a host cell. A vector can include one or more of the following elements: an origin of replication, one or more regulatory sequences (such as, for example, promoters and/or enhancers) that regulate the expression of the polypeptide of interest, and/or one or more selectable marker genes (such as, for example, antibiotic resistance genes and genes that can be used in colorimetric assays, for example, β-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Nonlimiting exemplary mammalian cells include, but are not limited to, NSO cells, PER.C6® cells (Crucell), and 293 and CHO cells, and their derivatives, such as 293-6E and DG44 cells, respectively. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) a provided herein.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, for example, in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder. In some embodiments, the subject to receive the treatment can be a patient, designating the fact that the subject has been identified as having a disorder of relevance to the treatment, or being at adequate risk of contracting the disorder.

A "disease" or "disorder" as used herein refers to a condition where treatment is needed and/or desired.

"Cancer" and "tumor," as used herein, are interchangeable terms that refer to any abnormal cell or tissue growth or proliferation in an animal. As used herein, the terms "cancer" and "tumor" encompass solid and hematological/lymphatic cancers and also encompass malignant, pre-malignant, and benign growth, such as dysplasia. Examples of cancer include but are not limited to, carcinoma, lymphoma, blastoma, sarcoma, and leukemia. More particular non-limiting examples of such cancers include kidney cancer (e.g., renal cell carcinoma, e.g., papillary renal cell carcinoma), squamous cell cancer, mesothelioma, teratoma, small-cell lung cancer, pituitary cancer, esophageal cancer, astrocytoma, soft tissue sarcoma, lung cancer (e.g., non-small cell lung cancer, adenocarcinoma of the lung, squamous carcinoma of the lung), cancer of the peritoneum, hepatocellular cancer, gastrointestinal cancer (e.g., stomach cancer), pancreatic cancer, cervical cancer, ovarian cancer, liver cancer, bladder cancer, hepatoma, breast cancer, colon cancer, colorectal cancer, rectal cancer, endometrial or uterine carcinoma, salivary gland carcinoma, liver cancer, prostate cancer, vulval cancer, thyroid cancer, thymoma, hepatic carcinoma, brain cancer, glioma, glioblastoma, endometrial cancer, testis cancer, cholangiocarcinoma, cholangiosarcoma, gallbladder carcinoma, gastric cancer, melanoma (e.g., uveal melanoma), pheochromocytoma, paraganglioma, adenoid cystic carcinoma, and various types of head and neck cancer (e.g., squamous head and neck cancer).

As used herein, "treatment" is an approach for obtaining beneficial or desired clinical results. "Treatment" as used herein, covers any administration or application of a therapeutic for disease in a mammal, including a human. For purposes of this disclosure, beneficial or desired clinical results include, but are not limited to, any one or more of: alleviation of one or more symptoms, diminishment of extent of disease, preventing or delaying spread (for example, metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods provided herein contemplate any one or more of these aspects of treatment. In-line with the above, the term treatment does not require one-hundred percent removal of all aspects of the disorder.

"Ameliorating" means a lessening or improvement of one or more symptoms as compared to not administering an anti-LILRB2 antibody. "Ameliorating" also includes shortening or reduction in duration of a symptom.

In the context of cancer, the term "treating" includes any or all of: inhibiting growth of cancer cells, inhibiting replication of cancer cells, lessening of overall tumor burden and ameliorating one or more symptoms associated with the disease.

The term "biological sample" means a quantity of a substance from a living thing or formerly living thing. Such substances include, but are not limited to, blood, (for example, whole blood), plasma, serum, urine, amniotic fluid, synovial fluid, endothelial cells, leukocytes, monocytes, other cells, organs, tissues, bone marrow, lymph nodes and spleen.

The term "control" refers to a composition known to not contain an analyte ("negative control") or to contain analyte ("positive control"). A positive control can comprise a known concentration of analyte. "Control," "positive control," and "calibrator" may be used interchangeably herein to refer to a composition comprising a known concentration of analyte. A "positive control" can be used to establish assay performance characteristics and is a useful indicator of the integrity of reagents (for example, analytes).

"Predetermined cutoff" and "predetermined level" refer generally to an assay cutoff value that is used to assess diagnostic/prognostic/therapeutic efficacy results by comparing the assay results against the predetermined cutoff/level, where the predetermined cutoff/level already has been linked or associated with various clinical parameters (for example, severity of disease, progression, non-progression, improvement, etc.). While the present disclosure may provide exemplary predetermined levels, it is well-known that cutoff values may vary depending on the nature of the immunoassay (for example, antibodies employed, etc.). It further is well within the skill of one of ordinary skill in the art to adapt the disclosure herein for other immunoassays to obtain immunoassay-specific cutoff values for those other immunoassays based on this disclosure. Whereas the precise value of the predetermined cutoff/level may vary between assays, correlations as described herein (if any) may be generally applicable.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In some embodiments, by "reduce" or "inhibit" is meant the ability to cause an overall decrease of 50% or greater. In some embodiments, by "reduce" or "inhibit" is meant the ability to cause an overall decrease of 75%, 85%, 90%, 95%, or greater. In some embodiments, the amount noted above is inhibited or decreased over a period of time, relative to a control dose (such as a placebo) over the same period of time. A "reference" as used herein, refers to any sample, standard, or level that is used for comparison purposes. A reference may be obtained from a healthy and/or non-diseased sample. In some examples, a reference may be obtained from an untreated sample. In some examples, a reference is obtained from a non-diseased on non-treated sample of a subject individual. In some examples, a reference is obtained from one or more healthy individuals who are not the subject or patient.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease. Unless otherwise specified, the terms "reduce," "inhibit," or "prevent" do not denote or require complete prevention over all time.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

A "therapeutically effective amount" of a substance/molecule, agonist or antagonist may vary according to factors such as the disease state, age, sex, and weight of the individual, and the ability of the substance/molecule, agonist or antagonist to elicit a desired response in the individual. A therapeutically effective amount is also one in which any toxic or detrimental effects of the substance/molecule, agonist or antagonist are outweighed by the therapeutically beneficial effects. A therapeutically effective amount may be delivered in one or more administrations. A therapeutically effective amount refers to an amount effective, at dosages and for periods of time necessary, to achieve the desired therapeutic and/or prophylactic result.

A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

A "PD-1 therapy" encompasses any therapy that modulates PD-1 binding to PD-L1 and/or PD-L2. PD-1 therapies may, for example, directly interact with PD-1 and/or PD-L1. In some embodiments, a PD-1 therapy includes a molecule that directly binds to and/or influences the activity of PD-1. In some embodiments, a PD-1 therapy includes a molecule that directly binds to and/or influences the activity of PD-L1. Thus, an antibody that binds to PD-1 or PD-L1 and blocks the interaction of PD-1 to PD-L1 is a PD-1 therapeutic. When a desired subtype of PD-1 therapy is intended, it will be designated by the phrase "PD-1 specific" for a therapy involving a molecule that interacts directly with PD-1, or "PD-L1 specific" for a molecule that interacts directly with PD-L1, as appropriate. Unless designated otherwise, all disclosure contained herein regarding PD-1 therapy applies to PD-1 therapy generally, as well as PD-1 specific and/or PD-L1 specific therapies. Nonlimiting exemplary PD-1 therapies include nivolumab (BMS-936558, MDX-1106, ONO-4538); pidilizumab, lambrolizumab/pembrolizumab (KEYTRUDA®, MK-3475); durvalumab; RG-7446; MSB-0010718C; AMP-224; BMS-936559 (an anti-PD-L1 antibody); AMP-514; MDX-1105; ANB-011; anti-LAG-3/PD-1; anti-PD-1 Ab (CoStim); anti-PD-1 Ab (Kadmon Pharm.); anti-PD-1 Ab (Immunovo); anti-TIM-3/PD-1 Ab (Anaptys-Bio); anti-PD-L1 Ab (CoStim/Novartis); MEDI-4736 (an anti-PD-L1 antibody, Medimmune/AstraZeneca); RG7446/MPDL3280A (an anti-PD-L1 antibody, Genentech/Roche); KD-033, PD-1 antagonist (Agenus); STI-A1010; STI-A1110; TSR-042; and other antibodies that are directed against programmed death-1 (PD-1) or programmed death ligand 1 (PD-L1).

Administration "in combination with" one or more further therapeutic agents includes simultaneous (concurrent) and consecutive or sequential administration in any order.

The term "concurrently" is used herein to refer to administration of two or more therapeutic agents, where at least part of the administration overlaps in time or where the administration of one therapeutic agent falls within a short period of time relative to administration of the other therapeutic agent. For example, the two or more therapeutic agents are administered with a time separation of no more than about a specified number of minutes.

The term "sequentially" is used herein to refer to administration of two or more therapeutic agents where the administration of one or more agent(s) continues after discontinuing the administration of one or more other agent(s). For example, administration of the two or more therapeutic agents are administered with a time separation of more than about a specified number of minutes.

As used herein, "in conjunction with" refers to administration of one treatment modality in addition to another treatment modality. As such, "in conjunction with" refers to administration of one treatment modality before, during or after administration of the other treatment modality to the individual.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (for example, a package or container) or kit comprising at least one reagent, for example, a medicament for treatment of a disease or disorder (for example, cancer), or a probe for specifically detecting a biomarker described herein. In some embodiments, the manufacture or kit is promoted, distributed, or sold as a unit for performing the methods described herein.

The terms "label" and "detectable label" mean a moiety attached to an antibody or its analyte to render a reaction (for example, binding) between the members of the specific binding pair, detectable. The labeled member of the specific binding pair is referred to as "detectably labeled." Thus, the term "labeled binding protein" refers to a protein with a label incorporated that provides for the identification of the binding protein. In some embodiments, the label is a detectable marker that can produce a signal that is detectable by visual or instrumental means, for example, incorporation of a radiolabeled amino acid or attachment to a polypeptide of biotinyl moieties that can be detected by marked avidin (for example, streptavidin containing a fluorescent marker or enzymatic activity that can be detected by optical or colorimetric methods). Examples of labels for polypeptides include, but are not limited to, the following: radioisotopes or radionuclides (for example, $^{3}$H, $^{14}$C$^{35}$S, $^{90}$Y, $^{99}$Tc, $^{111}$In, $^{125}$I, $^{131}$I, $^{177}$Lu, $^{166}$Ho, or $^{153}$Sm); chromogens, fluorescent labels (for example, FITC, rhodamine, lanthanide phosphors), enzymatic labels (for example, horseradish peroxidase, luciferase, alkaline phosphatase); chemiluminescent markers; biotinyl groups; predetermined polypeptide epitopes recognized by a secondary reporter (for example, leucine zipper pair sequences, binding sites for secondary antibodies, metal binding domains, epitope tags); and magnetic agents, such as gadolinium chelates. Representative examples of labels commonly employed for immunoassays include moieties that produce light, for example, acridinium compounds, and moieties that produce fluorescence, for example, fluorescein. In this regard, the moiety itself may not be detectably labeled but may become detectable upon reaction with yet another moiety.

The term "conjugate" refers to an antibody that is chemically linked to a second chemical moiety, such as a therapeutic or cytotoxic agent. The term "agent" includes a chemical compound, a mixture of chemical compounds, a biological macromolecule, or an extract made from biological materials. In some embodiments, the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. When employed in the context of an immunoassay, the conjugate antibody may be a detectably labeled antibody used as the detection antibody.

II. Anti-LILRB2 Antibodies

Novel antibodies directed against LILRB2 are provided. Anti-LILRB2 antibodies include, but are not limited to, humanized antibodies, chimeric antibodies, mouse antibodies, human antibodies, and antibodies comprising the heavy chain and/or light chain CDRs discussed herein. In some embodiments, an isolated antibody that binds to LILRB2 is provided. In some embodiments, a monoclonal antibody that binds to LILRB2 is provided.

In some aspects, an anti-LILRB2 antibody comprises at least one, two, three, four, five, or six CDRs selected from (a) CDR-H1 comprising the amino acid sequence of SEQ ID NO: 15; (b) CDR-H2 comprising the amino acid sequence of SEQ ID NO: 16; (c) CDR-H3 comprising the amino acid sequence of SEQ ID NO: 17; (d) CDR-L1 comprising the amino acid sequence of SEQ ID NO: 18; (e) CDR-L2 comprising the amino acid sequence of SEQ ID NO: 19; and (f) CDR-L3 comprising the amino acid sequence of SEQ ID NO: 20.

In some aspects, an anti-LILRB2 antibody comprises at least one, two, three, four, five, or six CDRs selected from (a) CDR-H1 comprising the amino acid sequence of SEQ ID NO: 95; (b) CDR-H2 comprising the amino acid sequence of SEQ ID NO: 96; (c) CDR-H3 comprising the amino acid sequence of SEQ ID NO: 97; (d) CDR-L1 comprising the amino acid sequence of SEQ ID NO: 98; (e) CDR-L2 comprising the amino acid sequence of SEQ ID NO: 99; and (f) CDR-L3 comprising the amino acid sequence of SEQ ID NO: 100.

In some aspects, an anti-LILRB2 antibody comprises at least one, two, three, four, five, or six CDRs selected from (a) CDR-H1 comprising the amino acid sequence of SEQ ID NO: 105; (b) CDR-H2 comprising the amino acid sequence of SEQ ID NO: 106; (c) CDR-H3 comprising the amino acid sequence of SEQ ID NO: 107; (d) CDR-L1 comprising the amino acid sequence of SEQ ID NO: 108; (e) CDR-L2 comprising the amino acid sequence of SEQ ID NO: 109; and (f) CDR-L3 comprising the amino acid sequence of SEQ ID NO: 110.

In some aspects, an anti-LILRB2 antibody comprises at least one, two, three, four, five, or six CDRs selected from (a) CDR-H1 comprising the amino acid sequence of SEQ ID NO: 115; (b) CDR-H2 comprising the amino acid sequence of SEQ ID NO: 116; (c) CDR-H3 comprising the amino acid sequence of SEQ ID NO: 117; (d) CDR-L1 comprising the amino acid sequence of SEQ ID NO: 118; (e) CDR-L2 comprising the amino acid sequence of SEQ ID NO: 119; and (f) CDR-L3 comprising the amino acid sequence of SEQ ID NO: 120.

In some embodiments, an anti-LILRB2 antibody is provided that competes with an anti-LILRB2 antibody described herein. In some embodiments, an antibody that competes for binding (i.e., cross-competes) with any of the antibodies provided herein can be made and/or used.

In some embodiments, the anti-LILRB2 antibody comprises at least one, at least two, or all three heavy chain CDR sequences selected from (a) CDR-H1 comprising the amino acid sequence of SEQ ID NO: 15; (b) CDR-H2 comprising the amino acid sequence of SEQ ID NO: 16; and (c) CDR-H3 comprising the amino acid sequence of SEQ ID NO: 17.

In some embodiments, the anti-LILRB2 antibody comprises at least one, at least two, or all three light chain CDR sequences selected from (a) CDR-L1 comprising the amino acid sequence of SEQ ID NO: 18; (b) CDR-L2 comprising the amino acid sequence of SEQ ID NO: 19; and (c) CDR-L3 comprising the amino acid sequence of SEQ ID NO: 20.

In some embodiments, the anti-LILRB2 antibody comprises at least one, at least two, or all three heavy chain CDR sequences selected from (a) CDR-H1 comprising the amino acid sequence of SEQ ID NO: 95; (b) CDR-H2 comprising the amino acid sequence of SEQ ID NO: 96; and (c) CDR-H3 comprising the amino acid sequence of SEQ ID NO: 97.

In some embodiments, the anti-LILRB2 antibody comprises at least one, at least two, or all three light chain CDR sequences selected from (a) CDR-L1 comprising the amino acid sequence of SEQ ID NO: 98; (b) CDR-L2 comprising the amino acid sequence of SEQ ID NO: 99; and (c) CDR-L3 comprising the amino acid sequence of SEQ ID NO: 100.

In some embodiments, the anti-LILRB2 antibody comprises at least one, at least two, or all three heavy chain CDR sequences selected from (a) CDR-H1 comprising the amino acid sequence of SEQ ID NO: 105; (b) CDR-H2 comprising the amino acid sequence of SEQ ID NO: 106; and (c) CDR-H3 comprising the amino acid sequence of SEQ ID NO: 107.

In some embodiments, the anti-LILRB2 antibody comprises at least one, at least two, or all three light chain CDR sequences selected from (a) CDR-L1 comprising the amino acid sequence of SEQ ID NO: 108; (b) CDR-L2 comprising the amino acid sequence of SEQ ID NO: 109; and (c) CDR-L3 comprising the amino acid sequence of SEQ ID NO: 110.

In some embodiments, the anti-LILRB2 antibody comprises at least one, at least two, or all three heavy chain CDR sequences selected from (a) CDR-H1 comprising the amino acid sequence of SEQ ID NO: 115; (b) CDR-H2 comprising the amino acid sequence of SEQ ID NO: 116; and (c) CDR-H3 comprising the amino acid sequence of SEQ ID NO: 117.

In some embodiments, the anti-LILRB2 antibody comprises at least one, at least two, or all three light chain CDR sequences selected from (a) CDR-L1 comprising the amino acid sequence of SEQ ID NO: 118; (b) CDR-L2 comprising the amino acid sequence of SEQ ID NO: 119; and (c) CDR-L3 comprising the amino acid sequence of SEQ ID NO: 120.

In some embodiments, any of the six CDRs provided herein can be combined as subparts with any of the other CDRs provided herein, for a total of six CDRs in a construct. Thus, in some embodiments, two CDRs from a first antibody (for example, CDR-H1 and CDR-H2) can be combined with four CDRs from a second antibody (CDR-H3, CDR-L1, CDR-L2, and CDR-L3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 13. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 13. In some embodiments, substitutions, insertions, or deletions occur in regions outside the CDRs (that is, in the FRs). Optionally, the anti-LILRB2 antibody comprises the $V_H$ sequence of SEQ ID NO: 13, including post-translational modifications of that sequence.

In some embodiments, the $V_H$ comprises: (a) CDR-H1 comprising the amino acid sequence of SEQ ID NO: 15; (b) CDR-H2 comprising the amino acid sequence of SEQ ID NO: 16; and (c) CDR-H3 comprising the amino acid sequence of SEQ ID NO: 17.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 14. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 14. In some embodiments, the substitutions, insertions, or deletions occur in regions outside the CDRs (that is, in the FRs). Optionally, the anti-LILRB2 antibody comprises the $V_L$ sequence of SEQ ID NO: 14, including post-translational modifications of that sequence.

In some embodiments, the $V_L$ comprises: (a) CDR-L1 comprising the amino acid sequence of SEQ ID NO: 18; (b) CDR-L2 comprising the amino acid sequence of SEQ ID NO: 19; and (c) CDR-L3 comprising the amino acid sequence of SEQ ID NO: 20.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 13 and a $V_L$ having at least 90%, 91%, 92%, 93%, 94%, 95%, 96%, 97%, 98%, 99%, or 100% sequence identity to the amino acid sequence of SEQ ID NO: 14. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 13. In some embodiments, a total of 1 to 10 amino acids have been substituted, inserted, and/or deleted in SEQ ID NO: 14. In some embodiments, substitutions, insertions, or deletions occur in regions outside the CDRs (that is, in the FRs). Optionally, the anti-LILRB2 antibody comprises the $V_H$ domain sequence in SEQ ID NO: 13 and the $V_L$ domain sequence of SEQ ID NO: 14, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 13 and SEQ ID NO: 14, respectively, including post-translational modifications of those sequences.

In some embodiments, an anti-LILRB2 antibody comprises a heavy chain comprising the amino acid sequence of SEQ ID NO: 11 and a light chain comprising the amino acid sequence of SEQ ID NO: 12.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 53. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 53. In some embodiments, substitutions, insertions, or deletions occur in regions outside the CDRs (that is, in the FRs). Optionally, the anti-LILRB2 antibody comprises the $V_H$ sequence of SEQ ID NO: 53, including post-translational modifications of that sequence.

In some embodiments, the $V_H$ comprises: (a) CDR-H1 comprising the amino acid sequence of SEQ ID NO: 15; (b) CDR-H2 comprising the amino acid sequence of SEQ ID NO: 16; and (c) CDR-H3 comprising the amino acid sequence of SEQ ID NO: 17.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 54. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 54. In some embodiments, the substitutions, insertions, or deletions occur in regions outside the CDRs (that is, in the FRs). Optionally, the anti-LILRB2 antibody comprises the $V_L$ sequence of SEQ ID NO: 54, including post-translational modifications of that sequence.

In some embodiments, the $V_L$ comprises: (a) CDR-L1 comprising the amino acid sequence of SEQ ID NO: 18; (b) CDR-L2 comprising the amino acid sequence of SEQ ID NO: 19; and (c) CDR-L3 comprising the amino acid sequence of SEQ ID NO: 20.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 53 and a $V_L$ having at least 90%, 91%, 92%, 93%, 94%, 95%, 96%, 97%, 98%, 99%, or 100% sequence identity to the amino acid sequence of SEQ ID NO: 54. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 53. In some embodiments, a total of 1 to 10 amino acids have been substituted, inserted, and/or deleted in SEQ ID NO: 54. In some embodiments, substitutions, insertions, or deletions occur in regions outside the CDRs (that is, in the FRs). Optionally, the anti-LILRB2 antibody comprises the $V_H$ domain sequence in SEQ ID NO: 53 and the $V_L$ domain sequence of SEQ ID NO: 54, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 53 and SEQ ID NO: 54, respectively, including post-translational modifications of those sequences.

In some embodiments, an anti-LILRB2 antibody comprises a heavy chain comprising the amino acid sequence of SEQ ID NO: 51 and a light chain comprising the amino acid sequence of SEQ ID NO: 52.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 63. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 63. In some embodiments, substitutions, insertions, or deletions occur in regions outside the CDRs (that is, in the FRs). Optionally, the anti-LILRB2 antibody comprises the $V_H$ sequence of SEQ ID NO: 63, including post-translational modifications of that sequence.

In some embodiments, the $V_H$ comprises: (a) CDR-H1 comprising the amino acid sequence of SEQ ID NO: 15; (b) CDR-H2 comprising the amino acid sequence of SEQ ID NO: 16; and (c) CDR-H3 comprising the amino acid sequence of SEQ ID NO: 17.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 64. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 64. In some embodiments, the substitutions, insertions, or deletions occur in regions outside the CDRs (that is, in the FRs). Optionally, the anti-LILRB2 antibody comprises the $V_L$ sequence of SEQ ID NO: 64, including post-translational modifications of that sequence.

In some embodiments, the $V_L$ comprises: (a) CDR-L1 comprising the amino acid sequence of SEQ ID NO: 18; (b) CDR-L2 comprising the amino acid sequence of SEQ ID NO: 19; and (c) CDR-L3 comprising the amino acid sequence of SEQ ID NO: 20.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 63 and a $V_L$ having at least 90%, 91%, 92%, 93%, 94%, 95%, 96%, 97%, 98%, 99%, or 100% sequence identity to the amino acid sequence of SEQ ID NO: 64. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 63. In some embodiments, a total of 1 to 10 amino acids have been substituted, inserted, and/or deleted in SEQ ID NO: 64. In some embodiments, substitutions, insertions, or deletions occur in regions outside the CDRs (that is, in the FRs). Optionally, the anti-LILRB2 antibody comprises the $V_H$ domain sequence in SEQ ID NO: 63 and the $V_L$ domain sequence of SEQ ID NO: 64, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 63 and SEQ ID NO: 64, respectively, including post-translational modifications of those sequences.

In some embodiments, an anti-LILRB2 antibody comprises a heavy chain comprising the amino acid sequence of SEQ ID NO: 61 and a light chain comprising the amino acid sequence of SEQ ID NO: 62.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 73. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 73. In some embodiments, substitutions, insertions, or deletions occur in regions outside the CDRs (that is, in the FRs). Optionally, the anti-LILRB2 antibody comprises the $V_H$ sequence of SEQ ID NO: 73, including post-translational modifications of that sequence.

In some embodiments, the $V_H$ comprises: (a) CDR-H1 comprising the amino acid sequence of SEQ ID NO: 15; (b) CDR-H2 comprising the amino acid sequence of SEQ ID NO: 16; and (c) CDR-H3 comprising the amino acid sequence of SEQ ID NO: 17.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 74. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 74. In some embodiments, the substitutions, insertions, or deletions occur in regions outside the CDRs (that is, in the FRs). Optionally, the anti-LILRB2 antibody comprises the $V_L$ sequence of SEQ ID NO: 74, including post-translational modifications of that sequence.

In some embodiments, the $V_L$ comprises: (a) CDR-L1 comprising the amino acid sequence of SEQ ID NO: 18; (b) CDR-L2 comprising the amino acid sequence of SEQ ID NO: 19; and (c) CDR-L3 comprising the amino acid sequence of SEQ ID NO: 20.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 73 and a $V_L$ having at least 90%, 91%, 92%, 93%, 94%, 95%, 96%, 97%, 98%, 99%, or 100% sequence identity to the amino acid sequence of SEQ ID NO: 74. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 73. In some embodiments, a total of 1 to 10 amino acids have been substituted, inserted, and/or deleted in SEQ ID NO: 74. In some embodiments, substitutions, insertions, or deletions occur in regions outside the CDRs (that is, in the FRs). Optionally, the anti-LILRB2 antibody comprises the $V_H$ domain sequence in SEQ ID NO: 73 and the $V_L$ domain sequence of SEQ ID NO: 74, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 73 and SEQ ID NO: 74, respectively, including post-translational modifications of those sequences.

In some embodiments, an anti-LILRB2 antibody comprises a heavy chain comprising the amino acid sequence of SEQ ID NO: 71 and a light chain comprising the amino acid sequence of SEQ ID NO: 72.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 83. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 83. In some embodiments, substitutions, insertions, or deletions occur in regions outside the CDRs (that is, in the FRs). Optionally, the anti-LILRB2 antibody comprises the $V_H$ sequence of SEQ ID NO: 83, including post-translational modifications of that sequence.

In some embodiments, the $V_H$ comprises: (a) CDR-H1 comprising the amino acid sequence of SEQ ID NO: 15; (b) CDR-H2 comprising the amino acid sequence of SEQ ID NO: 16; and (c) CDR-H3 comprising the amino acid sequence of SEQ ID NO: 17.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 84. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 84. In some embodiments, the substitutions, insertions, or deletions occur in regions outside the CDRs (that is, in the FRs). Optionally, the anti-LILRB2 antibody comprises the $V_L$ sequence of SEQ ID NO: 84, including post-translational modifications of that sequence.

In some embodiments, the $V_L$ comprises: (a) CDR-L1 comprising the amino acid sequence of SEQ ID NO: 18; (b) CDR-L2 comprising the amino acid sequence of SEQ ID NO: 19; and (c) CDR-L3 comprising the amino acid sequence of SEQ ID NO: 20.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 83 and a $V_L$ having at least 90%, 91%, 92%, 93%, 94%, 95%, 96%, 97%, 98%, 99%, or 100% sequence identity to the amino acid sequence of SEQ ID NO: 84. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 83. In some embodiments, a total of 1 to 10 amino acids have been substituted, inserted, and/or deleted in SEQ ID NO: 84. In some embodiments, substitutions, insertions, or deletions occur in regions outside the CDRs (that is, in the FRs). Optionally, the anti-LILRB2 antibody comprises the $V_H$ domain sequence in SEQ ID NO: 83 and the $V_L$ domain sequence of SEQ ID NO: 84, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 83 and SEQ ID NO: 84, respectively, including post-translational modifications of those sequences.

In some embodiments, an anti-LILRB2 antibody comprises a heavy chain comprising the amino acid sequence of SEQ ID NO: 81 and a light chain comprising the amino acid sequence of SEQ ID NO: 82.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 93. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 93. In some embodiments, substitutions, insertions, or deletions occur in regions outside the CDRs (that is, in the FRs). Optionally, the anti-LILRB2 antibody comprises the $V_H$ sequence of SEQ ID NO: 93, including post-translational modifications of that sequence.

In some embodiments, the $V_H$ comprises: (a) CDR-H1 comprising the amino acid sequence of SEQ ID NO: 95; (b) CDR-H2 comprising the amino acid sequence of SEQ ID NO: 96; and (c) CDR-H3 comprising the amino acid sequence of SEQ ID NO: 97.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 94. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 94. In some embodiments, the substitutions, insertions, or deletions occur in regions outside the CDRs (that is, in the FRs). Optionally, the anti-LILRB2 antibody comprises the $V_L$ sequence of SEQ ID NO: 94, including post-translational modifications of that sequence.

In some embodiments, the $V_L$ comprises: (a) CDR-L1 comprising the amino acid sequence of SEQ ID NO: 98; (b) CDR-L2 comprising the amino acid sequence of SEQ ID NO: 99; and (c) CDR-L3 comprising the amino acid sequence of SEQ ID NO: 100.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 93 and a $V_L$ having at least 90%, 91%, 92%, 93%, 94%, 95%, 96%, 97%, 98%, 99%, or 100% sequence identity to the amino acid sequence of SEQ ID NO: 94. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 93. In some embodiments, a total of 1 to 10 amino acids have been substituted, inserted, and/or deleted in SEQ ID NO: 94. In some embodiments, substitutions, insertions, or deletions occur in regions outside the CDRs (that is, in the FRs). Optionally, the anti-LILRB2 antibody comprises the $V_H$ domain sequence in SEQ ID NO: 93 and the $V_L$ domain sequence of SEQ ID NO: 94, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 93 and SEQ ID NO: 94, respectively, including post-translational modifications of those sequences.

In some embodiments, an anti-LILRB2 antibody comprises a heavy chain comprising the amino acid sequence of SEQ ID NO: 91 and a light chain comprising the amino acid sequence of SEQ ID NO: 92.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 103. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 103. In some embodiments, substitutions, insertions, or deletions occur in regions outside the CDRs (that is, in the FRs). Optionally, the anti-LILRB2 antibody comprises the $V_H$ sequence of SEQ ID NO: 103, including post-translational modifications of that sequence.

In some embodiments, the $V_H$ comprises: (a) CDR-H1 comprising the amino acid sequence of SEQ ID NO: 105; (b) CDR-H2 comprising the amino acid sequence of SEQ ID NO: 106; and (c) CDR-H3 comprising the amino acid sequence of SEQ ID NO: 107.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 104. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 104. In some embodiments, the substitutions, insertions, or deletions occur in regions outside the CDRs (that is, in the FRs). Optionally, the anti-LILRB2 antibody comprises the $V_L$ sequence of SEQ ID NO: 104, including post-translational modifications of that sequence.

In some embodiments, the $V_L$ comprises: (a) CDR-L1 comprising the amino acid sequence of SEQ ID NO: 108; (b) CDR-L2 comprising the amino acid sequence of SEQ ID NO: 109; and (c) CDR-L3 comprising the amino acid sequence of SEQ ID NO: 110.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 103 and a $V_L$ having at least 90%, 91%, 92%, 93%, 94%, 95%, 96%, 97%, 98%, 99%, or 100% sequence identity to the amino acid sequence of SEQ ID NO: 104. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 103. In some embodiments, a total of 1 to 10 amino acids have been substituted, inserted, and/or deleted in SEQ ID NO: 104. In some embodiments, substitutions, insertions, or deletions occur in regions outside the CDRs (that is, in the FRs). Optionally, the anti-LILRB2 antibody comprises the $V_H$ domain sequence in SEQ ID NO: 103 and the $V_L$ domain sequence of SEQ ID NO: 104, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 103 and SEQ ID NO: 104, respectively, including post-translational modifications of those sequences.

In some embodiments, an anti-LILRB2 antibody comprises a heavy chain comprising the amino acid sequence of SEQ ID NO: 101 and a light chain comprising the amino acid sequence of SEQ ID NO: 102.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 113. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 113. In some embodiments, substitutions, insertions, or deletions occur in regions outside the CDRs (that is, in the FRs). Optionally, the anti-LILRB2 antibody comprises the $V_H$ sequence of SEQ ID NO: 113, including post-translational modifications of that sequence.

In some embodiments, the $V_H$ comprises: (a) CDR-H1 comprising the amino acid sequence of SEQ ID NO: 115; (b) CDR-H2 comprising the amino acid sequence of SEQ ID NO: 116; and (c) CDR-H3 comprising the amino acid sequence of SEQ ID NO: 117.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 114. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 114. In some embodiments, the substitutions, insertions, or deletions occur in regions outside the CDRs (that is, in the FRs). Optionally, the anti-LILRB2 antibody comprises the $V_L$ sequence of SEQ ID NO: 114, including post-translational modifications of that sequence.

In some embodiments, the $V_L$ comprises: (a) CDR-L1 comprising the amino acid sequence of SEQ ID NO: 118; (b) CDR-L2 comprising the amino acid sequence of SEQ ID NO: 119; and (c) CDR-L3 comprising the amino acid sequence of SEQ ID NO: 120.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 113 and a $V_L$ having at least 90%, 91%, 92%, 93%, 94%, 95%, 96%, 97%, 98%, 99%, or 100% sequence identity to the amino acid sequence of SEQ ID NO: 114. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 113. In some embodiments, a total of 1 to 10 amino acids have been substituted, inserted, and/or deleted in SEQ ID NO: 114. In some embodiments, substitutions, insertions, or deletions occur in regions outside the CDRs (that is, in the FRs). Optionally, the anti-LILRB2 antibody comprises the $V_H$ domain sequence in SEQ ID NO: 113 and the $V_L$ domain sequence of SEQ ID NO: 114, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 113 and SEQ ID NO: 114, respectively, including post-translational modifications of those sequences.

In some embodiments, an anti-LILRB2 antibody comprises a heavy chain comprising the amino acid sequence of SEQ ID NO: 111 and a light chain comprising the amino acid sequence of SEQ ID NO: 112.

In some aspects, an anti-LILRB2 antibody comprises at least one, two, three, four, five, or six CDRs selected from (a) CDR-H1 comprising the amino acid sequence of SEQ ID NO: 5; (b) CDR-H2 comprising the amino acid sequence of SEQ ID NO: 6; (c) CDR-H3 comprising the amino acid sequence of SEQ ID NO: 7; (d) CDR-L1 comprising the amino acid sequence of SEQ ID NO: 8; (e) CDR-L2 comprising the amino acid sequence of SEQ ID NO: 9; and (f) CDR-L3 comprising the amino acid sequence of SEQ ID NO: 10.

In some embodiments, an anti-LILRB2 antibody is provided that competes with an anti-LILRB2 antibody described herein. In some embodiments, an antibody that competes for binding (i.e., cross-competes) with any of the antibodies provided herein can be made and/or used.

In some embodiments, the anti-LILRB2 antibody comprises at least one, at least two, or all three heavy chain CDR sequences selected from (a) CDR-H1 comprising the amino acid sequence of SEQ ID NO: 5; (b) CDR-H2 comprising the amino acid sequence of SEQ ID NO: 6; and (c) CDR-H3 comprising the amino acid sequence of SEQ ID NO: 7.

In some embodiments, the anti-LILRB2 antibody comprises at least one, at least two, or all three light chain CDR sequences selected from (a) CDR-L1 comprising the amino acid sequence of SEQ ID NO: 8; (b) CDR-L2 comprising the amino acid sequence of SEQ ID NO: 9; and (c) CDR-L3 comprising the amino acid sequence of SEQ ID NO: 10.

In some embodiments, any of the six CDRs provided herein can be combined as subparts with any of the other CDRs provided herein, for a total of six CDRs in a construct. Thus, in some embodiments, two CDRs from a first antibody (for example, CDR-H1 and CDR-H2) can be combined with four CDRs from a second antibody (CDR-H3, CDR-L1, CDR-L2, and CDR-L3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 3. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 3. In some embodiments, substitutions, insertions, or deletions occur in regions outside the CDRs (that is, in the FRs). Optionally, the anti-LILRB2 antibody comprises the $V_H$ sequence of SEQ ID NO: 3, including post-translational modifications of that sequence.

In some embodiments, the $V_H$ comprises: (a) CDR-H1 comprising the amino acid sequence of SEQ ID NO: 5; (b) CDR-H2 comprising the amino acid sequence of SEQ ID NO: 6; and (c) CDR-H3 comprising the amino acid sequence of SEQ ID NO: 7.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 4. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 4. In some embodiments, the substitutions, insertions, or deletions occur in regions outside the CDRs (that is, in the FRs). Optionally, the anti-LILRB2 antibody comprises the $V_L$ sequence of SEQ ID NO: 4, including post-translational modifications of that sequence.

In some embodiments, the $V_L$ comprises: (a) CDR-L1 comprising the amino acid sequence of SEQ ID NO: 8; (b) CDR-L2 comprising the amino acid sequence of SEQ ID NO: 9; and (c) CDR-L3 comprising the amino acid sequence of SEQ ID NO: 10.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 3 and a $V_L$ having at least 90%, 91%, 92%, 93%, 94%, 95%, 96%, 97%, 98%, 99%, or 100% sequence identity to the amino acid sequence of SEQ ID NO: 4. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 3. In some embodiments, a total of 1 to 10 amino acids have been substituted, inserted, and/or deleted in SEQ ID NO: 4. In some embodiments, substitutions, insertions, or deletions occur in regions outside the CDRs (that is, in the FRs). Optionally, the anti-LILRB2 antibody comprises the $V_H$ domain sequence in SEQ ID NO: 3 and the $V_L$ domain sequence of SEQ ID NO: 4, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 3 and SEQ ID NO: 4, respectively, including post-translational modifications of those sequences.

In some embodiments, an anti-LILRB2 antibody comprises a heavy chain comprising the amino acid sequence of SEQ ID NO: 1 and a light chain comprising the amino acid sequence of SEQ ID NO: 2.

In some aspects, an anti-LILRB2 antibody comprises at least one, two, three, four, five, or six CDRs selected from (a) CDR-H1 comprising the amino acid sequence of SEQ ID NO: 25; (b) CDR-H2 comprising the amino acid sequence of SEQ ID NO: 26; (c) CDR-H3 comprising the amino acid sequence of SEQ ID NO: 27; (d) CDR-L1 comprising the amino acid sequence of SEQ ID NO: 28; (e) CDR-L2 comprising the amino acid sequence of SEQ ID NO: 29; and (f) CDR-L3 comprising the amino acid sequence of SEQ ID NO: 30.

In some embodiments, an anti-LILRB2 antibody is provided that competes with an anti-LILRB2 antibody described herein. In some embodiments, an antibody that competes for binding (i.e., cross-competes) with any of the antibodies provided herein can be made and/or used.

In some embodiments, the anti-LILRB2 antibody comprises at least one, at least two, or all three heavy chain CDR sequences selected from (a) CDR-H1 comprising the amino acid sequence of SEQ ID NO: 25; (b) CDR-H2 comprising the amino acid sequence of SEQ ID NO: 26; and (c) CDR-H3 comprising the amino acid sequence of SEQ ID NO: 27.

In some embodiments, the anti-LILRB2 antibody comprises at least one, at least two, or all three light chain CDR sequences selected from (a) CDR-L1 comprising the amino acid sequence of SEQ ID NO: 28; (b) CDR-L2 comprising the amino acid sequence of SEQ ID NO: 29; and (c) CDR-L3 comprising the amino acid sequence of SEQ ID NO: 30.

In some embodiments, any of the six CDRs provided herein can be combined as subparts with any of the other CDRs provided herein, for a total of six CDRs in a construct. Thus, in some embodiments, two CDRs from a first antibody (for example, CDR-H1 and CDR-H2) can be combined with four CDRs from a second antibody (CDR-H3, CDR-L1, CDR-L2, and CDR-L3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 23. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 23. In some embodiments, substitutions, insertions, or deletions occur in regions outside the CDRs (that is, in the FRs). Optionally, the anti-LILRB2 antibody comprises the $V_H$ sequence of SEQ ID NO: 23, including post-translational modifications of that sequence.

In some embodiments, the $V_H$ comprises: (a) CDR-H1 comprising the amino acid sequence of SEQ ID NO: 25; (b) CDR-H2 comprising the amino acid sequence of SEQ ID NO: 26; and (c) CDR-H3 comprising the amino acid sequence of SEQ ID NO: 27.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 24. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 24. In some embodiments, the substitutions, insertions, or deletions occur in regions outside the CDRs (that is, in the FRs). Optionally, the anti-LILRB2 antibody comprises the $V_L$ sequence of SEQ ID NO: 24, including post-translational modifications of that sequence.

In some embodiments, the $V_L$ comprises: (a) CDR-L1 comprising the amino acid sequence of SEQ ID NO: 28; (b) CDR-L2 comprising the amino acid sequence of SEQ ID NO: 29; and (c) CDR-L3 comprising the amino acid sequence of SEQ ID NO: 30.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 23 and a $V_L$ having at least 90%, 91%, 92%, 93%, 94%, 95%, 96%, 97%, 98%, 99%, or 100% sequence identity to the amino acid sequence of SEQ ID NO: 24. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 23. In some embodiments, a total of 1 to 10 amino acids have been substituted, inserted, and/or deleted in SEQ ID NO: 24. In some embodiments, substitutions, insertions, or deletions occur in regions outside the CDRs (that is, in the FRs). Optionally, the anti-LILRB2 antibody comprises the $V_H$ domain sequence in SEQ ID NO: 23 and the $V_L$ domain sequence of SEQ ID NO: 24, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 23 and SEQ ID NO: 24, respectively, including post-translational modifications of those sequences.

In some embodiments, an anti-LILRB2 antibody comprises a heavy chain comprising the amino acid sequence of SEQ ID NO: 21 and a light chain comprising the amino acid sequence of SEQ ID NO: 22.

In some aspects, an anti-LILRB2 antibody comprises at least one, two, three, four, five, or six CDRs selected from (a) CDR-H1 comprising the amino acid sequence of SEQ ID NO: 35; (b) CDR-H2 comprising the amino acid sequence of SEQ ID NO: 36; (c) CDR-H3 comprising the amino acid sequence of SEQ ID NO: 37; (d) CDR-L1 comprising the amino acid sequence of SEQ ID NO: 38; (e) CDR-L2 comprising the amino acid sequence of SEQ ID NO: 39; and (f) CDR-L3 comprising the amino acid sequence of SEQ ID NO: 40.

In some embodiments, an anti-LILRB2 antibody is provided that competes with an anti-LILRB2 antibody described herein. In some embodiments, an antibody that competes for binding (i.e., cross-competes) with any of the antibodies provided herein can be made and/or used.

In some embodiments, the anti-LILRB2 antibody comprises at least one, at least two, or all three heavy chain CDR sequences selected from (a) CDR-H1 comprising the amino acid sequence of SEQ ID NO: 35; (b) CDR-H2 comprising the amino acid sequence of SEQ ID NO: 36; and (c) CDR-H3 comprising the amino acid sequence of SEQ ID NO: 37.

In some embodiments, the anti-LILRB2 antibody comprises at least one, at least two, or all three light chain CDR sequences selected from (a) CDR-L1 comprising the amino acid sequence of SEQ ID NO: 38; (b) CDR-L2 comprising the amino acid sequence of SEQ ID NO: 39; and (c) CDR-L3 comprising the amino acid sequence of SEQ ID NO: 40.

In some embodiments, any of the six CDRs provided herein can be combined as subparts with any of the other CDRs provided herein, for a total of six CDRs in a construct. Thus, in some embodiments, two CDRs from a first antibody (for example, CDR-H1 and CDR-H2) can be combined with four CDRs from a second antibody (CDR-H3, CDR-L1, CDR-L2, and CDR-L3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 33. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 33. In some embodiments, substitutions, insertions, or deletions occur in regions outside the CDRs (that is, in the FRs). Optionally, the anti-LILRB2 antibody comprises the $V_H$ sequence of SEQ ID NO: 33, including post-translational modifications of that sequence.

In some embodiments, the $V_H$ comprises: (a) CDR-H1 comprising the amino acid sequence of SEQ ID NO: 35; (b) CDR-H2 comprising the amino acid sequence of SEQ ID NO: 36; and (c) CDR-H3 comprising the amino acid sequence of SEQ ID NO: 37.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 34. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 34. In some embodiments, the substitutions, insertions, or deletions occur in regions outside the CDRs (that is, in the FRs). Optionally, the anti-LILRB2 antibody comprises the $V_L$ sequence of SEQ ID NO: 34, including post-translational modifications of that sequence.

In some embodiments, the $V_L$ comprises: (a) CDR-L1 comprising the amino acid sequence of SEQ ID NO: 38; (b) CDR-L2 comprising the amino acid sequence of SEQ ID NO: 39; and (c) CDR-L3 comprising the amino acid sequence of SEQ ID NO: 40.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 33 and a $V_L$ having at least 90%, 91%, 92%, 93%, 94%, 95%, 96%, 97%, 98%, 99%, or 100% sequence identity to the amino acid sequence of SEQ ID NO: 34. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 33. In some embodiments, a total of 1 to 10 amino acids have been substituted, inserted, and/or deleted in SEQ ID NO: 34. In some embodiments, substitutions, insertions, or deletions occur in regions outside the CDRs (that is, in the FRs). Optionally, the anti-LILRB2 antibody comprises the $V_H$ domain sequence in SEQ ID NO: 33 and the $V_L$ domain sequence of SEQ ID NO: 34, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 33 and SEQ ID NO: 34, respectively, including post-translational modifications of those sequences.

In some embodiments, an anti-LILRB2 antibody comprises a heavy chain comprising the amino acid sequence of SEQ ID NO: 31 and a light chain comprising the amino acid sequence of SEQ ID NO: 32.

In some aspects, an anti-LILRB2 antibody comprises at least one, two, three, four, five, or six CDRs selected from (a) CDR-H1 comprising the amino acid sequence of SEQ ID NO: 45; (b) CDR-H2 comprising the amino acid sequence of SEQ ID NO: 46; (c) CDR-H3 comprising the amino acid sequence of SEQ ID NO: 47; (d) CDR-L1 comprising the amino acid sequence of SEQ ID NO: 48; (e) CDR-L2 comprising the amino acid sequence of SEQ ID NO: 49; and (f) CDR-L3 comprising the amino acid sequence of SEQ ID NO: 50.

In some embodiments, an anti-LILRB2 antibody is provided that competes with an anti-LILRB2 antibody described herein. In some embodiments, an antibody that competes for binding (i.e., cross-competes) with any of the antibodies provided herein can be made and/or used.

In some embodiments, the anti-LILRB2 antibody comprises at least one, at least two, or all three heavy chain CDR sequences selected from (a) CDR-H1 comprising the amino acid sequence of SEQ ID NO: 45; (b) CDR-H2 comprising the amino acid sequence of SEQ ID NO: 46; and (c) CDR-H3 comprising the amino acid sequence of SEQ ID NO: 47.

In some embodiments, the anti-LILRB2 antibody comprises at least one, at least two, or all three light chain CDR sequences selected from (a) CDR-L1 comprising the amino acid sequence of SEQ ID NO: 48; (b) CDR-L2 comprising the amino acid sequence of SEQ ID NO: 49; and (c) CDR-L3 comprising the amino acid sequence of SEQ ID NO: 50.

In some embodiments, any of the six CDRs provided herein can be combined as subparts with any of the other CDRs provided herein, for a total of six CDRs in a construct. Thus, in some embodiments, two CDRs from a first antibody (for example, CDR-H1 and CDR-H2) can be combined with four CDRs from a second antibody (CDR-H3, CDR-L1, CDR-L2, and CDR-L3). In some embodiments, two or fewer residues in one or more of the CDRs can be replaced to obtain a variant thereof. In some embodiments, two or fewer residues can be replaced in 1, 2, 3, 4, 5, or 6 of the CDRs.

In particular embodiments, an anti-LILRB2 antibody comprises a variable heavy chain ($V_H$) domain sequence having at least 90%, 91%, 92%, 93%, 94%, 95%, 96%, 97%, 98%, 99%, or 100% sequence identity to the amino acid sequence of SEQ ID NO: 43. In some embodiments, a $V_H$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 43. In some embodiments, substitutions, insertions, or deletions occur in regions outside the CDRs (that is, in the FRs). Optionally, the anti-LILRB2 antibody comprises the $V_H$ sequence of SEQ ID NO: 43, including post-translational modifications of that sequence.

In some embodiments, the $V_H$ comprises: (a) CDR-H1 comprising the amino acid sequence of SEQ ID NO: 45; (b) CDR-H2 comprising the amino acid sequence of SEQ ID NO: 46; and (c) CDR-H3 comprising the amino acid sequence of SEQ ID NO: 47.

In some embodiments, an anti-LILRB2 antibody is provided, wherein the antibody comprises a variable light chain ($V_L$) domain having at least 90%, 91%, 92%, 93%, 94%, 95%, 96%, 97%, 98%, 99%, or 100% sequence identity to the amino acid sequence of SEQ ID NO: 44. In some embodiments, a $V_L$ sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 44. In some embodiments, the substitutions, insertions, or deletions occur in regions outside the CDRs (that is, in the FRs). Optionally, the anti-LILRB2 antibody comprises the $V_L$ sequence of SEQ ID NO: 44, including post-translational modifications of that sequence.

In some embodiments, the $V_L$ comprises: (a) CDR-L1 comprising the amino acid sequence of SEQ ID NO: 48; (b)

CDR-L2 comprising the amino acid sequence of SEQ ID NO: 49; and (c) CDR-L3 comprising the amino acid sequence of SEQ ID NO: 50.

In some embodiments, an anti-LILRB2 antibody comprises a $V_H$ domain sequence having at least 90%, 91%, 92%, 93%, 94%, 95%, 96%, 97%, 98%, 99%, or 100% sequence identity to the amino acid sequence of SEQ ID NO: 43 and a $V_L$ having at least 90%, 91%, 92%, 93%, 94%, 95%, 96%, 97%, 98%, 99%, or 100% sequence identity to the amino acid sequence of SEQ ID NO: 44. In some embodiments, a $V_H$ domain sequence having at least 90%, 91%, 92%, 93%, 94%, 95%, 96%, 97%, 98%, or 99% identity contains substitutions (for example, conservative substitutions), insertions, or deletions relative to the reference sequence, and a $V_L$ domain sequence having at least 90%, 91%, 92%, 93%, 94%, 95%, 96%, 97%, 98%, or 99% identity contains substitutions (for example, conservative substitutions), insertions, or deletions relative to the reference sequence, but an anti-LILRB2 antibody comprising that sequence retains the ability to bind to LILRB2. In some embodiments, a total of 1 to 10 amino acids have been substituted, inserted, and/or deleted in SEQ ID NO: 43. In some embodiments, a total of 1 to 10 amino acids have been substituted, inserted, and/or deleted in SEQ ID NO: 44. In some embodiments, substitutions, insertions, or deletions occur in regions outside the CDRs (that is, in the FRs). Optionally, the anti-LILRB2 antibody comprises the $V_H$ domain sequence in SEQ ID NO: 43 and the $V_L$ domain sequence of SEQ ID NO: 44, including post-translational modifications of one or both sequence.

In some embodiments, an anti-LILRB2 antibody comprises a $V_H$ domain as in any of the embodiments provided herein, and a $V_L$ domain as in any of the embodiments provided herein. In some embodiments, the antibody comprises the $V_H$ and $V_L$ domain sequences of SEQ ID NO: 43 and SEQ ID NO: 44, respectively, including post-translational modifications of those sequences.

In some embodiments, an anti-LILRB2 antibody comprises a heavy chain comprising the amino acid sequence of SEQ ID NO: 41 and a light chain comprising the amino acid sequence of SEQ ID NO: 42.

In some embodiments, the anti-LILRB2 antibody comprises the six CDRs as described in any of the embodiments above and specifically binds to LILRB2 (e.g., human LILRB2). In some embodiments, the anti-LILRB2 antibody comprises the six CDRs of any of the embodiments described above, specifically binds to LILRB2, and blocks binding of HLA-G and/or HLA-A2 to LILRB2 (e.g., human LILRB2). In some embodiments, the anti-LILRB2 antibody comprises the six CDRs as described in any of the embodiments above, specifically binds to LILRB2 (e.g., human LILRB2), and causes conversion of M2-like macrophages to M1-like macrophages.

In some embodiments, an anti-LILRB2 antibody comprises a variable heavy chain region and a variable light chain region. In some embodiments, an anti-LILRB2 antibody comprises at least one heavy chain comprising a variable heavy chain region and at least a portion of a heavy chain constant region, and at least one light chain comprising a variable light chain region and at least a portion of a light chain constant region. In some embodiments, an anti-LILRB2 antibody comprises two heavy chains, wherein each heavy chain comprises a variable heavy chain region and at least a portion of a constant heavy chain region, and two light chains, wherein each light chain comprises a variable light chain region and at least a portion of a constant light chain region. As used herein, a single-chain Fv (scFv), or any other antibody that comprises, for example, a single polypeptide chain comprising all six CDRs (three heavy chain CDRs and three light chain CDRs) is considered to have a heavy chain and a light chain. In some embodiments, the heavy chain is the region of the anti-LILRB2 antibody that comprises the three heavy chain CDRs. In some embodiments, the light chain is the region of the anti-LILRB2 antibody that comprises the three light chain CDRs.

In some embodiments, antibodies which compete with the anti-LILRB2 antibodies provided herein for binding to LILRB2 are provided. In some embodiments, antibodies cross-compete with the anti-LILRB2 antibodies provided herein for binding to an epitope on LILRB2.

In some embodiments, competition assays may be used to identify a monoclonal antibody that competes with an anti-LILRB2 antibody described herein for binding to LILRB2. Competition assays can be used to determine whether two antibodies bind the same epitope by recognizing identical or sterically overlapping epitopes or one antibody competitively inhibits binding of another antibody to the antigen. In some embodiments, such a competing antibody binds to the same epitope that is bound by an antibody described herein. Exemplary competition assays include, but are not limited to, routine assays such as those provided in Harlow and Lane (1988) Antibodies: A Laboratory Manual ch. 14 (Cold Spring Harbor Laboratory, Cold Spring Harbor, N.Y.). Detailed exemplary methods for mapping an epitope to which an antibody binds are provided in Morris (1996) "Epitope Mapping Protocols," in Methods in Molecular Biology vol. 66 (Humana Press, Totowa, N.J.). In some embodiments, two antibodies are said to bind to the same epitope if each blocks binding of the other by 50% or more. In some embodiments, the antibody that competes with an anti-LILRB2 antibody described herein is a chimeric, humanized or human antibody. In some embodiments, an antibody that competes with a chimeric, humanized, or human anti-LILRB2 antibody as described herein is provided.

In some embodiments, antibodies that bind to any one or more of the epitopes of the antibodies provided herein are provided. In some embodiments, antibodies that bind and overlap an epitope to which the present antibodies bind to are provided. In some embodiments, an antibody is provided that competes with at least one of the antibodies provided herein. In some embodiments, an antibody is provided that competes with at least two of the antibodies provided herein. In some embodiments, an antibody is provided that competes with at least three of the antibodies provided herein. In some embodiments, the antibody binds to an overlapping epitope as an antibody described in the examples herein. In some embodiments, the entire epitope is bound and/or obstructed by the competing antibody. In some embodiments, a part of the epitope is bound and/or obstructed by the competing antibody. In some embodiments, the competing antibody's paratope binds to at least a part of the epitope of an antibody provided herein. In some embodiments, the competing antibody's paratope binds the target, and a different section of the competing antibody's structure obstruct at least a part of the epitope of an antibody provided herein.

Exemplary Chimeric Antibodies

In some embodiments, an antibody provided herein is a chimeric antibody. Certain chimeric antibodies are described, for example, in U.S. Pat. No. 4,816,567; and Morrison et al., 1984, *Proc. Natl. Acad. Sci. USA,* 81:6851-6855. In one example, a chimeric antibody comprises a non-human variable region (for example, a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

Nonlimiting exemplary chimeric antibodies include chimeric antibodies comprising the heavy and/or light chain variable regions of any of the anti-LILRB2 antibodies described herein. Nonlimiting exemplary chimeric antibodies include chimeric antibodies comprising a CDR-H1, CDR-H2, and CDR-H3, and/or a CDR-L1, CDR-L2, and CDR-L3 of any of the anti-LILRB2 antibodies described herein. In some embodiments, the chimeric anti-LILRB2 antibody comprises the variable regions described above and binds to LILRB2. In some embodiments, the chimeric anti-LILRB2 antibody comprises the variable regions described above, binds to LILRB2, and causes conversion of M2-like macrophages to M1-like macrophages.

In some embodiments, a chimeric anti-LILRB2 antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 3, 13, 23, 33, 43, 53, 63, 73, 83, 93, 103, and 113 wherein the antibody binds LILRB2. In some embodiments, a chimeric anti-LILRB2 antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 4, 14, 24, 34, 44, 54, 64, 74, 84, 94, 104, and 114 wherein the antibody binds LILRB2. In some embodiments, a chimeric anti-LILRB2 antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 3, 13, 23, 33, 43, 53, 63, 73, 83, 93, 103, and 113; and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 4, 14, 24, 34, 44, 54, 64, 74, 84, 94, 104, and 114; wherein the antibody binds LILRB2.

Exemplary chimeric anti-LILRB2 antibodies also include chimeric antibodies that compete for binding to LILRB2 with an antibody or fragment thereof described herein. Thus, in some embodiments, a chimeric anti-LILRB2 antibody is provided that competes for binding to LILRB2 with any of the LILRB2 antibodies described herein, or fragment thereof. In some embodiments, the antibody competes for binding to LILRB2 and causes conversion of M2-like macrophages to M1-like macrophages.

In some embodiments, a chimeric antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, a chimeric antibody described herein comprises a human IgG constant region. In some embodiments, a chimeric antibody described herein comprises a human IgG4 heavy chain constant region. In some embodiments, a chimeric antibody described herein comprises a human IgG4 constant region and a human κ light chain.

As noted above, whether or not effector function is desirable may depend on the particular method of treatment intended for an antibody. Thus, in some embodiments, when effector function is desirable, a chimeric anti-LILRB2 antibody comprising a human IgG1 heavy chain constant region or a human IgG3 heavy chain constant region is selected. In some embodiments, when effector function is not desirable, a chimeric anti-LILRB2 antibody comprising a human IgG4 or IgG2 heavy chain constant region is selected.

Exemplary Humanized Antibodies

In some embodiments, humanized antibodies that bind LILRB2 are provided. Humanized antibodies are useful as therapeutic molecules because humanized antibodies reduce or eliminate the human immune response as compared to non-human antibodies, which can result in an immune response to an antibody therapeutic (such as the human anti-mouse antibody (HAMA) response), and decreased effectiveness of the therapeutic.

In some embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (for example, the antibody from which the CDR residues are derived), for example, to restore or improve antibody specificity or affinity.

Humanized antibodies and methods of making them are reviewed, for example, in Almagro and Fransson, 2008, *Front. Biosci.*, 13: 1619-1633, and are further described, for example, in Riechmann et al., 1988, *Nature*, 332:323-329; Queen et al., 1989, *Proc. Natl Acad. Sci. USA*, 86: 10029-10033; U.S. Pat. Nos. 5,821,337, 7,527,791, 6,982,321, and 7,087,409; Kashmiri et al., 2005, *Methods*, 36:25-34; Padlan, 1991, *Mol. Immunol.*, 28:489-498 (describing "resurfacing"); Dall'Acqua et al., 2005, *Methods*, 36:43-60 (describing "FR shuffling"); and Osbourn et al., 2005, *Methods*, 36:61-68 and Klimka et al., 2000, *Br. J. Cancer*, 83:252-260 (describing the "guided selection" approach to FR shuffling).

Human framework regions that can be used for humanization include but are not limited to: framework regions selected using the "best-fit" method (see, for example, Sims et al., 1993, *J. Immunol.* 151:2296); framework regions derived from the consensus sequence of human antibodies of a particular subgroup of light or heavy chain variable regions (see, for example, Carter et al., 1992, *Proc. Natl. Acad. Sci. USA*, 89:4285; and Presta et al., 1993, *J. Immunol.*, 151:2623); human mature (somatically mutated) framework regions or human germline framework regions (see, for example, Almagro and Fransson, 2008, *Front. Biosci.*, 13:1619-1633); and framework regions derived from screening FR libraries (see, for example, Baca et al., 1997, *J. Biol. Chem.*, 272:10678-10684 and Rosok et al., 1996, *J. Biol. Chem.*, 271:22611-22618).

Nonlimiting exemplary humanized antibodies include antibodies comprising a $V_H$ domain selected from SEQ ID NOs: 53, 63, 73, 83, 93, 103, and 113 and/or a $V_L$ domain selected from SEQ ID NOs: 54, 64, 74, 84, 94, 104, and 114, or any one, two, three, four, five, or six CDRs thereof. In some embodiments, the humanized anti-LILRB2 antibody comprises the CDRs described above and binds to LILRB2. In some embodiments, the humanized anti-LILRB2 antibody comprises the CDRs described above, binds to LILRB2 and causes conversion of M2-like macrophages to M1-like macrophages.

In some embodiments, a humanized anti-LILRB2 antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 53, 63, 73, 83, 93, 103, and 113 and wherein the antibody binds LILRB2. In some embodiments, a humanized anti-LILRB2 antibody comprises a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 54, 64, 74, 84, 94, 104, and 114, wherein the antibody binds LILRB2. In some embodiments, a humanized anti-LILRB2 antibody comprises a heavy chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 53, 63, 73, 83, 93, and 113 and a light chain comprising a variable region sequence that is at least 90%, at least 91%, at least 92%, at least 93%, at least 94%, at least 95%, at least 96%, at least 97%, at least 98%, or at least 99% identical to a sequence selected from SEQ ID NOs: 54, 64, 74, 84, 94, 104, and 114 wherein the antibody binds LILRB2.

In some embodiments, any one or more of the CDR sequences provided herein are maintained, while the remain heavy and/or light chain region (that is, FR1, FR2, FR3, and FR4) is at least 90%, at least 91%, at least 92%, at least 93%, at least 94%, at least 95%, at least 96%, at least 97%, at least 98%, or at least 99% identical to a sequence selected from SEQ ID NOs: 53, 54, 63, 64, 73, 74, 83, 84, 93, 94, 103, 104, 113, and 114.

In some embodiments, a humanized anti-LILRB2 antibody comprises at least one of the CDRs discussed herein. That is, in some embodiments, a humanized anti-LILRB2 antibody comprises at least one CDR selected from a CDR-H1 discussed herein, a CDR-H2 discussed herein, a CDR-H3 discussed herein, a CDR-L1 discussed herein, a CDR-L2 discussed herein, and a CDR-L3 discussed herein. Further, in some embodiments, a humanized anti-LILRB2 antibody comprises at least one mutated CDR based on a CDR discussed herein, wherein the mutated CDR comprises 1, 2, 3, or 4 amino acid substitutions relative to the CDR discussed herein. In some embodiments, one or more of the amino acid substitutions are conservative amino acid substitutions. One skilled in the art can select one or more suitable conservative amino acid substitutions for a particular CDR sequence, wherein the suitable conservative amino acid substitutions are not predicted to significantly alter the binding properties of the antibody comprising the mutated CDR.

Exemplary humanized anti-LILRB2 antibodies also include antibodies that compete for binding to LILRB2 with an antibody or fragment thereof described herein. In some embodiments, a humanized anti-LILRB2 antibody is provided that competes for binding to LILRB2 with any anti-LILRB2 antibody described herein, or fragment thereof, and causes conversion of M2-like macrophages to M1-like macrophages.

Exemplary Human Antibodies

In some embodiments, an anti-LILRB2 antibody provided herein is a human antibody. Human antibodies can be produced using various techniques known in the art. Human antibodies are described generally in van Dijk and van de Winkel, 2001, *Curr. Opin. Pharmacol.*, 5:368-374 and Lonberg, 2008, *Curr. Opin. Immunol.*, 20:450-459. In some embodiments, the human antibody is not a naturally occurring antibody. In some embodiments, the human antibody is a monoclonal antibody; thus, in some embodiments, each of the human antibodies in a set can bind to the same epitope on the antigen.

Human antibodies can be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, 2005, *Nat. Biotech.*, 23: 1117-1125. See also, for example, U.S. Pat. Nos. 6,075,181 and 6,150,584 describing XENOMOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCIMOUSE® technology). Human variable regions from intact antibodies generated by such animals may be further modified, for example, by combining with a different human constant region.

Human antibodies can also be made by hybridoma-based methods. Human myeloma and mouse-human heteromyeloma cell lines for the production of human monoclonal antibodies have been described. See, for example, Kozbor, 1984, *J. Immunol.*, 133: 3001; Brodeur et al., *Monoclonal-Antibody Production Techniques and Applications*, pp. 51-63 (Marcel Dekker, Inc., New York, 1987); and Boerner et al., 1991, *J. Immunol.*, 147:86). Human antibodies generated via human B-cell hybridoma technology are also described in Li et al., 2006, *Proc. Natl. Acad. Sci. USA*, 103:3557-3562. Additional methods include those described, for example, in U.S. Pat. No. 7,189,826 (describing production of monoclonal human IgM antibodies from hybridoma cell lines) and Ni, 2006, *Xiandai Mianyixue*, 26(4):265-268 (describing human-human hybridomas). Human hybridoma technology (Trioma technology) is also described in Vollmers and Brandlein, 2005, *Histology and Histopathology*, 20(3):927-937 and Vollmers and Brandlein, 2005, *Methods and Findings in Experimental and Clinical Pharmacology*, 27(3): 185-191.

Human antibodies can also be generated by isolating Fv clone variable domain sequences selected from human-derived phage display libraries. Such variable domain sequences may then be combined with a desired human constant domain. Techniques for selecting human antibodies from antibody libraries are described below.

Antibodies may be isolated by screening combinatorial libraries for antibodies with the desired activity or activities. For example, a variety of methods are known in the art for generating phage display libraries and screening such libraries for antibodies possessing the desired binding characteristics. Such methods are reviewed, for example, in Hoogenboom et al. in Methods in Molecular Biology 178: 1-37 (O'Brien et al., ed., Human Press, Totowa, N.J., 2001) and further described, for example, in the McCafferty et al., 1990, *Nature* 348:552-554; Clackson et al., 1991, *Nature*, 352: 624-628; Marks et al., 1992, *J. Mol. Biol.*, 222: 581-597; Marks and Bradbury, in *Methods in Molecular*

*Biology* 248: 161-175 (Lo, ed., Human Press, Totowa, N.J., 2003); Sidhu et al., 2004 *J. Mol. Biol.,* 338(2): 299-310; Lee et al., 2004, *J. Mol. Biol.* 340(5): 1073-1093; *Fellouse,* 2004, *Proc. Natl. Acad. Sci. USA,* 101(34): 12467-12472; and Lee et al., 2004, *J. Immunol. Methods,* 284(1-2): 119-132 and PCT publication WO 99/10494.

In certain phage display methods, repertoires of $V_H$ and $V_L$ genes are separately cloned by polymerase chain reaction (PCR) and recombined randomly in phage libraries, which can then be screened for antigen-binding phage as described in Winter et al., 1994, *Ann. Rev. Immunol.,* 12:433-455. Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (for example, from human) to provide a single source of antibodies to a wide range of non-self and also self-antigens without any immunization as described by Griffiths et al., 1993, *EMBO J,* 12:725-734. Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter 1992, *J. Mol. Biol.,* 227:381-388. Patent publications describing human antibody phage libraries include, for example: U.S. Pat. No. 5,750,373, and U.S. Patent Publication Nos. 2005/0079574, 2005/0119455, 2005/0266000, 2007/0117126, 2007/0160598, 2007/0237764, 2007/0292936, and 2009/0002360.

In some embodiments, a chimeric human anti-LILRB2 antibody is provided, where the antibody comprises the variable region from a human antibody that binds LILRB2 and the constant region from a different human antibody. In some embodiments, a chimeric human anti-LILRB2 antibody, where the antibody comprises the CDRs from a human antibody that binds LILRB2 and a framework from a different human antibody is provided. In some embodiments, the antibody is not a naturally occurring human antibody.

In some embodiments, a human anti-LILRB2 antibody comprises one or more human constant regions. In some embodiments, the human heavy chain constant region is of an isotype selected from IgA, IgG, and IgD. In some embodiments, the human light chain constant region is of an isotype selected from κ and λ. In some embodiments, a human antibody described herein comprises a human IgG constant region. In some embodiments, a human antibody described herein comprises a human IgG4 heavy chain constant region. In some embodiments, a human antibody described herein comprises a human IgG4 constant region and a human κ light chain.

In some embodiments, when effector function is desirable, a human anti-LILRB2 antibody comprising a human IgG1 heavy chain constant region or a human IgG3 heavy chain constant region is selected. In some embodiments, when effector function is not desirable, a human anti-LILRB2 antibody comprising a human IgG4 or IgG2 heavy chain constant region is selected.

As noted herein, the term "human antibody" denotes the genus of possible sequences for the antibody construct, rather than a source of the antibody.

Exemplary Antibody Constant Regions

In some embodiments, an antibody described herein comprises one or more human constant regions. In some embodiments, the human heavy chain constant region is of an isotype selected from IgA, IgG, and IgD. In some embodiments, the human light chain constant region is of an isotype selected from κ and λ. In some embodiments, an antibody described herein comprises a human IgG constant region. In some embodiments, an antibody described herein comprises a human IgG4 heavy chain constant region. In some embodiments, an antibody described herein comprises a human IgG4 constant region and a human κ light chain.

Throughout the present specification and claims unless explicitly stated or known to one skilled in the art, the numbering of the residues in an immunoglobulin heavy chain is that of the EU index as in Kabat et al., *Sequences of Proteins of Immunological Interest,* 5th Ed. Public Health Service, National Institutes of Health, Bethesda, Md. (1991), expressly incorporated herein by reference. The "EU index as in Kabat" refers to the residue numbering of the human IgG1 EU antibody.

As noted above, whether or not effector function is desirable may depend on the particular method of treatment intended for an antibody. Thus, in some embodiments, when effector function is desirable, an anti-LILRB2 antibody comprising a human IgG1 heavy chain constant region or a human IgG3 heavy chain constant region is selected. In some embodiments, when effector function is not desirable, an anti-LILRB2 antibody comprising a human IgG4 or IgG2 heavy chain constant region is selected.

In some embodiments, an antibody comprises a variant Fc region has at least one amino acid substitution compared to the Fc region of a wild-type IgG or a wild-type antibody. In some embodiments, the variant Fc region has two or more amino acid substitutions in the Fc region of the wild-type antibody. In some embodiments, the variant Fc region has three or more amino acid substitutions in the Fc region of the wild-type antibody. In some embodiments, the variant Fc region has at least one, two or three or more Fc region amino acid substitutions described herein. In some embodiments, the variant Fc region herein will possess at least about 80% homology with a native sequence Fc region and/or with an Fc region of a parent polypeptide. In some embodiments, the variant Fc region herein will possess at least about 90% homology with a native sequence Fc region and/or with an Fc region of a parent polypeptide. In some embodiments, the variant Fc region herein will possess at least about 95% homology with a native sequence Fc region and/or with an Fc region of a parent polypeptide.

In some embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, for example, Wright et al., 1997, *TIBTECH,* 15:26-32. The oligosaccharide may include various carbohydrates, for example, mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody may be made in order to create antibody variants with certain improved properties.

In some embodiments, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (for example, complex, hybrid and high mannose structures) as measured by MALDI-TOF mass spectrometry, as described in WO 2008/077546, for example. Asn297 refers to the asparagine residue located at about position 297 in the Fc region (EU numbering of Fc region residues); however, Asn297 may also be located about ±3 amino acids upstream or downstream of position 297, that is, between positions 294 and 300, due to minor sequence variations in antibodies. Such fucosylation variants may have improved ADCC function. See, for example, U.S. Patent Publication Nos. U.S. 2003/0157108 (Presta, L.); U.S. 2004/0093621 (Kyowa Hakko Kogyo Co., Ltd). Examples of publications related to "defucosylated" or "fucose-deficient" antibody variants include: U.S. 2003/0157108; WO 2000/61739; WO 2001/29246; U.S. 2003/0115614; U.S. 2002/0164328; U.S. 2004/0093621; U.S. 2004/0132140; U.S. 2004/0110704; U.S. 2004/0110282; U.S. 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al., 2004, *Biotech. Bioeng.* 87: 614. Examples of cell lines capable of producing defucosylated antibodies include Lec13 CHO cells deficient in protein fucosylation (Ripka et al., 1986, *Arch. Biochem. Biophys.* 249: 533-545; U.S. Patent Application No. U.S. 2003/0157108 A1 (Presta, L); and WO 2004/056312 A1, (Adams et al., especially at Example 11), and knockout cell lines, such as alpha-1,6-fucosyltransferase gene, FUT8, knockout CHO cells (see, for example, Yamane-Ohnuki et al., 2004, *Biotech. Bioeng.* 87: 614; Kanda, Y. et al., 2006, *Biotechnol. Bioeng.*, 94(4):680-688; and WO 2003/085107).

Antibody variants are further provided with bisected oligosaccharides, for example, in which a biantennary oligosaccharide attached to the Fc region of the antibody is bisected by GlcNAc. Such antibody variants may have reduced fucosylation and/or improved ADCC function. Examples of such antibody variants are described, for example, in WO 2003/011878 (Jean-Mairet et al.); U.S. Pat. No. 6,602,684 (Umana et al.); and U.S. 2005/0123546 (Umana et al.). Antibody variants with at least one galactose residue in the oligosaccharide attached to the Fc region are also provided. Such antibody variants may have improved CDC function. Such antibody variants are described, for example, in WO 1997/30087 (Patel et al.); WO 1998/58964 (Raju, S.); and WO 1999/22764 (Raju, S.).

Antibody variants are also provided with amino-terminal leader extensions. For example, one or more amino acid residues of the amino-terminal leader sequence are present at the amino-terminus of any one or more heavy or light chains of an antibody. An exemplary amino-terminal leader extension comprises or consists of three amino acid residues, VHS, present on one or both light chains of an antibody variant.

The in vivo or serum half-life of human FcRn high affinity binding polypeptides can be assayed, for example, in transgenic mice, in humans, or in non-human primates to which the polypeptides with a variant Fc region are administered. See also, for example, Petkova et al., 2006, *International Immunology* 18(12):1759-1769.

In some embodiments, the antibody variant mediates ADCC in the presence of human effector cells more effectively than a parent antibody. In some embodiments, the antibody variant is substantially more effective at mediating ADCC in vitro, when the amounts of polypeptide variant and parent antibody used in the assay are essentially the same. In some embodiments, the antibody variant is substantially more effective at mediating ADCC in vivo, when the amounts of polypeptide variant and parent antibody used in the assay are essentially the same. Generally, such variants will be identified using the in vitro ADCC assay as herein disclosed, but other assays or methods for determining ADCC activity, for example in an animal model etc., are contemplated.

Exemplary Antibody Conjugates

In some embodiments, an anti-LILRB2 antibody is conjugated to another molecule. In some embodiments, the additional molecule can be a detectable marker, such as a label. In some embodiments, the additional molecule can be a therapeutic molecule, such as a cytotoxic agent. In some embodiments, a label and/or a cytotoxic agent can be conjugated to the antibody. As used herein, a label is a moiety that facilitates detection of the antibody and/or facilitates detection of a molecule to which the antibody binds. Nonlimiting exemplary labels include, but are not limited to, radioisotopes, fluorescent groups, enzymatic groups, chemiluminescent groups, biotin, epitope tags, metal-binding tags, etc. One skilled in the art can select a suitable label according to the specific application.

As used herein, a cytotoxic agent is a moiety that reduces the proliferative capacity of one or more cells. A cell has reduced proliferative capacity when the cell becomes less able to proliferate, for example, because the cell undergoes apoptosis or otherwise dies, the cell fails to proceed through the cell cycle and/or fails to divide, the cell differentiates, etc. Nonlimiting exemplary cytotoxic agents include, but are not limited to, radioisotopes, toxins, and chemotherapeutic agents. One skilled in the art can select a suitable cytotoxic according to the intended application. In some embodiments, the cytotoxic agent is at least one of an antimetabolite, an alkylating agent, an antibiotic, a growth factor, a cytokine, an anti-angiogenic agent, an anti-mitotic agent, an anthracycline, toxin, or an apoptotic agent In some embodiments, a label and/or a cytotoxic agent is conjugated to an antibody using chemical methods in vitro. Nonlimiting exemplary chemical methods of conjugation are known in the art, and include services, methods and/or reagents commercially available from, for example, Thermo Scientific Life Science Research Produces (formerly Pierce; Rockford, Ill.), Prozyme (Hayward, Calif.), SACRI Antibody Services (Calgary, Canada), AbD Serotec (Raleigh, N.C.), etc. In some embodiments, when a label and/or cytotoxic agent is a polypeptide, the label and/or cytotoxic agent can be expressed from the same expression vector with at least one antibody chain to produce a polypeptide comprising the label and/or cytotoxic agent fused to an antibody chain. One skilled in the art can select a suitable method for conjugating a label and/or cytotoxic agent to an antibody according to the intended application.

In some embodiments, conjugation can be covalent. In some embodiments, conjugation can be non-covalent. In some embodiments, conjugation can be via a specific binding interaction, for example, through the binding of a secondary antibody.

Exemplary Leader Sequences

In order for some secreted proteins to express and secrete in large quantities, a leader sequence from a heterologous protein may be desirable. In some embodiments, employing heterologous leader sequences can be advantageous in that a resulting mature polypeptide can remain unaltered as the leader sequence is removed in the ER during the secretion process. The addition of a heterologous leader sequence can be useful to express and secrete some proteins.

Certain exemplary leader sequence sequences are described, for example, in the online Leader sequence Database maintained by the Department of Biochemistry, National University of Singapore. See Choo et al., 2005, *BMC Bioinformatics*, 6: 249; and PCT Publication No. WO 2006/081430.

III. Antibody Activity

Provided herein are anti-LILRB2 antibodies that provide specific functional characteristics. In particular aspects of the invention, anti-LILRB2 antibodies promote immunogenicity (e.g., as exhibited by M1-like macrophages) to respond to a pathology, e.g., cancer. Additionally or alternatively, anti-LILRB2 antibodies of the invention can inhibit an immunoregulatory (e.g., immunosuppressive) response, e.g., as exhibited by M2-like macrophages.

Blocking of HLA-A2 can be a model for disrupting the binding between LILRB2 and classical MHC class I molecules. Thus, in some embodiments of the invention, anti-LILRB2 antibodies block the binding of HLA-G or HLA-A2 to LILRB2 (e.g., human LILRB2). Blocking can be detected and/or quantified by any suitable means known in the art or described herein. For example, blocking of HLA-G or HLA-A2 can be detected and/or quantified using a tetramer blocking assay (e.g., using human monocytes), as described, e.g., in Example 10.

In some embodiments, an anti-LILRB2 antibody that blocks the binding of HLA-G to LILRB2 binds the same epitope (i.e., wholly or partially) of LILRB2 as HLA-G. In some embodiments, an anti-LILRB2 antibody that blocks the binding of HLA-G to LILRB2 binds at least one, at least two, at least three, at least four, at least five, at least six, at least seven, or at least eight residues of the LILRB2 epitope bound by HLA-G. In some embodiments, an anti-LILRB2 antibody blocks at least 50% (e.g., from 50-100%, from 55-95%, from 60-90%, from 65-85%, or from 70-80%, e.g., from 50-60%, from 60-70%, from 70-80%, from 80-90%, or from 90-100%, e.g., about 50%, about 55%, about 60%, about 65%, about 70%, about 75%, about 80%, about 85%, about 90%, about 95%, or about 100%) of HLA-G tetramer in a tetramer binding assay. In some embodiments, an anti-LILRB2 antibody blocks HLA-G tetramer at an $EC_{50}$ of less than 1.0 nM (e.g., less than 0.9 nM, less than 0.8 nM, less than 0.7 nM, less than 0.6 nM, less than 0.5 nM, less than 0.4 nM, less than 0.3 nM, less than 0.2 nM, less than 0.15 nM, less than 0.14 nM, less than 0.13 nM, less than 0.12 nM, less than 0.11 nM, less than 0.1 nM, less than 0.09 nM, or less than 0.08 nM) in a tetramer binding assay.

In some embodiments, an anti-LILRB2 antibody that blocks the binding of HLA-A2 to LILRB2 binds the same epitope (i.e., wholly or partially) of LILRB2 as HLA-A2. In some embodiments, an anti-LILRB2 antibody that blocks the binding of HLA-A2 to LILRB2 binds at least one, at least two, at least three, at least four, at least five, at least six, at least seven, or at least eight residues of the LILRB2 epitope bound by HLA-A2. In some embodiments, an anti-LILRB2 antibody blocks at least 50% (e.g., from 50-100%, from 55-95%, from 60-90%, from 65-85%, or from 70-80%, e.g., from 50-60%, from 60-70%, from 70-80%, from 80-90%, or from 90-100%, e.g., about 50%, about 55%, about 60%, about 65%, about 70%, about 75%, about 80%, about 85%, about 90%, about 95%, or about 100%) of HLA-A2 tetramer in a tetramer binding assay. In some embodiments, an anti-LILRB2 antibody blocks HLA-A2 tetramer at an $EC_{50}$ of less than 1.0 nM (e.g., less than 0.9 nM, less than 0.8 nM, less than 0.7 nM, less than 0.6 nM, less than 0.5 nM, less than 0.4 nM, less than 0.3 nM, less than 0.2 nM, less than 0.15 nM, less than 0.14 nM, less than 0.13 nM, less than 0.12 nM, less than 0.11 nM, less than 0.1 nM, less than 0.09 nM, or less than 0.08 nM) in a tetramer binding assay.

In some embodiments, anti-LILRB2 antibodies provided herein are capable of converting an M2-like macrophage population to an M1-like macrophage population. Conversion of an M2-like macrophage to an M1-like macrophage can be detected or quantified using any suitable method known in the art or described herein, e.g., a human monocyte-derive macrophage assay as described in Example 6 or a histoculture assay as described in Example 13.

In some embodiments, the conversion of an M2-like macrophage to an M1-like macrophage is indicated by an increased expression of one or more genes selected from the group consisting of CXCL9, CXCL11, IRF1, TAP1, IL6R, and IL15, e.g., an increase of expression of at least 1% (e.g., at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 1-fold, at least 2-fold, at least 3-fold, at least 4-fold, at least 5-fold, at least 10-fold, at least 20-fold, at least 30-fold, at least 40-fold, at least 50-fold, at least 100-fold, or more) of any one or more genes selected from the group consisting of CXCL9, CXCL11, IRF1, TAP1, IL6R, and IL15. In some embodiments, the conversion of an M2-like macrophage to an M1-like macrophage is indicated by a decreased expression of one or more genes selected from the group consisting of CCL2, PTPN22, KLRC3, IL10, IL18R1, G6PD, CD68, and BAT3, e.g., a decrease of expression of at least 1% (e.g., at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, or 100%) of any one or more genes selected from the group consisting of CCL2, PTPN22, KLRC3, IL10, IL18R1, G6PD, CD68, and BAT3.

In some embodiments, the conversion of an M2-like macrophage to an M1-like macrophage is indicated by an increased expression of one, two, or all three cytokines selected from the group consisting of TNFα, IL-1β, IL-6, CCL3, EGR2, TRAF1, IL1A, IRAK2, TNFalpha, IL7R, CCL2, IL8, CCL4, CXCL1, BCL2, EGR1, IL1RN, TNFSF15, DUSP4, ICAM1, TNFAIP3, TNFRSF9, CD83, TNFAIP6, CCL20, NFKB1, TNFRSF4, CXCL2, PTGS2, NFKBIA, NFKB2, CLEC4E, NFKBIZ, CCL5, CCL7, CLEC5A, CEBPB, TLR2, SRC, RELB, PLAUR, SOCS3, GBP1, CCL18, CSF1, CD40, NT5E, CCL23, CCL8, GBP5, ITGAX, C3, TNFSF15, ICAM5, DPP4, ZEB1, SPP1, IL23A, CD123, and IL6, e.g., an increase of expression of at least 1% (e.g., at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, at least 1-fold, at least 1.5-fold, at least 2-fold, at least 3-fold, at least 4-fold, at least 5-fold, at least 10-fold, at least 20-fold, at least 30-fold, at least 40-fold, at least 50-fold, at least 100-fold, or more) of any one or more genes selected from the group consisting of TNFα, IL-13, IL-6, CCL3, EGR2, TRAF1, IL1A, IRAK2, TNF, IL7R, CCL2, IL8, CCL4, CXCL1, BCL2, EGR1, IL1RN, TNFSF15, DUSP4, ICAM1, TNFAIP3, TNFRSF9, CD83, TNFAIP6, CCL20, NFKB1, TNFRSF4, CXCL2, PTGS2, NFKBIA, NFKB2, CLEC4E, NFKBIZ, CCL5, CCL7, CLEC5A, CEBPB, TLR2, SRC, RELB, PLAUR, SOCS3, GBP1, CCL18, CSF1, CD40, NT5E, CCL23, CCL8, GBP5, ITGAX, C3, TNFSF15, ICAM5, DPP4, ZEB1, SPP1, IL23A, CD123, and IL6. In some embodiments, the conversion of an M2-like macrophage to an M1-like macrophage is indicated by a decreased expression of IL-10, CCL2, TGFBR2, CXCL13, IL21R, CD36, CR1, C1QB, and TGFBI, e.g., a decrease of expression of at least 1% (e.g., at least 2%, at least 3%, at least 4%, at least 5%, at least 10%, at least 15%, at least 20%, at least 25%, at least 30%, at least 40%, at least 50%, at least 60%, at least 70%, at least 80%, at least 90%, or 100%) of any one or more genes selected from the group consisting of IL-10, CCL2, TGFBR2, CXCL13, IL21R, CD36, CR1, C1QB, and TGFBI.

In some embodiments, the anti-LILRB2 antibody provided herein binds to human LILRB2 with a greater affinity than to any one or more of human LILRB1, human LILRB3, human LILRB4, human LILRB5, human LILRA1, human LILRA2, human LILRA3, human LILRA4, human LILRA5, or human LILRA6. In some embodiments, the anti-LILRB2 antibody of the invention binds to human LILRB2 with at least 2-fold greater affinity (e.g., at least 3-fold, at least 4-fold, at least 5-fold, at least 10-fold, at least 20-fold, at least 30-fold, at least 40-fold, at least 50-fold, at least 100-fold, or more) greater affinity relative to any one or more of human LILRB1, human LILRB3, human LILRB4, human LILRB5, human LILRA1, human LILRA2, human LILRA3, human LILRA4, human LILRA5, or human LILRA6. In some embodiments, binding of the anti-LILRB2 antibody provided herein to any one or more of human LILRB1, human LILRB3, human LILRB4, human LILRB5, human LILRA1, human LILRA2, human LILRA3, human LILRA4, human LILRA5, or human LILRA6 is undetectable, e.g., bio-layer interferometry (e.g., less than 0.08 nm by OCTET®). In some embodiments, the $K_D$ of the anti-LILRB2 antibody provided herein to any one or more of LILRB1, human LILRB3, human LILRB4, human LILRB5, human LILRA1, human LILRA2, human LILRA3, human LILRA4, human LILRA5, or human LILRA6 is greater than 10 nM (e.g., greater than 15 nM, greater than 20 nM, greater than 25 nM, greater than 30 nM, greater than 35 nM, greater than 40 nM, greater than 45 nM, greater than 50 nM, greater than 60 nM, greater than 70 nM, greater than 80 nM, greater than 90 nM, greater than 100 nM, greater than 500 nM, greater than 1 M, greater than 10 M, or greater than 100 M).

IV. Antibody Expression and Production

Nucleic Acid Molecules Encoding Anti-LILRB2 Antibodies

Nucleic acid molecules comprising polynucleotides that encode one or more chains of an anti-LILRB2 antibody are provided herein. In some embodiments, a nucleic acid molecule comprises a polynucleotide that encodes a heavy chain or a light chain of an anti-LILRB2 antibody. In some embodiments, a nucleic acid molecule comprises both a polynucleotide that encodes a heavy chain and a polynucleotide that encodes a light chain, of an anti-LILRB2 antibody. In some embodiments, a first nucleic acid molecule comprises a first polynucleotide that encodes a heavy chain and a second nucleic acid molecule comprises a second polynucleotide that encodes a light chain.

In some embodiments, the heavy chain and the light chain are expressed from one nucleic acid molecule, or from two separate nucleic acid molecules, as two separate polypeptides. In some embodiments, such as when an antibody is an scFv, a single polynucleotide encodes a single polypeptide comprising both a heavy chain and a light chain linked together.

In some embodiments, a polynucleotide encoding a heavy chain or light chain of an anti-LILRB2 antibody comprises a nucleotide sequence that encodes at least one of the CDRs provided herein. In some embodiments, a polynucleotide encoding a heavy chain or light chain of an anti-LILRB2 antibody comprises a nucleotide sequence that encodes at least 3 of the CDRs provided herein. In some embodiments, a polynucleotide encoding a heavy chain or light chain of an anti-LILRB2 antibody comprises a nucleotide sequence that encodes at least 6 of the CDRs provided herein. In some embodiments, a polynucleotide encoding a heavy chain or light chain of an anti-LILRB2 antibody comprises a nucleotide sequence that encodes a leader sequence, which, when translated, is located at the N terminus of the heavy chain or light chain. As discussed above, the leader sequence may be the native heavy or light chain leader sequence, or may be another heterologous leader sequence.

In some embodiments, the nucleic acid is one that encodes for any of the amino acid sequences for the antibodies in the Sequence Table herein. In some embodiments, the nucleic acid is one that is at least 80% identical to a nucleic acid encoding any of the amino acid sequences for the antibodies in the Sequence Table herein, for example, at least 80, 85, 90, 91, 92, 93, 94, 95, 96, 97, 98, or 99% identical. In some embodiments, the nucleic acid is one that hybridizes to any one or more of the nucleic acid sequences provided herein. In some of the embodiments, the hybridization is under moderate conditions. In some embodiments, the hybridization is under highly stringent conditions, such as: at least about 6×SSC and 1% SDS at 65° C., with a first wash for 10 minutes at about 42° C. with about 20% (v/v) formamide in 0.1×SSC, and with a subsequent wash with 0.2×SSC and 0.1% SDS at 65° C.

Nucleic acid molecules can be constructed using recombinant DNA techniques conventional in the art. In some embodiments, a nucleic acid molecule is an expression vector that is suitable for expression in a selected host cell.

Vectors

Vectors comprising polynucleotides that encode anti-LILRB2 heavy chains and/or anti-LILRB2 light chains are provided. Vectors comprising polynucleotides that encode anti-LILRB2 heavy chains and/or anti-LILRB2 light chains are also provided. Such vectors include, but are not limited to, DNA vectors, phage vectors, viral vectors, retroviral vectors, etc. In some embodiments, a vector comprises a first polynucleotide sequence encoding a heavy chain and a second polynucleotide sequence encoding a light chain. In some embodiments, the heavy chain and light chain are expressed from the vector as two separate polypeptides. In some embodiments, the heavy chain and light chain are expressed as part of a single polypeptide, such as, for example, when the antibody is an scFv.

In some embodiments, a first vector comprises a polynucleotide that encodes a heavy chain and a second vector comprises a polynucleotide that encodes a light chain. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used. In some embodiments, a mass ratio of 1:2 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, for example, in Running Deer et al., 2004, *Biotechnol. Prog.* 20:880-889.

Host Cells

In some embodiments, anti-LILRB2 antibody heavy chains and/or anti-LILRB2 antibody light chains may be expressed in prokaryotic cells, such as bacterial cells; or in eukaryotic cells, such as fungal cells (such as yeast), plant cells, insect cells, and mammalian cells. Such expression may be carried out, for example, according to procedures known in the art. Exemplary eukaryotic cells that may be used to express polypeptides include, but are not limited to, COS cells, including COS 7 cells; 293 cells, including 293-6E cells; CHO cells, including CHO-S, DG44. Lec13 CHO cells, and FUT8 CHO cells; PER.C6® cells (Crucell); and NSO cells. In some embodiments, anti-LILRB2 antibody heavy chains and/or anti-LILRB2 antibody light chains may be expressed in yeast. See, for example, U.S. Publication No. U.S. 2006/0270045 A1. In some embodiments, a particular eukaryotic host cell is selected based on its ability to make desired post-translational modifications to the anti-LILRB2 antibody heavy chains and/or anti-LILRB2 antibody light chains. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Nonlimiting exemplary methods are described, for example, in Sambrook et al., *Molecular Cloning, A Laboratory Manual*, 3$^{rd}$ ed. Cold Spring Harbor Laboratory Press (2001). Nucleic acids may be transiently or stably transfected in the desired host cells, according to any suitable method.

Host cells comprising any of the polynucleotides or vectors described herein are also provided. In some embodiments, a host cell comprising an anti-LILRB2 antibody is provided. Any host cells capable of over-expressing heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

Purification of Antibodies

Anti-LILRB2 antibodies can be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A, Protein G, Protein A/G, or an antibody affinity column may be used to bind the constant region and to purify an anti-LILRB2 antibody. Hydrophobic interactive chromatography, for example, a butyl or phenyl column, may also suitable for purifying some polypeptides such as antibodies. Ion exchange chromatography (for example anion exchange chromatography and/or cation exchange chromatography) may also suitable for purifying some polypeptides such as antibodies. Mixed-mode chromatography (for example reversed phase/anion exchange, reversed phase/cation exchange, hydrophilic interaction/anion exchange, hydrophilic interaction/cation exchange, etc.) may also suitable for purifying some polypeptides such as antibodies. Many methods of purifying polypeptides are known in the art.

Cell-Free Production of Antibodies

In some embodiments, an anti-LILRB2 antibody is produced in a cell-free system. Nonlimiting exemplary cell-free systems are described, for example, in Sitaraman et al., 2009, *Methods Mol. Biol.* 498: 229-44; Spirin, 2004, *Trends Biotechnol.* 22: 538-45; Endo et al., 2003, *Biotechnol. Adv.* 21: 695-713.

Compositions

In some embodiments, antibodies prepared by the methods described above are provided. In some embodiments, the antibody is prepared in a host cell. In some embodiments, the antibody is prepared in a cell-free system. In some embodiments, the antibody is purified. In some embodiments, the antibody prepared in a host cell or a cell-free system is a chimeric antibody. In some embodiments, the antibody prepared in a host cell or a cell-free system is a humanized antibody. In some embodiments, the antibody prepared in a host cell or a cell-free system is a human antibody. In some embodiments, a cell culture media comprising an anti-LILRB2 antibody is provided. In some embodiments, a host cell culture fluid comprising an anti-LILRB2 antibody is provided.

In some embodiments, compositions comprising antibodies prepared by the methods described above are provided. In some embodiments, the composition comprises an antibody prepared in a host cell. In some embodiments, the composition comprises an antibody prepared in a cell-free system. In some embodiments, the composition comprises a purified antibody. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

In some embodiments, a composition comprising anti-LILRB2 antibody at a concentration of more than about any one of 10 mg/mL, 20 mg/mL, 30 mg/mL, 40 mg/mL, 50 mg/mL, 60 mg/mL, 70 mg/mL, 80 mg/mL, 90 mg/mL, 100 mg/mL, 125 mg/mL, 150 mg/mL, 175 mg/mL, 200 mg/mL, 225 mg/mL, or 250 mg/mL is provided. In some embodiments, the composition comprises a chimeric antibody prepared in a host cell or a cell-free system. In some embodiments, the composition comprises a humanized antibody prepared in a host cell or a cell-free system. In some embodiments, the composition comprises a human antibody prepared in a host cell or a cell-free system.

V. Therapeutic Compositions and Methods

Methods of Treating Diseases Using Anti-LILRB2 Antibodies

Antibodies and compositions comprising antibodies are provided for use in methods of treatment for humans or animals. Methods of treating disease comprising administering anti-LILRB2 antibodies are also provided. Nonlimiting exemplary diseases that can be treated with anti-LILRB2 antibodies include, but are not limited to cancer.

In more detail, examples of diseases, such as cancer, that can be treated according to the methods of the invention include solid and hematological/lymphatic cancers and also malignant, pre-malignant, and benign growth, such as dysplasia. Examples of cancer include but are not limited to, carcinoma, lymphoma, blastoma, sarcoma, and leukemia. More particular non-limiting examples of such cancers include kidney cancer (e.g., renal cell carcinoma, e.g., papillary renal cell carcinoma), squamous cell cancer, mesothelioma, teratoma, small-cell lung cancer, pituitary cancer, esophageal cancer, astrocytoma, soft tissue sarcoma, lung cancer (e.g., non-small cell lung cancer, adenocarcinoma of the lung, squamous carcinoma of the lung), cancer of the peritoneum, hepatocellular cancer, gastrointestinal cancer (e.g., stomach cancer), pancreatic cancer, cervical cancer, ovarian cancer, liver cancer, bladder cancer, hepatoma, breast cancer, colon cancer, colorectal cancer, rectal cancer, endometrial or uterine carcinoma, salivary gland carcinoma, liver cancer, prostate cancer, vulval cancer, thyroid cancer, thymoma, hepatic carcinoma, brain cancer, glioma, glioblastoma, endometrial cancer, testis cancer, cholangiocarcinoma, cholangiosarcoma, gallbladder carcinoma, gastric cancer, melanoma (e.g., uveal melanoma), pheochromocytoma, paraganglioma, adenoid cystic carcinoma, and various types of head and neck cancer (e.g., squamous head and neck cancer).

The anti-LILRB2 antibody can be administered as needed to subjects. Determination of the frequency of administration can be made by persons skilled in the art, such as an attending physician based on considerations of the condition being treated, age of the subject being treated, severity of the condition being treated, general state of health of the subject being treated and the like. In some embodiments, an effective dose of an anti-LILRB2 antibody is administered to a subject one or more times. In some embodiments, an effective dose of an anti-LILRB2 antibody is administered to the subject once a month, less than once a month, such as, for example, every two months or every three months. In some embodiments, an effective dose of an anti-LILRB2 antibody is administered less than once a month, such as, for example, every two weeks or every week. An effective dose of an anti-LILRB2 antibody is administered to the subject at least once. In some embodiments, the effective dose of an anti-LILRB2 antibody may be administered multiple times, including for periods of at least a month, at least six months, or at least a year.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, anti-LILRB2 antibodies may be administered in an amount in the range of about 10 µg/kg body weight to about 100 mg/kg body weight per dose. In some embodiments, anti-LILRB2 antibodies may be administered in an amount in the range of about 50 µg/kg body weight to about 5 mg/kg body weight per dose. In some embodiments, anti-LILRB2 antibodies may be administered in an amount in the range of about 100 µg/kg body weight to about 10 mg/kg body weight per dose. In some embodiments, anti-LILRB2 antibodies may be administered in an amount in the range of about 100 µg/kg body weight to about 20 mg/kg body weight per dose. In some embodiments, anti-LILRB2 antibodies may be administered in an amount in the range of about 0.5 mg/kg body weight to about 20 mg/kg body weight per dose.

In some embodiments, pharmaceutical compositions are administered in an amount effective to cause conversion of M2-like macrophages to M1-like macrophages.

The therapeutically effective amount is typically dependent on the weight of the subject being treated, his or her physical or health condition, the extensiveness of the condition to be treated, or the age of the subject being treated. In general, anti-LILRB2 antibodies may be administered in an amount in the range of about 10 µg/kg body weight to about 100 mg/kg body weight per dose. In some embodiments, anti-LILRB2 antibodies may be administered in an amount in the range of about 50 µg/kg body weight to about 5 mg/kg body weight per dose. In some embodiments, anti-LILRB2 antibodies may be administered in an amount in the range of about 100 µg/kg body weight to about 10 mg/kg body weight per dose. In some embodiments, anti-LILRB2 antibodies may be administered in an amount in the range of about 100 µg/kg body weight to about 20 mg/kg body weight per dose. In some embodiments, anti-LILRB2 antibodies may be administered in an amount in the range of about 0.5 mg/kg body weight to about 20 mg/kg body weight per dose.

Pharmaceutical Compositions

In some embodiments, compositions comprising anti-LILRB2 antibodies are provided in formulations with a wide variety of pharmaceutically acceptable carriers (see, for example, Gennaro, Remington: The Science and Practice of Pharmacy with Facts and Comparisons: Drugfacts Plus, 20th ed. (2003); Ansel et al., Pharmaceutical Dosage Forms and Drug Delivery Systems, 7$^{th}$ ed., Lippencott Williams and Wilkins (2004); Kibbe et al., Handbook of Pharmaceutical Excipients, 3$^{rd}$ ed., Pharmaceutical Press (2000)). Various pharmaceutically acceptable carriers, which include vehicles, adjuvants, and diluents, are available. Moreover, various pharmaceutically acceptable auxiliary substances, such as pH adjusting and buffering agents, tonicity adjusting agents, stabilizers, wetting agents and the like, are also available. Non-limiting exemplary carriers include saline, buffered saline, dextrose, water, glycerol, ethanol, and combinations thereof.

In some embodiments, a pharmaceutical composition comprising an anti-LILRB2 antibody is provided. In some embodiments, the pharmaceutical composition comprises a chimeric antibody. In some embodiments, the pharmaceutical composition comprises a humanized antibody. In some embodiments, the pharmaceutical composition comprises an antibody prepared in a host cell or cell-free system as described herein. In some embodiments, the pharmaceutical composition comprises pharmaceutically acceptable carrier.

In some embodiments, pharmaceutical compositions are administered in an amount effective for treatment of (including prophylaxis of) cancer. The therapeutically effective amount is typically dependent on the weight of the subject being treated, his or her physical or health condition, the extensiveness of the condition to be treated, or the age of the subject being treated. In general, anti-LILRB2 antibodies may be administered in an amount in the range of about 0.05 mg/kg body weight to about 100 mg/kg body weight per dose. In some embodiments, anti-LILRB2 antibodies may be administered in an amount in the range of about 10 µg/kg body weight to about 100 mg/kg body weight per dose. In some embodiments, anti-LILRB2 antibodies may be administered in an amount in the range of about 50 µg/kg body weight to about 5 mg/kg body weight per dose. In some embodiments, anti-LILRB2 antibodies may be administered in an amount in the range of about 100 µg/kg body weight to about 10 mg/kg body weight per dose. In some embodiments, anti-LILRB2 antibodies may be administered in an amount in the range of about 100 µg/kg body weight to about 20 mg/kg body weight per dose. In some embodiments, anti-LILRB2 antibodies may be administered in an amount in the range of about 0.5 mg/kg body weight to about 20 mg/kg body weight per dose. In some embodiments, anti-LILRB2 antibodies may be administered in an amount in the range of about 0.5 mg/kg body weight to about 10 mg/kg body weight per dose. In some embodiments, anti-LILRB2 antibodies may be administered in an amount in the range of about 0.05 mg/kg body weight to about 20 mg/kg body weight per dose. In some embodiments, anti-LILRB2 antibodies may be administered in an amount in the range of about 0.05 mg/kg body weight to about 10 mg/kg body weight per dose. In some embodiments, anti-LILRB2 antibodies may be administered in an amount in the range of about 5 mg/kg body weight or lower, for example less than 4, less than 3, less than 2, or less than 1 mg/kg of the antibody.

In some embodiments, anti-LILRB2 antibodies can be present in an amount in the range of about 50 µg/kg body weight to about 5 mg/kg body weight per dose. For example, in some embodiments, a dose for a 20 kg person can be within a range of about 1 mg to about 100 mg. In some embodiments, the dose can be within a range of 2 mg to 200 mg of the anti-LILRB2 antibody. In some embodiments, the dose can be within a range of 10 mg to 400 mg of the anti-LILRB2 antibody.

Routes of Administration

In some embodiments, anti-LILRB2 antibodies can be administered in vivo by various routes, including, but not limited to, intravenous, intra-arterial, parenteral, intratumoral, intraperitoneal or subcutaneous. The appropriate formulation and route of administration may be selected according to the intended application.

Combination Therapy

Anti-LILRB2 antibodies can be administered alone or with other modes of treatment, e.g., with an additional therapeutic agent. They can be provided before, substantially contemporaneous with, or after other modes of treatment, for example, surgery, chemotherapy, radiation therapy, or the administration of a biologic, such as another therapeutic antibody. In some embodiments, an anti-LILRB2 antibody is administered in conjunction with another anti-cancer agent.

In some embodiments, an anti-LILRB2 antibody provided herein is administered with a PD-1 therapy. Exemplary PD-1 therapies include, but are not limited to, nivolumab (BMS-936558, MDX-1106, ONO-4538); pidilizumab, lambrolizumab/pembrolizumab (KEYTRUDA, MK-3475); durvalumab; RG-7446; avelumab (MSB-0010718C); AMP-224; BMS-936559 (an anti-PD-L1 antibody); AMP-514; MDX-1105; ANB-011; anti-LAG-3/PD-1; anti-PD-1 Ab (CoStim); anti-PD-1 Ab (Kadmon Pharm.); anti-PD-1 Ab (Immunovo); anti-TIM-3/PD-1 Ab (AnaptysBio); anti-PD-L1 Ab (CoStim/Novartis); MEDI-4736 (an anti-PD-L1 antibody, Medimmune/AstraZeneca); RG7446/MPDL3280A (an anti-PD-L1 antibody, Genentech/Roche); KD-033, PD-1 antagonist (Agenus); STI-A1010; STI-A1110; TSR-042; and other antibodies and other agents that are directed against programmed death-1 (PD-1) or programmed death ligand 1 (PD-L1) (e.g., JTX-4014, US 2018/0118829).

In some embodiments, a subject is selected for treatment with an anti-LILRB2 antibody provided herein and a PD-1 therapy if the subject's tumor is PD-L1$^{HIGH}$. Determining the level of PD-L1 may be determined, for example, using IHC. In some embodiments, a subject is first treated with a PD-1 therapy, and is later treated with an anti-LILRB2 antibody provided herein, with or without continuing the PD-1 therapy. Thus, methods provided herein include treatment of a subject with an anti-LILRB2 antibody, wherein the subject has previously been treated with a PD-1 therapy.

In some embodiments, an anti-LILRB2 antibody provided herein is administered to patients who show the presence of macrophages in one or more tumors. The presence of macrophages can be determined by, e.g., mRNA signature or IHC.

In some embodiments, an anti-LILRB2 antibody provided herein is administered with one or more therapies selected from: an anti-CD47 antibody (e.g., CC90002 (Celgene) or Hu5F9-G4 (Forty Seven, Inc.)); an anti-SIRP alpha antibody (e.g., OSE-172 (OSE Immunotherapuetics)); pegylated IL-2 (e.g., NKTR-214 (Nektar Therapeutics)); an anti-VEGF antibody (e.g., bevacizumab (AVASTIN®)); TTI-621 or TTI-624 (Trillium Therapeutics SIRPa-Fc); ALX148 (Alexo, SIRPa-Fc), and an IDO inhibitor (e.g., epacadostat (Incyte)).

In some embodiments, a subject is selected for treatment with an anti-LILRB2 antibody provided herein and an ICOS therapy (e.g., JTX-2011, e.g., as described in U.S. Patent Publication No. 2016/0304610, incorporated herein by reference in its entirety). In some embodiments, a subject is first treated with an ICOS therapy, and is later treated with an anti-LILRB2 antibody provided herein, with or without continuing the ICOS therapy. Thus, methods provided herein include treatment of a subject with an anti-LILRB2 antibody, wherein the subject has previously been treated with an ICOS therapy.

In some embodiments, the anti-LILRB2 antibody provided herein is administered with an agonist anti-OX40 antibody (such as Medi6469, Medlmmune; MOXRO916/RG7888, Roche). In some embodiments, the anti-LILRB2 antibody provided herein is administered with an anti-CTLA4 antibody (such as ipilimumab, YERVOY®, BMS-734016; MDX-101).

In some embodiments, an additional therapeutic agent is a chemotherapeutic agent. Exemplary chemotherapeutic agents that may be combined with the anti-LILRB2 antibodies provided herein include, but are not limited to, capectiabine, cyclophosphamide, dacarbazine, temozolomide, cyclophosphamide, docetaxel, doxorubicin, daunorubicin, cisplatin, carboplatin, epirubicin, eribulin, 5-FU, gemcitabine, irinotecan, ixabepilone, methotrexate, mitoxantrone, oxaliplatin, paclitaxel, nab-paclitaxel, ABRAXANE® (protein-bound paclitaxel), pemetrexed, vinorelbine, and vincristine. In some embodiments, an anti-LILRB2 antibody provided herein is administered with at least one kinase inhibitor. Nonlimiting exemplary kinase inhibitors include erlotinib, afatinib, gefitinib, crizotinib, dabrafenib, trametinib, vemurafenib, and cobimetanib.

In some embodiments, the additional therapeutic agent is an IDO inhibitor. Nonlimiting exemplary IDO inhibitors are described, e.g., in US 2016/0060237; and US 2015/0352206. Nonlimiting exemplary IDO inhibitors include Indoximod (New Link Genetics), INCB024360 (Incyte Corp), 1-methyl-D-tryptophan (New Link Genetics), and GDC-0919 (Genentech).

In some embodiments, an anti-LILRB2 antibody provided herein is administered in combination with an immune-modifying drug (IMiD). Nonlimiting exemplary IMiDs include thalidomide, lenalidomide, and pomalidomide.

In some embodiments, the anti-LILRB2 antibody is administered with a second therapeutic method for treatment. Thus, the administration of an antibody provided herein can be in combination with another system of treatment.

In some embodiments, an additional therapeutic agent is a cancer vaccine. Cancer vaccines have been investigated as a potential approach for antigen transfer and activation of dendritic cells. In particular, vaccination in combination with immunologic checkpoints or agonists for co-stimulatory pathways have shown evidence of overcoming tolerance and generating increased anti-tumor response. A range of cancer vaccines have been tested that employ different approaches to promoting an immune response against the tumor (see, e.g., Emens, 2008, *Expert Opin. Emerg. Drugs*, 13(2): 295-308). Approaches have been designed to enhance the response of B cells, T cells, or professional antigen-presenting cells against tumors. Exemplary types of cancer vaccines include, but are not limited to, peptide-based vaccines that employ targeting distinct tumor antigens, which may be delivered as peptides/proteins or as genetically-engineered DNA vectors, viruses, bacteria, or the like; and cell biology approaches, for example, for cancer vaccine development against less well-defined targets, including, but not limited to, vaccines developed from patient-derived dendritic cells, autologous tumor cells or tumor cell lysates, allogeneic tumor cells, and the like.

Nonlimiting exemplary cancer vaccines include Sipuleucel-T, which is derived from autologous peripheral-blood mononuclear cells (PBMCs) that include antigen-presenting cells (see, e.g., Kantoff P W et al., 2010, *N Engl J Med* 363:411-22). In Sipuleucel-T generation, the patient's PBMCs are activated ex vivo with PA2024, a recombinant fusion protein of prostatic acid phosphatase (a prostate antigen) and granulocyte-macrophage colony-stimulating factor (an immune-cell activator). Another approach to a candidate cancer vaccine is to generate an immune response against specific peptides mutated in tumor tissue, such as melanoma (see, e.g., Carreno et al., 2015, *Science* 348: 6236). Such mutated peptides may, in some embodiments, be referred to as neoantigens. As a nonlimiting example of the use of neoantigens in tumor vaccines, neoantigens in the tumor predicted to bind the major histocompatibility complex protein HLA-A*02:01 are identified for individual patients with a cancer, such as melanoma. Dendritic cells from the patient are matured ex vivo, then incubated with neoantigens. The activated dendritic cells are then administered to the patient. In some embodiments, following administration of the cancer vaccine, robust T-cell immunity against the neoantigen is detectable.

In some such embodiments, the cancer vaccine is developed using a neoantigen. In some embodiments, the cancer vaccine is a DNA vaccine, such as a mammaglobin-A DNA vaccine (see, e.g., Gillanders et al., 2014, *Clin. Canc. Res.*, 20: 5964-75). In some embodiments, the cancer vaccine is an engineered virus comprising a cancer antigen, such as PROSTVAC (rilimogene galvacirepvec/rilimogene glafolivec). In some embodiments, the cancer vaccine comprises engineered tumor cells, such as GVAX, which is a granulocyte-macrophage colony-stimulating factor (GM-CSF) gene-transfected tumor cell vaccine (see, e.g., Nemunaitis, 2005, *Expert Rev Vaccines*, 4: 259-74).

In some embodiments, an anti-LILRB2 antibody described herein is administered before, concurrently, or after a cancer vaccine. In some embodiments, cancer vaccines developed using neoantigens are used in combination with the anti-LILRB2 antibodies described herein. In some such embodiments, the combination is used to treat a cancer with a high mutational burden, such as melanoma, lung, bladder, or colorectal cancer.

In some embodiments, an anti-LILRB2 antibody provided herein is administered in combination with a chimeric antigen receptor T cell therapy (CAR-T therapy). The CAR-T cell may be genetically modified to express a receptor that recognizes an antigen expressed by tumor cell. The antigen may be an antigen specifically expressed by the tumor or an antigen expressed by both cancerous cells and healthy tissue. In some embodiments, the CAR-T cell is an anti-BCMA CAR-T cell. In some embodiments, CAR-T therapy is adoptive CAR-T therapy, in which a patients T cells are removed and modified to express the chimeric antigen receptor, and then returned to the patient. See, e.g., Dai et al., 2016, *J Natl Cancer Inst*, 108 (7): djv439, doi: 10.1093/jnci/djv439; Gill et al., 2015, *Blood Rev*, pii: S0268-960X(15)00080-6, doi: 10.1016/j.blre.2015.10.003; Gill et al., 2015, *Immunol. Rev*, 263(1):68-89. doi: 10.1111/imr.12243.

Kits/Articles of Manufacture

Provided herein are also kits, medicines, compositions, and unit dosage forms for use in any of the methods described herein.

Kits can include one or more containers comprising an anti-LILRB2 antibody (or unit dosage forms and/or articles of manufacture). In some embodiments, a unit dosage is provided wherein the unit dosage contains a predetermined amount of a composition comprising an anti-LILRB2 antibody, with or without one or more additional agents. In some embodiments, such a unit dosage is supplied in single-use prefilled syringe for injection. In some embodiments, the composition contained in the unit dosage can comprise saline, sucrose, or the like; a buffer, such as phosphate, or the like; and/or be formulated within a stable and effective pH range. In some embodiments, the composition can be provided as a lyophilized powder that may be reconstituted upon addition of an appropriate liquid, for example, sterile water. In some embodiments, the composition comprises one or more substances that inhibit protein aggregation, including, but not limited to, sucrose and arginine. In some embodiments, a composition comprises heparin and/or a proteoglycan.

In some embodiments, the amount of the anti-LILRB2 antibody used in the unit dose can be any of the amounts provided herein for the various methods and/or compositions described.

In some embodiments, kits further comprise instructions for use in the treatment of cancer in accordance with any of the methods described herein. The kit may further comprise a description of selection an individual suitable or treatment. Instructions supplied in the kits are typically written instructions on a label or package insert (for example, a paper sheet included in the kit), but machine-readable instructions (for example, instructions carried on a magnetic or optical storage disk) are also acceptable. In some embodiments, the kit further comprises another therapeutic agent.

The kits are in suitable packaging. Suitable packaging includes, but is not limited to, vials, bottles, jars, flexible packaging (for example, sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, temperature is in degrees Centigrade, and pressure is at or near atmospheric.

Example 1. HLA-G Cell Culture Experiments

The following example investigates the role of HLA-G in suppressing myeloid cell function. FIG. 1 shows a model of a LILRB2-expressing myeloid cell and an HLA-G-expressing tumor cell. A blocking anti-LILRB2 antibody is depicted between the LILRB2 expressed on the myeloid cell and the HLA-G expressed on the tumor cell. Multimeric HLA-G expressed as tetramers were used in primary human myeloid cell assays to investigate the role of HLA-G in suppressing dendritic cell function.

Non-adherent immature dendritic cells (iDCs) were collected and washed twice in 1×DPBS (Gibco), and then were plated at 1×10$^5$ cells per well in a 96-well round bottom tissue culture treated plate in RPMI1640 supplemented with GLUTAMAX™ (Gibco) and 10% HI-FBS (Sigma). iDCs were either plated in media alone, or matured in media containing PGE2, IL-1β, and TNFα in the presence or absence of HLA-G tetramer (Fred Hutchinson Cancer Research Center) and incubated at 37° C.+5% $CO_2$. After 24 hours, supernatants were collected for cytokine analysis via cytometric bead array (CBA) according to manufacturer's protocol (BD) and analyzed using an Accuri C6 analyzer (BD). Cells were stained with antibodies specific for important antigen presentation molecules and cell expression of these markers was assessed using a FACSCELESTA™ flow cytometer analyzer (BD).

DCs matured in the presence of HLA-G tetramer exhibited a decrease in expression of maturation markers CD80 and CD86 (FIGS. 2A-2F). This inhibitory effect was abolished when HLA-G tetramers were incubated with LILRB2$^{low}$ donor dendritic cells (FIGS. 2G-2L). These results demonstrate that soluble HLA-G blocks the maturation and ability for dendritic cells to develop into potent antigen presenting cells, and that HLA-G-mediated suppression is dependent on LILRB2 expressed on dendritic cells.

Example 2. Generation of Antibodies

Mice and rats were immunized with human LILRB2 protein or cells overexpressing human LILRB2 with a DNA plasmid encoding for human LILRB2. All antibodies except J-16 and J-18 to J-20 are of murine origin; J-16 and J-18 to J-20 are derived from rat immunizations. Hybridoma clone supernatants were screened for specificity to human LILRB2 over other LILR family members using cell lines overexpressing full length LILR proteins. Hybridoma clones of interest were scaled up and supernatant was purified for more extensive antibody screening before clones of interest were sequenced and produced recombinantly as human IgG4 chimeras. (See FIGS. 3A and 3B.)

Example 3. Chimeric Antibody Screening: Initial Anti-LILRB2 Screen Set-Up

Due to the high degree of sequence similarity among the eleven reported human LILR family members, antibodies were screened for specificity against all family members at hybridoma clone, hybridoma scale-up, chimeric, and humanized antibody stages. Specificity was checked both on cells as well as with recombinant protein using the FORTEBIO® OCTET® at the chimeric antibody stage.

On cells, specificity was defined by antibody binding below a two-fold of isotype control cutoff. Positive control antibodies were utilized to establish expression of family members on cell surface, and antibodies were also evaluated in comparison to positive control.

For soluble recombinant protein assays, recombinant LILR family proteins were expressed as 6×His and/or human Fc1 fusion proteins. Antibodies were loaded on anti-human capture (AHC) sensors at 10 µg/mL, and sensors were baselined in kinetics buffer. Control antibodies were similarly loaded onto sensor. If human Fc fusion proteins were used, sensors were blocked with human Fc protein and baselined in kinetics buffer. Sensors were then tested for association with family member proteins at 300 nM. Binding is considered a response above 0.08 nm cutoff on the OCTET® instrument Chimeric (hIgG4) anti-LILRB2 antibodies were selected based on specificity to cell-expressed hLILRB2 over the ten other human LILR family members, ability to block the ligand interactions to cell-expressed LILRB2, and ability to convert M2-like macrophages to M1-like macrophages having an inflammatory activation status in a primary human macrophage assay. Select LILRB2-specific, ligand-blocking antibodies were additionally screened for binding to non-human primate (NHP) monocytes. An isotype control antibody was included in all screens to determine background signals. Described below are the specific criteria and strategy performed to identify ligand-blocking, hLILRB2-specific, chimeric antibodies. Results are summarized in FIGS. 3A and 3B and described in detail below.

Antibody Binning Summary

A subset of antibodies against LILRB2 were binned using the OCTET® Red96 in sandwich format. Briefly, antibody #1 (indicated in column 1) was loaded onto an AHC sensor at 10 µg/mL. Tips were baselined in kinetics buffer, blocked with hFc1, baselined in kinetics buffer, then loaded with human LILRB2. Tips were again baselined in kinetics buffer and loaded with 10 µg/mL of antibody #2 (indicated in row 1). The response values shown in Table 2, below, is the binding of antibody #2 in the sandwich format described.

TABLE 2

Competitive binding assay results

|  | J-17 | J-19 | J-11 | J-03 | J-16 | J-07 | J-04 |
|---|---|---|---|---|---|---|---|
| J-17 | −0.11 | −0.10 | −0.27 | 0.43 | 0.52 | 0.40 | 0.46 |
| J-19 | −0.21 | −0.21 | 0.28 | 0.54 | 0.63 | 0.45 | 0.54 |
| J-11 | −0.39 | 0.71 | −0.24 | 0.51 | 0.65 | 0.47 | 0.54 |
| J-03 | 0.05 | 0.15 | 0.01 | −0.08 | −0.08 | −0.07 | −0.07 |
| J-16 | 0.09 | 0.47 | 0.30 | −0.28 | −0.36 | −0.26 | −0.31 |
| J-07 | 0.04 | 0.27 | 0.10 | −0.29 | −0.30 | −0.28 | −0.30 |
| J-04 | 0.42 | 0.67 | 0.51 | −0.10 | −0.10 | −0.10 | −0.10 |

Antibodies identified as specific binders to LILRB2 and potent blockers of HLA-G binding to LILRB2 (J-19, J-11, and J-17) fall in close but not entirely overlapping epitope bins. J-11 and J-19 did not block binding of each other to LILRB2, but both were blocked by J-17. Antibodies that are specific to LILRB2 but do not block HLA-G, J-04, J-03, and J-07, bind in a separate bin from the three antibodies that are specific and block HLA-G, but the same bin as an antibody that blocks HLA-G binding to LILRB2 but is cross-reactive to LILRA1, J-16. Results are shown in Table 3, below.

TABLE 3

| Antibody binning results | | | | | | | |
|---|---|---|---|---|---|---|---|
| mAb1 | J-17 | J-19 | J-11 | J-03 | J-16 | J-07 | J-04 |
| Blocked mAb | J-19 | J-17 | J-17 | J-16 | J-03 | J-16 | J-16 |
| Blocked mAb | J-11 | | | J-07 | J-07 | J-03 | J-03 |
| Blocked mAb | | | | J-04 | J-04 | J-04 | J-07 |
| bin | A/B | A | B | C | C | C | C |

Example 4. Chimeric Antibody Screening: Screening Against Cross-Reactivity with LILR Family Members The purpose of this screen was to identify antibodies with specific binding to hLILRB2 expressed on cells, with a counter-screen against cell-expressed hLILRB1, hLILRB3, hLILRB4, hLILRB5, hLILRA1, hLILRA2, hLILRA3, hLILRA4, hLILRA5, and hLILRA6. 25 chimeric (hIgG4) antibodies were screened for cellular hLILRB2-specificity. Positive hits for hLILRB2 binding were identified as antibodies that bound hLILRB2-CHO-s greater than two-fold over isotype control mAb binding. Antibodies that also bound non-LILRB2 expressing cells greater than two-fold over isotype control mAb binding were designated as non-LILRB2-specific, or cross-reactive.

Figures 3, 3B, 4:
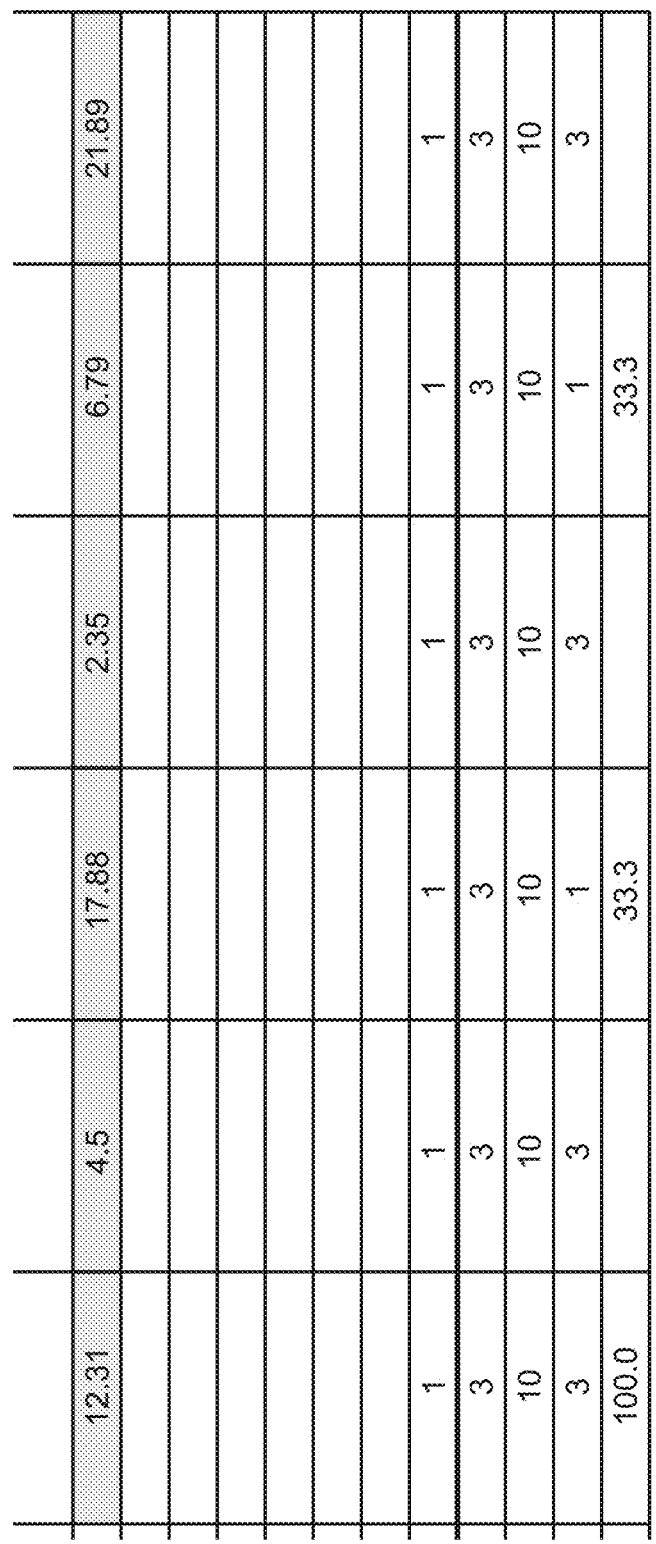
Figure 4:
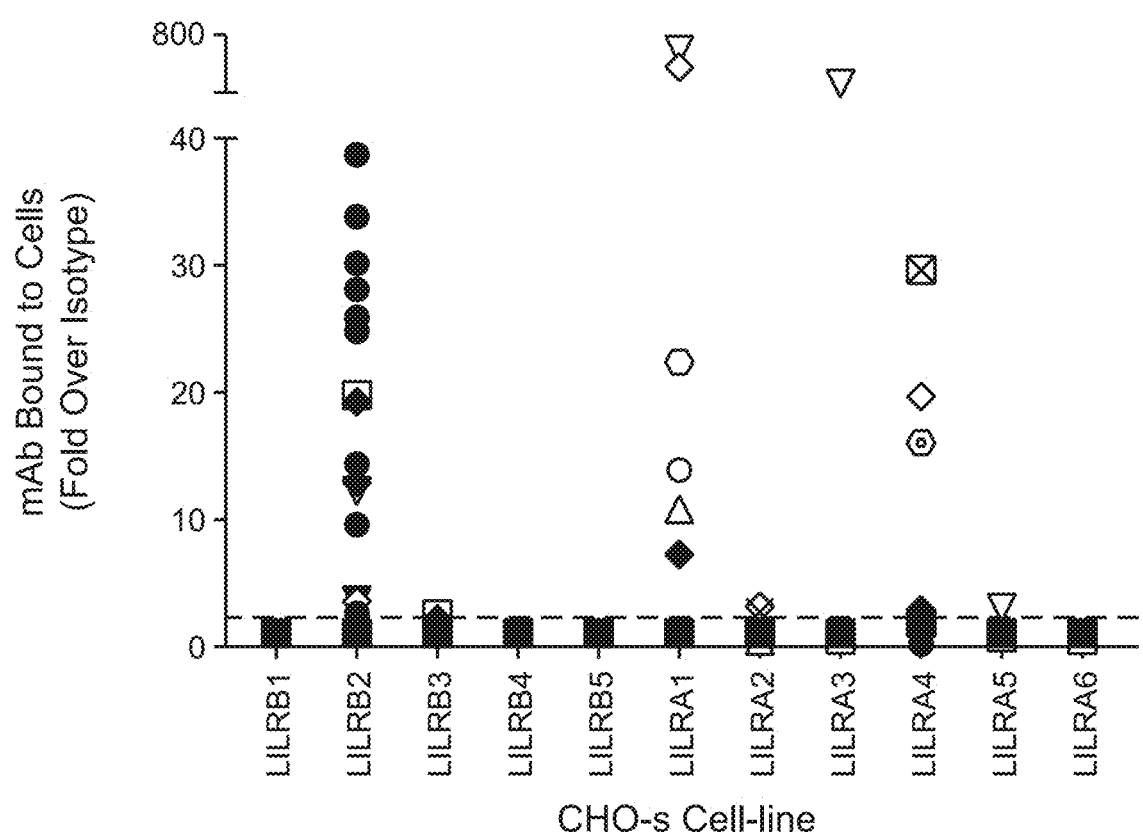
FIG. 4 is a graph showing results of a cell-based LILR family cross-reactivity screen of anti-LILRB2 chimeric mAbs. hLILRB2-specific (filled symbols) and cross-reactive (open symbols) antibodies from the screen are shown. Antibodies detected with greater than two-fold binding over isotype control mAb were identified as hLILR cross-reactive antibodies (the dotted line represents this threshold).

As shown in FIG. 4, 76% of chimeric antibodies tested were confirmed to bind cell-expressed human LILRB2. 78% of these hLILRB2-binding antibodies exhibited specific binding to hLILRB2 over the other ten hLILR family members over-expressed on CHO-s. Antibodies detected with a binding of 2-fold greater than isotype control for another LILR over-expressing cell line in addition to hLILRB2 CHO-s were found to be cross-reactive to hLILRB3, hLILRA1, hLILRA2, and/or hLILRA3. No hLILRB1, hLILRB4, hLILRA4, hLILRA5, or hLILRA6 cross-reactive antibodies were identified in this screen.

Example 5. Chimeric Antibody Screening: Screening for HLA-G Blocking Anti-LILRB2 Chimeric mAbs and HLA-A2 Blocking Anti-LILRB2 Chimeric mAbs Antibodies were additionally screened for ability to block ligand-receptor interactions in a cell-based assay. Upon HLA-G binding LILRB2, myeloid cells are rendered immunosuppressive. Thus, identifying anti-LILRB2 antibodies that are capable of blocking HLA-G:LILRB2 interactions are predicted to be beneficial in promoting anti-tumor responses. In addition to HLA-G, another LILRB2 ligand capable of suppressing myeloid cells are classical major histocompatibility complex (MHC) class I molecules, such as HLA-A2.

In the secondary screen, 1×10$^5$ CHO-s cells over-expressing human LILRB2 were plated in 96-well round-bottom tissue culture-treated plate and washed twice with 1×DPBS (Gibco) and incubated with 10 µg/mL primary antibody (anti-LILRB2 mAbs or control) prepared in 50 µL FACS buffer (1×DPBS containing 2% HI-FBS (Sigma)+0.05% Sodium Azide). After incubation with mAbs for 30 minutes at 4° C., cells were washed twice in FACS buffer and then resuspended in 50 µL of FACS buffer containing 5 µg/mL APC-conjugated HLA-A2 or HLA-G tetramer (Fred Hutch). Cells were incubated protected from light for 30-60 minutes at 4° C. After incubation with tetramer, cells were washed in FACS buffer and re-suspended in fix buffer (1.5% paraformaldehyde diluted in 1×DPBS). Samples were analyzed using the Celesta flow cytometer analyzer (BD Biosciences). Data represent percent tetramer blocked by mAbs relative to tetramer alone, calculated according to the following equation:

$$\% \text{ tetramer blocked} = 100 - \left( \frac{(MFI_{Tetramer+mAb})}{MFI_{Tetramer}} \times 100 \right)$$

Figure 5:
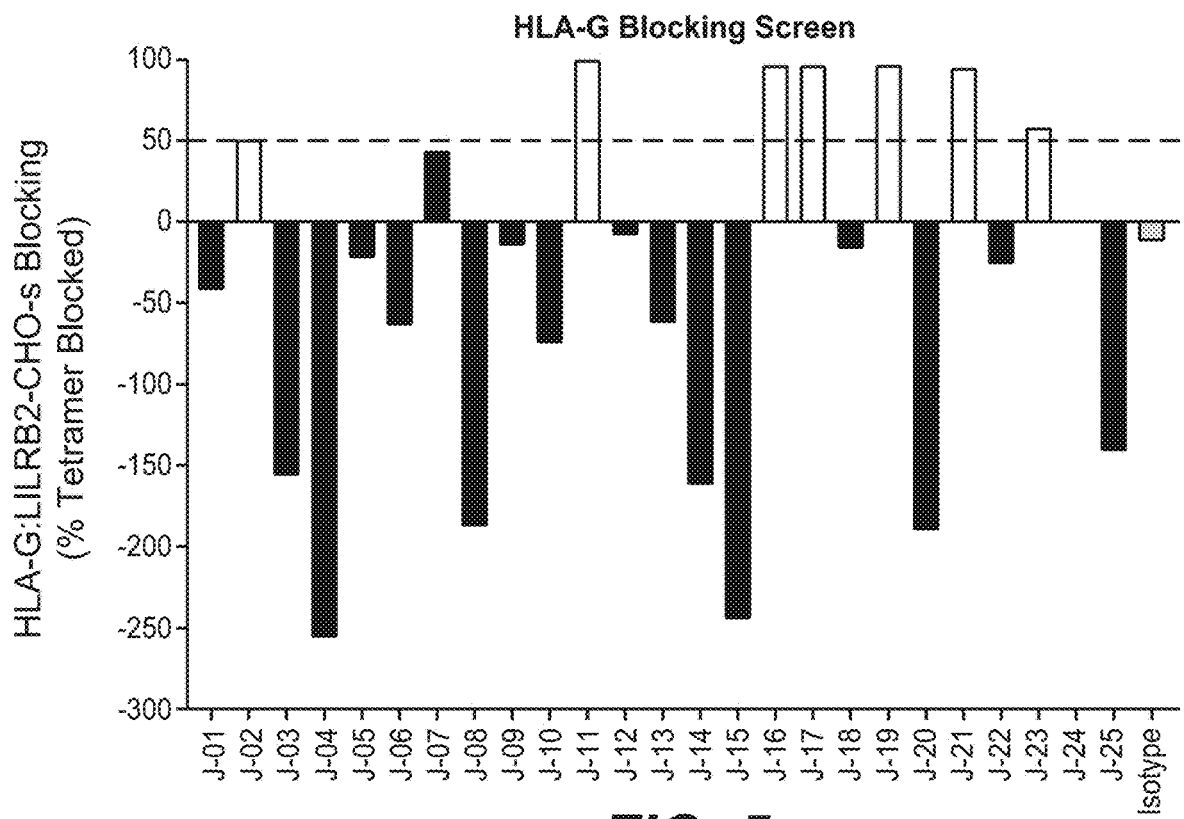
FIG. 5 is a graph showing results of cell-based HLA-G blocking by anti-LILRB2 mAbs. HLA-G blocking anti-LILRB2 chimeric mAbs are shown in white bars and were identified as mAbs able to block at least 50% HLA-G binding to hLILRB2+ cells (dotted line). Non-blocking LILRB2 chimeric mAbs are represented in black bars, and an isotype control mAb is in a gray bar.

The results of a study distinguishing HLA-G blocking antibodies from HLA-G non-blocking antibodies is shown in FIG. 5. Antibodies capable of blocking HLA-G:LILRB2 interactions on cells is identified as the percent of tetramer bound to LILRB2+ cells in the presence of antibody compared to tetramer bound to cells in the absence of antibody. Seven out of the 25 anti-LILRB2 antibodies blocked HLA-G tetramer binding to hLILRB2+ CHO-s by at least 50%. None of the isotype control antibodies blocked HLA-G from binding LILRB2+ cells.

Figure 6:
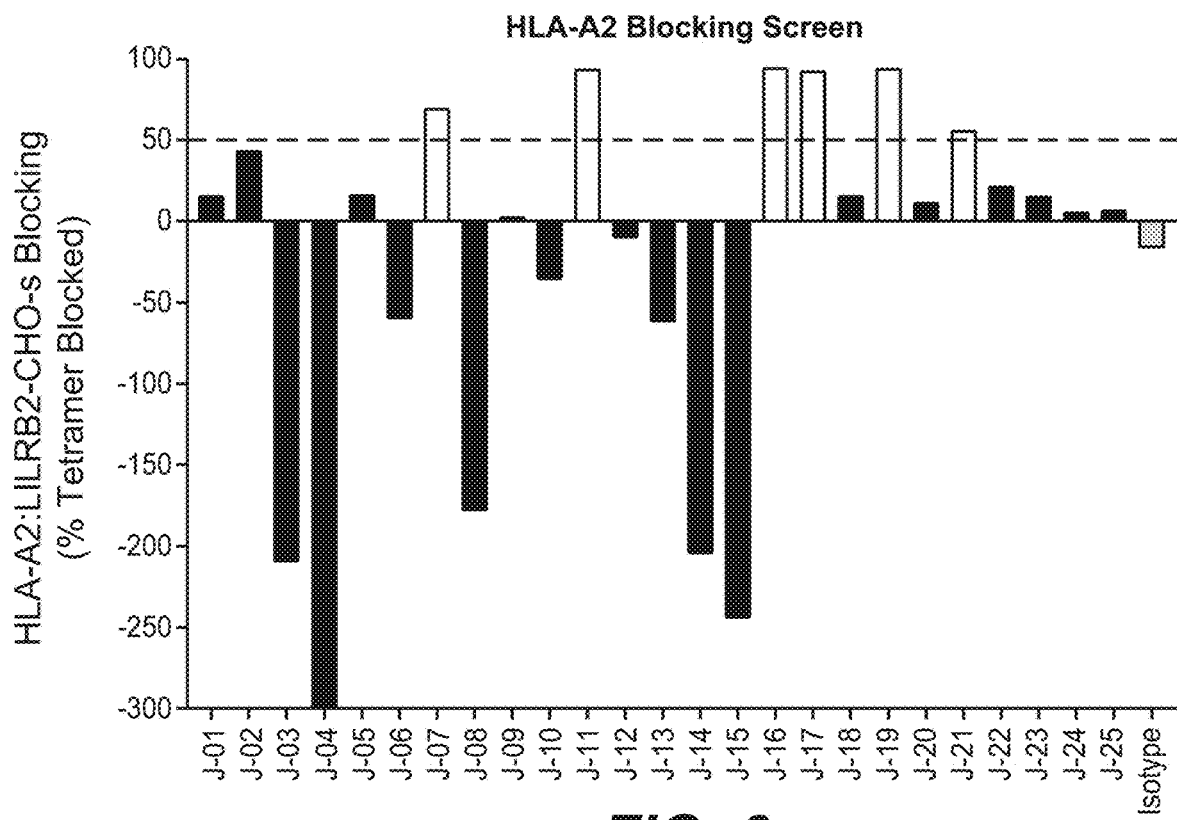
FIG. 6 is a graph showing results of cell-based HLA-A2 blocking by anti-LILRB2 mAbs. HLA-A2 blocking anti-LILRB2 chimeric mAbs are shown in white bars and were identified as mAbs able to block at least 50% HLA-A2 binding to hLILRB2+ cells (dotted line). Non-blocking LILRB2 chimeric mAbs are represented in black bars, and an isotype control mAb is in a gray bar.

The results of a study distinguishing HLA-A2 blocking antibodies from HLA-A2 non-blocking antibodies is shown in FIG. 6. Antibodies capable of blocking HLA-A2:LILRB2 interactions on cells is identified as the percent of tetramer bound to LILRB2+ cells in the presence of antibody compared to tetramer bound to cells in the absence of antibody. Six out of the 25 anti-LILRB2 antibodies blocked HLA-A2 tetramer binding to hLILRB2+ CHO-s by at least 50%. None of the isotype control antibodies blocked HLA-A2 from binding LILRB2+ cells.

Example 6. Chimeric Antibody Screening: Screening Anti-LILRB2 Chimeric mAbs for Biological Activity in Cell Culture Human Macrophage Monoculture-Cytokine Release Assay Primary Human Monocytes from Healthy Donor Peripheral Blood were Differentiated into macrophages in the presence of M-CSF. After seven days of differentiation, 1×10$^5$ human monocyte differentiated macrophages (HMDMs) were plated per well in a 96-well round-bottom tissue culture treated plated in a final volume of 200 µL containing 100 ng/mL LPS in the absence or presence of 1 µg/mL soluble mAbs in cell culture media (RPMI (Gibco)+10% FBS (Sigma)). After incubation for 24 hours at 37° C. with 5% CO$_2$, supernatant was collected and cytokine bead array (CBA) was performed according to manufacturer's protocol (BD Biosciences) to measure cytokines produced in response to mAbs. Samples were analyzed using the Accuri C6 cytometer analyzer (BD Biosciences). Data represent mean of two-to-four donors.

Figure 7A:
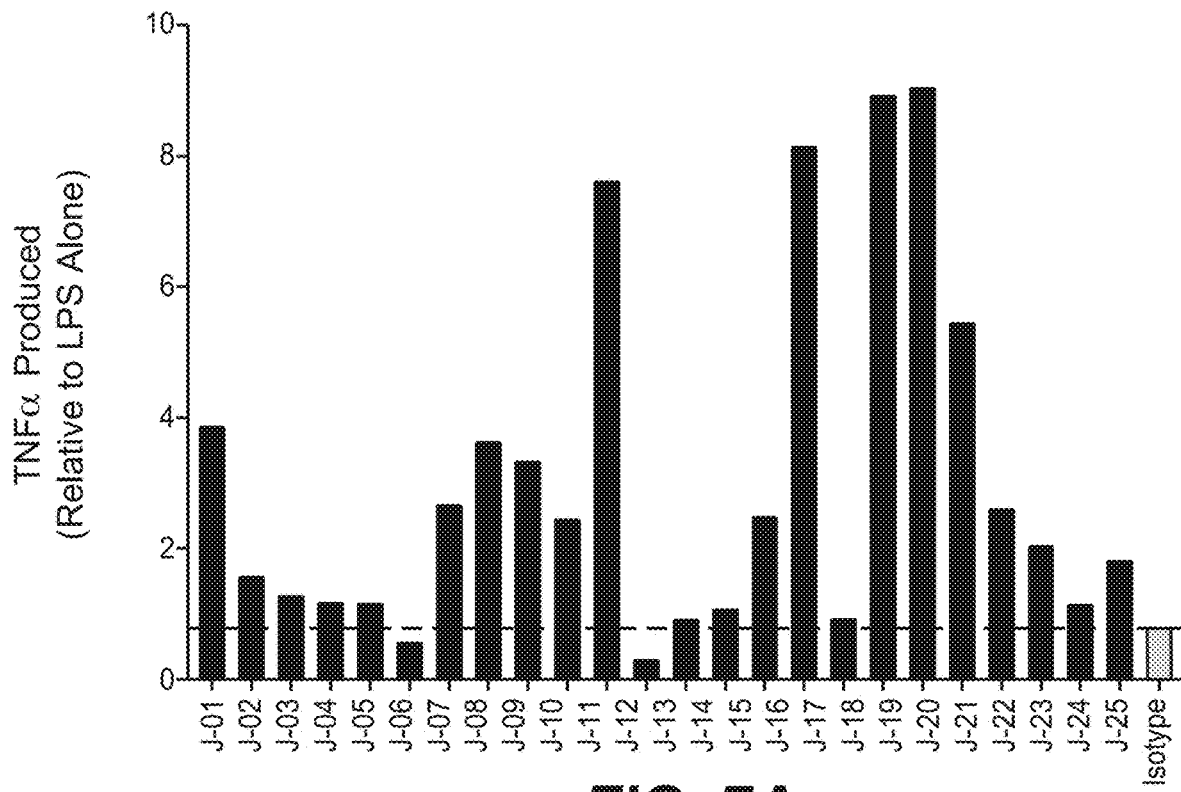
FIGS. 7A and 7B are graphs showing results of cell-based functional assays of anti-LILRB2 mAbs.
Figure 7B:
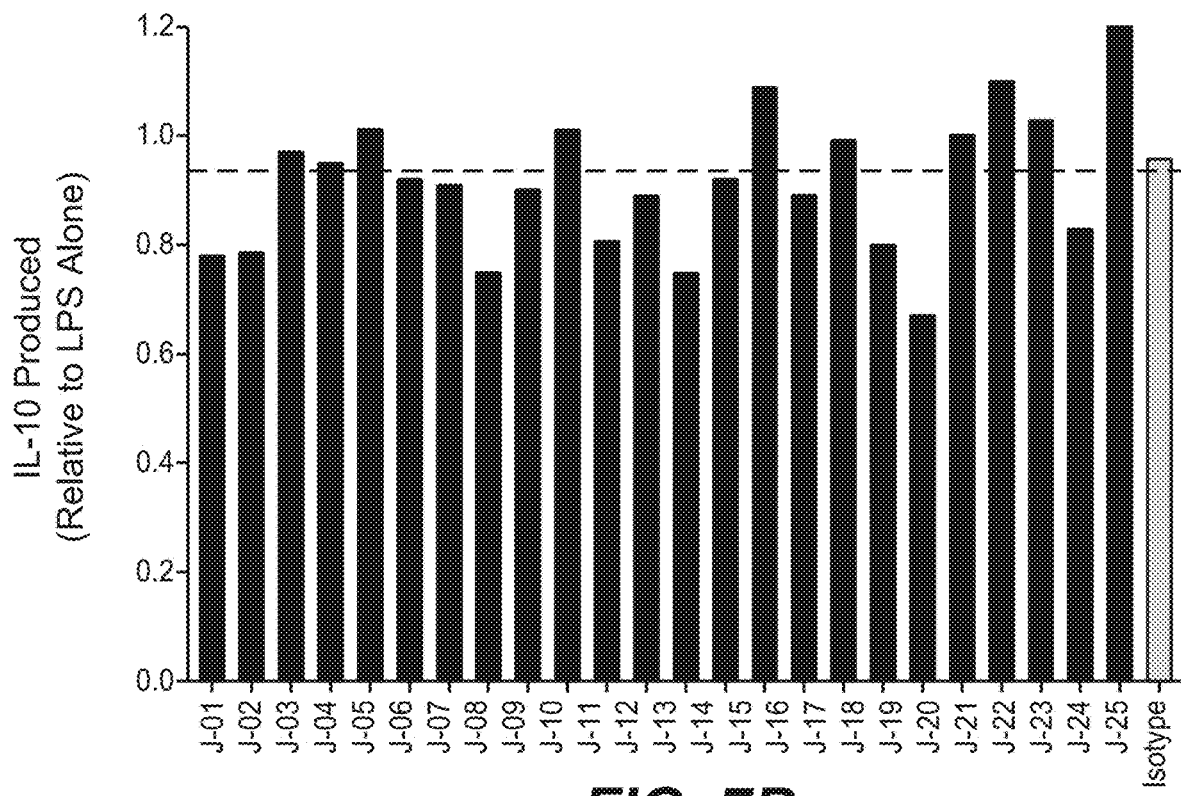

M1/inflammatory and M2/anti-inflammatory cytokine production by primary HMDMs were detected upon treatment with soluble anti-LILRB2 mAbs, as shown in FIGS. 7A and 7B. M1/inflammatory cytokines measured included TNFα, as well as IL-6 and IL-1β (data not shown). M2/anti-inflammatory cytokines measured included IL-10, as well as CCL-2 (data not shown). Production of cytokines is described as normalized levels relative to LPS treatment alone.

Figure 8A:
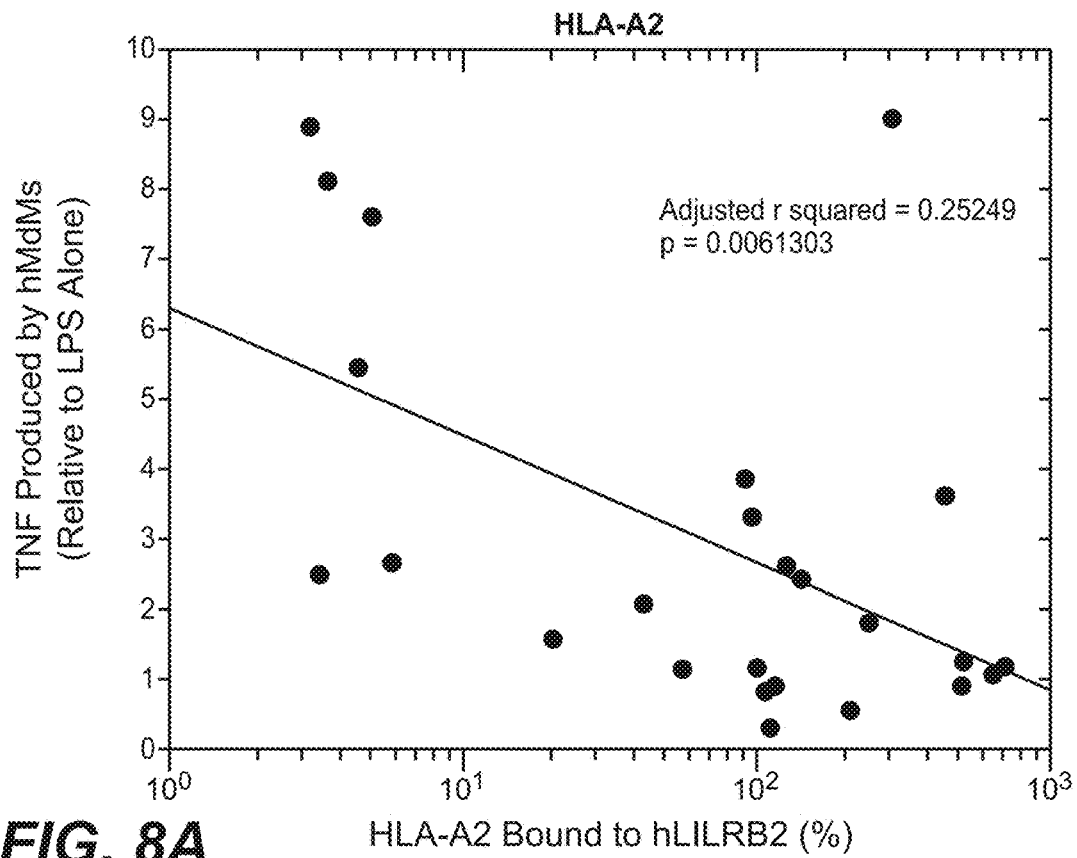
FIGS. 8A and 8B are graphs showing correlation of ligand blocking vs M1-promoting cytokines by anti-LILRB2 mAbs. A positive correlation between HLA-G blocking (FIG. 8A) and HLA-A2 blocking (FIG. 8B) and TNFα produced in response to anti-LILRB2 mAbs (black circles) was observed in primary cell assays. Negative control mAbs are shown in gray.
Figure 8B:
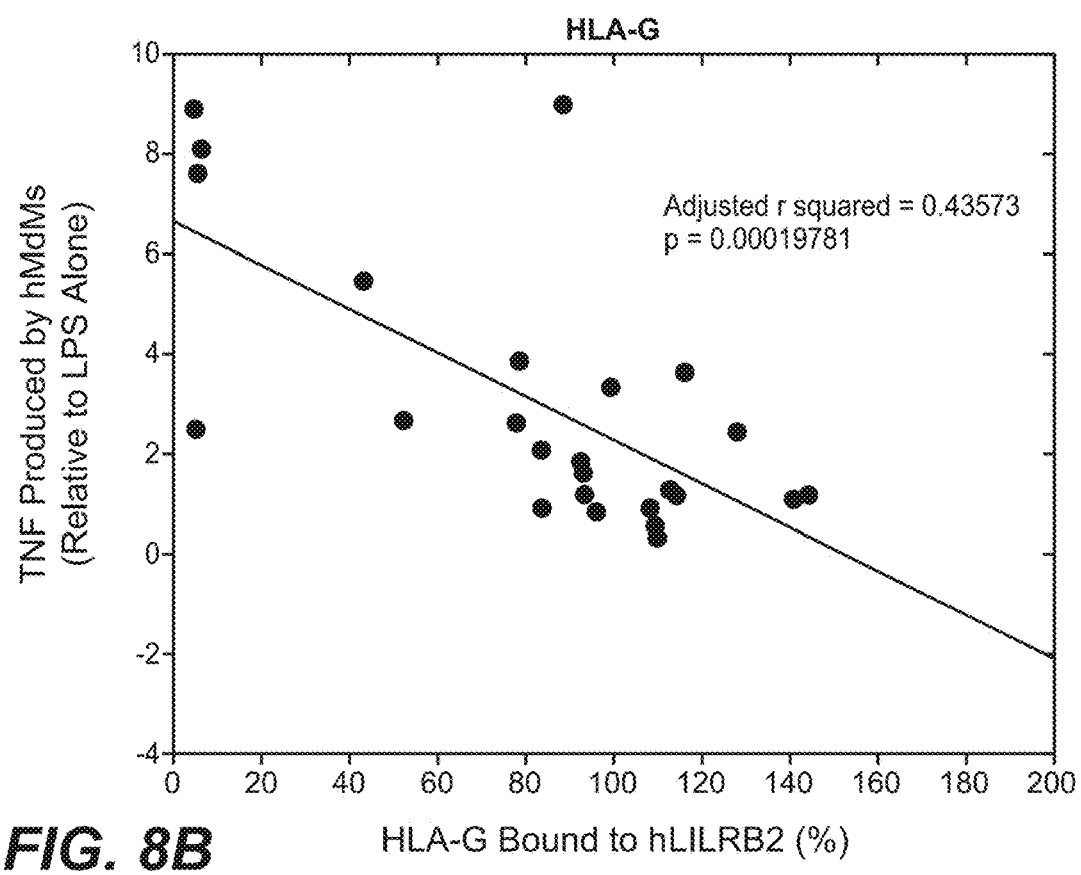

A positive correlation between M1-promoting activity (as measured by TNFα increase) and the ability for anti-LILRB2 mAbs to block HLA-G/A:LILRB2 interactions was observed (FIGS. 8A and 8B).

Human Macrophage Monoculture-Nanostring Assay

Primary human monocytes were differentiated into macrophages in the presence of M-CSF.

After seven days of differentiation, $1\times10^5$ HMDMs were plated per well in a 96-well round-bottom tissue culture treated plate in a final volume of 200 µL containing 100 ng/mL LPS in the absence or presence of 10 µg/mL soluble anti-hLILRB2 mAbs in cell culture media (RPMI (Gibco)+ 10% FBS (Sigma)). Similar conditions were prepared to evaluate mAb activity in the absence of LPS. Cells were incubated at 37° C. with 5% $CO_2$, and separate wells were plated to assess gene changes at four and 24 hours post-treatment. At each time point, supernatant was collected and RNA was extracted from the cells, quantified using Quibit, and QC'd using AATI's Fragment Analyzer. If sufficient RNA was extracted from the sample, gene expression was performed using NanoString nCounter using the Human Immunology V2 panel as well as a custom macrophage-specific spike-in. Gene expression was normalized to the expression of housekeeping genes, then noise thresholding was performed using the data from negative probes. Gene expression was transformed to the log 2 space and data from samples that were treated with LILRB2 binders were normalized to data from the palivizumab treated sample from the same donor. Data represent results from four donors.

Log 2 (gene expression) for each donor and each treatment were normalized to the log 2 (gene expression) in response to palivizumab control. Tables 4 and 5 list the differentially expressed genes, in the presence or absence of LPS, respectively, calculated using the ttest function in MATLAB. Genes that had median log 2 (fold change) across all donors either greater than 1 (i.e. 2 fold increase) or less than −1 (i.e., 2 fold decrease) with p<0.05 in response to all anti-LILRB2 antibodies in the absence of LPS after four hours of exposure to the drugs (Table 4) and genes that were differentially expressed in response to all anti-LILRB2 antibodies in the presence of LPS after 24 hours of exposure to the drugs (Table 5). These changes were consistent across donors and are the basis for the monoculture signature scores defined in the Histoculture section.

TABLE 4

Monoculture anti-LILRB2 differential gene expression at four hours without LPS

| CCL4 | CCL2 | TNFAIP6 | CLEC4E | CCL18 | CASP10 | CIITA |
|---|---|---|---|---|---|---|
| IL8 | IL7R | BCL2 | NFKB2 | GBP1 | CASP2 | |
| CCL3 | DUSP4 | CXCL2 | CCL5 | SOCS3 | TLR7 | |
| IL1B | TNFSF15 | CCL20 | CCL7 | CSF1 | MAF | |
| CXCL1 | IL1RN | NFKB1 | SRC | CD40 | IFI16 | |
| TRAF1 | ICAM1 | NFKBIA | CEBPB | CCL23 | IL16 | |
| IL1A | TNFAIP3 | TNFRSF4 | TLR2 | NTSE | KLRC4 | |
| TNF | CCL8 | EGR1 | CLEC5A | MBP | KLRK1 | |
| IRAK2 | CD83 | NFKBIZ | RELB | TGFBR2 | TLR8 | |
| EGR2 | TNFRSF9 | PTGS2 | PLAUR | BLNK | TNFSF10 | |

TABLE 5

Monoculture anti-LILRB2 differential gene expression at 24 hours with LPS

| IL6 | IL23A | C3 | IL21R |
|---|---|---|---|
| NTSE | CXCL2 | CCL4 | CXCL13 |
| IL1A | ZEB1 | GBP5 | |
| CD123 | PTGS2 | SRC | |
| IL8 | TNFSF15 | CCL2 | |
| CCL20 | TNF | TGFBI | |
| IL1RN | DPP4 | CR1 | |
| CXCL1 | ICAM5 | C1QB | |

TABLE 5-continued

Monoculture anti-LILRB2 differential gene expression at 24 hours with LPS

| IL1B | ITGAX | CD36 |
|---|---|---|
| SPP1 | CCL3 | TRAF5 |

Example 7. Chimeric Antibody Screening: Screening Anti-LILRB2 Chimeric mAbs for Cross-Reactivity to Non-Human Primates Methods
Primary Cell Binding LILRB2 expression in humans is restricted to innate immune cell types including monocytes and neutrophils. Select HLA-G/A blocking, anti-LILRB2 mAbs capable of promoting the conversion of M2 to M1-like macrophages were tested for potential to bind human, cyno and rhesus monocytes in whole blood. Whole blood obtained from healthy human, cyno, and rhesus donors was obtained in sodium heparin tubes. Upon receipt, 100 µL undiluted whole blood was incubated with Fc-receptor blocking reagent (TruStain, Biologend) according to manufacturer's protocol. After a 15-minute incubation, biotinylated mAbs were added to the blood at 25 µg/mL and incubated at room temperature. After 20 minutes, diluted streptavidin-APC (BioLegend) and the human/NHP cross-reactive anti-CD14-BV421 clone M5E2 (BioLegend) were added and incubated for 20 minutes at room temperature. Red blood cells were lysed and samples fixed using 1× Lyse/Fix solution (BD Biosciences) according to manufacturer's protocol. Samples were analyzed using a Celesta flow cytometer analyzer (BD Biosciences). Monocytes were identified across species as side scatter $(SSC)^{hi}$ $CD14^{hi}$ cells, neutrophils were identified as $SSC^{hi}CD14^{lo}$ cell, and lymphocytes were identified as $SSC^{lo}$ $CD14^{neg}$ cells.

On-Cell Binding to Over-Expressed Rhesus-LILRB2

Anti-hLILRB2 mAb binding to rhesus LILRB2 (LILRBb) protein was assessed by incubating LILRBb-CHOs cells with select anti-hLILRB2 mABs for 30 minutes. After incubation, cells were washed and incubated with anti-hIgG-APC (Jackson Labs) according to manufacturer's protocol. Cell binding was assessed by flow cytometry using a Celesta flow cytometer analyzer (BD Biosciences).

Results

Figure 9A:
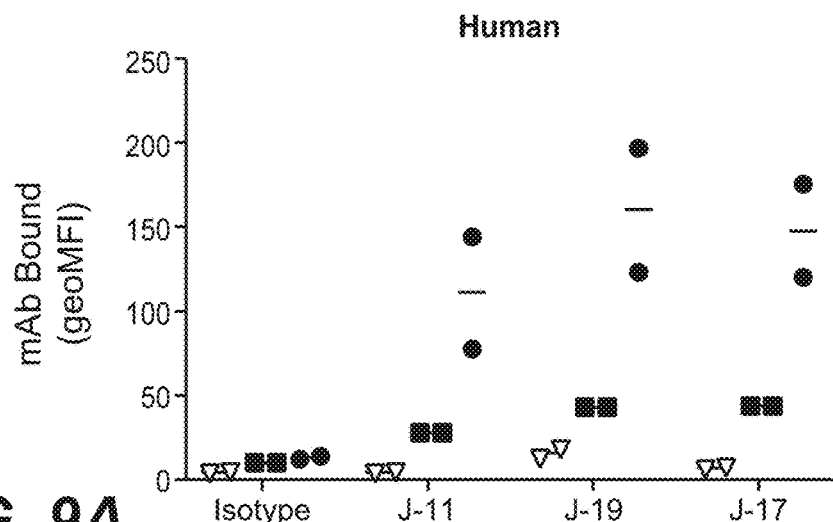
FIGS. 9A-9C are graphs showing primary cell human-NHP cross-reactivity assessment of anti-LILRB2 mAbs. Antibodies were incubated with human (FIG. 9A), cyno (FIG. 9B), and rhesus (FIG. 9C) whole blood. Anti-LILRB2 mAbs showed greater binding LILRB2+ populations including monocytes (circles) and neutrophils (squares) relative to lymphocytes (triangles). All anti-LILRB2 mAbs bound human monocytes and neutrophils, and a single anti-LILRB2 mAb was found to exhibit cross-species binding to cyno and rhesus monocytes and neutrophils. Bars indicate mean of two donors per species.
Figure 9B:
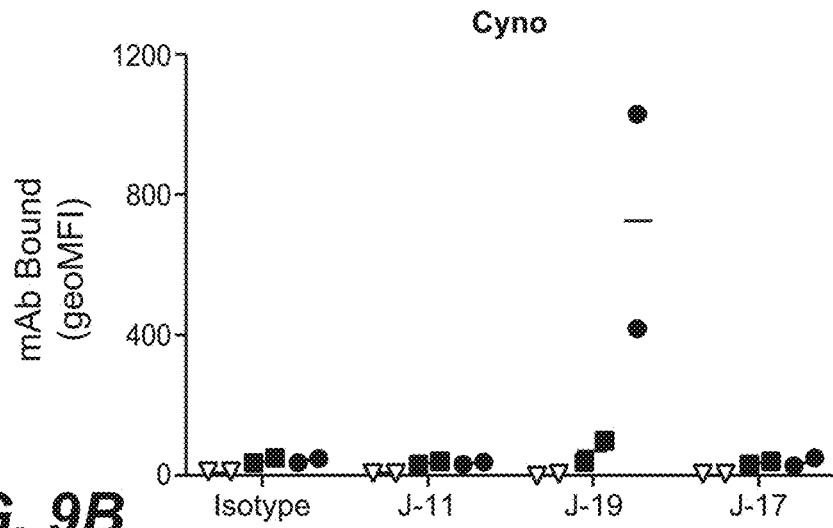
Figure 9C:
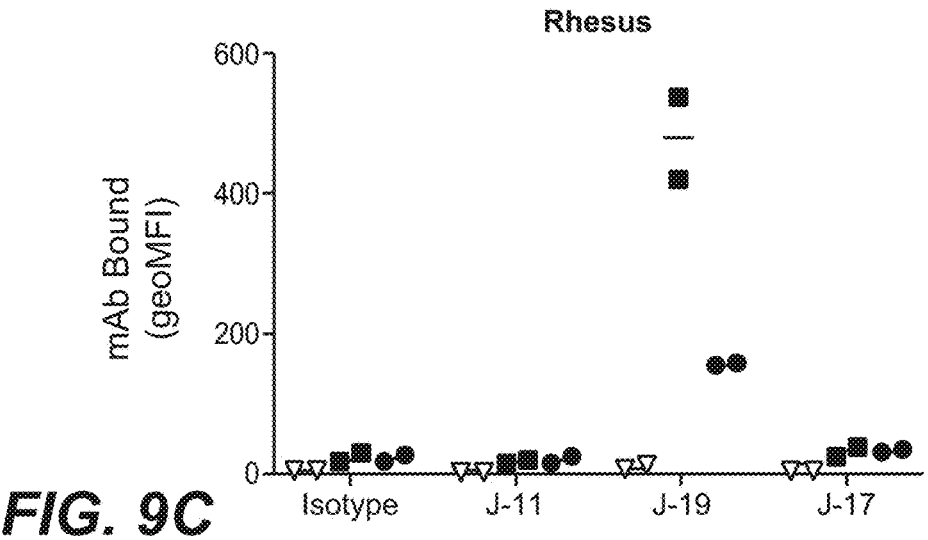
Figure 10A:
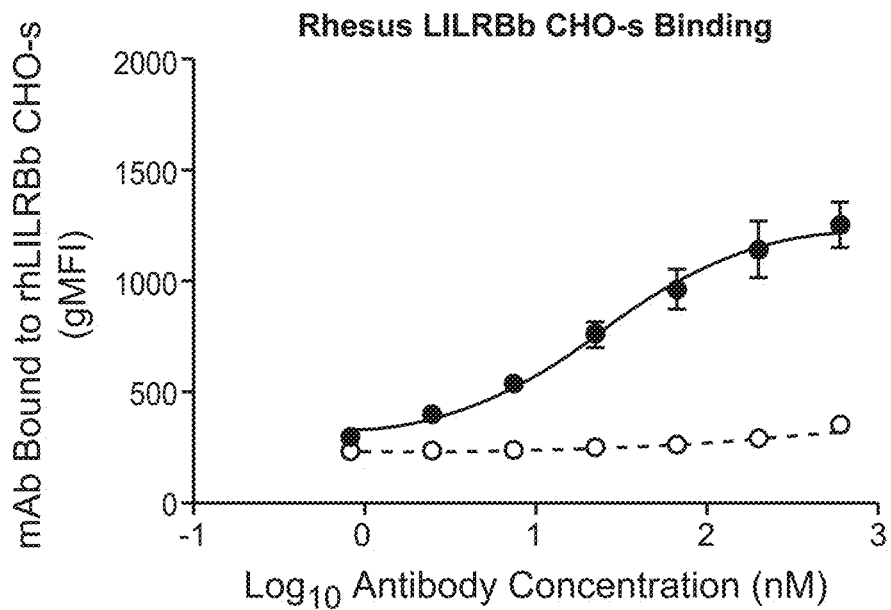
FIGS. 10A and 10B are graphs showing on-cell binding assessment to CHO-expressed putative rhesus LILRB2 (LILRBb). Select anti-hLILRB2 chimeric mAb (black) bound selectively to putative rhesus LILRBb (FIG. 10A) in a dose-dependent and specific manner. This anti-hLILRB2 mAb did not bind the closely related protein in rhesus, LILRBa (FIG. 10B). Isotype control mAb (gray) did not bind either cell line.
Figure 10B:
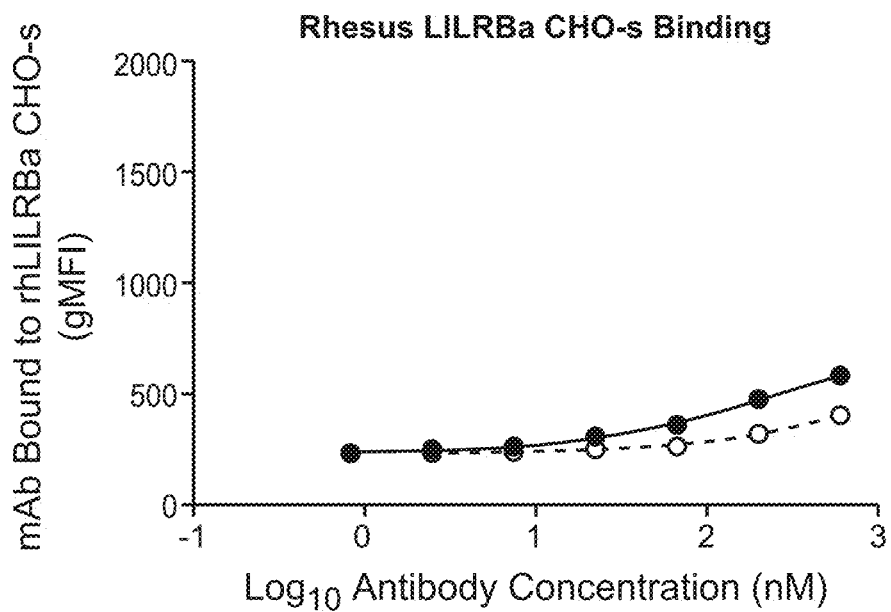

All anti-LILRB2 mAbs tested in this assay preferentially bound monocytes and neutrophils over lymphocytes in human whole blood (FIGS. 9A-9C). A single anti-LILRB2 mAb exhibited cross-species reactivity to both cyno and human, with a similar preferential binding to monocytes and neutrophils over lymphocytes. Isotype control antibodies did not bind significantly to any cell types in human or NHP blood. FIGS. 10A and 10B confirm that these results translate to cells that over-expressing NHP LILRB2 (LILRBb), such that the same anti-hLILRB2 that preferentially cross-binds to NHP monocytes and neutrophils also binds specifically to rhesus LILRB2 (LILRBb) over-expressed CHO-s in a dose-dependent manner and does not cross-react to closely related family members in rhesus including LILRBa.

Example 8. Humanization, Affinity Characterization, and Assessment Strategy for Lead Chimeric Antibodies Lead chimeras were humanized by grafting the CDRs of lead antibodies into human frameworks while maintaining certain amino acids to support loop structure and chain interface. A total of five heavy chain variable regions and five light chain variable regions were generated and expressed in combination to create a total of 25 humanized variants in the human IgG4 backbone. These variants were expressed as recombinant protein and filtered based on protein titer and affinity to the human LILRB2 target. Antibodies were further characterized for functional and biophysical properties to narrow down the panel and select humanized leads.

Using a Mass-2 (Sierra Sensors) high capacity amine chip preimmobilized with AffiniPure Goat Anti-Human IgG, Fcγ Fragment Specific antibody, humanized antibodies were captured on the anti-human surface and then binding to human LILRB2-His was measured by flowing six different concentrations from 65 to 0.27 nM of the analyte over the antibody surface. The anti-LILRB2 surface was removed (10 mM Glycine, pH 2.0) and recaptured between all concentrations or buffer only cycles. The data was analyzed using the Sierra Analyzer software (version 3.1.14). All curves were double subtracted and fit to a 1:1 Langmuir Fit. Results are shown in Table 6, below.

TABLE 6

Binding kinetics of antibodies

| Antibody Reference | $k_a$ [1/(M · s)] | $k_d$ [1/s] | $K_D$ [M] |
| --- | --- | --- | --- |
| J-19.h | $5.15 \times 10^5$ | $1.35 \times 10^{-3}$ | $2.62 \times 10^{-9}$ |
| J-11.h | $3.70 \times 10^5$ | $9.13 \times 10^{-4}$ | $2.47 \times 10^{-9}$ |
| J-17.h | $1.56 \times 10^6$ | $4.43 \times 10^{-4}$ | $2.85 \times 10^{-9}$ |
| J-19.h1 | $3.91 \times 10^5$ | $1.07 \times 10^{-3}$ | $2.73 \times 10^{-9}$ |
| J-19.h2 | $5.21 \times 10^5$ | $2.38 \times 10^{-3}$ | $4.58 \times 10^{-9}$ |
| J-19.h3 | $5.18 \times 10^5$ | $1.01 \times 10^{-3}$ | $1.96 \times 10^{-9}$ |
| J19.h4 | $5.13 \times 10^5$ | $1.20 \times 10^{-3}$ | $2.33 \times 10^{-9}$ |

Humanized (hIgG4) anti-LILRB2 antibodies were further characterized based on specificity to cell-expressed hLILRB2 over the ten other human LILR family members, ability to block the ligand interactions to cell-expressed LILRB2, and ability to convert M2-like macrophages to an M1-like inflammatory activation status in a primary human macrophage assay. Antibodies were additionally screened for binding to non-human primate (NHP) monocytes. Humanized variants were additionally assessed for specific EC/ICso's for affinity to cell-expressed LILRB2, ligand blocking, and cytokine production in a primary human macrophage functional assay. An isotype control antibody was included in all screens to determine background signals. EC/ICso's were calculated based on transformed, non-normalized data using GraphPad Prism software. Results are summarized in FIGS. 11A and 11B and described in detail below.

Example 9. Humanized Antibody Characterization: LILR Family Cross-Reactivity Screening The purpose of this assessment was to verify anti-LILRB2 antibodies maintain specificity to hLILRB2 expressed on cells post humanization, without binding other related LILR family members including hLILRB1, hLILRB3, hLILRB4, hLILRB5, hLILRA1, hLILRA2, hLILRA3, hLILRA4, hLILRA5, and hLILRA6. Positive hits for hLILRB2 binding were identified as antibodies that bound greater than or equal to a three-fold over isotype control antibody binding. None of the variants tested exceed three-fold greater non-specific binding relative to isotype. Additionally, $EC_{50}$ cell-based affinity measurements were determined.

Methods

To test for specificity to hLILRB2 and not towards any of the ten LILR family members, a multiplexed cell-based barcoding approach was used by staining cells with Far Red and/or Violet Cell Trace dyes (Thermo Scientific) according to manufacturer's protocol or left unstained. In brief, cells were washed twice with 1×DPBS and then incubated with diluted dye in 1×DPBS for 20 minutes at 37° C., mixing gently every 5-10 minutes. Dye labeling was quenched by adding equal volume of 100% HI-FBS (Sigma) to the cells. Note that LILRB1, LILRB2, LILRB3, LILRB4, and LILRB5 cell lines are also GFP-positive, while LILRA1, LILRA2, LILRA3, LILRA4, LILRA5, and LILRA6 cell lines are GFP-negative. The cells were then washed twice in 1×DPBS and then all 11 cell lines were combined per well in a 96-well round bottom tissue-culture treated plate. At least $25 \times 10^3$ cells of each cell-line were plated per well. Cells were then re-suspended in primary antibody (anti-LILRB2 mAbs or control) prepared in FACS buffer (1×DPBS containing 2% HI-FBS (Sigma)+0.05% Sodium Azide). After incubation at 4° C. for 30 minutes, cells were washed twice with 1×DPBS and re-suspended in anti-human IgG-PE (BioLegend) diluted 1:200 in FACS buffer. Following a 30 minute incubation at 4° C., protected from light, cells were washed in 1×DPBS and re-suspended in fix buffer (1.5% paraformaldehyde diluted in 1×DPBS). Samples were analyzed using the Celesta flow cytometer analyzer (BD Biosciences). Geometric mean fluorescence intensity (gMFI) of PE was determined for each antibody across each cell line. Background MFI was detected with isotype control and relative binding of antibodies tested was measured as a fold over isotype.

Results

Figure 12:
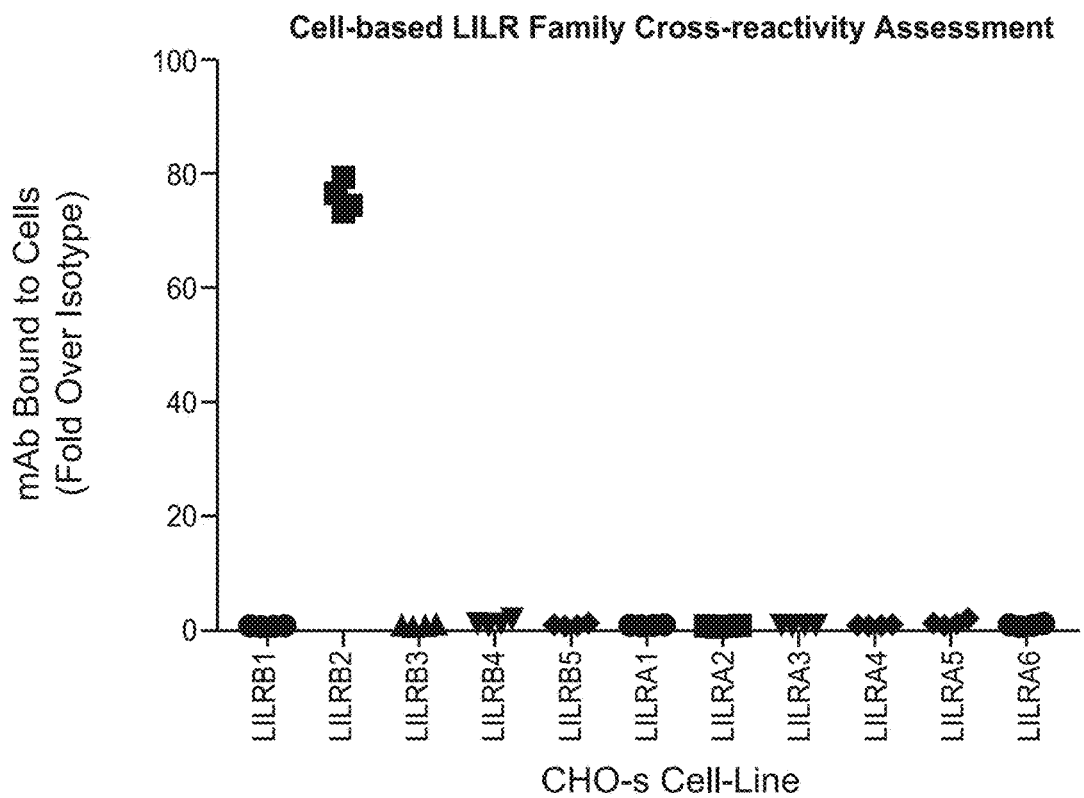
FIG. 12 is a graph showing results of a cell-based LILR family cross-reactivity screen of anti-LILRB2 humanized mAbs. hLILRB2-specific (filled symbols) antibodies from the screen are shown. No LILR-cross-reactive antibodies were identified.
Figure 13:
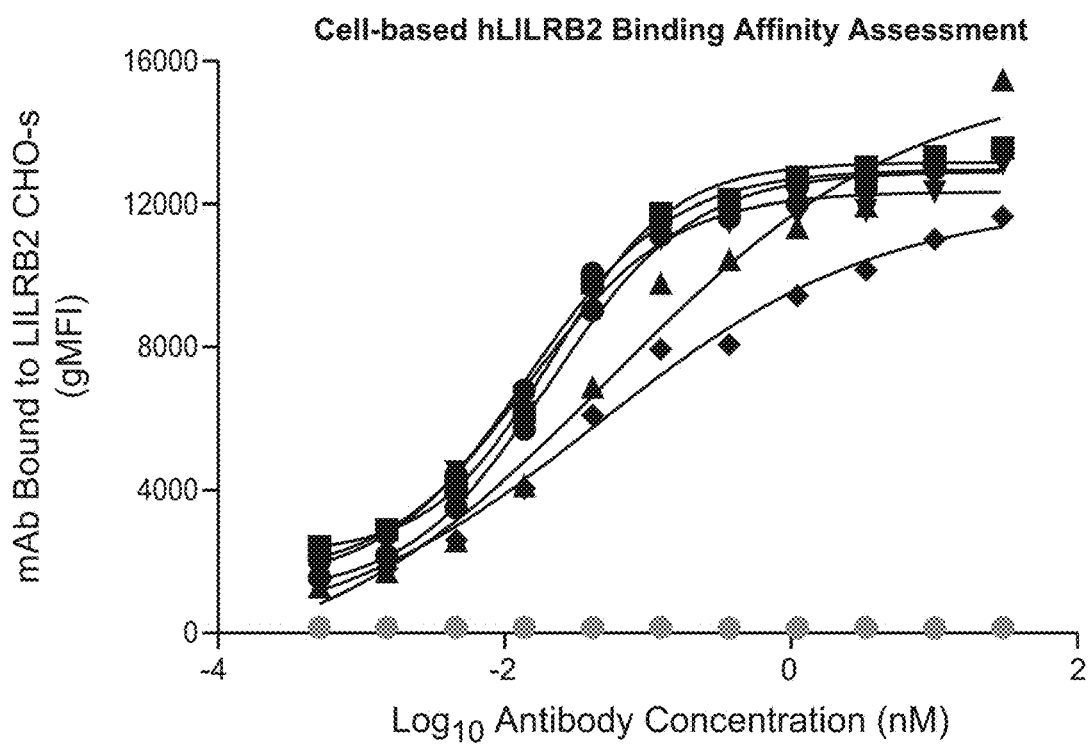
FIG. 13 is a graph showing cell-based affinity determination of humanized anti-hLILRB2 mAbs. All anti-hLILRB2 mAbs tested exhibited dose-dependent specific binding to cell-expressed hLILRB2 (black), while the isotype control mAb did not bind hLILRB2 (gray).

Of the anti-hLILRB2 humanized antibodies tested for binding and specificity to hLILRB2, all of the antibodies bound highly to hLILRB2 and did not cross-bind any of the ten additional hLILR family members in a cell-based binding assay (FIG. 12). The $EC_{50}$ of each antibody to LILRB2-expressing CHO-s was within the sub-nanomolar range (FIG. 13).

Example 10. Humanized Antibody Characterization: Blocking of HLA-G and HLA-A2 to hLILRB2+ Cells The potency of select humanized variants in blocking the interaction of HLA-G and HLA-A2 with primary human macrophage-expressed hLILRB2 were assessed. Primary human monocytes were differentiated into macrophages in the presence of M-CSF. After seven days of differentiation, $1 \times 10^5$ HMDMs were plated in 96-well round-bottom tissue culture-treated plate and washed twice with 1×DPBS (Gibco) and then incubated with 50 μL primary antibody (anti-LILRB2 mAbs or control) prepared in FACS buffer (1×DPBS containing 2% HI-FBS (Sigma)+0.05% Sodium Azide). After incubation with mAbs for 30 minutes at 4° C., cells were washed twice in FACS buffer and then resuspended in 50 µL of FACS buffer containing 5 µg/mL APC-conjugated HLA-G or HLA-A2 tetramer (Fred Hutch). Cells were incubated protected from light for 30-60 minutes at 4° C. After incubation with tetramer, cells were washed in FACS buffer and re-suspended in fix buffer (1.5% paraformaldehyde diluted in 1×DPBS). Samples were analyzed using the Celesta flow cytometer analyzer (BD Biosciences).

Figure 14:
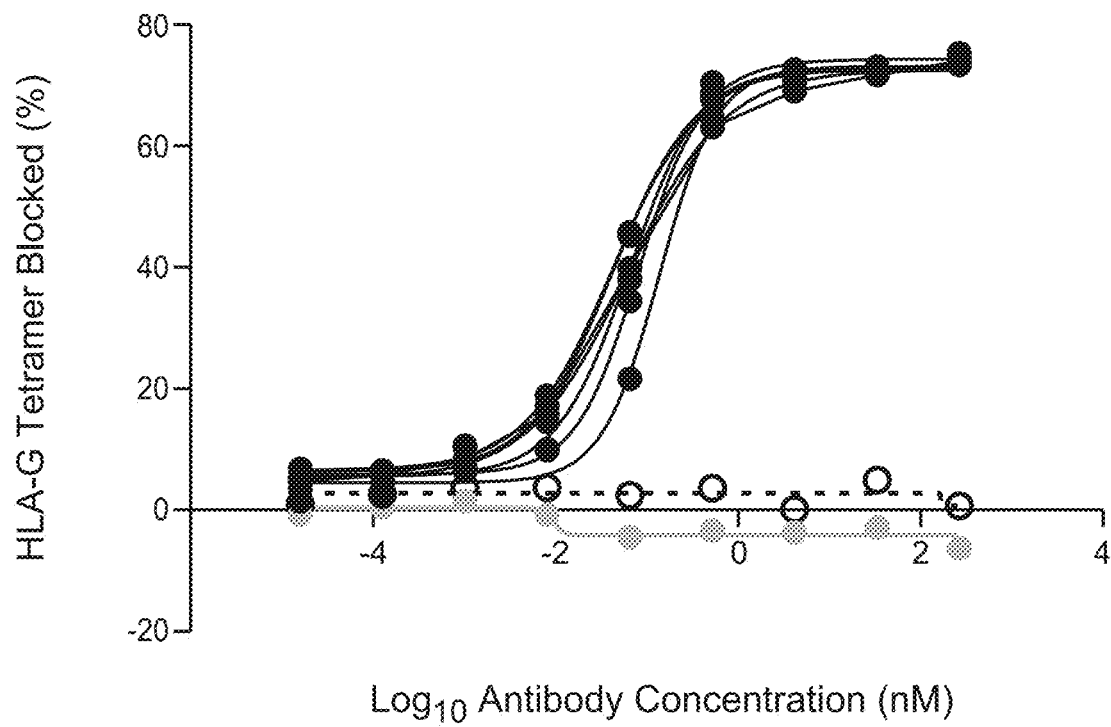
FIG. 14 is a graph showing cell-based HLA-G blocking by anti-LILRB2 humanized mAbs. Humanized anti-hLILRB2 mAbs (black, filled circles) block HLA-G: hLILRB2 interactions on primary human macrophages within the sub-nanomolar range. Isotype control mAb (gray) and non-blocking, chimeric anti-hLILRB2 mAb (open circles) did not disrupt the interaction between HLA-G and cell-expressed hLILRB2.

As shown in FIG. 14, all anti-hLILRB2 humanized antibodies tested blocked HLA-G interaction to cell-expressed hLILRB2 with an $EC_{50}$'s in the nanomolar range. $EC_{50}$ values for each of the variants tested are shown in FIG. 11B. Control antibodies including isotype controls and non-ligand blocking anti-hLILRB2 chimeric antibodies did not display any activity in this assay.

Figure 15:
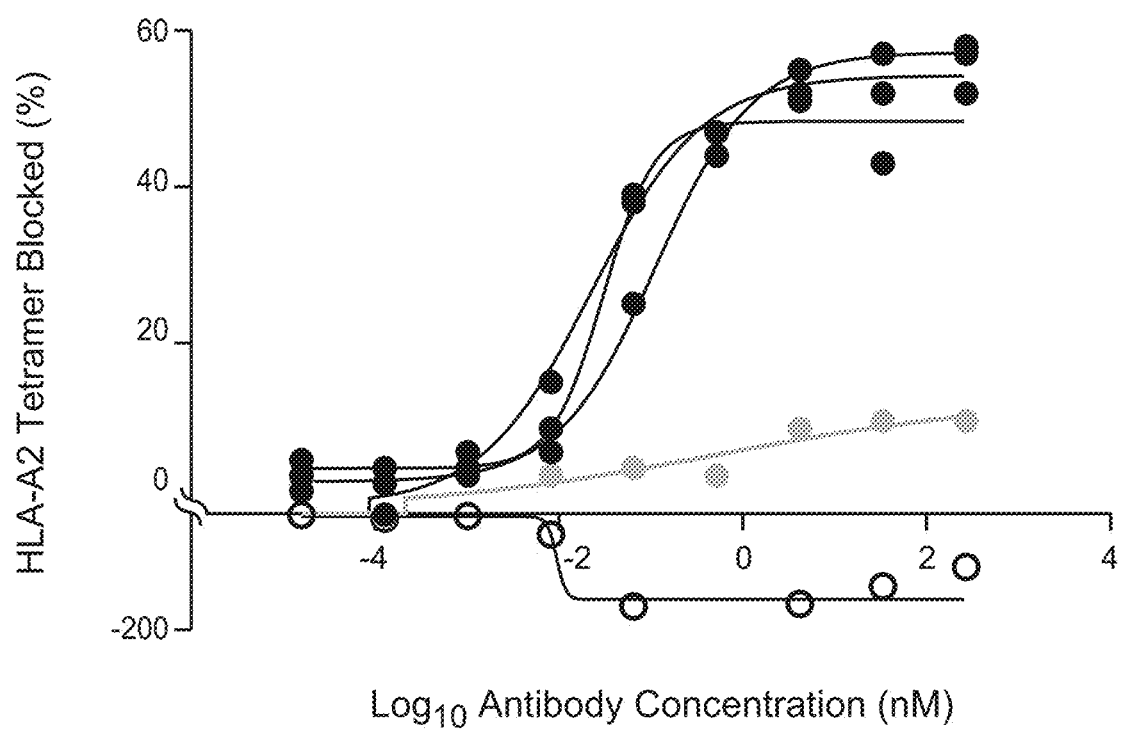
FIG. 15 is a graph showing cell-based HLA-A2 blocking by anti-LILRB2 humanized mAbs. Humanized anti-hLILRB2 mAbs (black, filled circles) block HLA-A2: hLILRB2 interactions on primary human macrophages within the sub-nanomolar range. Isotype control mAb (gray) and non-blocking, chimeric anti-hLILRB2 mAb (open circles) did not disrupt the interaction between HLA-A2 and cell-expressed hLILRB2.

As shown in FIG. 15, all anti-hLILRB2 humanized antibodies tested blocked HLA-A2 interaction to cell-expressed hLILRB2 with an $EC_{50}$'s in the nanomolar range. $EC_{50}$ values for each of the variants tested are shown in FIG. 11B.

Example 11. Humanized Antibody Characterization: Biological Activity of Humanized Anti-LILRB2 mAbs in Cell Culture Tumor associated macrophages (TAMs) display a functional activation status consistent with an M2-like, immunosuppressive macrophage. Without wishing to be bound by theory, antagonizing the inhibitory receptor, LILRB2, on macrophages is hypothesized to prevent the induction of immunosuppressive macrophages and promote hyper-inflammatory responses. To characterize the functional activity of anti-LILRB2 antibodies, $EC/IC_{50}$'s were determined as a potency measurement of anti-LILRB2 mAbs capable of converting M2 into M1-like macrophages in a human monocyte-derived macrophage (HMDM) cytokine release assay. Antibodies with sub-nM activity ($EC_{50}$) in this assay were designated as M1-promoting mAbs.

Methods

After seven days of differentiation, $1\times10^5$ HMDMs were plated per well in a 96-well round-bottom tissue culture treated plate in a final volume of 200 µL containing 100 ng/mL LPS in the absence or presence mAbs in cell culture media (RPMI (Gibco)+10% FBS (Sigma)). After incubation for 24 hours at 37° C. with 5% $CO_2$, supernatant was collected and CBA was performed according to manufacturer's protocol (BD Biosciences) to measure cytokines produced in response to mAbs. Samples were analyzed using the Accuri C6 cytometer analyzer (BD Biosciences).

Results

Figure 16A:
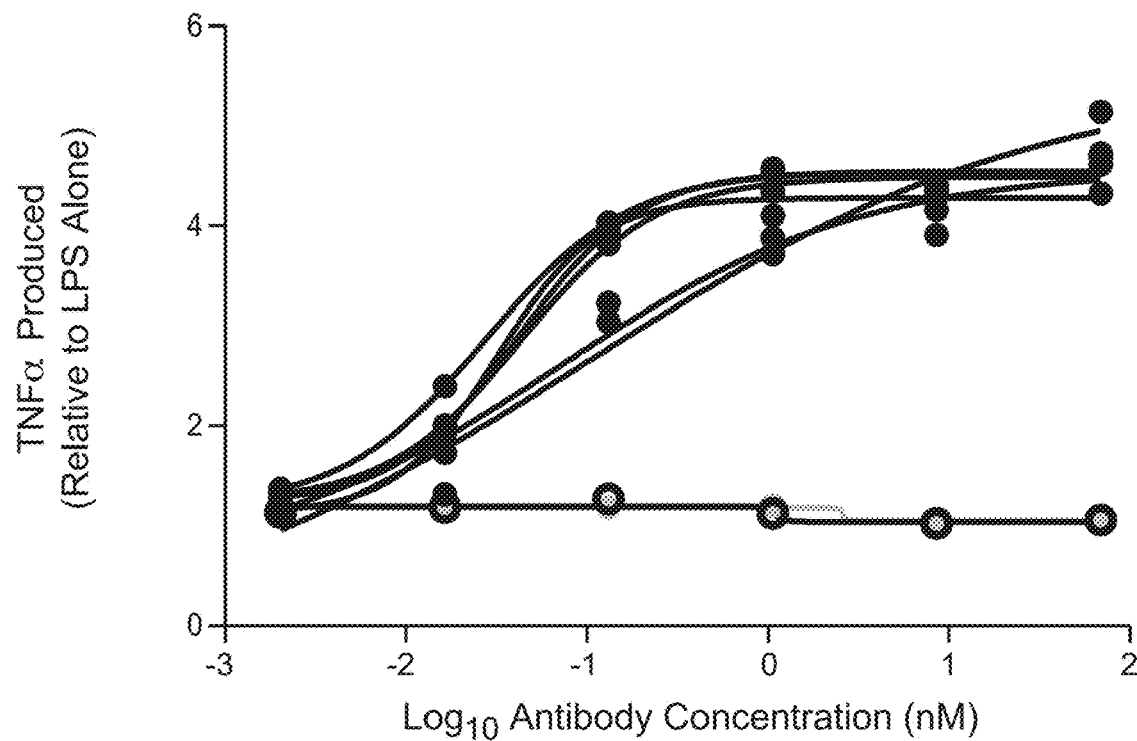
FIGS. 16A and 16B are graphs showing results of a cell-based functional assay of anti-LILRB2 humanized mAbs. Humanized anti-hLILRB2 mAbs (black, filled circles) exhibit M1-promoting activity as measured by TNFα production (FIG. 16A) and suppressive-M2 activity as measured by a reduction in IL-10 production (FIG. 16B) by LPS-stimulated HMDMs. Negative control mAbs including isotype control (gray) and non-ligand blocking anti-hLILRB2 chimeric mAb (open circles) did not show activity in this assay.
Figure 16B:
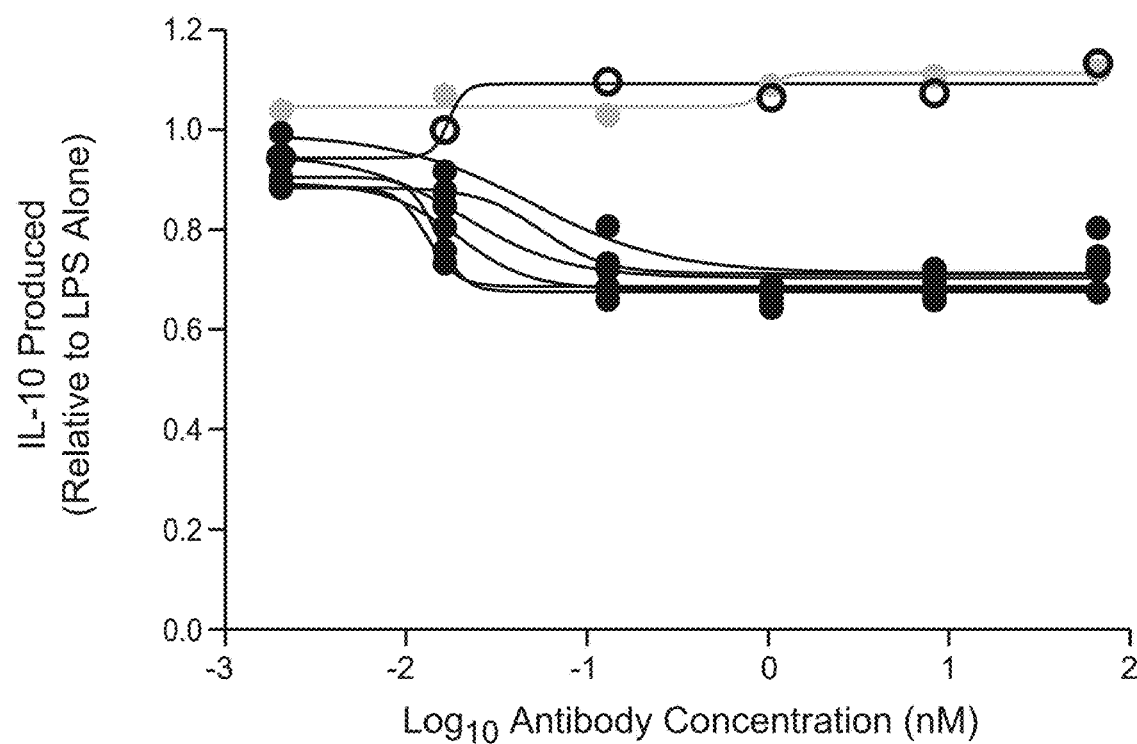

As shown in FIGS. 16A and 16B, all anti-hLILRB2 humanized mAbs displayed M1-promoting activity, while suppressing the production M2-associated cytokines including IL-10 and CCL-2. 67% of humanized anti-hLILRB2 mAbs tested were shown to have sub-nanomolar activity in this assay. $EC_{50}$ values for each of the variants tested are shown in FIG. 10B.

Example 12. Humanized Antibody Characterization: Selective Binding to Non-Human Primate LILRB2 (LILRBb)

To assess humanized mAbs for cross-species reactivity, hLILRB2-specific, ligand-blocking mAbs were assessed for additional selective binding to putative rhesus LILRB2 (LILRBb) over-expressed cells and not to closely related NHP LILR family members.

Methods

Anti-hLILRB2 mAb binding to rhesus LILRB2 (LILRBb) protein was assessed by incubating LILRBb-CHOs cells with select anti-hLILRB2 mAbs for 30 minutes. After incubation, cells were washed and incubated with anti-hIgG-APC (Jackson Labs) according to manufacturer's protocol. Cell binding was assessed by flow cytometry using a Celesta flow cytometer analyzer (BD Biosciences).

Results

Figure 17A:
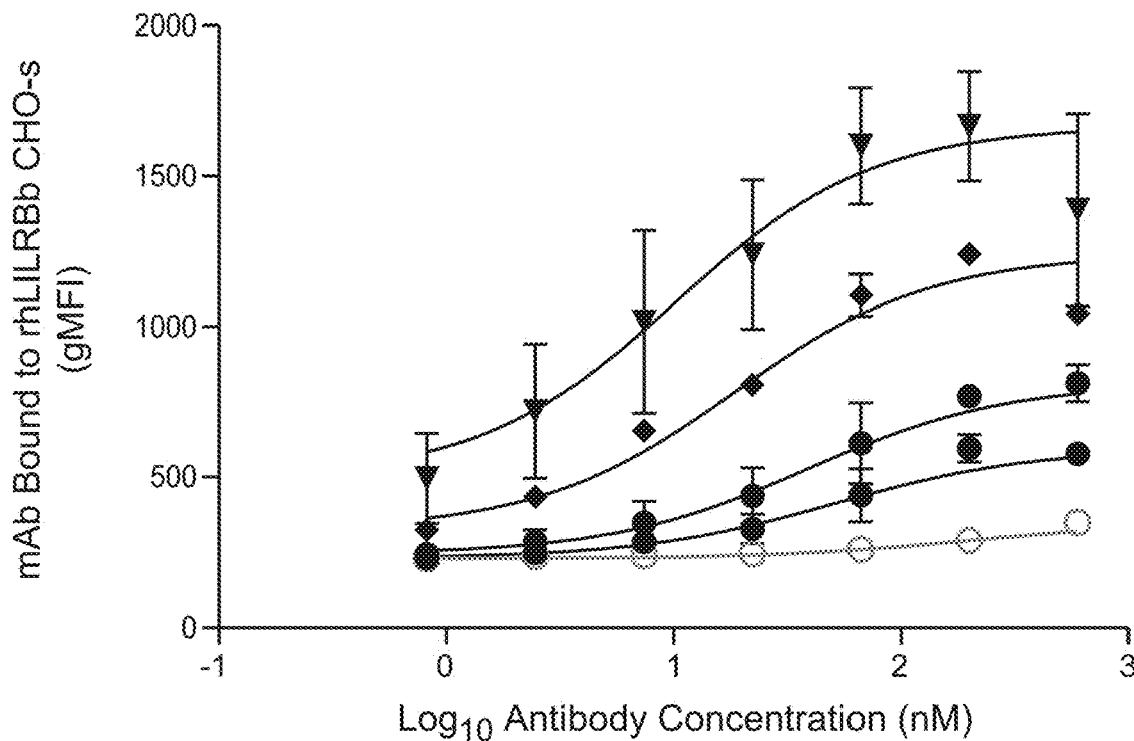
FIGS. 17A and 17B are graphs showing results of an on-cell binding assessment to CHO-expressed rhesus LILRB2 (LILRBb). Select anti-hLILRB2 humanized mAb (black) bound selectively to rhesus LILRBb (FIG. 17A) in a dose-dependent and specific manner. This anti-hLILRB2 mAb did not bind the closely related protein in rhesus, LILRBa (FIG. 17B). Isotype control mAb (gray) did not bind either cell line.
Figure 17B:
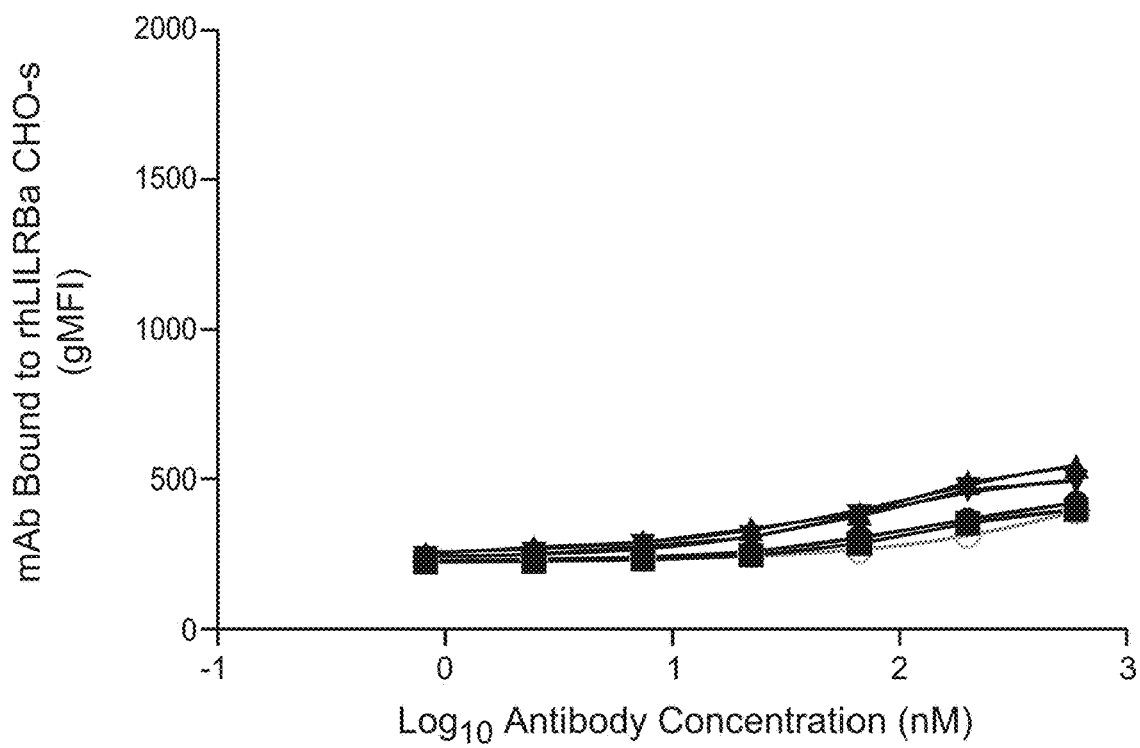

All anti-hLILRB2 humanized mAbs bound to rhesus LILRB2 (LILRBb) in dose-dependent and specific manner (FIG. 17A). These anti-hLILRB2 mAbs did not bind the closely-related rhesus LILRBa protein expressed on cells (FIG. 17B).

Example 13. Gene Expression Analysis: Histoculture Experiments

Fresh human kidney tumor samples were obtained postsurgery. A section of each tumor was cut and fixed for IHC. Approximately 300-µM slices of remaining tumor were placed in a six-well plate. Indicated treatments were added into the medium and plates were incubated at 37° C. Each slice was treated with 10 µg/mL of one of six drugs for 24 hours. The six treatments included in the experiment are J-19, J-17, and J-11 (all LILRB2 binders and ligand blockers), J-04 (a LILRB2 binder that does not block ligand binding), an anti-TIM3 antibody, and palivizumab, which was used as a negative control.

Figure 18:
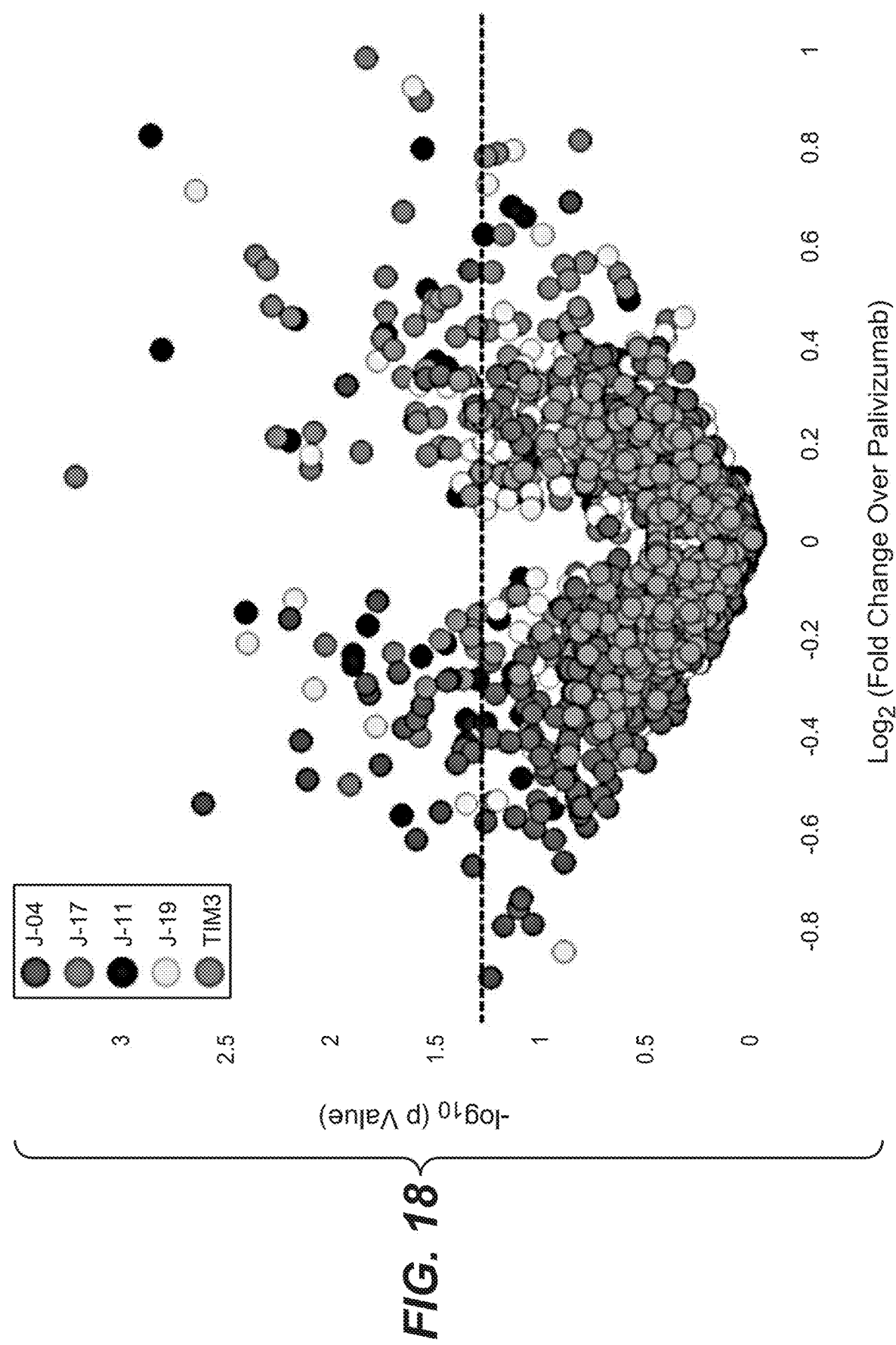
FIG. 18 is a volcano plot showing log 2 (fold change) in gene expression in response to treatment with respect to palivizumab control vs. −log 10 (nominal p value). Each dot depicts the average normalized change in gene expression across all samples receiving the same treatment. Calculations were performed in MATLAB®, and p values were calculated by performing using the ttest function (the null hypothesis is that the average normalized log 2 (fold change) in gene expression across all samples for a particular treatment is 0).

Tumor slices were lysed using Qiagen's TissueLyser processor, and formalin-fixed paraffin-embedded (FFPE) samples were deparaffinized. RNA was extracted from FFPE and fresh tumor samples, quantified using Quibit, and, in certain cases, QC'd using AATI's Fragment Analyzer. If sufficient RNA was extracted from the sample, gene expression was performed using NanoString nCounter using the Human Immunology V2 panel as well as a custom macrophage-specific spike-in. Gene expression was normalized to the expression of housekeeping genes, and noise thresholding was performed using the data from negative probes. Gene expression was transformed to the log 2 space and data from samples that were treated with LILRB2 binders or anti-TIM3 were normalized to data from the palivizumab treated sample from the same patient. FIG. 18 shows change in gene expression in response to treatment relative to palivizumab control. Differential gene expression relative to palivizumab control is quantified in Table 7, below. Each gene in the list showed differential expression to at least two treatments with a nominal p value less than 0.055. The fold change in gene expression was either positive for all treatments or negative for all treatments.

TABLE 7

| Histoculture differential gene expression | | | | | |
|---|---|---|---|---|---|
| Gene | J-04 | J-17 | J-11 | J-19 | TIM3 |
| CD68 | −0.29 | −0.20 | −0.24 | −0.31 | |
| CXCL9 | | 0.98 | 0.80 | 0.72 | 0.67 |
| G6PD | | −0.21 | −0.26 | −0.25 | −0.17 |
| IL10 | −0.41 | −0.40 | −0.37 | −0.38 | |
| IL6R | 0.33 | 0.45 | 0.36 | 0.31 | |
| ETS1 | 0.31 | 0.34 | | | 0.14 |
| KCNJ2 | 0.55 | 0.49 | 0.82 | | |

TABLE 7-continued

Histoculture differential gene expression

| Gene | J-04 | J-17 | J-11 | J-19 | TIM3 |
|---|---|---|---|---|---|
| MASP1 |  | 0.46 |  | 0.36 | 0.32 |
| ZEB1 | 0.33 | 0.41 |  |  | 0.21 |
| BAT3 |  |  | −0.15 | −0.12 |  |
| CCL2 |  | −0.50 | −0.57 |  |  |
| CLEC4A |  |  | 0.28 | 0.29 |  |
| CXCL11 |  |  |  | 0.93 | 0.78 |
| GUSB |  | 0.15 |  | 0.11 |  |
| IFITM1 |  | 0.48 | 0.42 |  |  |
| IL15 |  |  | 0.35 |  | 0.22 |
| IL18R1 |  | −0.22 |  |  | −0.30 |
| IRF1 |  | 0.47 |  |  | 0.39 |
| ITGA6 |  |  | 0.39 | 0.29 |  |
| KLRC3 | −0.44 |  | −0.24 |  |  |
| PIGR |  | 0.58 |  | 0.71 |  |
| PTPN22 | −0.62 |  | −0.21 |  |  |
| SDHA |  | 0.25 |  | 0.20 |  |
| SLC2A1 | 0.27 |  | 0.45 |  |  |
| TAP1 |  | 0.24 |  |  | 0.24 |

Figure 19:
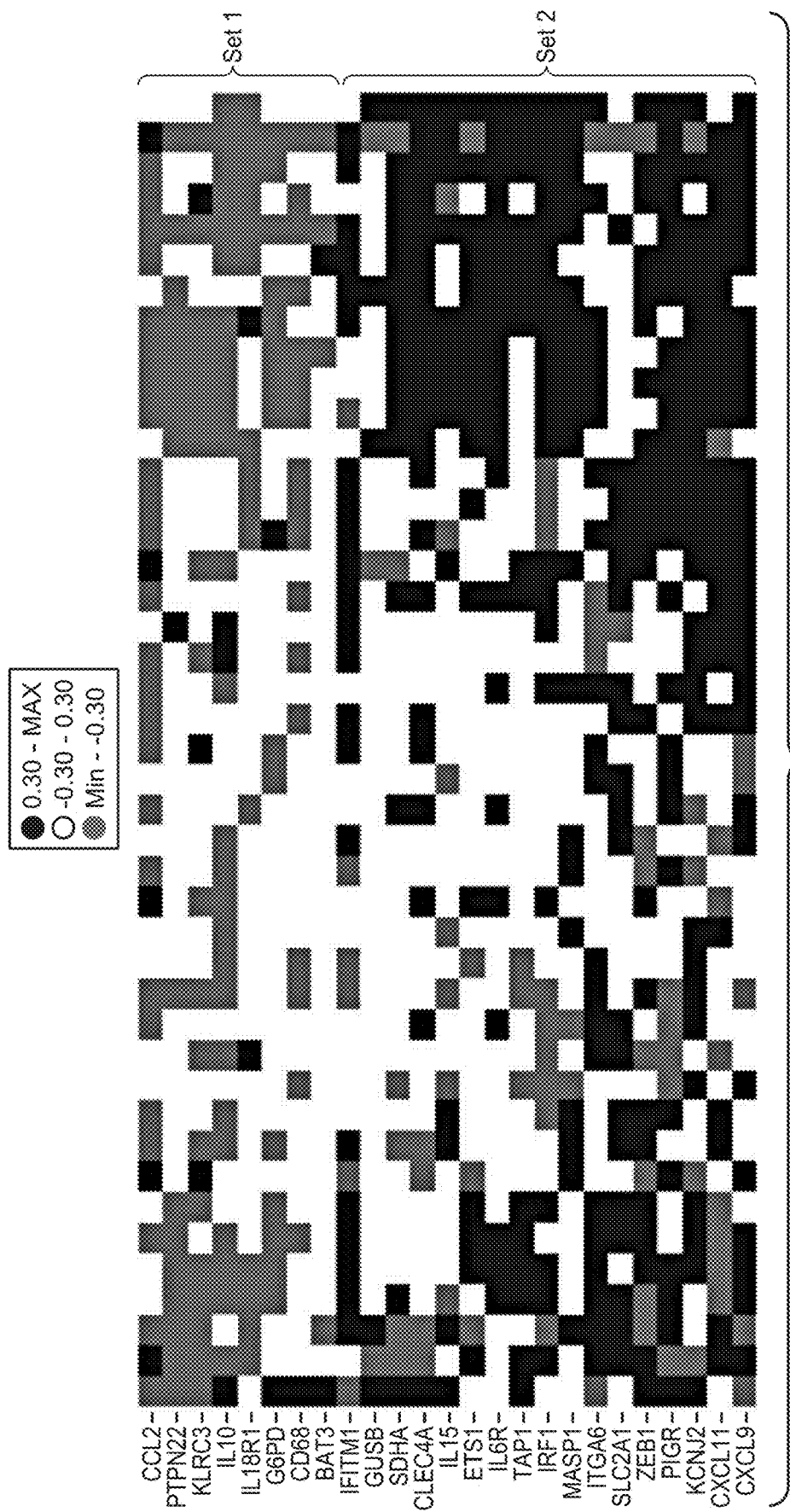
FIG. 19 is a hierarchical clustering heatmap showing the log 2 (fold change) in gene expression of each gene (row) in each treated sample (column) normalized to an IgG4 control for each kidney histoculture sample. Each gene in the list showed differential expression to at least two treatments with a nominal p value less than 0.055 (see Table 7). The expression of Set 1 genes is generally downregulated in response to treatment (gray boxes) and the expression of Set 2 genes is generally upregulated in response to treatment (black boxes). The noise threshold is set at 0.3 based on housekeeping gene expression distribution. A Euclidean distance metric was used in the complete linkage clustering, which was performed in Spotfire.

A hierarchical clustering heatmap showing the log 2 (fold change) in expression of each gene (row) in each treated sample (column) is shown in FIG. 19. Each gene in the list showed differential expression to at least two treatments with a nominal p value less than 0.055. The expression of Set 1 genes is generally downregulated in response to treatment (gray boxes) and the expression of Set 2 genes is generally upregulated in response to treatment (black boxes).

A response score for each sample was calculated by adding the sum of the log 2 (fold change) of a subset of genes in Set 2 to the negative sum of the log 2 (fold change) of a subset of genes in Set 1 and dividing by the number of genes included, according to the following equation:

$$\text{PD score} = \frac{1}{\text{\# Set 1 genes} + \text{\# Set 2 genes}} \left( \sum_{Set2} \log2(\text{fold change}) - \sum_{Set1} \log2(\text{fold change}) \right)$$

Figure 20:
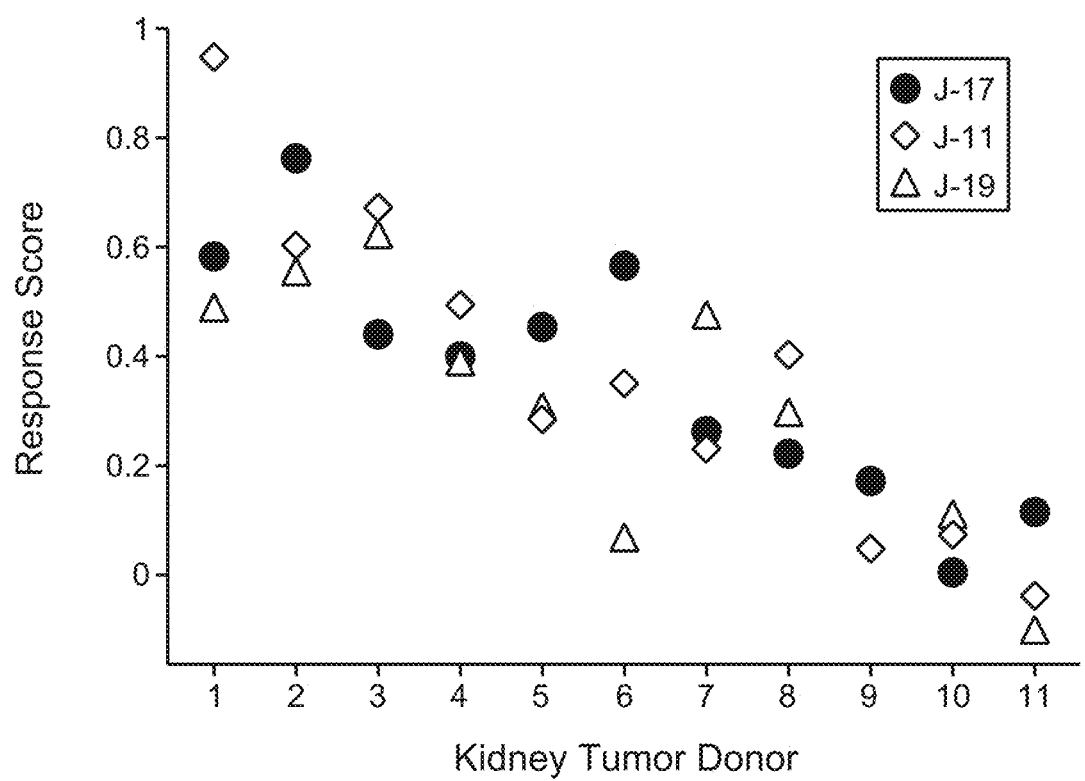
FIG. 20 is a graph showing a response score for each donor to each ligand-blocking anti-LILRB2 antibodies.

The response score for each donor to each ligand-blocking anti-LILRB2 drug is shown in FIG. 20. Response to treatment is consistent across treatments within donor, thus allowing for classification of donors by their response to anti-LILRB2 treatment. Donors with an average response score greater than 0.5 are classified as "full responders"; those with an average response score between 0.3 and 0.5 are classified as "partial responders"; those with scores below 0.3 are classified as "non-responders."

Figure 21A:
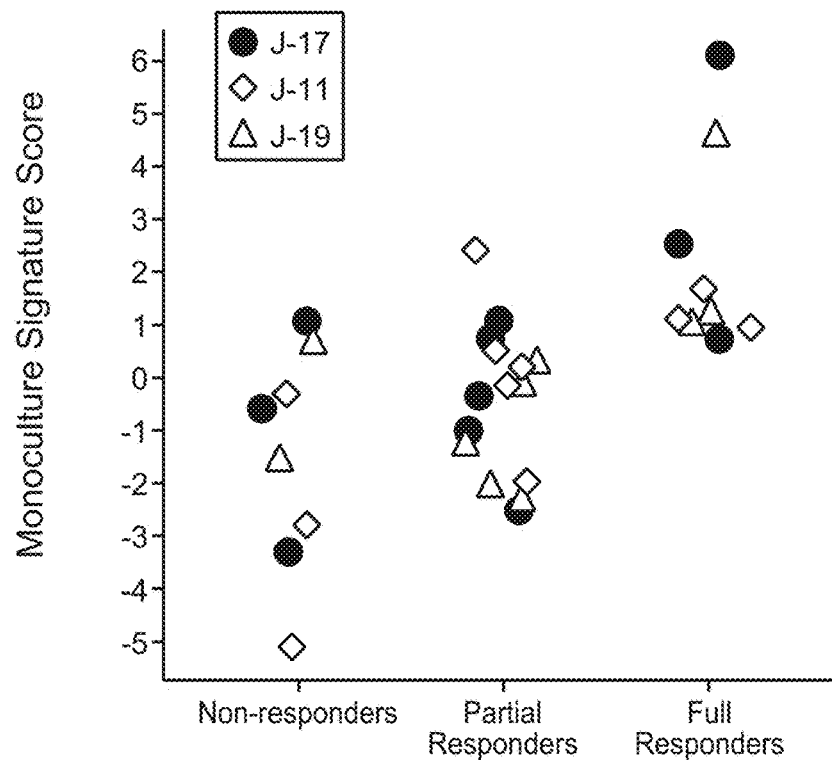
FIGS. 21A and 21B are graphs showing monoculture signature scores for each of three anti-LILRB2 antibodies for each non-responder, partial responder, and full responder.
Figure 21B:
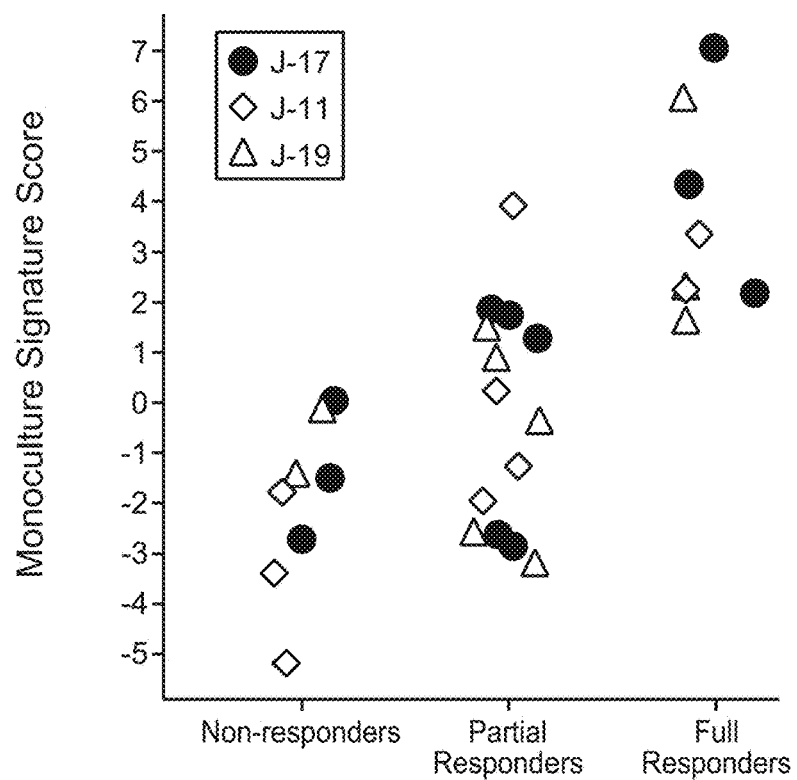

Monoculture signatures were derived based on the mean log 2 (fold change) in gene expression across donors in response to anti-LILRB2 ligand-blocking drugs in the absence of LPS after 4 hours and in the presence of LPS after 24 hours (FIGS. 21A and 21B). Monoculture signature scores were calculated for each histoculture sample treated with an anti-LILRB2 ligand-blocking drug by projection of the log 2 (fold change) in gene expression onto the vector defined by the monoculture signature. The monoculture signature scores (four hours in the absence of LPS and 24 hours in the presence of LPS) are significantly higher (p<0.01) in full responders compared to partial and non-responders.

In sum, the monoculture results showed that LILRB2-binding drugs cause macrophages to differentially express a number of genes consistently across donors. The set of genes that was modulated in this system constitutes a monoculture signature that incorporates both magnitude and directionality. To confirm that these pathways would also be modulated in more complex systems, histoculture experiments were performed. Analysis of histoculture data shows that exposure of kidney tumor slices to LILRB2-binding drugs results in upregulation of inflammatory chemokine expression, as well as differential expression of known myeloid-specific genes. The genes are co-regulated and are only differentially expressed in a subset of samples. This subset of genes constitutes the PD response signature, which is used to calculate response scores and classify samples based on response to drugs. It should be noted that donors that respond to one anti-LILRB2 drug generally respond to all of them. Additionally, when the histoculture data was projected onto the monoculture signature, the responders showed statistically significant monoculture scores. Thus, the modulation of myeloid-specific genes was consistent with findings in in vitro experiments, suggesting that the same biological pathways are being affected.

Example 14. Toxicology

Figure 22:
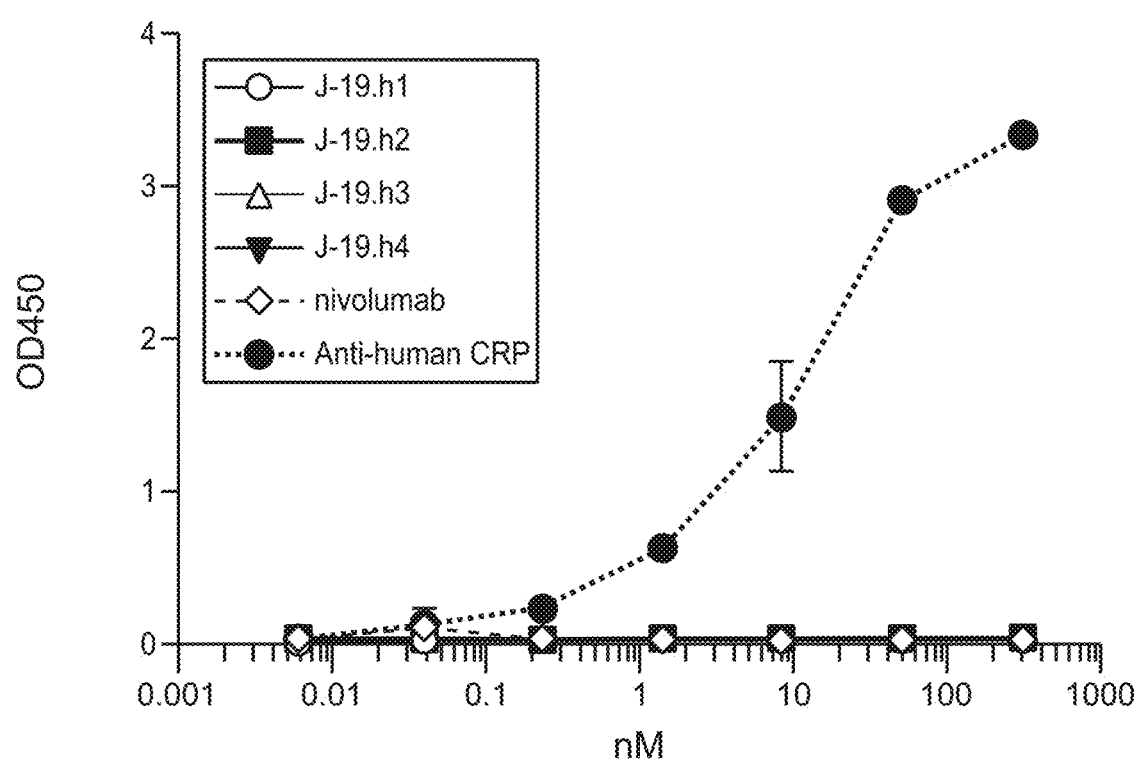
FIG. 22 is a graph showing binding of serum protein to antibodies over antibody concentration. No serum protein binding to LILRB2 antibodies was observed.
Figure 23A:
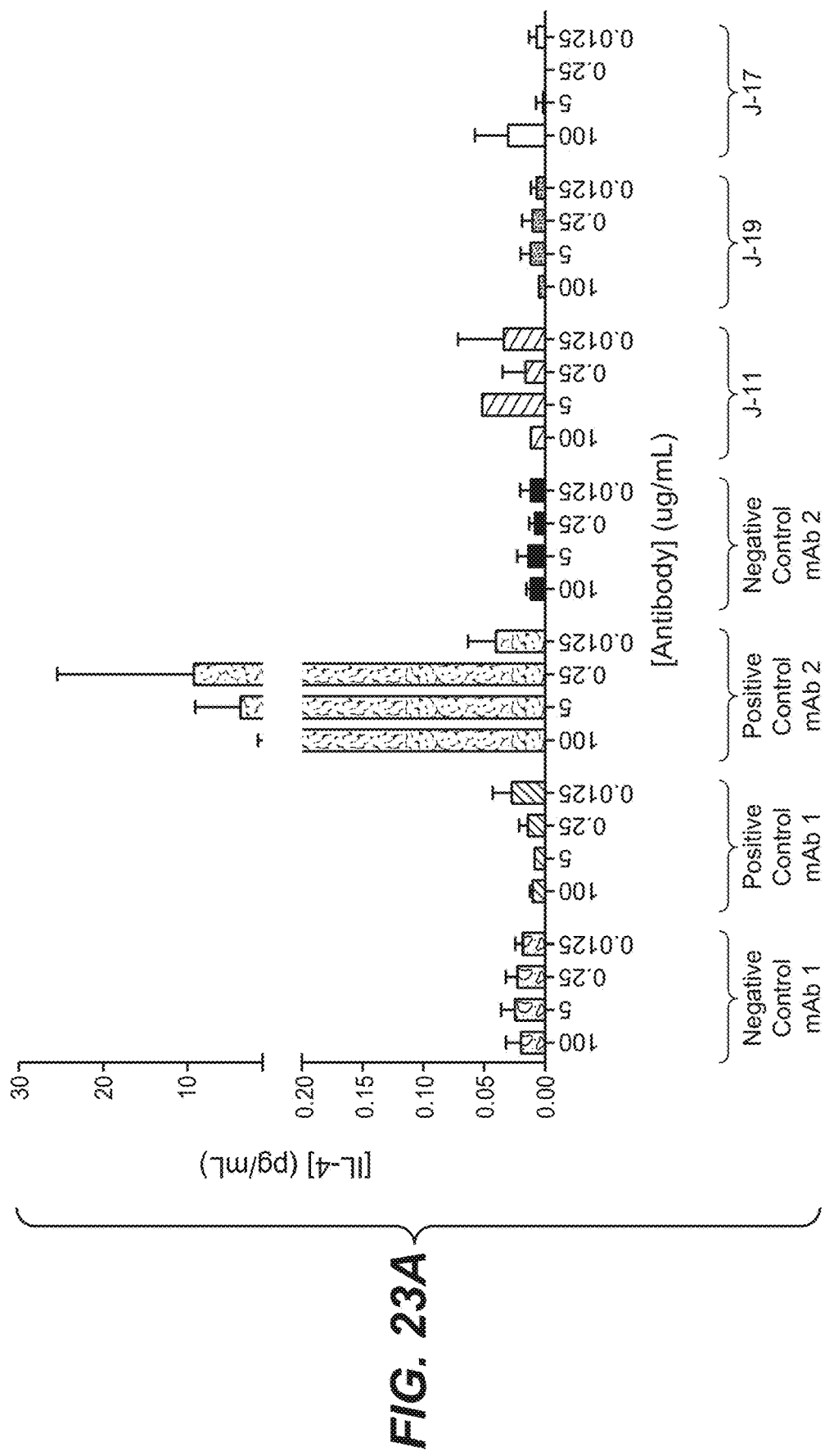
FIGS. 23A-23D are graphs showing the results of a whole blood cytokine release assay.
Figure 23B:
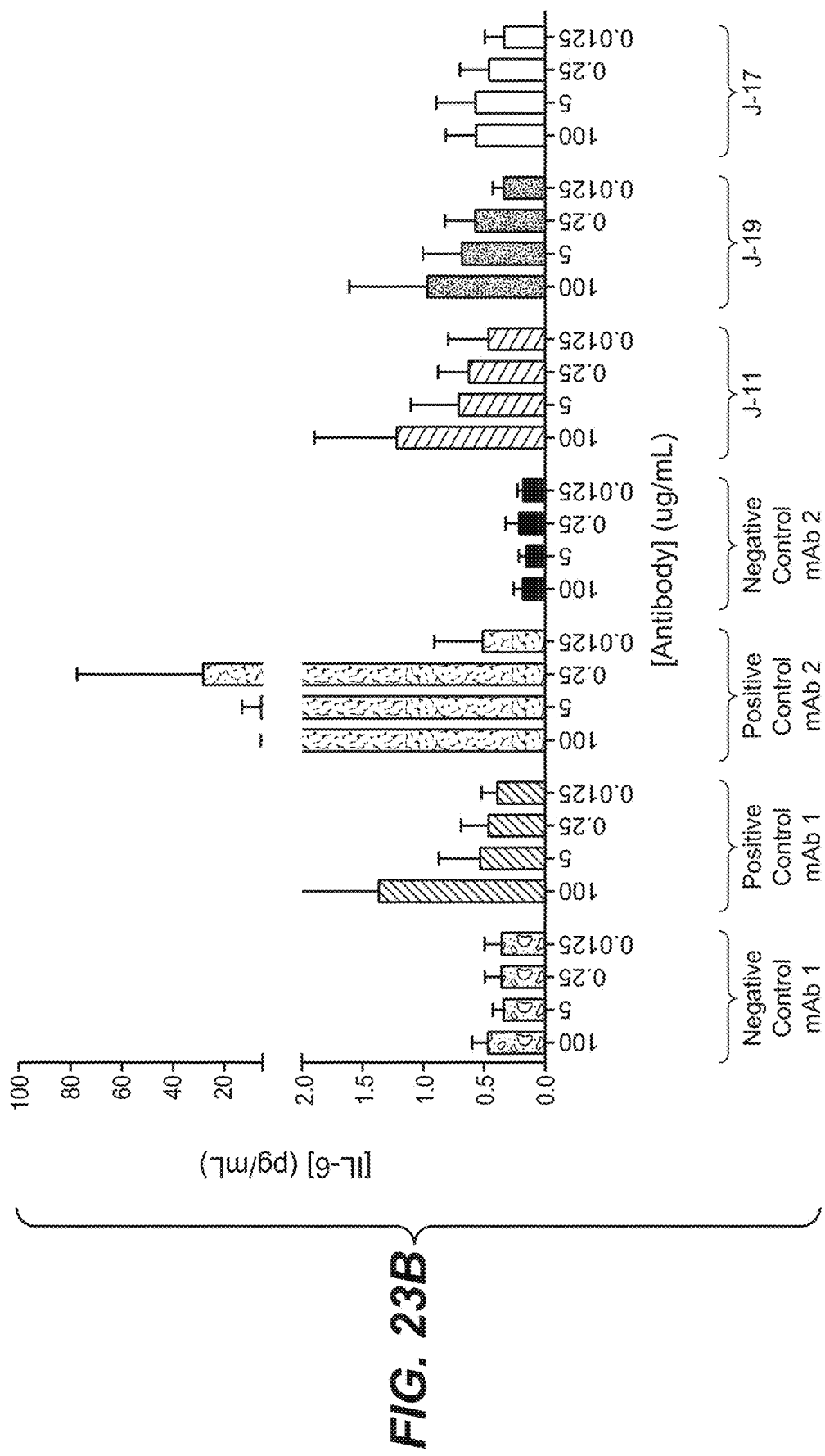
Figure 23C:
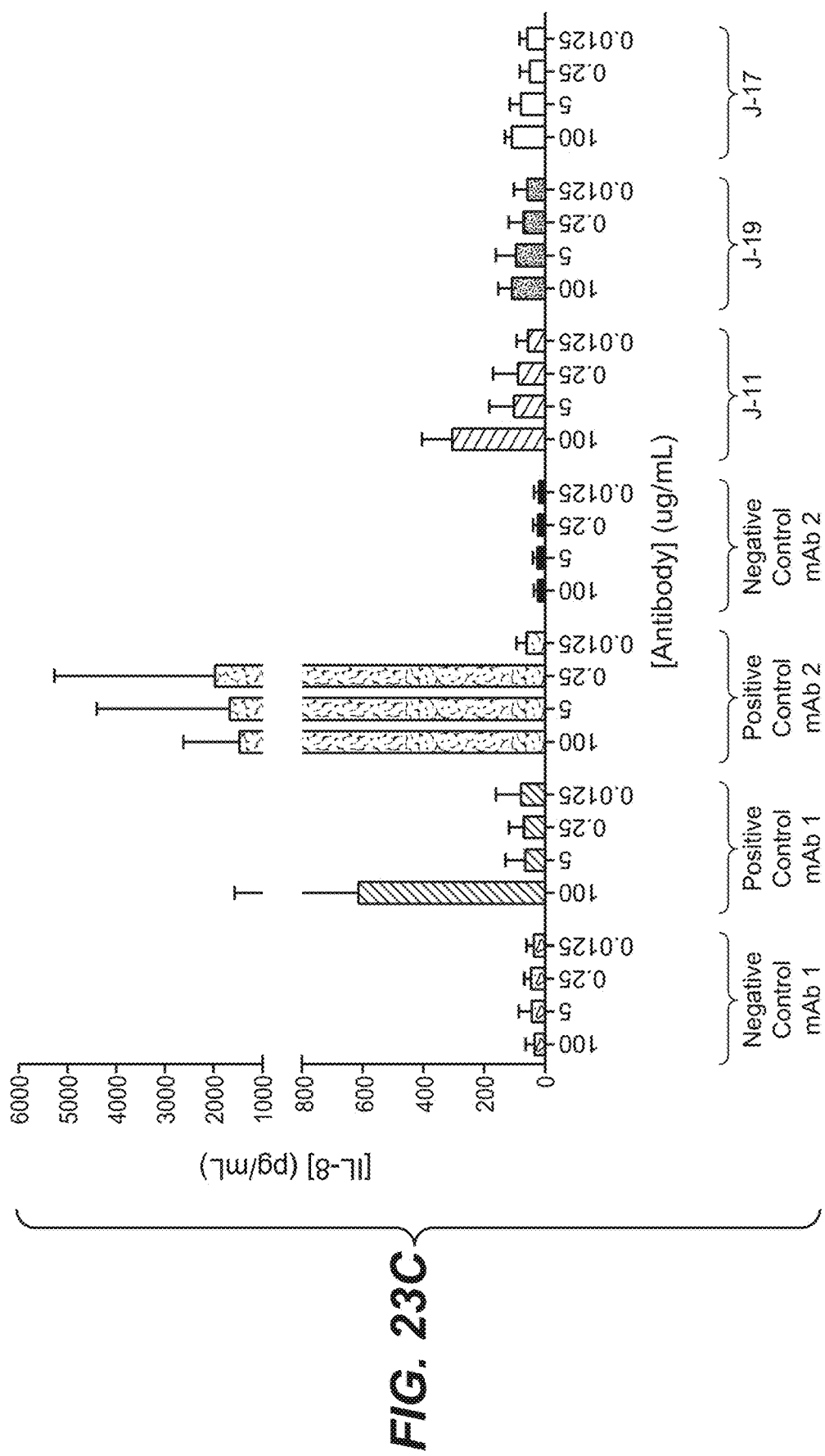
Figure 23D:
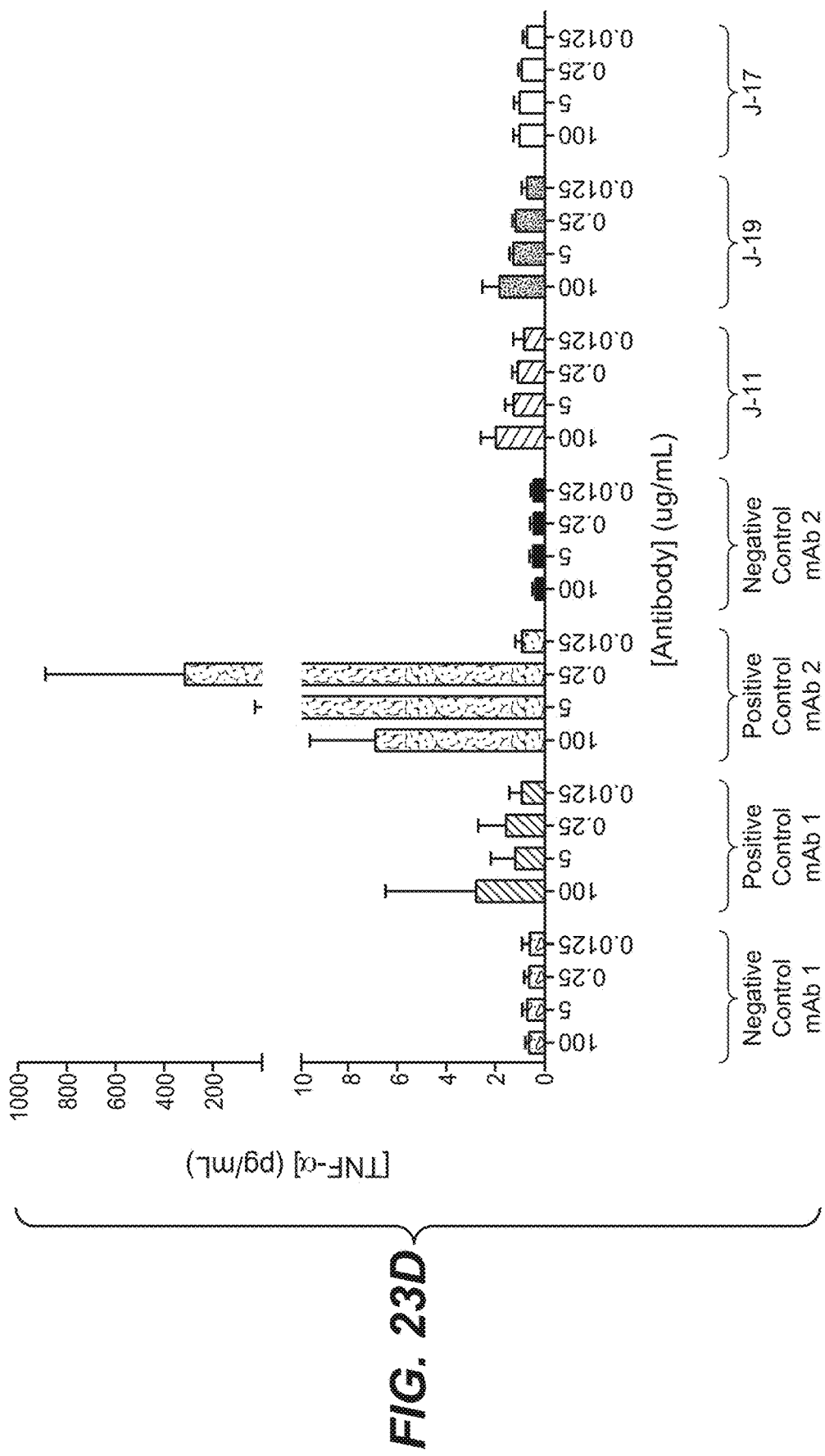

Specificity of anti-LILRB2 antibodies was determined by assessing binding of antibodies to red blood cells and platelets by flow cytometry or to serum proteins by ELISA. No off-target binding was observed in these assays (FIG. 22).

The potential for anti-LILRB2 antibodies to elicit cytokine storm was assessed in a human whole blood cytokine release assay using titrations of soluble antibodies. The assay was incubated for 24 hours at 37° C. Plasma was then isolated and cytokines were measured using a 10-cytokine MSD panel. Data are mean+/−SD of three donors. As shown in FIGS. 23A-23D, anti-LILRB2 antibodies did not exhibit induction of cytokines associated with cytokine storm (e.g., IL-4, IL-6, IL-18, or TNFα) in this assay.

Figure 24A:
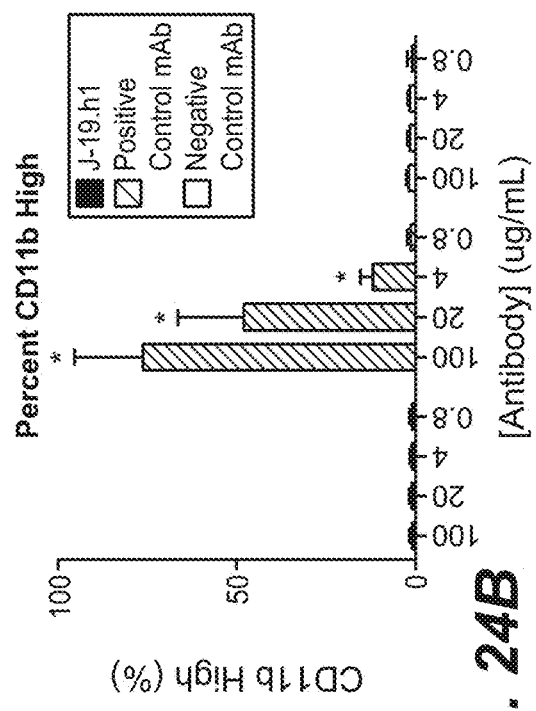
FIGS. 24A-24D are graphs showing the results of a neutrophil activation assay.
Figure 24B:
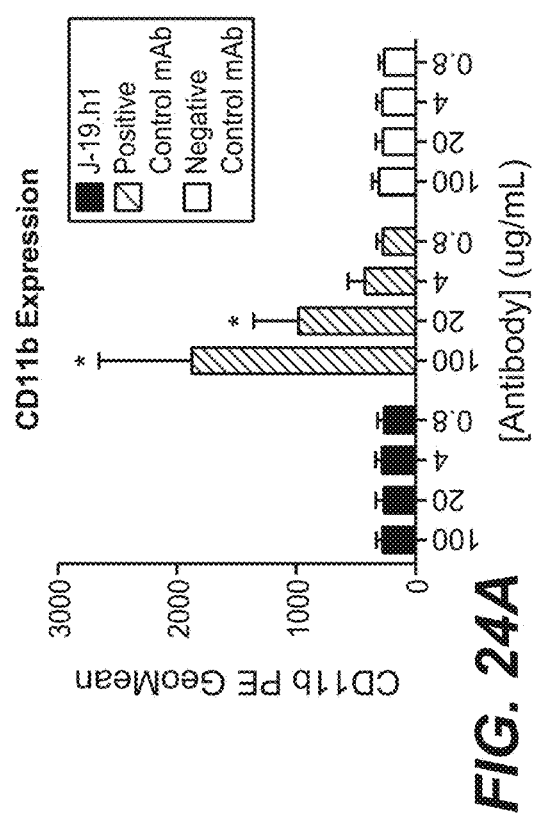
Figure 24C:
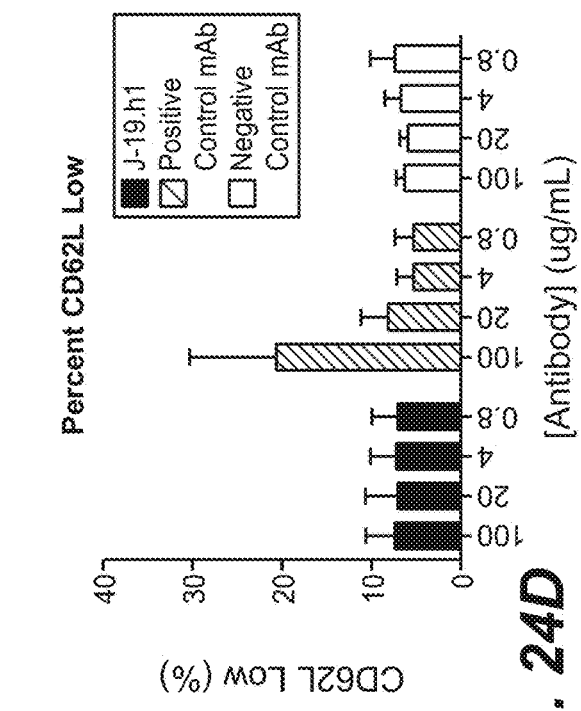
Figure 24D:
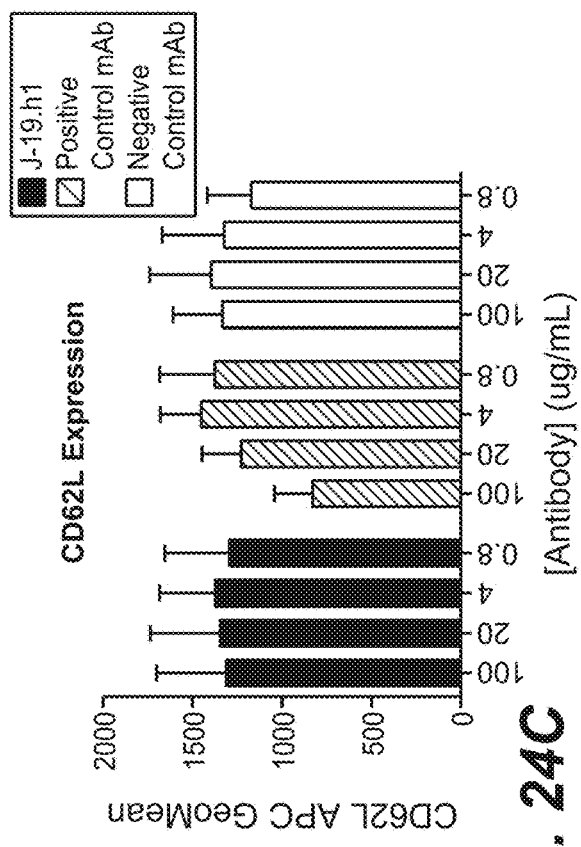

The potential for anti-LILRB2 antibodies to induce neutrophil activation was assessed in human whole blood using titrations of soluble antibodies. The assay was incubated for two hours at 37° C. Changes in neutrophil activation markers (increase in CD11 b and decrease in CD62L) were assessed by flow cytometry. Data are mean+/−SD of 2 donors. Anti-LILRB2 antibodies did not induce neutrophil activation, as indicated by low CD11 b expression (FIGS. 24A and 24B) and retention of CD62L (FIGS. 24C and 24D).

Example 15. Pharmacokinetics

Figure 25:
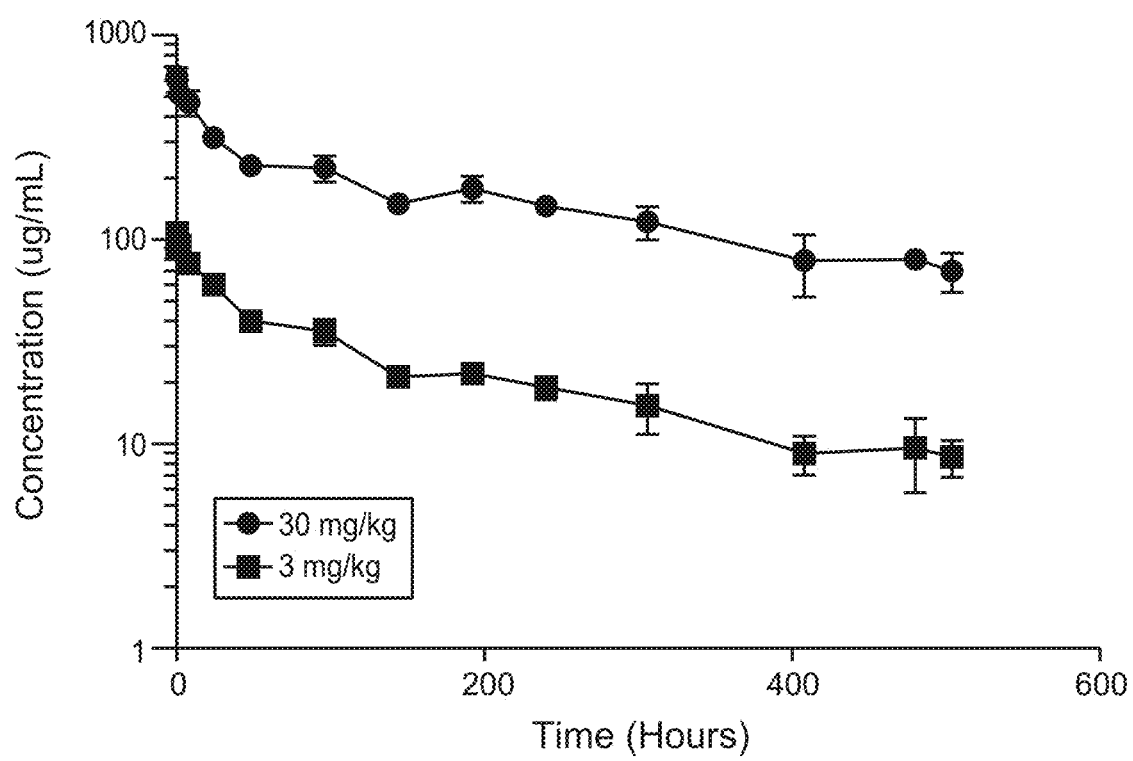
FIG. 25 is a graph showing the serum concentration of anti-LILBR2 antibody in cynomolgus monkeys over time, after a 30 mg/kg dose or a three mg/kg dose. Data are the average+/−SD of three individual monkeys.

Cynomolgus monkeys (n=3 per group) received a single intravenous infusion of the indicated concentration of anti-LILRB2 antibody. Serum concentrations of drug were measured using an electrochemiluminescent assay, and the results, shown in FIG. 25, indicate that single-dose pharmacokinetics in cynomolgus monkeys exhibits a half-life typical of human IgG4 antibodies.

Figure 26A:
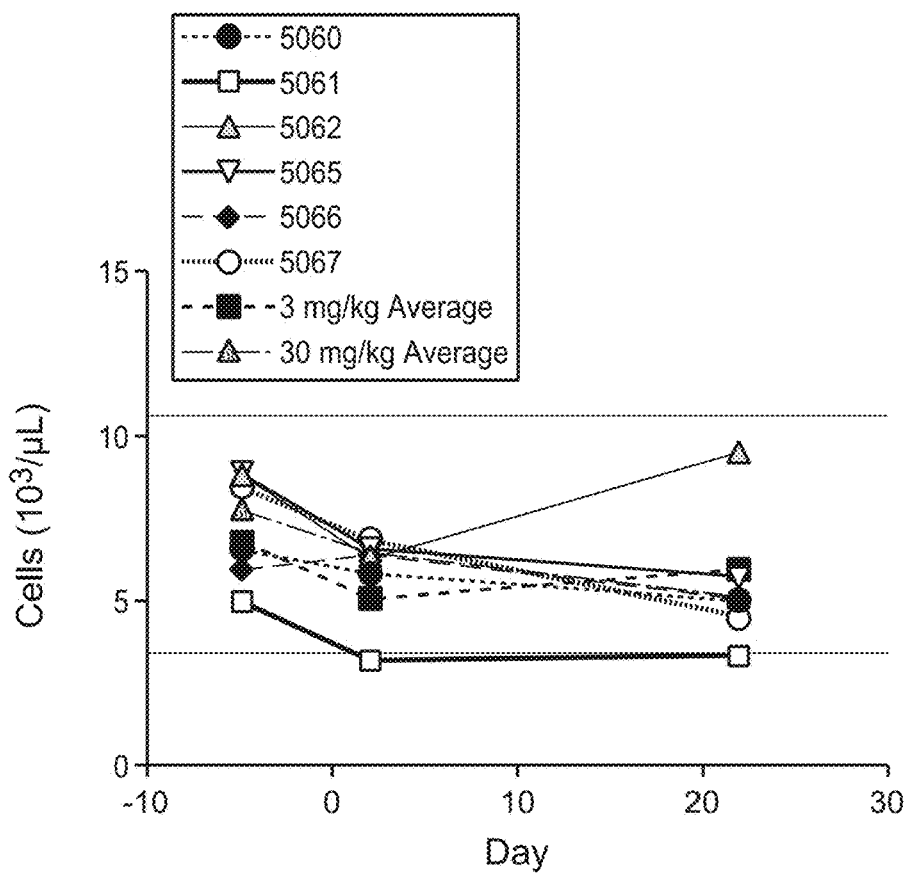
FIGS. 26A and 26B are graphs showing peripheral blood neutrophil populations measured by complete blood count (CBC) assay in cynomolgus monkeys pre-study and following dosing of anti-LILRB2 antibodies. Data are presented as absolute number of cells (FIG. 26A) and as a percent of total (FIG. 26B).
Figure 26B:
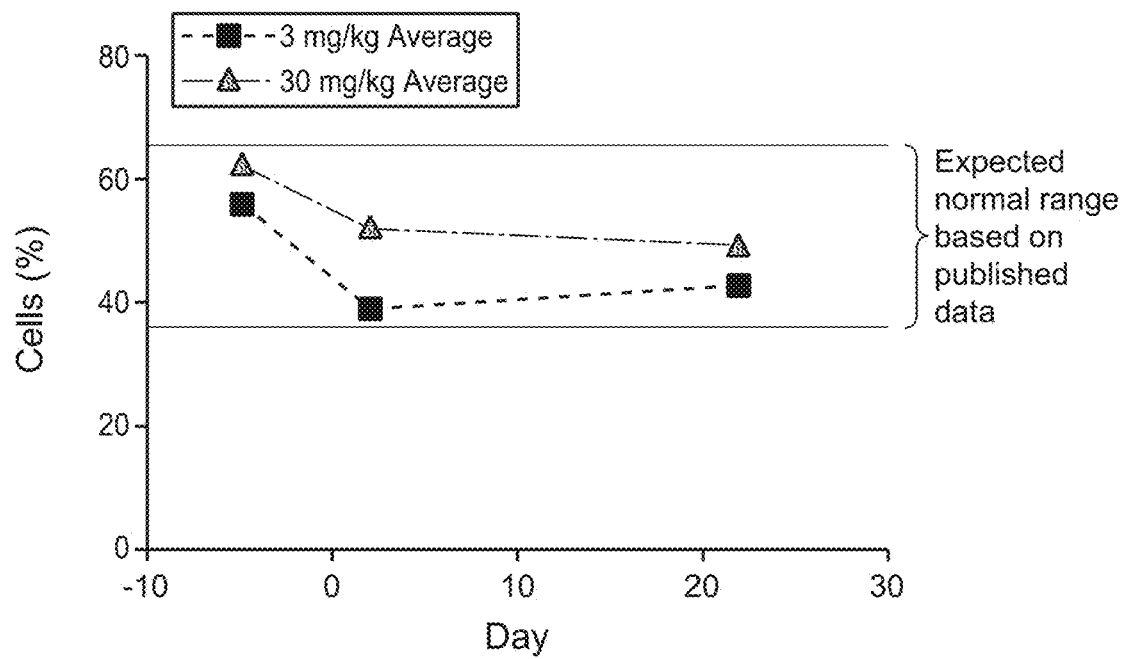
Figure 27A:
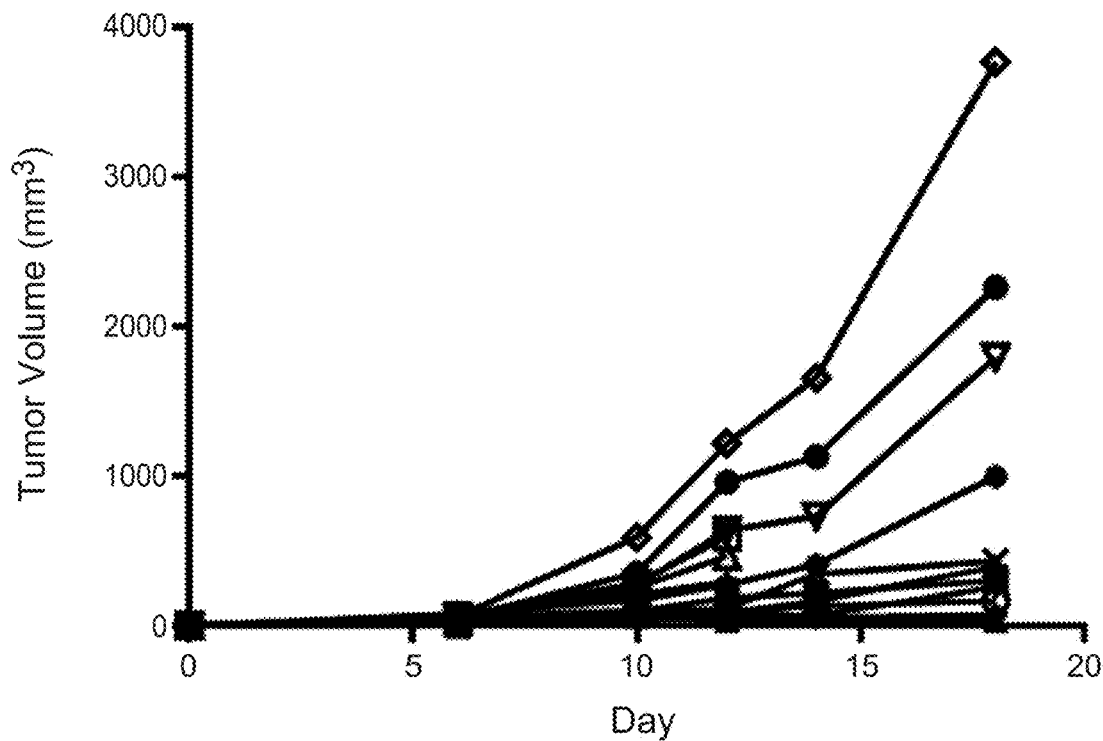
FIGS. 27A and 27B are graphs showing growth of tumors in mice over time after inoculation with B16.SIY cells.
Figure 27B:
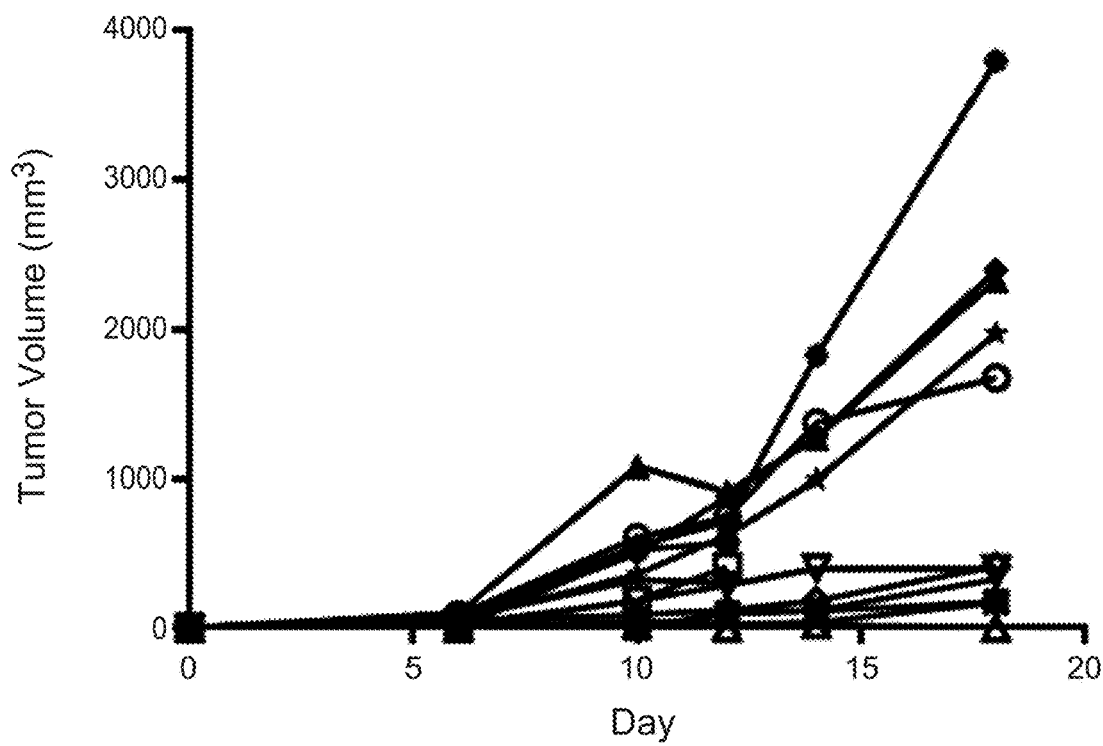
Figure 28A:
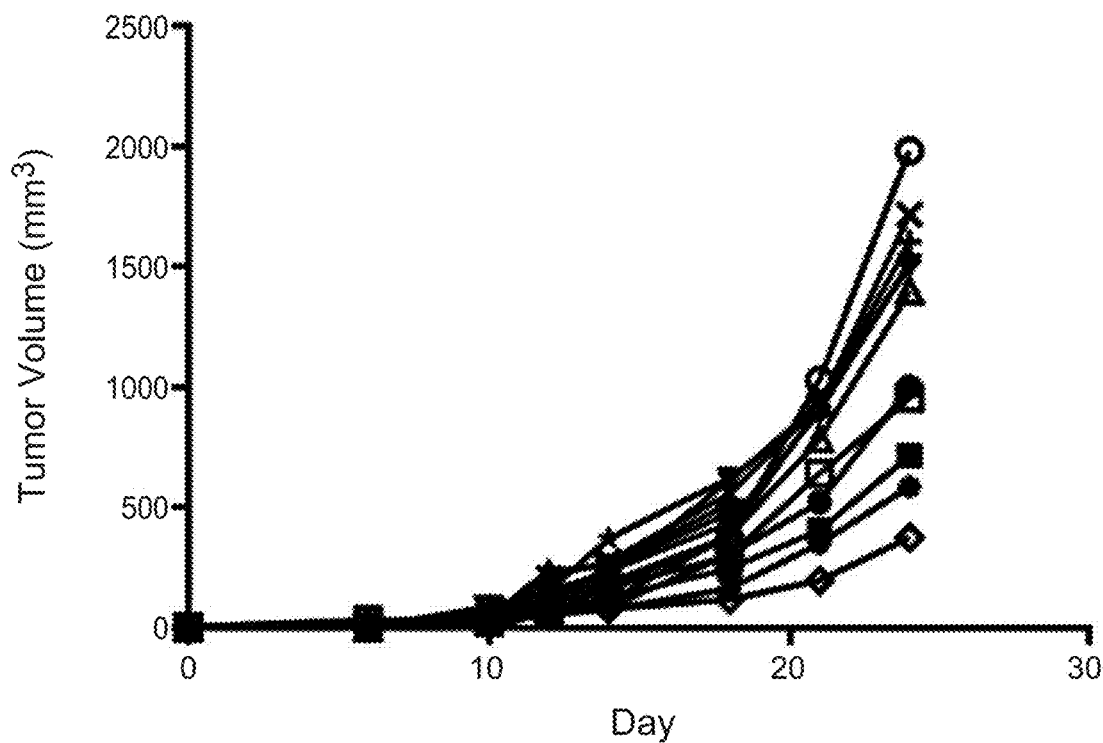
FIGS. 28A and 28B are graphs showing growth of tumors in mice over time after inoculation with LLC cells.
Figure 28B:
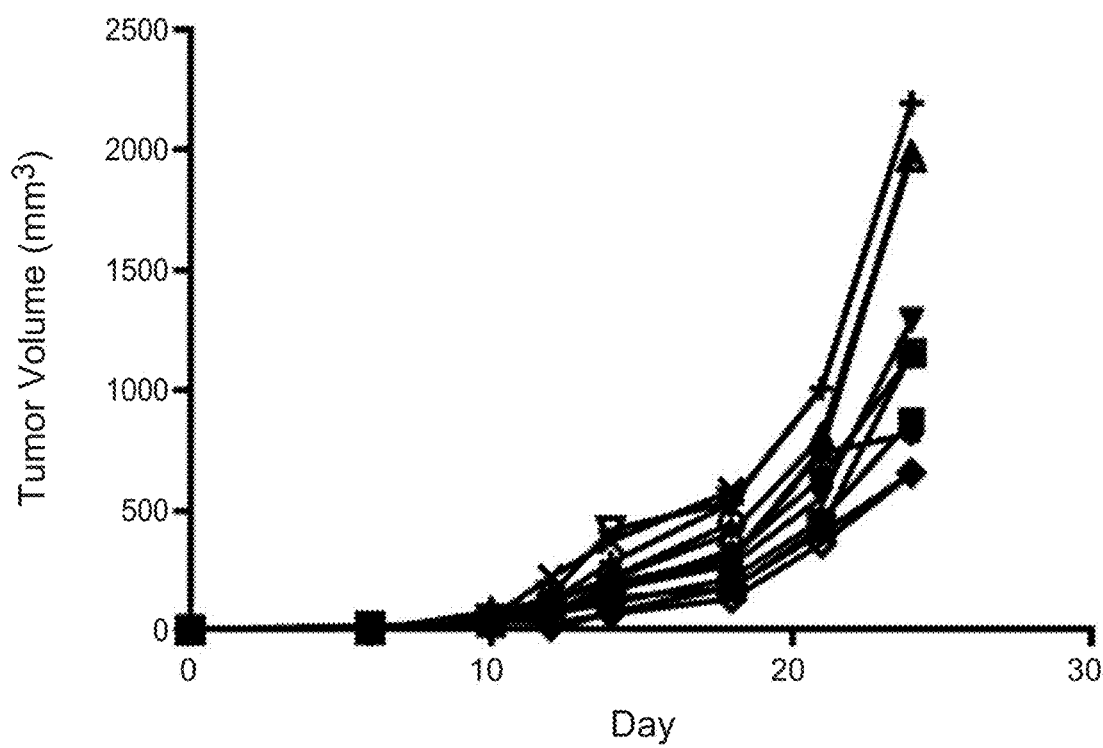

To assess the effect of anti-LILRB2 on neutrophil populations, a CBC assay was conducted in cynomolgus monkeys pre-study and following dosing of anti-LILRB2 antibodies. As shown in FIGS. 26A and 26B, peripheral blood neutrophils remained within normal range and displayed a nonsignificant downward trend.

Example 16. Pirb Knockout Mice Experiment

Eight- to twelve-week old Pirb homozygous knockout mice or wild type littermate controls were inoculated subcutaneously with B16.SIY (1×10$^6$), LLC (2×10$^5$), or MC38 (5×10$^5$) tumor cells. Once palpable tumors were felt, mice were monitored and tumor measurements recorded at least twice weekly until tumors exceeded 2,000 mm$^3$ or mice had a body weight decrease of over 20%. Some mice were sacrificed early for analysis of the tumor-infiltrating cells. All experiments were conducted in accordance with institutional guidelines for animal care and use.

Figure 29A:
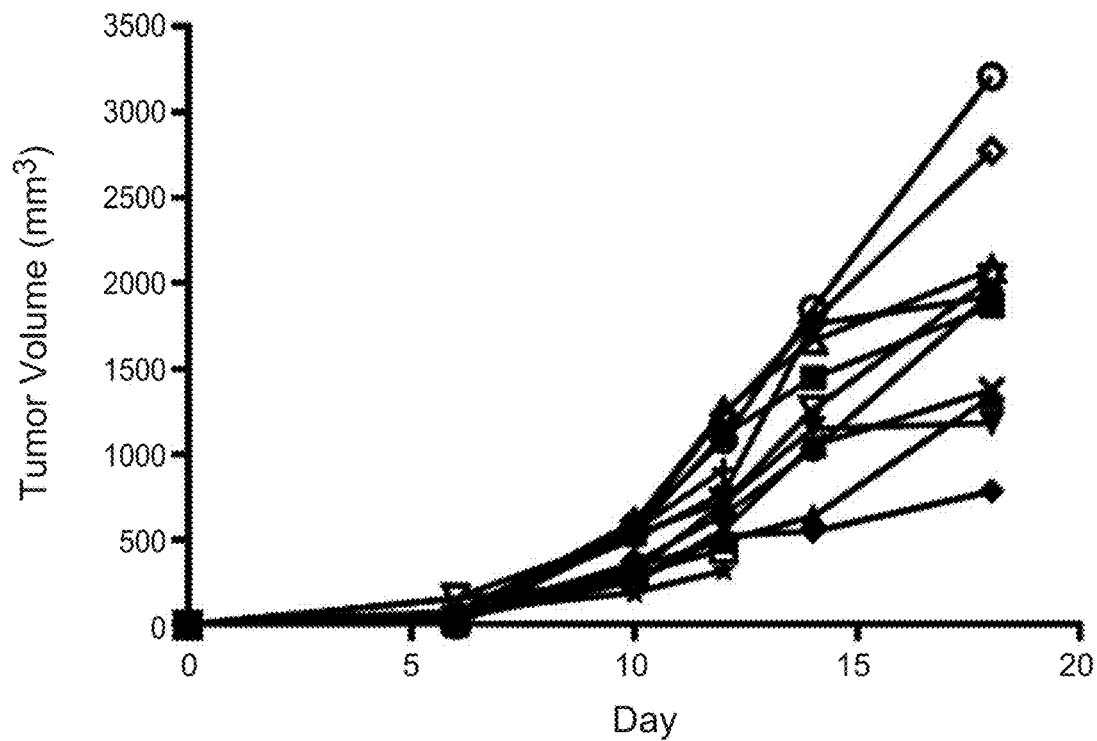
FIGS. 29A and 29B are graphs showing growth of tumors in mice over time after inoculation with MC38 cells.
Figure 29B:
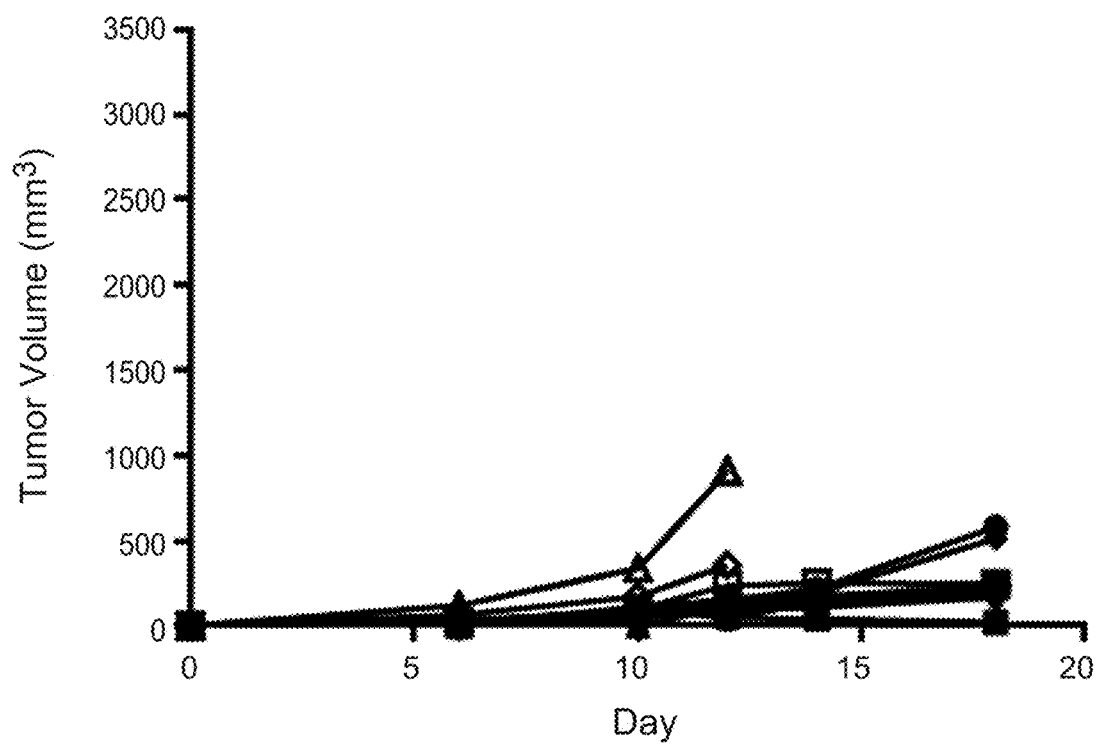

Tumors were detected in all wild type mice and in line with historical growth kinetics at Jounce Therapeutics. While no significant difference was observed in the growth of B16.SIY or LLC tumors between wild type and Pirb knockout mice (FIGS. 27A, 27B, 28A, and 28B), a significant decrease in MC38 tumor growth was found in Pirb knockout as compared to wild type mice (FIGS. 29A and 29B). Analysis of the MC38 tumor-infiltrating cells was consistent with a phenotype of tumor-associated macrophages that exhibited less immunosuppressive characteristics (lower IL-4R) and increased antigen presentation capacity (higher MHC class II) in Pirb knockout mice as compared to wild type controls (data not shown).

Example 17. Alanine Scan Analysis

The heavy chain and light chain variable regions of J-19.h1 are set forth in FIG. 30. The complementarity-determining region (CDR) of the heavy and light chains of J-19.h1 as defined by the Kabat CDR definition are indicated in FIG. 30 by underlining. Key binding residues of J-19.h1 necessary for binding the target, LILRB2, were identified by mutating individual residues in the CDRs. The scan was conducted by mutating 34 heavy chain and 18 light chain residues in the CDRs individually to alanine. Mutations to CDRL2 were not included as this region of J-19.h1 was not determined to contribute to LILRB2 binding. A full mutation of J-19.h1 to the germline CDRL2 sequence did not change binding affinity for the target.

All variants were produced transiently in a Chinese Hamster Ovarian cell line and purified using into citrate buffer on an automated liquid handler. Affinities were determined using a ForteBio Octet Red96. J-19.h1 variants were normalized to 10 ug/mL and loaded onto anti-human capture sensors. The loaded sensors were then soaked in kinetics buffer to establish a baseline and dipped into wells containing LILRB2 at two concentrations of 50 nM and 5 nM, followed by a dissociation step into buffer. Kinetics data was calculated using the ForteBio data analysis software.

Resulting affinities of J-19.h1 variants to LILRB2 showed key residues, highlighted grey, are critical to LILRB2 binding. Mutation to alanine resulted in affinities that were 5-fold less than the control or resulted in complete abrogation of binding. Residues with a dotted underline had affinities between 2 and 5-fold of the control. All other residues in the CDR maintained similar affinity to LILRB2 when mutated to alanine.

Example 18. qPCR Primers

Commercially available qPCR assays for LILRB2 from both Applied Biosystems (TaqMan) and Biorad (PrimePCR) did not show specificity for their target when run on cDNA derived from the RNA of LILR family member over-expressing cell lines. The LILR family members have high homology with each other and primer sets therefore can produce off target effects during PCR.

The following primer sets were tested on the over-expressing cell lines and one primer set showed specificity under certain PCR conditions. The cDNA libraries were generated using both the BioRad iScript Reverse Transcription Supermix and the Fluidigm Reverse Transcription master mix. The primer sets, when not accompanied with a probe, were run using the BioRad SsoFast EvaGreen Supermix with Low ROX master mix. The primer sets with probes were run using the Applied Biosystems TaqMan Fast Advanced Master Mix. The primers were ordered from IDT as oligos and the probes were labeled with FAM.

TABLE 8

Primer and probe sequences

| | Forward Primer | Reverse Primer | Probe (if any) |
|---|---|---|---|
| Set 1 | CACACAGCTCAACC TGGACA | TGGGTAGGCTCCTG TCATCA | |
| Set 2 | AGCTCAACCTGGAC AGCAC | CTTGGGGATGGTCC CTGTCT | |
| Set 3 | ACACACAGCTCAAC CTGGAC | CAGGCAGACTCAGA TCAGCA | |
| Set 4 | CACACAGCTCAACC TGGACA | CTGCAGGCAGACTC AGATCA | |
| Set 5 | CCTGCATTTCTCCT CTGTGC | CTGTCCAGGTTGAG CTGTGT | |
| Set 6 | TCGCACAGGTGCTA TGGTTA | GCACTGAGAGTGAT GGCTTCTTA | |
| Set 7 | AGTAGAAGGAGACT CAGGACTG | TCCCAAAGTTCCCA GCATC | AGCCTGGA CCCCTAAC AAAGACC |
| Set 8 | TTCCACACTTTCCT TCTGACC | GGGAATTCAGCCTG GTACTTAG | TGCCCCAC TCCGTCTA AGATCAAT ACA |
| Set 9 | CGTCACCCTCAGTT GTCAG | TCCGTGTAATCCAA GATGCTG | CCTTGAAG CCCAGGAG TACCGTCT A |
| Set 10 | CCTACTTCCCTGCA TTTCTCC | CAGGCAGACTCAGA TCAGC | AGCTCAAC CTGGACGG CACA |
| Set 11 | TTCTTCCCCTACTT CCCTGCATTTC | CTTCAAGGCTCCCC TGACAAC | |
| Set 12 | GAAGTCAACTTTTC TTCCCCTAC | CAAGGCTCCCCTGA CAACT | |
| Set 13 | CACACAGCTCAACC TGGACA | AGACTCAGCCCGAG ACAGAT | |
| Set 14 | GTCAACTTTTCTTC CCCTACTTC | AAGGCTCCCCTGAC AACTG | |
| Set 15 | AAGAAGCCATCACT CTCAGTGC | GTAGGAGCGGCTCA CAGG | |

The forward primers for sets 1-15 are SEQ ID NOs: 135-149; the reverse primers for sets 1-15 are SEQ ID NOs: 150-164; the probes for sets 7-10 are SEQ ID NOs: 165-168; each in order as set forth in Table 8.

Set 9 listed above proved to be specific for LILRB2 when assayed across the numerous LILR family member over-expressing cell lines when run as a TaqMan assay (both Applied Biosystems master mix and IDT GE master mix), as well as a primer set EvaGreen assay (BioRad Master mix).

The following PCR cycling conditions were followed: Cycle 1: 95° C. for 60 seconds; Cycle 2: 96° C. for 5 seconds; Cycle 3: 65° C. for 20 seconds; Repeat cycles 2-3 for 40 cycles total; Melting curve for EvaGreen chemistry from 60-95° C. Primer and probe sequences: Forward: CGTCAC-CCTCAGTTGTCAG (SEQ ID NO: 143); Reverse: TCCGTGTAATCCAAGATGCTG (SEQ ID NO: 158); Probe: CCTTGAAGCCCAGGAGTACCGTCTA (SEQ ID NO: 167).

The addition of up to 5 nucleotides to either end of the primers should not affect PCR specificity per the UCSC In-Silico PCR tool (bold is wet-validated primer set). https://genome.ucsc.edu/cgi-bin/hgPcr?hgsid=693240227_npi8w0U7m F4EWHuVaOYA4nlqdtsZ AGTCC-CGTCACCCTCAGTT-GTCAG-GGGAG (SEQ ID NO: 169); TCGTA-TCCGTG-TAATCCAAGATGCTG-ATTTT (SEQ ID NO: 170).

Example 19. PD Signature Score Analysis of Fresh Tumor Samples

Fresh human tumor samples were obtained post-surgery. A section of each tumor was cut and fixed for IHC. 300 µM slices of remaining tumor were placed in a 6-well plate. Treatments were added into the medium and plates were incubated at 37° C. Tumor slices were stored in RNAlater after incubation. Each slice was treated with 10 µg/mL of drug for 24 hours; in instances where samples were treated with more than one drug, 10 µg/mL of each drug was used.

Tumor slices were lysed using Qiagen's TissueLyser processor and FFPE samples were deparaffinized. RNA was extracted from FFPE and fresh tumor samples, quantified using Quibit, and QC'd using AATI's Fragment Analyzer. If sufficient RNA was extracted from the sample, gene expression was performed using NanoString nCounter using the Human Immunology V2 panel as well as a custom macrophage-specific spike-in. Gene expression was normalized to the expression of housekeeping genes, then noise thresholding was performed using the data from negative probes and data was transformed to the log 2 space. This data will henceforth be referred to as "normalized gene expression." Normalized gene expression data was then further normalized to the average data from the palivizumab treated samples from the same patient. This data will henceforth be referred to as "palivizumab-normalized gene expression."

Pharmacodynamic (PD) signature scores were calculated for each sample. Monoculture signatures are derived from the mean log 2 (fold change compared to palivizumab-treated samples) in gene expression across monocyte-derived macrophages from 4 donors in response to anti-LILRB2 ligand-blocking drugs in the absence of LPS after 4 hours. "Monoculture signature scores" were calculated for each treated histoculture sample by projecting the palivizumab-normalized gene expression onto the vector defined by the monoculture signature. "IFNγ signature scores" were calculated by averaging the palivizumab-normalized gene expression of the 6 genes identified by Hirsch et al. ($32^{nd}$ Annual Meeting and Pre-Conference Programs of the Society for Immunotherapy of Cancer (SITC 2017): Part One, P39; J. Immunother. Cancer 5 (Suppl. 2):86, 2017) displaying modulated expression in response to anti-PD1 treatment. "Keytruda signature scores" were calculated by averaging the palivizumab-normalized gene expression of the 18 genes identified by Ayers et al. (J. Clin. Invest. 127:2930-2940, 2017) as being predictive of clinical response to pembrolizumab.

To evaluate noise in the system and determine response cutoffs, 173 tumor slices (samples) from 80 kidney, lung, and head and neck tumors were treated with the control antibody palivizumab for 24 hours. At least two samples from each tumor were treated with palivizumab. The noise threshold for each PD response signature was defined as the $95^{th}$ percentile of the distribution of the signature scores across the 173 samples. Tumors are classified as "responders" to a particular drug if the average PD signature score across all samples from that tumor treated with that drug is greater than the noise threshold for that signature.

Baseline (untreated) samples from most tumors were characterized. Cell type specific signatures were calculated by averaging the normalized gene expression of genes that are associated with particular cell types. The Keytruda signature was calculated for each baseline sample by averaging the normalized gene expression of the 18 genes identified by Ayers et al. (supra) as being predictive of clinical response to pembrolizumab.

Results of the experiments described above are shown in FIGS. 31-34.

Figure 31:
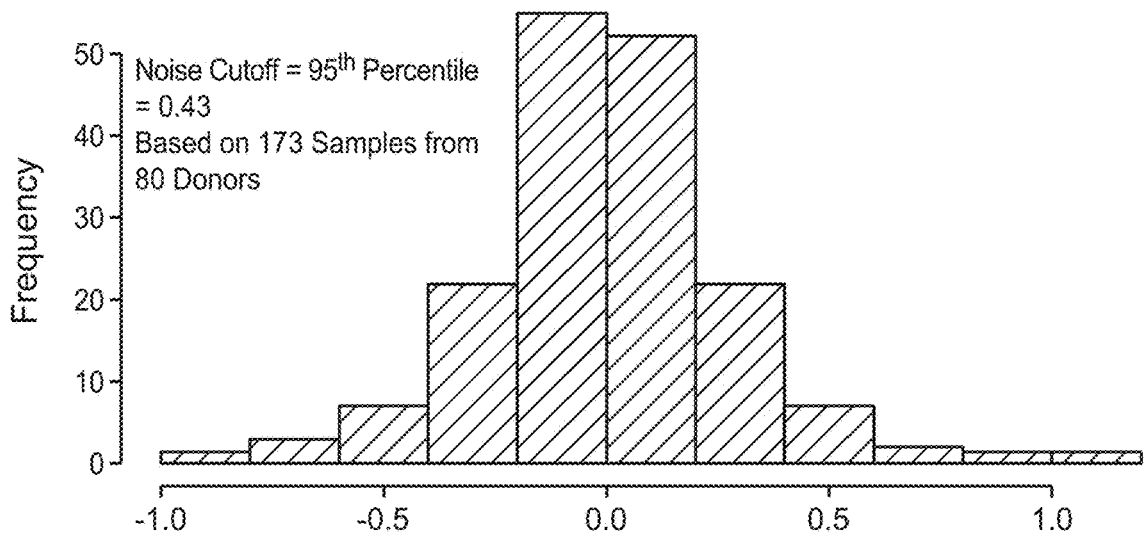
FIG. 31 is a histogram of the IFNγ PD response scores from 173 tumor samples from 80 tumors treated with palivizumab for 24 hours.

FIG. 31 is a histogram of the IFNγ PD response scores from 173 tumor samples from 80 tumors treated with palivizumab for 24 hours. In each tumor, at least two samples were treated with palivizumab. The noise threshold for the signature is defined as the $95^{th}$ percentile of the distribution. For the IFNγ signature, the noise threshold is 0.43.

Figure 32:
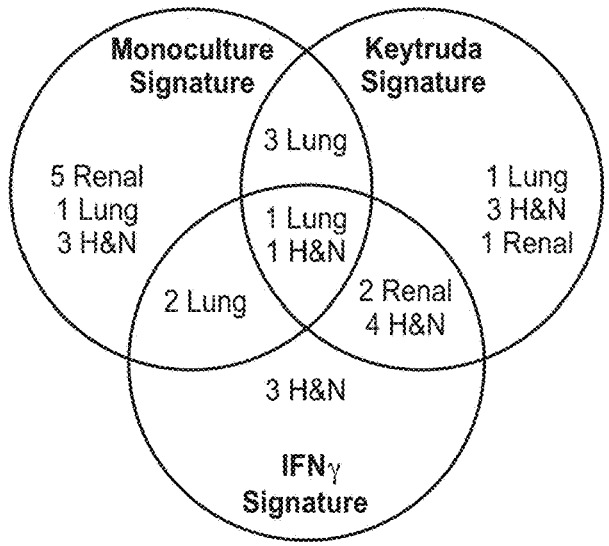
FIG. 32 is a Venn diagram and chart describing the PD response rates to J-19.h1 across 3 indications: renal cell carcinoma, head and neck cancer, and lung cancer.

FIG. 32 is a Venn diagram and chart describing the PD response rates to J-19.h1 across 3 indications: renal cell carcinoma, head and neck cancer, and lung cancer. Tumors are classified as "responders" if the average PD response score across all J-19.H1 treated slices for that tumor is greater than the noise threshold. As noted above, the noise threshold for each PD signature is defined as the $95^{th}$ percentile of the distribution of PD response scores of palivizumab treated samples across tumors with more than one palivizumab treated sample. In histoculture, J-19.H1 induces different PD responses across indications, suggesting multiple mechanisms of action: the monoculture signature indicates macrophage polarization; the IFN gamma signature suggests similar response to checkpoint inhibitors; the Keytruda signature is a sign of tumor priming for response to checkpoint inhibitors.

Figure 33:
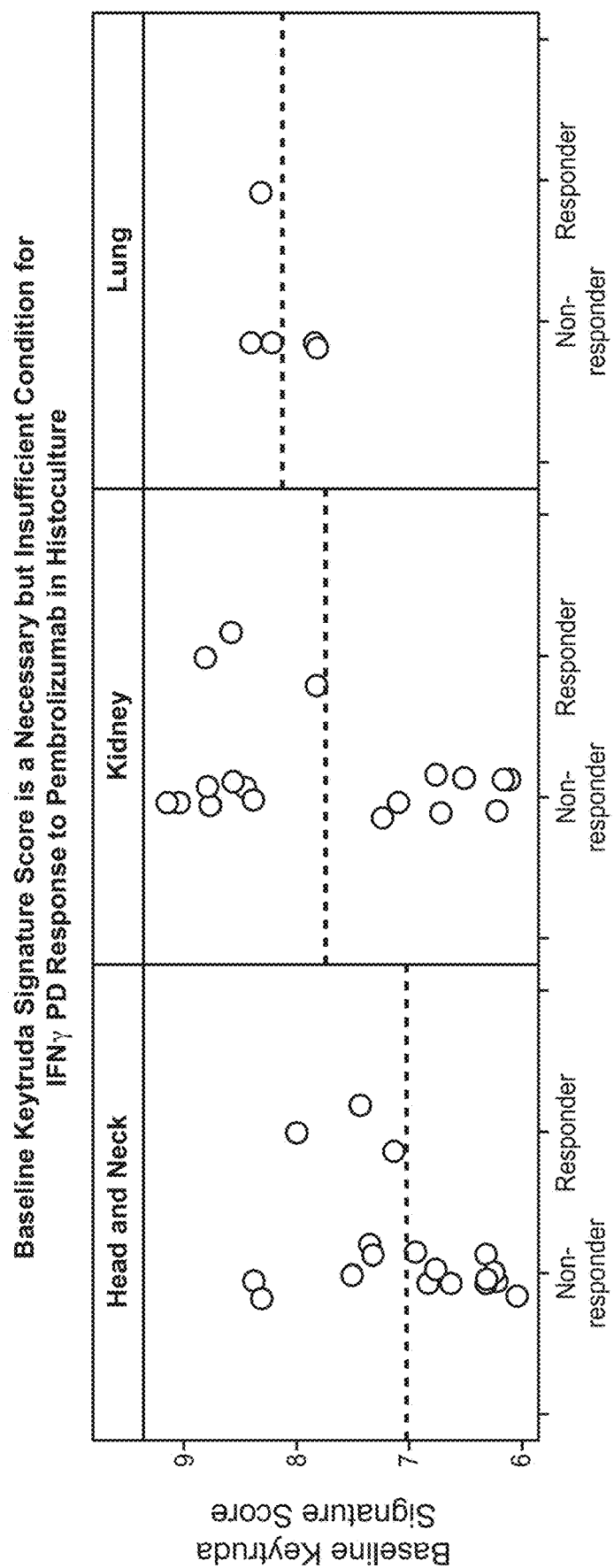
FIG. 33 is a series of graphs showing Keytruda signature scores calculated for untreated samples, based on normalized gene expression (raw gene expression is normalized to housekeeping genes and negative control probes, then log 2 transformed).

FIG. 33 is a series of graphs showing Keytruda signature scores calculated for untreated samples, based on normalized gene expression (raw gene expression is normalized to housekeeping genes and negative control probes, then log 2 transformed). Tumors are classified as IFNγ PD responders if the average response of all samples in that tumor treated with J-19.H1 is greater than the noise threshold of the IFNγ signature. Each dot represents the Keytruda signature score of an untreated tumor sample. Dotted lines show the average baseline Keytruda signature score for the samples profiled in each indication. The baseline Keytruda signature score is a necessary but insufficient condition for IFN gamma PD response to pembrolizumab in histoculture, which is consistent with clinical observations reported by others, thus suggesting the relevance of the histoculture model to clinical outcomes.

Figure 34:
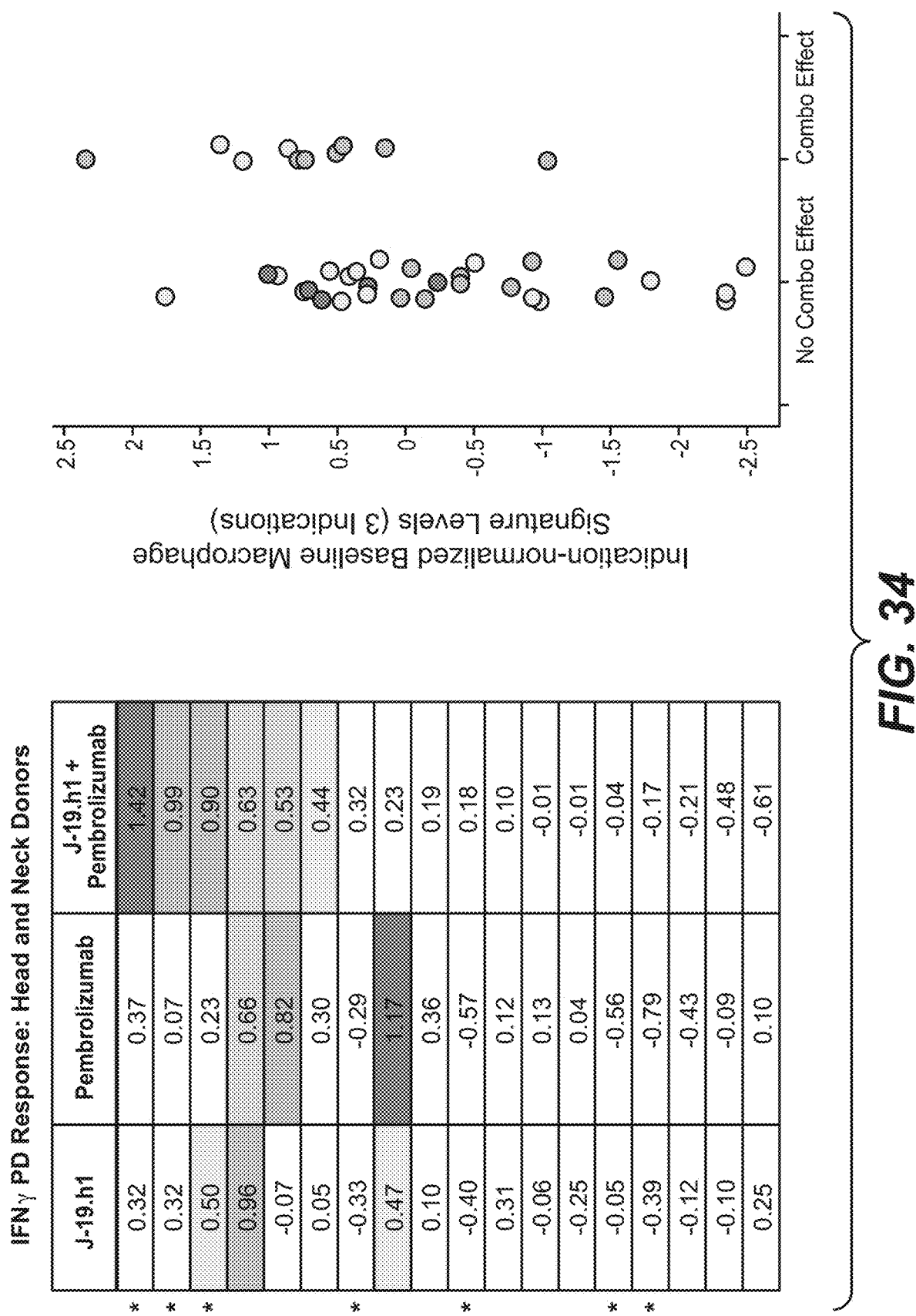
FIG. 34, left panel, is a table showing average IFNγ PD signature scores calculated for 18 head and neck tumors in response to J-19.h1, pembrolizumab, or J-19.h1 combined with pembrolizumab.

FIG. 34, left panel, is a table showing average IFNγ PD signature scores calculated for 18 head and neck tumors in response to J-19.h1, pembrolizumab, or J-19.H1 combined with pembrolizumab. Cells highlighted in grey indicate tumors for which the response to treatment is greater than the noise threshold. Rows with an asterisk beside them denote tumors for which J-19.h1 potentiates response; i.e., the IFNγ PD signature score in response to J-19.H1+pembrolizumab is greater than or equal to the score in response to pembrolizumab alone+0.43 (the noise threshold for the IFNγ PD signature). Tumors that have potentiated response with J-19.H1 are referred to as having a "combo effect" in the right panel. FIG. 34, right panel, is a graph showing a comparison of the indication-normalized tumor macrophage content of tumors prior to treatment. The graph shows the baseline macrophage content of tumors that display a combination effect in response to J-19.H1+pembrolizumab compared to those that do not show any potentiation due to J-19.H1. The comparison is made for tumors across 3 indications: renal cell carcinoma, lung cancer and head, and neck cancer. Tumor macrophage content is calculated by averaging the expression of genes associated with macrophages in untreated samples and is normalized within each indication. The IFN gamma PD response to pembrolizumab in histoculture is potentiated by J-19.H1 in samples enriched with macrophages.

Example 20. Antibody Mutants

The heavy chain variable region of J-19.h1 is set forth below:

```
                                            (SEQ ID NO: 53)
QITLKESGPTLVKPTQTLTLTCTFSGFSLNTYAMGVSWIRQPPGKALE

WLASIWWNGNKYNNPSLKSRLTVTKDTSKNQVVLTMTNMDPVDTATYY

CAHSRIIR*FTDYVMDAWGQGTLVTVSS
```

CDRH1, CDRH2, and CDRH3 are indicated by underlining, in order. R* denotes a residue in CDRH3 that, when mutate to alanine (J-19.h5), measured higher affinity for LILRB2 compared to J-19.h1. This measurement was determined using a ForteBio Octet Red96. The variant was normalized to 10 ug/mL and loaded onto an anti-human capture sensor. The loaded sensor was then soaked in kinetics buffer to establish a baseline and dipped into wells containing LILRB2 at two concentrations of 50 nM and 5 nM, followed by a dissociation step into buffer. Kinetics data was calculated using the ForteBio data analysis software. Results showed J-19.h5 having a two-fold higher affinity for LILRB2 compared to the unmutated version of J-19.h1.

Additional variants were made of J-19.h1, in which the arginine was mutated to aspartate (J-19.h6) and glutamate (J-19.h7). All variants were produced transiently using a Chinese Hamster Ovarian cell line and purified using citrate buffer on an automated liquid handler. Affinity to LILRB2 was measured exactly as it was previously to J-19.h5. The data indicated that these two variants have even greater affinity to LILRB2 compared to J-19.h1 and J-19.h5.

Affinities for the four antibodies (J-19.h1, J-19.h5, J-19.h6, and J-19.h7) were confirmed through surface plasmon resonance (SPR) using a SierraSensor Mass-2. The antibodies were captured using an anti-human Fc chip at a concentration of 2 ug/mL. LILRB2 was flowed over the captured antibodies at seven concentrations (65, 21.67, 7.22, 2.41, 0.802, 0.267, 0.089 nM). J-19.h5 and J-19.h6 were run in triplicates, while J-19.h7 and J-19.h1 were run in duplicates. Below is a table describing the association, dissociation, and Kd of the four antibodies.

TABLE 9

Kinetic Measurements of J-19.h1 and Higher Affinity Mutants

| Analyte | Ligand | Ka (1/Ms) | Kd (1/s) | KD (M) | Replicates | Fold difference over J-19.h1 |
|---|---|---|---|---|---|---|
| LILRB2 | J-19.h5 | 8.76E+05 | 1.15E−03 | 1.31E−09 | 3 | 1.91 |
| | J-19.h6 | 8.25E+05 | 5.92E−04 | 7.18E−10 | 3 | 3.47 |
| | J-19.h7 | 8.65E+05 | 7.88E−04 | 9.12E−10 | 2 | 2.73 |
| | J-19.h1 | 7.05E+05 | 1.76E−03 | 2.49E−09 | 2 | 1 |

OTHER EMBODIMENTS

The disclosure may be embodied in other specific forms without departing from the spirit or essential characteristics thereof. The foregoing embodiments are therefore to be considered in all respects illustrative rather than limiting of the disclosure. Scope of the disclosure is thus indicated by the appended claims rather than by the foregoing description, and all changes that come within the meaning and range of equivalency of the claims are therefore intended to be embraced herein. All references cited herein are incorporated herein by reference.

TABLE 10

Table of Sequences

| SEQ ID NO: | Description | Sequence |
|---|---|---|
| 1 | J-11.h heavy chain | QVQLQQSGAELMKPGASVKLSCKATGYILTGYWIEWVKQR PGHGLEWIGEILPGSGSTNYNENFKGKATFTADTSSNTAY MQLSSLTTEDSAIYYCARAVLGYFDYWGQGTTLTVSSAST KGPSVFPLAPCSRSTSESTAALGCLVKDYFPEPVTVSWNS GALTSGVHTFPAVLQSSGLYSLSSVVTVPSSSLGTKTYTC NVDHKPSNTKVDKRVESKYGPPCPPCPAPEFLGGPSVFLF PPKPKDTLMISRTPEVTCVVVDVSQEDPEVQFNWYVDGVE VHNAKTKPREEQFNSTYRVVSVLTVLHQDWLNGKEYKCKV SNKGLPSSIEKTISKAKGQPREPQVYTLPPSQEEMTKNQV |

TABLE 10-continued

Table of Sequences

| | | |
|---|---|---|
| | | SLTCLVKGFYPSDIAVEWESNGQPENNYKTTPPVLDSDGS<br>FFLYSRLTVDKSRWQEGNVFSCSVMHEALHNHYTQKSLSL<br>SLGK |
| 2 | J-11.h light chain | DIVMTQSHKFMSTSVGDRVSITCKASQDVSTAVAWYQQKP<br>GQSPKLLIYWASTRHTGVPDRFTGSGSGTDYTLTISSVQA<br>EDLALYYCHQHYSTYTFGGGTKLEIKRTVAAPSVFIFPPS<br>DEQLKSGTASVVCLLNNFYPREAKVQWKVDNALQSGNSQE<br>SVTEQDSKDSTYSLSSTLTLSKADYEKHKVYACEVTHQGL<br>SSPVTKSFNRGEC |
| 3 | J-11.h $V_H$ | QVQLQQSGAELMKPGASVKLSCKATGYILTGYWIEWVKQR<br>PGHGLEWIGEILPGSGSTNYNENFKGKATFTADTSSNTAY<br>MQLSSLTTEDSAIYYCARAVLGYFDYWGQGTTLTVSS |
| 4 | J-11.h $V_L$ | DIVMTQSHKFMSTSVGDRVSITCKASQDVSTAVAWYQQKP<br>GQSPKLLIYWASTRHTGVPDRFTGSGSGTDYTLTISSVQA<br>EDLALYYCHQHYSTYTFGGGTKLEIK |
| 5 | J-11.h CDR-H1 | GYWIE |
| 6 | J-11.h CDR-H2 | EILPGSGSTNYNENFKG |
| 7 | J-11.h CDR-H3 | AVLGYFDY |
| 8 | J-11.h CDR-L1 | KASQDVSTAVA |
| 9 | J-11.h CDR-L2 | WASTRHT |
| 10 | J-11.h CDR-L3 | HQHYSTYT |
| 11 | J-19.h heavy chain | QVTLKESGPGILQPSHTLSLTCSFSGFSLNTYAMGVSWIR<br>QPSGKGLEWLASIWWNGNKYNNPSLKSRLTVSKDTSNNQA<br>FLKVTSVDTADTATYYCAHSRIIRFTDYVMDAWGQGASVT<br>VSSASTKGPSVFPLAPCSRSTSESTAALGCLVKDYFPEPV<br>TVSWNSGALTSGVHTFPAVLQSSGLYSLSSVVTVPSSSLG<br>TKTYTCNVDHKPSNTKVDKRVESKYGPPCPPCPAPEFLGG<br>PSVFLFPPKPKDTLMISRTPEVTCVVVDVSQEDPEVQFNW<br>YVDGVEVHNAKTKPREEQFNSTYRVVSVLTVLHQDWLNGK<br>EYKCKVSNKGLPSSIEKTISKAKGQPREPQVYTLPPSQEE<br>MTKNQVSLTCLVKGFYPSDIAVEWESNGQPENNYKTTPPV<br>LDSDGSFFLYSRLTVDKSRWQEGNVFSCSVMHEALHNHYT<br>QKSLSLSLGK |
| 12 | J-19.h light chain | DIQMTQSPASLSTFLGEPVTIECRASEDIYNDLAWYQQKP<br>GKSPQLLIYNANSLHTGVPSRFSGSGSGTQYSLKINSLQS<br>EDVASYFCQQYYDYPLTFGSGTKLEIKRTVAAPSVFIFPP<br>SDEQLKSGTASVVCLLNNFYPREAKVQWKVDNALQSGNSQ<br>ESVTEQDSKDSTYSLSSTLTLSKADYEKHKVYACEVTHQG<br>LSSPVTKSFNRGEC |
| 13 | J-19.h $V_H$ | QVTLKESGPGILQPSHTLSLTCSFSGFSLNTYAMGVSWIR<br>QPSGKGLEWLASIWWNGNKYNNPSLKSRLTVSKDTSNNQA<br>FLKVTSVDTADTATYYCAHSRIIRFTDYVMDAWGQGASVT<br>VSS |
| 14 | J-19.h $V_L$ | DIQMTQSPASLSTFLGEPVTIECRASEDIYNDLAWYQQKP<br>GKSPQLLIYNANSLHTGVPSRFSGSGSGTQYSLKINSLQS<br>EDVASYFCQQYYDYPLTFGSGTKLEIK |
| 15 | J-19.h CDR-H1 | TYAMGVS |
| 16 | J-19.h CDR-H2 | SIWWNGNKYNNPSLKS |
| 17 | J-19.h CDR-H3 | SRIIRFTDYVMDA |
| 18 | J-19.h CDR-L1 | RASEDIYNDLA |
| 19 | J-19.h CDR-L2 | NANSLHT |
| 20 | J-19.h CDR-L3 | QQYYDYPLT |
| 21 | J-17.h heavy chain | QIQLVQSGPELKKPGETVKISCKASGYTFTTYGLSWVKQT<br>PGKGLKWMGWINTYSGVPTYTDDFKGRFAFSLETSASTAY<br>LQINNLKNEDTATYFCARPYDFDQVGFAYWGQGTLVTVSA<br>ASTKGPSVFPLAPCSRSTSESTAALGCLVKDYFPEPVTVS<br>WNSGALTSGVHTFPAVLQSSGLYSLSSVVTVPSSSLGTKT<br>YTCNVDHKPSNTKVDKRVESKYGPPCPPCPAPEFLGGPSV |

TABLE 10-continued

Table of Sequences

| | | |
|---|---|---|
| | | FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK |
| 22 | J-17.h light chain | SIVMTQTPKFLLVSAGDRVSITCKASQTVSSDVAWYQQKA GQSPKLLIYYASNRYTGVPDRFTGSGYGTDFTFTISTVQA EDLAVYFCQQDYSSPFTFGGGSKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| 23 | J-17.h $V_H$ | QIQLVQSGPELKKPGETVKISCKASGYTFTTYGLSWVKQT PGKGLKWMGWINTYSGVPTYTDDFKGRFAFSLETSASTAY LQINNLKNEDTATYFCARPYDFDQVGFAYWGQGTLVTVSA |
| 24 | J-17.h $V_L$ | SIVMTQTPKFLLVSAGDRVSITCKASQTVSSDVAWYQQKA GQSPKLLIYYASNRYTGVPDRFTGSGYGTDFTFTISTVQA EDLAVYFCQQDYSSPFTFGGGSKLEIK |
| 25 | J-17.h CDR-H1 | TYGLS |
| 26 | J-17.h CDR-H2 | WINTYSGVPTYTDDFKG |
| 27 | J-17.h CDR-H3 | PYDFDQVGFAY |
| 28 | J-17.h CDR-L1 | KASQTVSSDVA |
| 29 | J-17.h CDR-L2 | YASNRYT |
| 30 | J-17.h CDR-L3 | QQDYSSPFT |
| 31 | J-04 heavy chain | QVQLQQSGAELVRPGASVTLSCKASGYTFADYEIHWVKQT PVHGLEWIGAIDPETGGTAYNQKFKGKAILTADKSSSTAY MELRSLTSEDSAVYYCTRYYDYDDAMDYWGQGTSVTVSSA STKGPSVFPLAPCSRSTSESTAALGCLVKDYFPEPVTVSW NSGALTSGVHTFPAVLQSSGLYSLSSVVTVPSSSLGTKTY TCNVDHKPSNTKVDKRVESKYGPPCPPCPAPEFLGGPSVF LFPPKPKDTLMISRTPEVTCVVVDVSQEDPEVQFNWYVDG VEVHNAKTKPREEQFNSTYRVVSVLTVLHQDWLNGKEYKC KVSNKGLPSSIEKTISKAKGQPREPQVYTLPPSQEEMTKN QVSLTCLVKGFYPSDIAVEWESNGQPENNYKTTPPVLDSD GSFFLYSRLTVDKSRWQEGNVFSCSVMHEALHNHYTQKSL SLSLGK |
| 32 | J-04 light chain | QIVLTQSPAIMSASPGEKVTMTCSASSSVSFMHWYQQKSG TSPKRWIYGTSKLASGVPARFSGSGSGTSYSLTISSMEAE DAATYYCQQWNGNPFTFGSGTKLETKRTVAAPSVFIFPPS DEQLKSGTASVVCLLNNFYPREAKVQWKVDNALQSGNSQE SVTEQDSKDSTYSLSSTLTLSKADYEKHKVYACEVTHQGL SSPVTKSFNRGEC |
| 33 | J-04 $V_H$ | QVQLQQSGAELVRPGASVTLSCKASGYTFADYEIHWVKQT PVHGLEWIGAIDPETGGTAYNQKFKGKAILTADKSSSTAY MELRSLTSEDSAVYYCTRYYDYDDAMDYWGQGTSVTVSS |
| 34 | J-04 $V_L$ | QIVLTQSPAIMSASPGEKVTMTCSASSSVSFMHWYQQKSG TSPKRWIYGTSKLASGVPARFSGSGSGTSYSLTISSMEAE DAATYYCQQWNGNPFTFGSGTKLETK |
| 35 | J-04 CDR-H1 | DYEIH |
| 36 | J-04 CDR-H2 | AIDPETGGTAYNQKFKG |
| 37 | J-04 CDR-H3 | YYDYDDAMDY |
| 38 | J-04 CDR-L1 | SASSSVSFMH |
| 39 | J-04 CDR-L2 | GTSKLAS |
| 40 | J-04 CDR-L3 | QQWNGNPFT |
| 41 | J-03 heavy chain | QVQLQQSGAELVRPGASVTLSCKASGYKFTDYEMHWVKQT PVHGLEWIGAIDPETNGTAYNKKFKGKAILTADKSSSTAY MELRSLTSEDSAVYYCTRGDYDFSAWFAYWGQGTLVTVSA ASTKGPSVFPLAPCSRSTSESTAALGCLVKDYFPEPVTVS |

TABLE 10-continued

Table of Sequences

| | | |
|---|---|---|
| | | WNSGALTSGVHTFPAVLQSSGLYSLSSVVTVPSSSLGTKT YTCNVDHKPSNTKVDKRVESKYGPPCPPCPAPEFLGGPSV FLFPPKPKDTLMISRTPEVTCVVVDVSQEDPEVQFNWYVD GVEVHNAKTKPREEQFNSTYRVVSVLTVLHQDWLNGKEYK CKVSNKGLPSSIEKTISKAKGQPREPQVYTLPPSQEEMTK NQVSLTCLVKGFYPSDIAVEWESNGQPENNYKTTPPVLDS DGSFFLYSRLTVDKSRWQEGNVFSCSVMHEALHNHYTQKS LSLSLGK |
| 42 | J-03 light chain | DIVLTQSPASLAVSLGQRATISCRASESVDNYDISFMHWY QQKPGQPPKLLIYRASNLESGIPARFSGSGSRTDFTLTIN PVETDDVATYYCQQSNKDPRTFGGGTKLEIKRTVAAPSVF IFPPSDEQLKSGTASVVCLLNNFYPREAKVQWKVDNALQS GNSQESVTEQDSKDSTYSLSSTLTLSKADYEKHKVYACEV THQGLSSPVTKSFNRGEC |
| 43 | J-03 $V_H$ | QVQLQQSGAELVRPGASVTLSCKASGYKFTDYEMHWVKQT PVHGLEWIGAIDPETNGTAYNKKFKGKAILTADKSSSTAY MELRSLTSEDSAVYYCTRGDYDFSAWFAYWGQGTLVTVSA |
| 44 | J-03 $V_L$ | DIVLTQSPASLAVSLGQRATISCRASESVDNYDISFMHWY QQKPGQPPKLLIYRASNLESGIPARFSGSGSRTDFTLTIN PVETDDVATYYCQQSNKDPRTFGGGTKLEIK |
| 45 | J-03 CDR-H1 | DYEMH |
| 46 | J-03 CDR-H2 | AIDPETNGTAYNKKFKG |
| 47 | J-03 CDR-H3 | GDYDFSAWFAY |
| 48 | J-03 CDR-L1 | RASESVDNYDISFMH |
| 49 | J-03 CDR-L2 | RASNLES |
| 50 | J-03 CDR-L3 | QQSNKDPRT |
| 51 | J-19.h1 heavy chain | QITLKESGPTLVKPTQTLTLTCTFSGFSLNTYAMGVSWIR QPPGKALEWLASIWWNGNKYNNPSLKSRLTVTKDTSKNQV VLTMTNMDPVDTATYYCAHSRIIRFTDYVMDAWGQGTLVT VSSASTKGPSVFPLAPCSRSTSESTAALGCLVKDYFPEPV TVSWNSGALTSGVHTFPAVLQSSGLYSLSSVVTVPSSSLG TKTYTCNVDHKPSNTKVDKRVESKYGPPCPPCPAPEFLGG PSVFLFPPKPKDTLMISRTPEVTCVVVDVSQEDPEVQFNW YVDGVEVHNAKTKPREEQFNSTYRVVSVLTVLHQDWLNGK EYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHYT QKSLSLSLGK |
| 52 | J-19.h1 light chain | DIQMTQSPSSLSTSVGDRVTITCRASEDIYNDLAWYQQKP GKAPKLLIYNANSLHTGVASRFSGSGSGTDFTFTISSLQP EDVATYFCQQYYDYPLTFGQGTKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| 53 | J-19.h1 $V_H$ | QITLKESGPTLVKPTQTLTLTCTFSGFSLNTYAMGVSWIR QPPGKALEWLASIWWNGNKYNNPSLKSRLTVTKDTSKNQV VLTMTNMDPVDTATYYCAHSRIIRFTDYVMDAWGQGTLVT VSS |
| 54 | J-19.h1 $V_L$ | DIQMTQSPSSLSTSVGDRVTITCRASEDIYNDLAWYQQKP GKAPKLLIYNANSLHTGVASRFSGSGSGTDFTFTISSLQP EDVATYFCQQYYDYPLTFGQGTKLEIK |
| 55 | J-19.h1 CDR-H1 | TYAMGVS |
| 56 | J-19.h1 CDR-H2 | SIWWNGNKYNNPSLKS |
| 57 | J-19.h1 CDR-H3 | SRIIRFTDYVMDA |
| 58 | J-19.h1 CDR-L1 | RASEDIYNDLA |
| 59 | J-19.h1 CDR-L2 | NANSLHT |
| 60 | J-19.h1 CDR-L3 | QQYYDYPLT |

TABLE 10-continued

Table of Sequences

| | | |
|---|---|---|
| 61 | J-19.h2 heavy chain | QITLKESGPTLVKPTQTLTLTCTFSGFSLNTYAMGVSWIRQPPGKALEWLASIWWNGNKYNNPSLKSRLTVTKDTSKNQVVLTMTNMDPVDTATYYCAHSRIIRFTDYVMDAWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 62 | J-19.h2 light chain | DIVMTQSPSSLSASVGDTVTITCRASEDIYNDLAWYQQKPGKAPQLLLYNANSLHTGVPSRFSGSGSGTDYTLTISTLQPEDFATYYCQQYYDYPLTFGPGTKVHIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 63 | J-19.h2 $V_H$ | QITLKESGPTLVKPTQTLTLTCTFSGFSLNTYAMGVSWIRQPPGKALEWLASIWWNGNKYNNPSLKSRLTVTKDTSKNQVVLTMTNMDPVDTATYYCAHSRIIRFTDYVMDAWGQGTLVTVSS |
| 64 | J-19.h2 $V_L$ | DIVMTQSPSSLSASVGDTVTITCRASEDIYNDLAWYQQKPGKAPQLLLYNANSLHTGVPSRFSGSGSGTDYTLTISTLQPEDFATYYCQQYYDYPLTFGPGTKVHIK |
| 65 | J-19.h2 CDR-H1 | TYAMGVS |
| 66 | J-19.h2 CDR-H2 | SIWWNGNKYNNPSLKS |
| 67 | J-19.h2 CDR-H3 | SRIIRFTDYVMDA |
| 68 | J-19.h2 CDR-L1 | RASEDIYNDLA |
| 69 | J-19.h2 CDR-L2 | NANSLHT |
| 70 | J-19.h2 CDR-L3 | QQYYDYPLT |
| 71 | J-19.h3 heavy chain | QVTLKESGPSLVKPTQTLTLTCTFSGFSLNTYAMGVSWIRQPPGKALEWLASIWWNGNKYNNPSLKSRLTITKDTSKNQVVLKVTNMDPADTATYYCAHSRIIRFTDYVMDAWGQGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 72 | J-19.h3 light chain | DIVMTQSPSSLSASVGDTVTITCRASEDIYNDLAWYQQKPGKAPQLLLYNANSLHTGVPSRFSGSGSGTDYTLTISTLQPEDFATYYCQQYYDYPLTFGPGTKVHIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 73 | J-19.h3 $V_H$ | QVTLKESGPSLVKPTQTLTLTCTFSGFSLNTYAMGVSWIRQPPGKALEWLASIWWNGNKYNNPSLKSRLTITKDTSKNQVVLKVTNMDPADTATYYCAHSRIIRFTDYVMDAWGQGTTVTVSS |
| 74 | J-19.h3 $V_L$ | DIVMTQSPSSLSASVGDTVTITCRASEDIYNDLAWYQQKPGKAPQLLLYNANSLHTGVPSRFSGSGSGTDYTLTISTLQPEDFATYYCQQYYDYPLTFGPGTKVHIK |
| 75 | J-19.h3 CDR-H1 | TYAMGVS |
| 76 | J-19.h3 CDR-H2 | SIWWNGNKYNNPSLKS |
| 77 | J-19.h3 CDR-H3 | SRIIRFTDYVMDA |
| 78 | J-19.h3 CDR-L1 | RASEDIYNDLA |

TABLE 10-continued

Table of Sequences

| 79 | J-19.h3 CDR-L2 | NANSLHT |
| 80 | J-19.h3 CDR-L3 | QQYYDYPLT |
| 81 | J-19.h4 heavy chain | QVTLKESGPALVKPTHTLTLTCTFSGFSLNTYAMGVSWIRQPPGKALEWLASIWWNGNKYNNPSLKSRLTISKDTSKNQVVLTMTNMDPEDTATFYCAHSRIIRFTDYVMDAWGRGTTVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 82 | J-19.h4 light chain | DIVMTQSPSSLSASVGDTVTITCRASEDIYNDLAWYQQKPGKAPQLLLYNANSLHTGVPSRFSGSGSGTDYTLTISTLQPEDFATYYCQQYYDYPLTFGPGTKVHIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 83 | J-19.h4 V$_H$ | QVTLKESGPALVKPTHTLTLTCTFSGFSLNTYAMGVSWIRQPPGKALEWLASIWWNGNKYNNPSLKSRLTISKDTSKNQVVLTMTNMDPEDTATFYCAHSRIIRFTDYVMDAWGRGTTVTVSS |
| 84 | J-19.h4 V$_L$ | DIVMTQSPSSLSASVGDTVTITCRASEDIYNDLAWYQQKPGKAPQLLLYNANSLHTGVPSRFSGSGSGTDYTLTISTLQPEDFATYYCQQYYDYPLTFGPGTKVHIK |
| 85 | J-19.h4 CDR-H1 | TYAMGVS |
| 86 | J-19.h4 CDR-H2 | SIWWNGNKYNNPSLKS |
| 87 | J-19.h4 CDR-H3 | SRIIRFTDYVMDA |
| 88 | J-19.h4 CDR-L1 | RASEDIYNDLA |
| 89 | J-19.h4 CDR-L2 | NANSLHT |
| 90 | J-19.h4 CDR-L3 | QQYYDYPLT |
| 91 | J-19.h5 heavy chain | QITLKESGPTLVKPTQTLTLTCTFSGFSLNTYAMGVSWIRQPPGKALEWLASIWWNGNKYNNPSLKSRLTVTKDTSKNQVVLTMTNMDPVDTATYYCAHSRIIAFTDYVMDAWGQGTLVTVSSASTKGPSVFPLAPCSRSTSESTAALGCLVKDYFPEPVTVSWNSGALTSGVHTFPAVLQSSGLYSLSSVVTVPSSSLGTKTYTCNVDHKPSNTKVDKRVESKYGPPCPPCPAPEFLGGPSVFLFPPKPKDTLMISRTPEVTCVVVDVSQEDPEVQFNWYVDGVEVHNAKTKPREEQFNSTYRVVSVLTVLHQDWLNGKEYKCKVSNKGLPSSIEKTISKAKGQPREPQVYTLPPSQEEMTKNQVSLTCLVKGFYPSDIAVEWESNGQPENNYKTTPPVLDSDGSFFLYSRLTVDKSRWQEGNVFSCSVMHEALHNHYTQKSLSLSLGK |
| 92 | J-19.h5 light chain | DIQMTQSPSSLSTSVGDRVTITCRASEDIYNDLAWYQQKPGKAPKLLIYNANSLHTGVASRFSGSGSGTDFTFTISSLQPEDVATYFCQQYYDYPLTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC |
| 93 | J-19.h5 V$_H$ | QITLKESGPTLVKPTQTLTLTCTFSGFSLNTYAMGVSWIRQPPGKALEWLASIWWNGNKYNNPSLKSRLTVTKDTSKNQVVLTMTNMDPVDTATYYCAHSRIIAFTDYVMDAWGQGTLVTVSS |
| 94 | J-19.h5 V$_L$ | DIQMTQSPSSLSTSVGDRVTITCRASEDIYNDLAWYQQKPGKAPKLLIYNANSLHTGVASRFSGSGSGTDFTFTISSLQPEDVATYFCQQYYDYPLTFGQGTKLEIK |
| 95 | J-19.h5 CDR-H1 | TYAMGVS |
| 96 | J-19.h5 CDR-H2 | SIWWNGNKYNNPSLKS |

TABLE 10-continued

Table of Sequences

| | | |
|---|---|---|
| 97 | J-19.h5 CDR-H3 | SRIIAFTDYVMDA |
| 98 | J-19.h5 CDR-L1 | RASEDIYNDLA |
| 99 | J-19.h5 CDR-L2 | NANSLHT |
| 100 | J-19.h5 CDR-L3 | QQYYDYPLT |
| 101 | J-19.h6 heavy chain | QITLKESGPTLVKPTQTLTLTCTFSGFSLNTYAMGVSWIR QPPGKALEWLASIWWNGNKYNNPSLKSRLTVTKDTSKNQV VLTMTNMDPVDTATYYCAHSRIIDFTDYVMDAWGQGTLVT VSSASTKGPSVFPLAPCSRSTSESTAALGCLVKDYFPEPV TVSWNSGALTSGVHTFPAVLQSSGLYSLSSVVTVPSSSLG TKTYTCNVDHKPSNTKVDKRVESKYGPPCPPCPAPEFLGG PSVFLFPPKPKDTLMISRTPEVTCVVVDVSQEDPEVQFNW YVDGVEVHNAKTKPREEQFNSTYRVVSVLTVLHQDWLNGK EYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHYT QKSLSLSLGK |
| 102 | J-19.h6 light chain | DIQMTQSPSSLSTSVGDRVTITCRASEDIYNDLAWYQQKP GKAPKLLIYNANSLHTGVASRFSGSGSGTDFTFTISSLQP EDVATYFCQQYYDYPLTFGQGTKLEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| 103 | J-19.h6 V$_H$ | QITLKESGPTLVKPTQTLTLTCTFSGFSLNTYAMGVSWIR QPPGKALEWLASIWWNGNKYNNPSLKSRLTVTKDTSKNQV VLTMTNMDPVDTATYYCAHSRIIDFTDYVMDAWGQGTLVT VSS |
| 104 | J-19.h6 V$_L$ | DIQMTQSPSSLSTSVGDRVTITCRASEDIYNDLAWYQQKP GKAPKLLIYNANSLHTGVASRFSGSGSGTDFTFTISSLQP EDVATYFCQQYYDYPLTFGQGTKLEIK |
| 105 | J-19.h6 CDR-H1 | TYAMGVS |
| 106 | J-19.h6 CDR-H2 | SIWWNGNKYNNPSLKS |
| 107 | J-19.h6 CDR-H3 | SRIIDFTDYVMDA |
| 108 | J-19.h6 CDR-L1 | RASEDIYNDLA |
| 109 | J-19.h6 CDR-L2 | NANSLHT |
| 110 | J-19.h6 CDR-L3 | QQYYDYPLT |
| 111 | J-19.h7 heavy chain | QITLKESGPTLVKPTQTLTLTCTFSGFSLNTYAMGVSWIR QPPGKALEWLASIWWNGNKYNNPSLKSRLTVTKDTSKNQV VLTMTNMDPVDTATYYCAHSRIIEFTDYVMDAWGQGTLVT VSSASTKGPSVFPLAPCSRSTSESTAALGCLVKDYFPEPV TVSWNSGALTSGVHTFPAVLQSSGLYSLSSVVTVPSSSLG TKTYTCNVDHKPSNTKVDKRVESKYGPPCPPCPAPEFLGG PSVFLFPPKPKDTLMISRTPEVTCVVVDVSQEDPEVQFNW YVDGVEVHNAKTKPREEQFNSTYRVVSVLTVLHQDWLNGK EYKCKVSNKGLPSSIEKTISKAKGQPREPQVYTLPPSQEE MTKNQVSLTCLVKGFYPSDIAVEWESNGQPENNYKTTPPV LDSDGSFFLYSRLTVDKSRWQEGNVFSCSVMHEALHNHYT QKSLSLSLGK |
| 112 | J-19.h7 light chain | DIQMTQSPSSLSTSVGDRVTITCRASEDIYNDLAWYQQKP GKAPKLLIYNANSLHTGVASRFSGSGSGTDFTFTISSLQP EDVATYFCQQYYDYPLTFGQGTKLElKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC |
| 113 | J-19.h7 V$_H$ | QITLKESGPTLVKPTQTLTLTCTFSGFSLNTYAMGVSWIR QPPGKALEWLASIWWNGNKYNNPSLKSRLTVTKDTSKNQV VLTMTNMDPVDTATYYCAHSRIIEFTDYVMDAWGQGTLVT VSS |
| 114 | J-19.h7 V$_L$ | DIQMTQSPSSLSTSVGDRVTITCRASEDIYNDLAWYQQKP GKAPKLLIYNANSLHTGVASRFSGSGSGTDFTFTISSLQP EDVATYFCQQYYDYPLTFGQGTKLEIK |

TABLE 10-continued

Table of Sequences

| | | | |
|---|---|---|---|
| 115 | J-19.h7 CDR-H1 | | TYAMGVS |
| 116 | J-19.h7 CDR-H2 | | SIWWNGNKYNNPSLKS |
| 117 | J-19.h7 CDR-H3 | | SRIIEFTDYVMDA |
| 118 | J-19.h7 CDR-L1 | | RASEDIYNDLA |
| 119 | J-19.h7 CDR-L2 | | NANSLHT |
| 120 | J-19.h7 CDR-L3 | | QQYYDYPLT |

| SEQ ID NO: | Protein | Acc. No. | Sequence |
|---|---|---|---|
| 121 | LILRA1 | O75019 | MTPIVTVLICLRLSLGPRTHVQAGTLPKPTLWAEPGSVIT QGSPVTLWCQGILETQEYRLYREKKTAPWITRIPQEIVKK GQFPIPSITWEHTGRYRCFYGSHTAGWSEPSDPLELVVTG AYIKPTLSALPSPVVTSGGNVTLHCVSQVAFGSFILCKEG EDEHPQCLNSQPRTHGWSRAIFSVGPVSPSRRWSYRCYAY DSNSPHVWSLPSDLLELLVLGVSKKPSLSVQPGPIVAPGE SLTLQCVSDVSYDRFVLYKEGERDFLQLPGPQPQAGLSQA NFTLGPVSRSYGGQYRCSGAYNLSSEWSAPSDPLDILIAG QFRGRPFISVHPGPTVASGENVTLLCQSWGPFHTFLLTKA GAADAPLRLRSIHEYPKYQAEFPMSPVTSAHSGTYRCYGS LSSNPYLLSHPSDSLELMVSGAAETLSPPQNKSDSKAGAA NTLSPSQNKTASHPQDYTVENLIRMGIAGLVLVVLGILLF EAQHSQRSL |
| 122 | LILRA2 | Q8N149 | MTPILTVLICLGLSLGPRTHVQAGHLPKPTLWAEPGSVII QGSPVTLRCQGSLQAEEYHLYRENKSASWVRRIQEPGKNG QFPIPSITWEHAGRYHCQYYSHNHSSEYSDPLELVVTGAY SKPTLSALPSPVVTLGGNVTLQCVSQVAFDGFILCKEGED EHPQRLNSHSHARGWSWAIFSVGPVSPSRRWSYRCYAYDS NSPYVWSLPSDLLELLVPGVSKKPSLSVQPGPMVAPGESL TLQCVSDVGYDRFVLYKEGERDFLQRPGWQPQAGLSQANF TLGPVSPSHGGQYRCYSAHNLSSEWSAPSDPLDILITGQF YDRPSLSVQPVPTVAPGKNVTLLCQSRGQFHTFLLTKEGA GHPPLHLRSEHQAQQNQAEFRMGPVTSAHVGTYRCYSSLS SNPYLLSLPSDPLELVVSEAAETLSPSQNKTDSTTTSLGQ HPQDYTVENLIRMGVAGLVLVVLGILLFEAQHSQRSLQDA AGR |
| 123 | LILRA3 | Q8N6C8 | MTPILTVLICLGLSLDPRTHVQAGPLPKPTLWAEPGSVIT QGSPVTLRCQGSLETQEYHLYREKKTALWITRIPQELVKK GQFPILSITWEHAGRYCCIYGSHTAGLSESSDPLELVVTG AYSKPTLSALPSPVVTSGGNVTIQCDSQVAFDGFILCKEG EDEHPQCLNSHSHARGSSRAIFSVGPVSPSRRWSYRCYGY DSRAPYVWSLPSDLLGLLVPGVSKKPSLSVQPGPVVAPGE KLTFQCGSDAGYDRFVLYKEWGRDFLQRPGRQPQAGLSQA NFTLGPVSRSYGGQYTCSGAYNLSSEWSAPSDPLDILITG QIRARPFLSVRPGPTVASGENVTLLCQSQGGMHTFLLTKE GAADSPLRLKSKRQSHKYQAEFPMSPVTSAHAGTYRCYGS LSSNPYLLTHPSDPLELVVSGAAETLSPPQNKSDSKAGE |
| 124 | LILRA4 | P59901 | MTLILTSLLFFGLSLGPRTRVQAENLPKPILWAEPGPVIT WHNPVTIWCQGTLEAQGYRLDKEGNSMSRHILKTLESENK VKLSIPSMMWEHAGRYHCYYQSPAGWSEPSDPLELVVTAY SRPTLSALPSPVVTSGVNVTLRCASRLGLGRFTLIEEGDH RLSWTLNSHQHNHGKFQALFPMGPLTFSNRGTFRCYGYEN NTPYVWSEPSDPLQLLVSGVSRKPSLLTLQGPVVTPGENL TLQCGSDVGYIRYTLYKEGADGLPQRPGRQPQAGLSQANF TLSPVSRSYGGQYRCYGAHNVSSEWSAPSDPLDILIAGQI SDRPSLSVQPGPTVTSGEKVTLLCQSWDPMFTFLLTKEGA AHPPLRLRSMYGAHKYQAEFPMSPVTSAHAGTYRCYGSRS SNPYLLSHPSEPLELVVSGATETLNPAQKKSDSKTAPHLQ DYTVENLIRMGVAGLVLLFLGILLFEAQHSQRSPPRCSQE ANSRKDNAPFRVVEPWEQI |
| 125 | LILRA5 | A6NI73 | MAPWSHPSAQLQPVGGDAVSPALMVLLCLGLSLGPRTHVQ AGNLSKATLWAEPGSVISRGNSVTIRCQGTLEAQEYRLVK EGSPEPWDTQNPLEPKNKARFSIPSMTEHHAGRYRCYYYS PAGWSEPSDPLELVVTGFYNKPTLSALPSPVVTSGENVTL QCGSRLRFDRFILTEEGDHKLSWTLDSQLTPSGQFQALFP VGPVTPSHRWMLRCYGSRRHILQVWSEPSDLLEIPVSGAA DNLSPSQNKSDSGTASHLQDYAVENLIRMGMAGLILVVLG ILIFQDWHSQRSPQAAAGR |

TABLE 10-continued

Table of Sequences

| 126 | LILRA6 | Q6PI73 | MTPALTALLCLGLSLGPRTRVQAGPFPKPTLWAEPGSVIS<br>WGSPVTIWCQGSLEAQEYQLDKEGSPEPLDRNNPLEPKNK<br>ARFSIPSMTQHHAGRYRCHYYSSAGWSEPSDPLELVMTGF<br>YNKPTLSALPSPVVASGGNMTLRCGSQKGYHHFVLMKEGE<br>HQLPRTLDSQQLHSGGFQALFPVGPVTPSHRWRFTCYYYY<br>TNTPRVWSHPSDPLEILPSGVSRKPSLLTLQGPVLAPGQS<br>LTLQCGSDVGYDRFVLYKEGERDFLQRPGQQPQAGLSQAN<br>FTLGPVSPSHGGQYRCYGAHNLSSEWSAPSDPLNILMAGQ<br>IYDTVSLSAQPGPTVASGENVTLLCQSRGYFDTFLLTKEG<br>AAHPPLRLRSMYGAHKYQAEFPMSPVTSAHAGTYRCYGSY<br>SSNPHLLSFPSEPLELMVSGHSGGSSLPPTGPPSTPASHA<br>KDYTVENLIRMGMAGLVLVFLGILLFEAQHSQRNPQDAAG<br>R |
| 127 | LILRB1 | Q8NHL6 | MTPILTVLICLGLSLGPRTHVQAGHLPKPTLWAEPGSVIT<br>QGSPVTLRCQGGQETQEYRLYREKKTALWITRIPQELVKK<br>GQFPIPSITWEHAGRYRCYYGSDTAGRSESSDPLELVVTG<br>AYIKPTLSAQPSPVVNSGGNVILQCDSQVAFDGFSLCKEG<br>EDEHPQCLNSQPHARGSSRAIFSVGPVSPSRRWWYRCYAY<br>DSNSPYEWSLPSDLLELLVLGVSKKPSLSVQPGPIVAPEE<br>TLTLQCGSDAGYNRFVLYKDGERDFLQLAGAQPQAGLSQA<br>NFTLGPVSRSYGGQYRCYGAHNLSSEWSAPSDPLDILIAG<br>QFYDRVSLSVQPGPTVASGENVTLLCQSQGWMQTFLLTKE<br>GAADDPWRLRSTYQSQKYQAEFPMGPVTSAHAGTYRCYGS<br>QSSKPYLLTHPSDPLELVVSGPSGGSSPTTGPTSTSGPE<br>DQPLTPTGSDPQSGLRHLGVVIGILVAVILLLLLLLLF<br>LILRHRRQGKHWTSTQRKADFQHPAGAVGPEPTDRGLQWR<br>SSPAADAQEENLYAAVKHTQPEDGVEMDTRSPHDEDPQAV<br>TYAEVKHSRPRREMASPPSPLSGEFLDTKDRQAEEDRQMD<br>TEAAASEAPQDVTYAQLHSLTLRREATEPPPSQEGPSPAV<br>PSIYATLAIH |
| 128 | LILRB2 | Q8N423 | MTPIVTVLICLGLSLGPRTHVQTGTIPKPTLWAEPDSVIT<br>QGSPVTLSCQGSLEAQEYRLYREKKSASWITRIRPELVKN<br>GQFHIPSITWEHTGRYGCQYYSRARWSELSDPLVLVMTGA<br>YPKPTLSAQPSPVVTSGGRVTLQCESQVAFGGFILCKEGE<br>EEHPQCLNSQPHARGSSRAIFSVGPVSPNRRWSHRCYGYD<br>LNSPYVWSSPSDLLELLVPGVSKKPSLSVQPGPVVAPGES<br>LTLQCVSDVGYDRFVLYKEGERDLRQLPGRQPQAGLSQAN<br>FTLGPVSRSYGGQYRCYGAHNLSSECSAPSDPLDILITGQ<br>IRGTPFISVQPGPTVASGENVTLLCQSWRQFHTFLLTKAG<br>AADAPLRLRSIHEYPKYQAEFPMSPVTSAHAGTYRCYGSL<br>NSDPYLLSHPSEPLELVVSGPSMGSSPPPTGPISTPAGPE<br>DQPLTPTGSDPQSGLRHLGVVIGILVAVVLLLLLLLLLF<br>LILRHRRQGKHWTSTQRKADFQHPAGAVGPEPTDRGLQWR<br>SSPAADAQEENLYAAVKDTQPEDGVEMDTRAAASEAPQDV<br>TYAQLHSLTLRRKATEPPPSQEREPPAEPSIYATLAIH |
| 129 | LILRB2 | NP_005865.3 | MTPIVTVLICLGLSLGPRTRVQTGTIPKPTLWAEPDSVIT<br>QGSPVTLSCQGSLEAQEYRLYREKKSASWITRIRPELVKN<br>GQFHIPSITWEHTGRYGCQYYSRARWSELSDPLVLVMTGA<br>YPKPTLSAQPSPVVTSGGRVTLQCESQVAFGGFILCKEGE<br>DEHPQCLNSQPHARGSSRAIFSVGPVSPNRRWSHRCYGYD<br>LNSPYVWSSPSDLLELLVPGVSKKPSLSVQPGPVMAPGES<br>LTLQCVSDVGYDRFVLYKEGERDLRQLPGRQPQAGLSQAN<br>FTLGPVSRSYGGQYRCYGAHNLSSECSAPSDPLDILITGQ<br>IRGTPFISVQPGPTVASGENVTLLCQSWRQFHTFLLTKAG<br>AADAPLRLRSIHEYPKYQAEFPMSPVTSAHAGTYRCYGSL<br>NSDPYLLSHPSEPLELVVSGPSMGSSPPPTGPISTPAGPE<br>DQPLTPTGSDPQSGLRHLGVVIGILVAVVLLLLLLLLLF<br>LILRHRRQGKHWTSTQRKADFQHPAGAVGPEPTDRGLQWR<br>SSPAADAQEENLYAAVKDTQPEDGVEMDTRAAASEAPQDV<br>TYAQLHSLTLRRKATEPPPSQEREPPAEPSIYATLAIH |
| 130 | LILRB3 | O75022 | MTPALTALLCLGLSLGPRTRVQAGPFPKPTLWAEPGSVIS<br>WGSPVTIWCQGSQEAQEYRLHKEGSPEPLDRNNPLEPKNK<br>ARFSIPSMTEHHAGRYRCHYYSSAGWSEPSDPLEMVMTGA<br>YSKPTLSALPSPVVASGGNMTLRCGSQKGYHHFVLMKEGE<br>HQLPRTLDSQQLHSRGFQALFPVGPVTPSHRWRFTCYYYY<br>TNTPWVWSHPSDPLEILPSGVSRKPSLLTLQGPVLAPGQS<br>LTLQCGSDVGYNRFVLYKEGERDFLQRPGQQPQAGLSQAN<br>FTLGPVSPSNGGQYRCYGAHNLSSEWSAPSDPLNILMAGQ |

TABLE 10-continued

Table of Sequences

| | | | |
|---|---|---|---|
| | | | IYDTVSLSAQPGPTVASGENVTLLCQSWWQFDTFLLTKEG
AAHPPLRLRSMYGAHKYQAEFPMSPVTSAHAGTYRCYGSY
SSNPHLLSHPSEPLELVVSGHSGGSSLPPTGPPSTPGLGR
YLEVLIGVSVAFVLLLFLLLFLLLRRQRHSKHRTSDQRKT
DFQRPAGAAETEPKDRGLLRRSSPAADVQEENLYAAVKDT
QSEDRVELDSQSPHDEDPQAVTYAPVKHSSPRREMASPPS
SLSGEFLDTKDRQVEEDRQMDTEAAASEASQDVTYAQLHS
LTLRRKATEPPPSQEGEPPAEPSIYATLAIH |
| 131 | LILRB4 | Q8NHJ6 | MIPTFTALLCLGLSLGPRTHMQAGPLPKPTLWAEPGSVIS
WGNSVTIWCQGTLEAREYRLDKEESPAPWDRQNPLEPKNK
ARFSIPSMTEDYAGRYRCYYRSPVGWSQPSDPLELVMTGA
YSKPTLSALPSPLVTSGKSVTLLCQSRSPMDTFLLIKERA
AHPLLHLRSEHGAQQHQAEFPMSPVTSVHGGTYRCFSSHG
FSHYLLSHPSDPLELIVSGSLEDPRPSPTRSVSTAAGPED
QPLMPTGSVPHSGLRRHWEVLIGVLVVSILLLSLLLFLLL
QHWRQGKHRTLAQRQADFQRPPGAAEPEPKDGGLQRRSSP
AADVQGENFCAAVKNTQPEDGVEMDTRQSPHDEDPQAVTY
AKVKHSRPRREMASPPSPLSGEFLDTKDRQAEEDRQMDTE
AAASEAPQDVTYAQLHSFTLRQKATEPPPSQEGASPAEPS
VYATLAIH |
| 132 | LILRB5 | O75023 | MTLTLSVLICLGLSVGPRTCVQAGTLPKPTLWAEPASVIA
RGKPVTLWCQGPLETEEYRLDKEGLPWARKRQNPLEPGAK
AKFHIPSTVYDSAGRYRCYYETPAGWSEPSDPLELVATGF
YAEPTLLALPSPVVASGGNVTLQCDTLDGLLTFVLVEEEQ
KLPRTLYSQKLPKGPSQALFPVGPVTPSCRWRFRCYYYYR
KNPQVWSNPSDLLEILVPGVSRKPSLLIPQGSVVARGGSL
TLQCRSDVGYDIFVLYKEGEHDLVQGSGQQPQAGLSQANF
TLGPVSRSHGGQYRCYGAHNLSPRWSAPSDPLDILIAGLI
PDIPALSVQPGPKVASGENVTLLCQSWHQIDTFFLTKEGA
AHPPLCLKSKYQSYRHQAEFSMSPVTSAQGGTYRCYSAIR
SYPYLLSSPSYPQELVVSGPSGDPSLSPTGSTPTPGPEDQ
PLTPTGLDPQSGLGRHLGVVTGVSVAFVLLLFLLLFLLLR
HRHQSKHRTSAHFYRPAGAAGPEPKDQGLQKRASPVADIQ
EEILNAAVKDTQPKDGVEMDARAAASEAPQDVTYAQHSL
TLRREATEPPPSQEREPPAEPSIYAPLAIH |
| 133 | Macaca
fascicularis
LILRB2
(putative) | XP_015297203 | MTPILMVLICLGLSLGPRTHVQAGILPKPTLWAEPGSVIS
EGSPVTLRCQGSLQVQEYHLYREKNPASWVRQIRQELVKK
GYFAIGFITWEHTGQYRCQYYSHSWWSEPSDPLELVVTGA
YSKPTLSALPSPVVASGGNVTLQCDSQVAFDSFTLCKEGE
DEHPQRLNCQSHARGWSWAVFSVGPVSPSRRWSYRCYGYI
SSAPNVWSLPSDLLELLVPGVSKKPSLSVQPGPVVAPGDK
LTLQCGSDAGYDRFALYKEGEGDFLQRPVRQPQAGLSQAN
FLLGPVSRSHGGQYRCSGAHNLSSEWSAPSDPLDILIAGQ
IRGRPFLSVQPGPKVVSGENVTLLCQSSWQFHAFLLTQAG
AADAHLHLRSMYKYPKYQAEFPMSPVTSAHAGTYRCYGSR
SSNPYLLSVPSDPLELVVSGPSGGPSSPTTGPTSTCAGPE
DQPLTPTGSAPQSGLGRHLGVVTGVLVAFVLLLFLLLLLF
LVLRYRRQGKRWTSAQRKADFQHPAGAVEPEPRDRGLQRR
SSPAADTQEENLYAAVKDTQPEDGVELDSRAAASEDPQDV
TYAQLQSLTLRREATEPPPSQERAPPVESSIYATLTIH |
| 134 | Macaca
mulatta
LILRBb
(putative) | Q1I0P6_MACMU | GLSLGSRTRVQAGTLPKPTLWAEPDSVITQGSPVTLRCQG
SLQVQEYRLYRERKPASWVRRIRQELVKKGYFAIGFITWE
HTGQYHCQYYSHSWWPEPSDPLELVMTGAYSKPTLSALPS
PMVASGGNVTLQCDSQVAFDGFILCKEGEDEHPQRLNSHF
HAYGWSRAVFSVGPVSPSRRWSYRCYGYDSRSPYVWSLPS
DLLELLVPGVSKKPSLSVQPGPVVAPGDKLTLQCGSDAGY
NRFALYKEGEGNFLQHPGRQRQAGLSQANFLLGPVSRSHG
GQYRCYGAHNLSSEWSAPSDPLDILIAGQIRGRPSLLVQP
GRTVASGENVTLLCQSSWQFHVFLLTQAGAADAHLHLRSM
YKYPKYQAEFPMSPVTSAHAGTYRCYGSHSSDSYLLSVPS
DPLELVVSGPSGGPSSPTTGPTSTCGPEDQPLTPTGSAPQ
SGLGRHLGVVTGVLVAFVLLLFLLLLLFLVLRHRRQGKRW
TSAQRKADFQHPAGAVEPEPRDRGLQRRSSPAANTQEENL
YAAMKDTQPEDGVELDSQAAASEDPQDVTYAQLQSLTLRR
ETTEPPPSQERAPPVESSIY |

In the event of an inconsistency between a sequence in the sequence listing and a sequence in the specification, the sequence in the specification should be considered as controlling.

What is claimed is:

1. A method of treating cancer in a subject in need thereof, or enhancing an anti-tumor immune response in a subject in need thereof, the method comprising administering to the subject a therapeutically effective amount of an antibody comprising the following complementarity determining regions (CDRs):
   (a) a CDR-H1 comprising the amino acid sequence of SEQ ID NO: 15;
   (b) a CDR-H2 comprising the amino acid sequence of SEQ ID NO: 16;
   (c) a CDR-H3 comprising the amino acid sequence of SEQ ID NO: 17;
   (d) a CDR-L1 comprising the amino acid sequence of SEQ ID NO: 18;
   (e) a CDR-L2 comprising the amino acid sequence of SEQ ID NO: 19; and
   (f) a CDR-L3 comprising the amino acid sequence of SEQ ID NO: 20.

2. The method of claim 1, further comprising administering the antibody in combination with a second therapeutic agent.

3. The method of claim 1, wherein the antibody comprises a $V_H$ region comprising an amino acid sequence that is at least 90% identical to the amino acid sequence of SEQ ID NO: 53 and a $V_L$ region comprising an amino acid sequence that is at least 90% identical to the amino acid sequence of SEQ ID NO: 54.

4. The method of claim 1, wherein the antibody comprises a $V_H$ region comprising the amino acid sequence of SEQ ID NO: 53 and a variable light chain $V_L$ region comprising the amino acid sequence of SEQ ID NO: 54.

5. The method of claim 1, wherein the antibody comprises a heavy chain comprising the amino acid sequence of SEQ ID NO: 51 and a light chain comprising the amino acid sequence of SEQ ID NO: 52.

6. The method of claim 1, wherein the antibody comprises:
   (a) a variable heavy chain ($V_H$) region comprising an amino acid sequence that is at least 90% identical to the amino acid sequence of SEQ ID NO: 13 and a variable light chain ($V_L$) region comprising an amino acid sequence that is at least 90% identical to the amino acid sequence of SEQ ID NO: 14;
   (b) a $V_H$ region comprising an amino acid sequence that is at least 90% identical to the amino acid sequence of SEQ ID NO: 63 and a $V_L$ region comprising an amino acid sequence that is at least 90% identical to the amino acid sequence of SEQ ID NO: 64;

(c) a $V_H$ region comprising an amino acid sequence that is at least 90% identical to the amino acid sequence of SEQ ID NO: 73 and a $V_L$ region comprising an amino acid sequence that is at least 90% identical to the amino acid sequence of SEQ ID NO: 74; or (d) a $V_H$ region comprising an amino acid sequence that is at least 90% identical to the amino acid sequence of SEQ ID NO: 83 and a $V_L$ region comprising an amino acid sequence that is at least 90% identical to the amino acid sequence of SEQ ID NO: 84.

7. The method of claim 1, wherein the antibody comprises:

(a) a $V_H$ region comprising the amino acid sequence of SEQ ID NO: 13 and a $V_L$ region comprising the amino acid sequence of SEQ ID NO: 14;

(b) a $V_H$ region comprising the amino acid sequence of SEQ ID NO: 63 and a $V_L$ region comprising the amino acid sequence of SEQ ID NO: 64;

(c) a $V_H$ region comprising the amino acid sequence of SEQ ID NO: 73 and a $V_L$ region comprising the amino acid sequence of SEQ ID NO: 74; or (d) a $V_H$ region comprising the amino acid sequence of SEQ ID NO: 83 and a $V_L$ region comprising the amino acid sequence of SEQ ID NO: 84.

8. The method of claim 1, wherein the antibody comprises:

(a) a heavy chain comprising the amino acid sequence of SEQ ID NO: 11 and a light chain comprising the amino acid sequence of SEQ ID NO: 12;

(b) a heavy chain comprising the amino acid sequence of SEQ ID NO: 61 and a light chain comprising the amino acid sequence of SEQ ID NO: 62;

(c) a heavy chain comprising the amino acid sequence of SEQ ID NO: 71 and a light chain comprising the amino acid sequence of SEQ ID NO: 72; or (d) a heavy chain comprising the amino acid sequence of SEQ ID NO: 81 and a light chain comprising the amino acid sequence of SEQ ID NO: 82.

9. The method of claim 1, wherein:

(a) the antibody is a monoclonal antibody;

(b) the antibody is a chimeric antibody, a humanized antibody, a CDR-grafted antibody, or a human antibody;

(c) the antibody comprises an Fc region selected from the group consisting of a native Fc region, a variant Fc region, and a functional Fc region;

(d) the antibody is a conjugate antibody or is detectably labeled;

(e) the antibody is an IgG1 antibody, an IgG2 antibody, or an IgG3 antibody;

(f) the antibody is an IgG4 antibody;

(g) the heavy chain of the antibody additionally comprises a C-terminal lysine; or (h) the antibody binds to LILRB2 with a dissociation constant ($K_D$) of less than 3.0 nM.

10. The method of claim 1, wherein the method further comprises administering an immunotherapy.

11. The method of claim 10, wherein the immunotherapy comprises a PD-1 or PD-L1 therapy.

12. The method of claim 11, wherein the PD-1 or PD-L1 therapy is selected from the group consisting of nivolumab, pidilizumab, lambrolizumab/pembrolizumab, durvalumab, RG-7446, avelumab, AMP-224, BMS-936559, AMP-514, MDX-1105, ANB-011, anti-LAG-3/PD-1, MEDI-4736, RG7446/MPDL3280A, KD-033, STI-A1010, STI-A1110, TSR-042, and JTX-4014.

13. The method of claim 10, wherein the immunotherapy comprises an ICOS therapy.

14. The method of claim 13, wherein the ICOS therapy comprises JTX-2011.

15. The method of claim 10, wherein the immunotherapy comprises a CTLA therapy.

16. The method of claim 15, wherein the CTLA therapy comprises ipilimumab.

17. The method of claim 2, wherein the second therapeutic agent comprises a cancer vaccine.

18. The method of claim 17, wherein the cancer vaccine is selected from Sipuleucel-T, rilimogene galvacirpvec, and rilimogene glafolivec.

19. The method of claim 1, wherein the cancer is a solid cancer.

20. The method of claim 1, wherein the cancer is selected from the group consisting of carcinoma, lymphoma, blastoma, sarcoma, and leukemia.

21. The method of claim 1, wherein the cancer is selected from the group consisting of kidney cancer, squamous cell cancer, mesothelioma, teratoma, small-cell lung cancer, pituitary cancer, esophageal cancer, astrocytoma, soft tissue sarcoma, lung cancer, cancer of the peritoneum, hepatocellular cancer, gastrointestinal cancer, stomach cancer, pancreatic cancer, cervical cancer, ovarian cancer, liver cancer, bladder cancer, hepatoma, breast cancer, colon cancer, colorectal cancer, rectal cancer, endometrial or uterine carcinoma, salivary gland carcinoma, liver cancer, prostate cancer, vulval cancer, thyroid cancer, thymoma, hepatic carcinoma, brain cancer, glioma, glioblastoma, endometrial cancer, testis cancer, cholangiocarcinoma, cholangiosarcoma, gallbladder carcinoma, gastric cancer, melanoma, pheochromocytoma, paraganglioma, adenoid cystic carcinoma, and head and neck cancer.

* * * * *